(12) United States Patent
Cee et al.

(10) Patent No.: US 7,776,857 B2
(45) Date of Patent: Aug. 17, 2010

(54) AURORA KINASE MODULATORS AND METHOD OF USE

(75) Inventors: Victor Cee, Thousand Oaks, CA (US); Holly Deak, Brookline, MA (US); Bingfan Du, Cambridge, MA (US); Stephanie Geuns-Meyer, Medford, MA (US); Brian L. Hodous, Cambridge, MA (US); Zihao Hua, Tewksbury, MA (US); Matthew Martin, Cambridge, MA (US); Isaac Marx, Somerville, MA (US); Hanh Nho Nguyen, Arlington, MA (US); Philip Olivieri, Charlestown, MA (US); Kathleen Panter, Cambridge, MA (US); Karina Romero, Cambridge, MA (US); Laurie Schenkel, Boston, MA (US); Ryan White, Somerville, MA (US)

(73) Assignee: Amgen Inc., Thousand Oaks, CA (US)

( * ) Notice: Subject to any disclaimer, the term of this patent is extended or adjusted under 35 U.S.C. 154(b) by 89 days.

(21) Appl. No.: 12/080,669

(22) Filed: Apr. 3, 2008

(65) Prior Publication Data
US 2009/0069297 A1  Mar. 12, 2009

Related U.S. Application Data

(60) Provisional application No. 60/922,205, filed on Apr. 5, 2007.

(51) Int. Cl.
*C07D 237/30* (2006.01)
(52) U.S. Cl. .......................... 514/248; 544/237; 546/123
(58) Field of Classification Search .................. 544/237
See application file for complete search history.

(56) References Cited

U.S. PATENT DOCUMENTS

| | | | |
|---|---|---|---|
| 6,143,764 A | 11/2000 | Kubo | |
| 6,903,101 B1 | 6/2005 | Dumas | |
| 6,919,338 B2 | 7/2005 | Mortlock | |

FOREIGN PATENT DOCUMENTS

| | | |
|---|---|---|
| WO | 9713771 A1 | 4/1997 |
| WO | 9802434 A1 | 1/1998 |
| WO | 9802437 A1 | 1/1998 |
| WO | 0050405 A1 | 8/2000 |
| WO | 0110859 A1 | 2/2001 |
| WO | 0121597 A1 | 3/2001 |
| WO | 0194353 A1 | 12/2001 |
| WO | WO0200649 | 1/2002 |
| WO | 02092087 A1 | 11/2002 |
| WO | 03055491 A1 | 7/2003 |
| WO | 03082289 A1 | 10/2003 |
| WO | 2004000833 A1 | 12/2003 |
| WO | 2004016612 A1 | 2/2004 |
| WO | 2004037814 A1 | 5/2004 |
| WO | 2004039774 A1 | 5/2004 |
| WO | 2005047279 A1 | 5/2005 |
| WO | 2005118572 A1 | 12/2005 |
| WO | 2005121125 A1 | 12/2005 |
| WO | 2006085330 A1 | 8/2006 |
| WO | 2007084815 A2 | 7/2007 |

OTHER PUBLICATIONS

R. Giet and C. Prigent, J. Cell. Sci., 112:3591-3601 (1999).
Y. Miyoshi et al., Int. J. Cancer, 92:370-373 (2001).
Angew. Chem. Int. Ed. 2003, 42, 5993-5996.
Garnier, E.; Andoux, J.; Pasquinet, E.; Suzenet, F.; Poullain, D.; Lebret, B.; Guillaumet, G. J. Org. Chem. 2004, 69, 7809.

*Primary Examiner*—James O Wilson
*Assistant Examiner*—Brian McDowell
(74) *Attorney, Agent, or Firm*—G. Prabhakar Reddy

(57) ABSTRACT

The present invention relates to chemical compounds having a general formula I

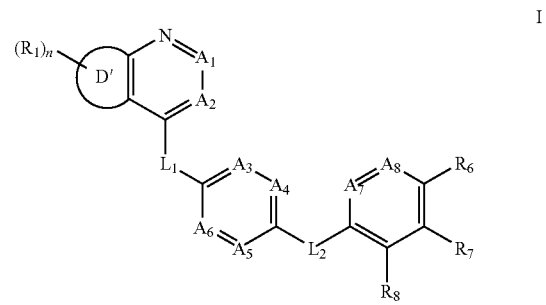

wherein $A^{1-8}$, $D'$, $L^1$, $L^2$, $R^1$, $R^{6-8}$ and n are defined herein, and synthetic intermediates, which are capable of modulating various protein kinase receptor enzymes and, thereby, influencing various disease states and conditions related to the activities of such kinases. For example, the compounds are capable of modulating Aurora kinase thereby influencing the process of cell cycle and cell proliferation to treat cancer and cancer-related diseases. The invention also includes pharmaceutical compositions, including the compounds, and methods of treating disease states related to the activity of Aurora kinase.

17 Claims, No Drawings

AURORA KINASE MODULATORS AND METHOD OF USE

This application claims the benefit of U.S. Provisional Application No. 60/922,205, filed Apr. 5, 2007, which is hereby incorporated herein by reference in its entirety.

FIELD OF THE INVENTION

The invention relates to the field of pharmaceutical agents and, more specifically, is directed to compounds and compositions useful for modulating Aurora kinase, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different cancers, over the last couple of decades, numerous groups have invested a tremendous amount of time, effort and financial resources. However, to date, of the available cancer treatments and therapies, only a few offer any considerable degree of success.

Cancer is often characterized by unregulated cell proliferation. Damage to one or more genes, responsible for the cellular pathways, which control progress of proliferation through the cell cycle, typically causes the loss of normal regulation of cell proliferation. These genes code for various proteins, which participate in a cascade of events, including protein phosphorylation, leading to cell-cycling progression and cell proliferation. Various kinase proteins have been identified, which play roles in the cell cycling cascade and in protein phosphorylation in particular.

One class of proteins found to play a part in cell cycling and, therefore, cell proliferation is the Aurora kinase family of proteins. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also commonly referred to as Aurora 2, Aurora 1, and Aurora 3, respectively.

The specific function of each Aurora kinase member in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases appear to be viable targets for the treatment of cancer. Aurora kinases are overexpressed in various types of cancers, including colon, breast, lung, pancrease, prostate, bladder, head, neck, cervix, and ovarian cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

Further, inhibition of one or more of the Aurora kinases by several parties has been shown to inhibit cell proliferation and trigger apoptosis in several tumor cell lines. Particularly, inhibition of Aurora has been found to arrest cell cycling and promote programmed cell death via apoptosis. Accordingly, there has been a strong interest in finding inhibitors of Aurora kinase proteins.

Thus, the inhibition of Aurora kinases has been regarded as a promising approach for the development of novel anti-cancer agents. For example, WO 04/039774 describes aza-quinazolinones for treating cancer via inhibiton of Aurora kinase, WO 04/037814 describes indazolinones for treating cancer via inhibiton of Aurora-2 kinase, WO 04/016612 describes 2, 6, 9-substituted purine derivatives for treating cancer via inhibiton of Aurora kinase, WO 04/000833 describes tri- and tetra-substituted pyrimidine compounds useful for treating Aurora-meiated diseases, WO 04/092607 describes crystals useful for screening, designing and evaluating compounds as agonists or antagonists of Aurora kinase and U.S. Pat. No. 6,919,338 and WO 03/055491 each describe substituted quinazoline derivatives as inhibitors of Aurora-2 kinase.

BRIEF DESCRIPTION OF THE INVENTION

The present invention provides a new class of compounds useful for modulating one or more of the Aurora kinase enzymes and for treating Aurora kinase-mediated conditions and/or diseases, including cancer. In one embodiment of the invention, the compounds, including pharmaceutically acceptable salts thereof, are generally defined by Formula I

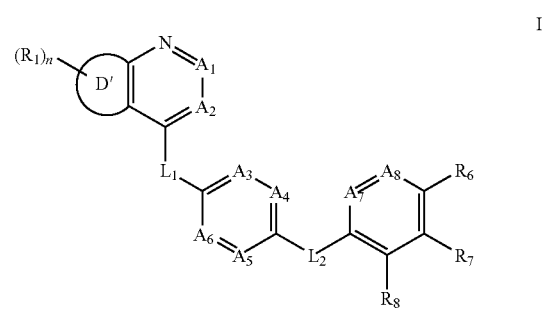

wherein $A^{1-8}$, D', $L^1$, $L^2$, $R^1$, $R^{6-8}$ and n are defined herein.

In another embodiment, the invention provides compounds of Formulas II, III and IV, which are similar in structure to Formula I above.

The invention also provides processes for making compounds of Formulas I-IV, as well as intermediates useful in such processes.

The compounds provided by the invention have Aurora kinase modulatory activity and, in particular, Aurora kinase inhibitory activity. To this end, the invention also provides the use of these compounds, as well as pharmaceutically acceptable salts thereof, in the preparation and manufacture of a pharmaceutical composition or medicament for therapeutic, prophylactic, acute or chronic treatment of Aurora kinase mediated diseases and disorders, including without limitation, cancer. Thus, the compounds of the invention are useful in the manufacture of anti-cancer medicaments. For example, in one embodiment, the invention provides a pharmaceutical composition (also referred to herein as a medicament) comprising a therapeutically-effective amount of a compound of Formula I, II, III or IV in association with at least one pharmaceutically-acceptable carrier, adjuvant or diluent.

DETAILED DESCRIPTION OF THE INVENTION

In one embodiment of the invention, compounds useful for treating Aurora kinase and related disorders, including cancer and inflammation, are defined by Formula I:

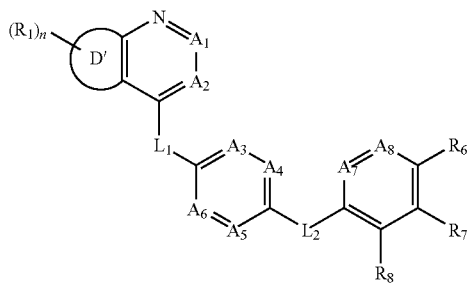

I or stereoisomer, tautomer, solvate, pharmaceutically acceptable salt or prodrug thereof, wherein each of $A^1$ and $A^2$, independently, is N or $CR^2$, provided no more than one of $A^1$ and $A^2$ is N;

each of $A^3$, $A^4$, $A^5$ and $A^6$, independently, is N or $CR^3$, provided that no more than two of $A^3$, $A^4$, $A^5$ and $A^6$ is N;

each of $L^1$ and $L^2$, independently, is —O—, —$NR^4$—, —S—, —C(O)—, —S(O)—, —$SO_2$— or —$CR^4R^4$—, wherein each $R^4$, independently, is H, halo, OH, $C_{1-6}$alkoxyl, NH—$C_{1-6}$alkyl, CN or $C_{1-6}$alkyl;

each of $A^7$ and $A^8$, independently, is N or $CR^5$, provided at least one of $A^7$ and $A^8$ is N;

D' is a 5- or 6-membered ring of carbon atoms optionally including 1-3 heteroatoms selected from O, N and S, and the ring optionally substituted independently with n number of substituents of $R^1$;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^2$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^5$ is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

each of $R^6$, $R^7$ and $R^8$, independently, is $R^9$;

alternatively, either of $R^6$ or $R^8$, independently, taken together with $R^1$ and the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4;

provided that (1) when D' is a phenyl ring, $A^1$ is CH and $A^2$ is $CR^2$ in Formula I above, than $R^2$ is not CN; or (2) when $A^1$ is CH, $A^2$ is N and $L^1$ is —$NR^4$—, then D' is not

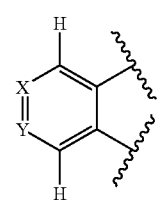

wherein one of X and Y is N and the other of X and Y is an optionally substituted carbon atom.

Accordingly, while the above embodiment includes quinoline D ring compounds, the present invention does not encompass those compounds of Formula I where when either of $A^1$ or $A^2$, independently, is $CR^2$, then $R^2$ is a cyano group. In addition, the present invention does not include those compounds of Formula I wherein the D ring is pyrimidine ring having $A^1$ as CH and $A^2$ as N while the D' ring is

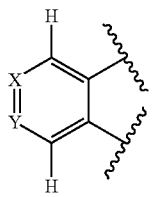

wherein one of X and Y is N and the other of X and Y is an optionally substituted carbon atom.

In another embodiment, Formula I includes compounds wherein $A^1$ is N and $A^2$ is $CR^2$, in conjunction with any of the above or below embodiments.

In another embodiment, Formula I includes compounds wherein $A^1$ is $CR^2$ and $A^2$ is N, in conjunction with any of the above or below embodiments.

In another embodiment, Formula I includes compounds wherein each of $A^1$ and $A^2$ independently, is $CR^2$, in conjunction with any of the above or below embodiments.

In another embodiment, Formula I includes compounds wherein each of $A^1$ and $A^2$ independently, is $CR^2$ wherein $R^2$ is either H or a halogen, in conjunction with any of the above or below embodiments.

In another embodiment, Formula I includes compounds wherein D' is a 5-membered ring of carbon atoms optionally including 1-3 heteroatoms selected from O, N and S, and the ring optionally substituted independently with n number of substituents of $R^1$, in conjunction with any of the above or below embodiments.

In another embodiment, Formula I includes compounds wherein D' is a 6-membered ring of carbon atoms optionally including 1-3 heteroatoms selected from O, N and S, and the ring optionally substituted independently with n number of substituents of $R^1$, in conjunction with any of the above or below embodiments.

In another embodiment, Formula I includes compounds wherein D' is

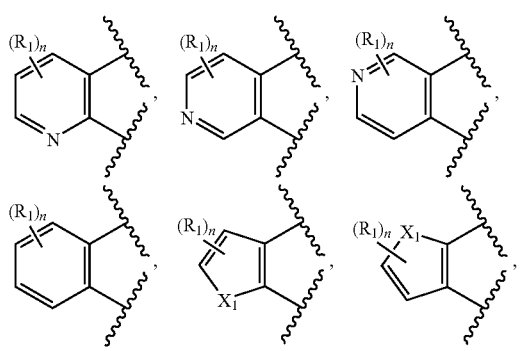

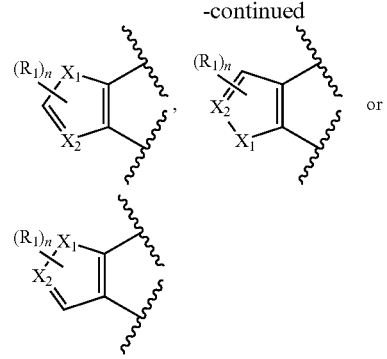

wherein $X^1$ is O, S or $NR^1$, $X^2$ is $CR^1$ or N and $R^1$ and n are as defined in Formula I, in conjunction with any of the above or below embodiments.

In another embodiment, Formula I includes compounds wherein D' is

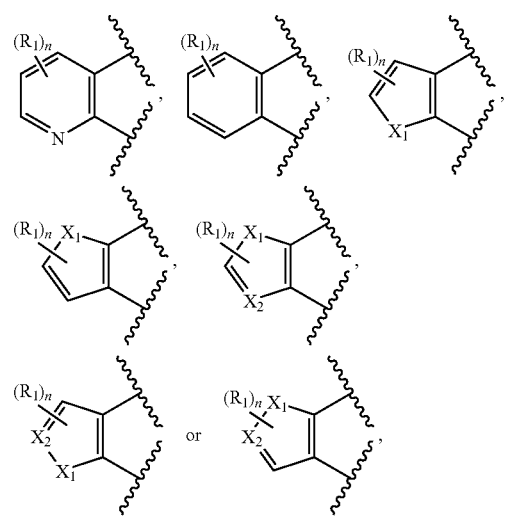

wherein $X^1$ is O, S or $NR^1$, $X^2$ is $CR^1$ or N and $R^1$ and n are as defined in Formula I, in conjunction with any of the above or below embodiments.

In another embodiment, Formula I includes compounds wherein each of $A^3$, $A^4$, $A^5$ and $A^6$ is $CR^3$, in conjunction with any of the above or below embodiments.

In another embodiment, Formula I includes compounds wherein three of $A^3$, $A^4$, $A^5$ and $A^6$ is CH, and one of $A^3$, $A^4$, $A^5$ and $A^6$ is $CR^3$, in conjunction with any of the above or below embodiments.

In another embodiment, Formula I includes compounds wherein each of $A^3$, $A^4$, $A^5$ and $A^6$ is CH, in conjunction with any of the above or below embodiments.

In another embodiment, Formula I includes compounds wherein $A^3$ is N and each of $A^4$, $A^5$ and $A^6$ is $CR^3$, in conjunction with any of the above or below embodiments.

In another embodiment, Formula I includes compounds wherein $A^4$ is N and each of $A^3$, $A^5$ and $A^6$ is $CR^3$, in conjunction with any of the above or below embodiments.

In another embodiment, Formula I includes compounds wherein $A^5$ is N and each of $A^3$, $A^4$ and $A^6$ is $CR^3$, in conjunction with any of the above or below embodiments.

In another embodiment, Formula I includes compounds wherein $A^6$ is N and each of $A^3$, $A^4$ and $A^4$ is $CR^3$, in conjunction with any of the above or below embodiments.

In another embodiment, Formula I includes compounds wherein each of $A^3$ and $A^6$ is N and each of $A^4$ and $A^5$ is $CR^3$, in conjunction with any of the above or below embodiments.

In another embodiment, Formula I includes compounds wherein each of $A^4$ and $A^5$ is N and each of $A^3$ and $A^6$ is $CR^3$, in conjunction with any of the above or below embodiments.

In another embodiment, Formula I includes compounds wherein each of $A^3$ and $A^4$ is N and each of $A^5$ and $A^6$ is $CR^3$, in conjunction with any of the above or below embodiments.

In another embodiment, Formula I includes compounds wherein $A^7$ is N and $A^8$ is $CR^5$, in conjunction with any of the above or below embodiments.

In another embodiment, Formula I includes compounds wherein $A^3$ is N and $A^7$ is $CR^5$, in conjunction with any of the above or below embodiments.

In another embodiment, Formula I includes compounds wherein each of $A^7$ and $A^8$ is N, in conjunction with any of the above or below embodiments.

In another embodiment, Formula I includes compounds wherein $L^1$ is —O—, in conjunction with any of the above or below embodiments.

In another embodiment, Formula I includes compounds wherein $L^1$ is —$NR^4$—, in conjunction with any of the above or below embodiments.

In another embodiment, Formula I includes compounds wherein $L^1$ is —NH—, in conjunction with any of the above or below embodiments.

In another embodiment, Formula I includes compounds wherein $L^1$ is —S—, in conjunction with any of the above or below embodiments.

In another embodiment, Formula I includes compounds wherein $L^1$ is —C(O)—, in conjunction with any of the above or below embodiments.

In another embodiment, Formula I includes compounds wherein $L^1$ is —S(O)—, in conjunction with any of the above or below embodiments.

In another embodiment, Formula I includes compounds wherein $L^1$ is —$SO_2$—, in conjunction with any of the above or below embodiments.

In another embodiment, Formula I includes compounds wherein $L^1$ is —$CR^4R^4$—, in conjunction with any of the above or below embodiments.

In another embodiment, Formula I includes compounds wherein $L^1$ is —O—, —$NR^4$— or —S—, in conjunction with any of the above or below embodiments.

In another embodiment, Formula I includes compounds wherein $L^1$ is —O— or —S—, in conjunction with any of the above or below embodiments.

In another embodiment, Formula I includes compounds wherein $L^2$ is —O—, in conjunction with any of the above or below embodiments.

In another embodiment, Formula I includes compounds wherein $L^2$ is —$NR^1$—, in conjunction with any of the above or below embodiments.

In another embodiment, Formula I includes compounds wherein $L^2$ is —NH—, in conjunction with any of the above or below embodiments.

In another embodiment, Formula I includes compounds wherein $L^2$ is —S—, in conjunction with any of the above or below embodiments.

In another embodiment, Formula I includes compounds wherein $L^2$ is —C(O)—, in conjunction with any of the above or below embodiments.

In another embodiment, Formula I includes compounds wherein $L^2$ is —S(O)—, in conjunction with any of the above or below embodiments.

In another embodiment, Formula I includes compounds wherein $L^2$ is —$SO_2$—, in conjunction with any of the above or below embodiments.

In another embodiment, Formula I includes compounds wherein $L^2$ is —$CR^4R^4$—, in conjunction with any of the above or below embodiments.

In another embodiment, Formula I includes compounds wherein $R^1$ is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$ or —$C(O)R^9$, in conjunction with any of the above or below embodiments.

In another embodiment, Formula I includes compounds wherein $R^1$ is $COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$ or —$NR^9S(O)_2R^9$, in conjunction with any of the above or below embodiments.

In another embodiment, Formula I includes compounds wherein $R^1$ is a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$, in conjunction with any of the above or below embodiments.

In another embodiment, Formula I includes compounds wherein each $R^2$, independently, is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$, in conjunction with any of the above or below embodiments.

In another embodiment, Formula I includes compounds wherein each $R^2$, independently, is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine, in conjunction with any of the above or below embodiments.

In another embodiment, Formula I includes compounds wherein each $R^2$, independently, is $R^2$ is H, halo, haloalkyl, haloalkoxyl, OH, SH, $NO_2$, $NH_2$, $C_{1-6}$-alkyl, $C_{2-6}$-alkenyl, $C_{2-6}$-alkynyl, $C_{1-6}$-alkylamino-, $C_{1-6}$-alkoxyl, $C_{1-6}$-thioalkoxyl or —$C(O)R^9$, in conjunction with any of the above or below embodiments.

In another embodiment, Formula I includes compounds wherein each $R^3$, independently, is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$, in conjunction with any of the above or below embodiments.

In another embodiment, Formula I includes compounds wherein each $R^3$, independently, is $R^2$ is H, halo, haloalkyl, haloalkoxyl, OH, SH, $NO_2$, $NH_2$, $C_{1-6}$-alkyl, $C_{2-6}$-alkenyl, $C_{2-4}$-alkynyl, $C_{1-6}$-alkylamino-, $C_{1-6}$-alkoxyl, $C_{1-6}$-thioalkoxyl or —$C(O)R^9$, in conjunction with any of the above or below embodiments.

In another embodiment, Formula I includes compounds wherein each $R^3$, independently, is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine, in conjunction with any of the above or below embodiments.

In another embodiment, Formula I includes compounds wherein each $R^4$, independently, is H, halo, OH, $C_{1-6}$alkoxyl, NH—$C_{1-6}$alkyl, CN or $C_{1-6}$alkyl, in conjunction with any of the above or below embodiments.

In another embodiment, Formula I includes compounds wherein each $R^4$, independently, is H, CN or $C_{1-6}$alkyl, in conjunction with any of the above or below embodiments.

In another embodiment, Formula I includes compounds wherein each $R^4$, independently, is H or $C_{1-6}$alkyl, in conjunction with any of the above or below embodiments.

In another embodiment, Formula I includes compounds wherein $R^5$ is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)$R^9$, in conjunction with any of the above or below embodiments.

In another embodiment, Formula I includes compounds wherein $R^5$ is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine, in conjunction with any of the above or below embodiments.

In another embodiment, Formula I includes compounds wherein $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula I includes compounds wherein $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula I includes compounds wherein each of $R^7$ and $R^8$ independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, in conjunction with any of the above or below embodiments.

In another embodiment, Formula I includes compounds wherein either of $R^7$ or $R^8$, independently, is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula I includes compounds wherein $R^8$ taken together with $R^7$ and the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$, in conjunction with any of the above or below embodiments.

In another embodiment, Formula I includes compounds wherein $R^8$ taken together with $R^7$ and the carbon atoms to which they are attached form a ring selected from phenyl, cyclohexyl, thienyl, furyl, pyridyl, pyrimidyl and cyclopenyl, the ring optionally substituted independently with 1-4 substituents of $R^9$, in conjunction with any of the above or below embodiments.

In another embodiment, Formula I includes compounds wherein $R^8$ taken together with $R^7$ and the carbon atoms to which they are attached form a ring selected from phenyl, pyridyl and pyrimidyl, the ring optionally substituted independently with 1-4 substituents of $R^9$, in conjunction with any of the above or below embodiments.

In another embodiment, Formula I includes compounds wherein $R^8$ taken together with $R^7$ and the carbon atoms to which they are attached form a phenyl ring, optionally substituted independently with 1-4 substituents of $R^9$, in conjunction with any of the above or below embodiments.

In another embodiment, Formula I includes compounds wherein $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and $R^7$ and $R^8$, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$, in conjunction with any of the above or below embodiments.

In another embodiment, Formula I includes compounds wherein $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-10}$alkyl, $C_{1-10}$alkoxyl, $C_{3-6}$cycloalkyl, $C_{1-10}$-alkylamino-, $C_{1-10}$-dialkylamino-, benzyl or phenyl; and $R^7$ and $R^8$, taken together with the carbon atoms to which they are attached form a phenyl ring, optionally including 1-3 heteroatoms selected from O, N, or S, and the ring optionally substituted independently with 1-4 substituents of $R^9$, in conjunction with any of the above or below embodiments.

In another embodiment, Formula I includes compounds wherein
each of $A^1$ and $A^2$, independently, is $CR^2$;
$L^1$ is —O—, —S— or —NR$^4$—;
$L^2$ is —NR$^4$—; and
$R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, the compounds of the present invention include compounds of Formula II:

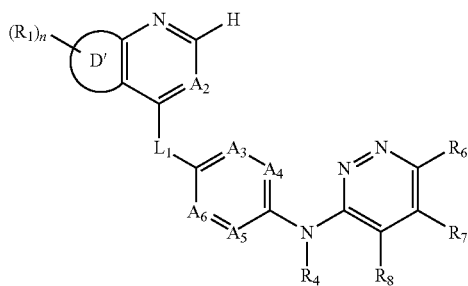

II or stereoisomer, tautomer, solvate, pharmaceutically acceptable salt or prodrug thereof, wherein
$A^2$ is N or $CR^2$;
each of $A^3$, $A^4$, $A^5$ and $A^6$, independently, is N or $CR^3$, provided that no more than two of $A^3$, $A^4$, $A^5$ and $A^6$ is N;

$L^1$ is —O—, —S—, or —NR$^4$—;
D' is a 5- or 6-membered ring of carbon atoms optionally including 1-3 heteroatoms selected from O, N and S, and the ring optionally substituted independently with n number of substituents of $R^1$;
each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —SR$^9$, —OR$^9$, —NR$^9$R$^9$, —C(O)R$^9$, —COOR$^9$, —OC(O)R$^9$, —C(O)C(O)R$^9$, —C(O)NR$^9$R$^9$, —NR$^9$C(O)R$^9$, —NR$^9$C(O)NR$^9$R$^9$, —NR$^9$(COOR$^9$), —OC(O)NR$^9$R$^9$, —S(O)$_2$R$^9$, —S(O)$_2$R$^9$, —S(O)$_2$NR$^9$R$^9$, —NR$^9$S(O)$_2$NR$^9$R$^9$, —NR$^9$S(O)$_2$R$^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

$R^2$ is H, halo, haloalkyl, haloalkoxyl, oxo, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)R$^9$;
each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)R$^9$;
each $R^4$, independently, is H or $C_{1-6}$alkyl;
$R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;
each of $R^7$ and $R^8$, independently, is $R^9$;
alternatively, $R^7$ and $R^8$ independently, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$;
each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, SR$^{10}$, OR$^{10}$, NR$^4$R$^{10}$, C(O)R$^{10}$, COOR$^{10}$, C(O)NR$^4$R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$R$^{10}$, NR$^4$S(O)$_2$R$^{10}$, NR$^4$S(O)$_2$NR$^4$R$^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-substituents of halo, haloalkyl, haloalkoxyl, CN, $NO_2$, N142, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4;

provided that (1) when $A^2$ is N and $L^1$ is —$NR^4$—, then D' is not

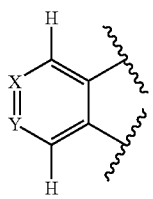

wherein one of X and Y is N and the other of X and Y is an optionally substituted carbon atom.

In another embodiment, Formula II includes compounds wherein D' is

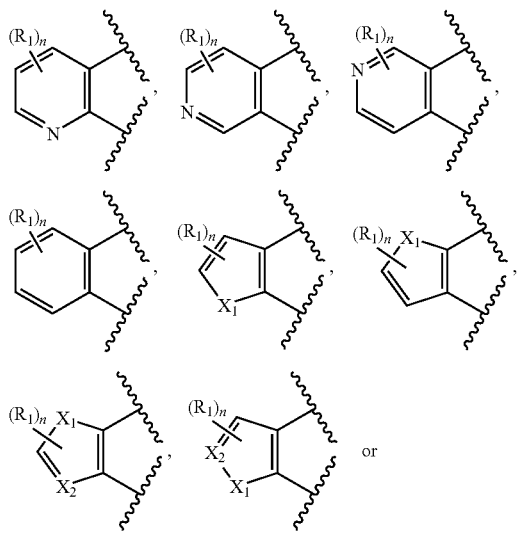

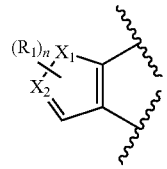

wherein X is O, S or $NR^1$ and $R^1$ and n are as defined in the immediately preceeding embodiment; and $L^1$ is —O— or —S—, in conjunction with any of the above or below embodiments.

In another embodiment, Formula II includes compounds wherein $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and $R^7$ and $R^8$, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$, in conjunction with any of the above or below embodiments.

In another embodiment, the compounds of the present invention include compounds of Formula II-A:

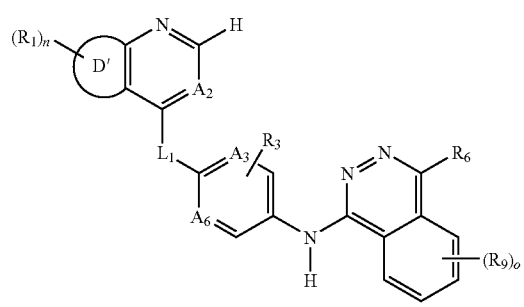

II-A or stereoisomer, tautomer, solvate, pharmaceutically acceptable salt or prodrug thereof, wherein $A^2$ is N or $CR^2$;

each of $A^3$ and $A^6$, independently, is N or $CR^3$, provided that no more than one of $A^3$ and $A^6$ is N;

$L^1$ is —O—, —S—, or —$NR^4$—;

D' is a 5- or 6-membered ring of carbon atoms optionally including 1-3 heteroatoms selected from O, N and S, and the ring optionally substituted independently with n number of substituents of $R^1$;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

$R^2$ is H, halo, haloalkyl, haloalkoxyl, OH, SH, $NO_2$, $NH_2$, $C_{1-6}$-alkyl, $C_{2-4}$-alkenyl, $C_{2-6}$-alkynyl, $C_{1-6}$-alkylamino-, $C_{1-6}$-alkoxyl, $C_{1-6}$-thioalkoxyl or —$C(O)R^9$;

each $R^3$, independently, is H, halo, haloalkyl, haloalkoxyl, OH, SH, $NO_2$, $NH_2$, $C_{1-6}$alkyl, $C_{2-6}$-alkenyl, $C_{2-6}$-alkynyl, $C_{1-6}$-alkylamino-, $C_{1-6}$-alkoxyl, $C_{1-6}$-thioalkoxyl or —$C(O)R^9$;

$R^4$ is H or $C_{1-6}$alkyl;

$R^6$ is $R^9$;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

n is 0, 1, 2, 3 or 4; and o is 0, 1, 2, 3 or 4.

In another embodiment, the compounds of the present invention include compounds of Formula III:

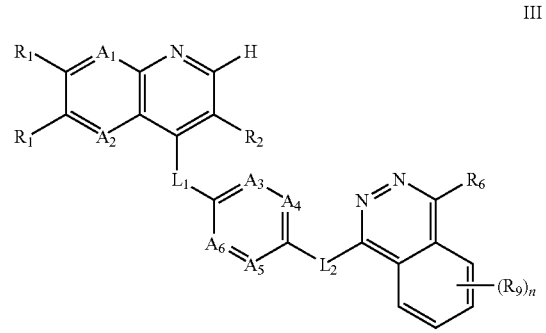

III or stereoisomer, tautomer, solvate, pharmaceutically acceptable salt or prodrug thereof, wherein one of $A^1$ and $A^2$ is N and the other of one of $A^1$ and $A^2$ is $CR^2$;

each of $A^3$, $A^4$, $A^5$ and $A^6$, independently, is N or $CR^3$, provided that no more than two of $A^3$, $A^4$, $A^5$ and $A^6$ is N;

each of $L^1$ and $L^2$, independently, is —O—, —$NR^4$—, —S—, —C(O)—, —S(O)—, —$SO_2$— or —$CR^4R^4$—, wherein each $R^4$, independently, is H or $C_{1-6}$alkyl;

each $R^1$, independently, is H, halo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

$R^2$ is H, halo, haloalkyl, haloalkoxyl, oxo, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^6$ is $R^9$;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

In another embodiment, Formula III compounds include compounds wherein $A^1$ is $CR^2$ and $A^2$ is N;

each of $A^3$, $A^4$, $A^5$ and $A^6$ independently, is $CR^3$;

$L^1$ is —O—, —$NR^4$— or —S—;

$L^2$ is —$NR^4$—;

each $R^1$, independently, is H, halo, $CF_3$, $C_2F_5$, haloalkoxyl, CN, OH, SH, $NO_2$, $NH_2$, acetyl, methyl, methoxyl, ethyl, ethoxyl, propyl, propoxyl, isopropyl, cyclopropyl, butyl, isobutyl, tert-butyl, cyclobutyl, pentyl, cyclopentyl, hexyl, cyclohexyl, methylamine, dimethylamine, ethylamine, diethylamine, propylamine, isopropylamine, dipropylamine, diisopropylamine, —C(O)$R^9$, —COO$R^9$, —C(O)NH$R^9$, —NHC(O)$R^9$, —NHC(O)NH$R^9$, —NH(COO$R^9$), —S(O)$_2$$R^9$, —S(O)$_2$$R^9$, —S(O)$_2$NH$R^9$, —NHS(O)$_2$NH$R^9$, —NHS(O)$_2$$R^9$ or a ring selected from phenyl, pyridyl, pyrimidinyl, pyridazinyl, pyazinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl, cycloheptyl or pyranyl, said ring optionally substituted independently with 1-5 substituents of $R^9$;

$R^2$ is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine;

each $R^3$, independently, is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine;

each $R^4$, independently, is H or $C_{1-6}$alkyl; and $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula III compounds include compounds wherein $A^1$ is $CR^2$ and $A^2$ is N;

one of $A^3$, $A^4$, $A^5$ and $A^6$ is N and others of $A^3$, $A^4$, $A^5$ and $A^6$ are each $CR^3$;

$L^1$ is —O—, —$NR^4$— or —S—;

$L^2$ is —$NR^4$—;

each $R^1$, independently, is H, halo, $CF_3$, $C_2F_5$, haloalkoxyl, CN, OH, SH, $NO_2$, $NH_2$, acetyl, methyl, methoxyl, ethyl, ethoxyl, propyl, propoxyl, isopropyl, cyclopropyl, butyl, isobutyl, tert-butyl, cyclobutyl, pentyl, cyclopentyl, hexyl, cyclohexyl, methylamine, dimethylamine, ethylamine, diethylamine, propylamine, isopropylamine, dipropylamine, diisopropylamine, —C(O)$R^9$, —COO$R^9$, —C(O)NH$R^9$, —NHC(O)$R^9$, —NHC(O)NH$R^9$, —NH(COO$R^9$), —S(O)$_2$$R^9$, —S(O)$_2$$R^9$, —S(O)$_2$NH$R^9$, —NHS(O)$_2$NH$R^9$, —NHS(O)$_2$$R^9$ or a ring selected from phenyl, pyridyl, pyrimidinyl, pyridazinyl, pyazinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl, cycloheptyl or pyranyl, said ring optionally substituted independently with 1-5 substituents of $R^9$;

$R^2$ is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylaamine;

each $R^3$, independently, is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine;

each $R^4$, independently, is H or $C_{1-6}$alkyl; and $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-4}$cycloalkyl, $C_{1-10}$-alkylamino-, $C_{1-10}$-dialkylamino-, benzyl or phenyl.

In another embodiment, the compounds of the present invention include compounds of Formula III-A:

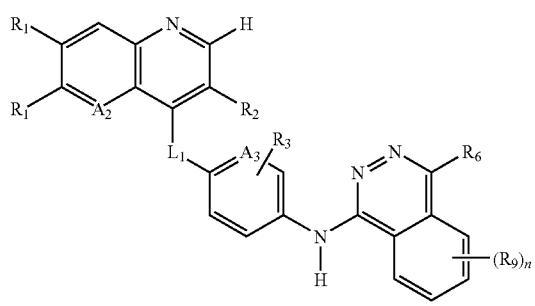

III-A or stereoisomer, tautomer, solvate, pharmaceutically acceptable salt or prodrug thereof, wherein $A^2$ is $CR^2$ or N;

$A^3$ is N or $CR^3$;

$L^1$ is —O—, —$NR^4$—, —S—, —C(O)—, —S(O)—, —$SO_2$— or —$CR^4R^4$—, wherein each $R^4$, independently, is H or $C_{1-6}$alkyl;

each $R^1$, independently, is H, halo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —C(O)$R^9$, —COO$R^9$, —OC(O)$R^9$, —C(O)C(O)$R^9$, —C(O)NR$^9R^9$, —NR$^9$C(O)$R^9$, —NR$^9$C(O)NR$^9R^9$, —NR$^9$(COO$R^9$), —OC(O)NR$^9R^9$, —S(O)$_2R^9$, —S(O)$_2R^9$, —S(O)$_2$NR$^9R^9$, —NR$^9$S(O)$_2$NR$^9R^9$, —NR$^9$S(O)$_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^2$, independently, is H, halo, haloalkyl, haloalkoxyl, oxo, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)$R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)$R^9$;

$R^6$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, C(O)$R^{10}$, COO$R^{10}$, C(O)NR$^4R^{10}$, $NR^4$C(O)$R^{10}$, $NR^4$C(O)NR$^4R^{10}$, $NR^4$ (COO$R^{10}$), S(O)$_2R^{10}$, S(O)$_2$NR$^4R^{10}$, $NR^4$S(O)$_2R^{10}$, $NR^4$S(O)$_2$NR$^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, C(O)$R^{10}$, COO$R^{10}$, C(O)NR$^4R^{10}$, $NR^4$C(O)$R^{10}$, $NR^4$C(O)NR$^4R^{10}$, $NR^4$ (COO$R^{10}$), S(O)$_2R^{10}$, S(O)$_2$NR$^4R^{10}$, $NR^4$S(O)$_2R^{10}$, $NR^4$S (O)$_2$NR$^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

In yet another embodiment, the invention provides compounds generally defined by Formula IV:

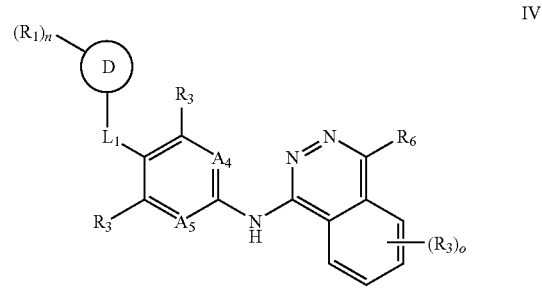

IV or stereoisomer, tautomer, solvate, pharmaceutically acceptable salt or prodrug thereof, wherein each of $A^4$ and $A^5$, independently, is N or $CR^3$;

$L^1$ is —O—, —$NR^4$—, —S—, —C(O)—, —S(O)—, —$SO_2$— or —$CR^4R^4$—, wherein each $R^4$, independently, is H, halo, OH, $C_{1-6}$alkoxyl, NH—$C_{1-6}$alkyl, CN or $C_{1-6}$alkyl;

D is a fully saturated or partially or fully unsaturated 8-12 membered bicyclic ring system, said ring system formed of carbon atoms optionally including 1-3 heteroatoms if monocyclic or 1-6 heteroatoms if bicyclic, said heteroatoms selected from O, N, or S, and said ring optionally substituted independently with n number of substituents of $R^1$;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $-SR^9$, $-OR^9$, $-NR^9R^9$, $-C(O)R^9$, $-COOR^9$, $-OC(O)R^9$, $-C(O)C(O)R^9$, $-C(O)NR^9R^9$, $-NR^9C(O)R^9$, $-NR^9C(O)NR^9R^9$, $-NR^9(COOR^9)$, $-OC(O)NR^9R^9$, $-S(O)_2R^9$, $-S(O)_2R^9$, $-S(O)_2NR^9R^9$, $-NR^9S(O)_2NR^9R^9$, $-NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^3$, independently, is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or $-C(O)C_{1-10}$-alkyl;

$R^5$ is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or $-C(O)R^9$;

$R^6$ is $R^9$;

$R^9$ is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4; and o is 0, 1, 2, 3 or 4.

In another embodiment, Formula IV compound include compounds wherein each of $A^4$ and $A^5$, independently, is $CR^3$, in conjunction with any of the above or below embodiments.

In another embodiment, Formula IV compound include compounds wherein $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula IV compound include compounds wherein $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula IV compound include compounds wherein ring D is a 8-, 9- or 10-membered fused bicyclic ring of carbon atoms optionally including 1-3 heteroatoms selected from O, N and S, and the ring optionally substituted independently with n number of substituents of $R^1$, in conjunction with any of the above or below embodiments.

The many different embodiments for the various elements, chemical moieties or R or L groups described and defined hereinabove with respect to compounds of Formula I also apply, and are included herein, to compounds of Formula II, II-A, III, III-A and IV where appropriate, as appreciated by those of ordinary skill in the art.

In yet another embodiment, Formulas I, II, II-A, III, III-A and IV include the exemplary compounds and derivatives, prodrugs, solvates, tautomers and pharmaceutically acceptable salt forms thereof, intermediates related thereto, examples of which are described in the Examples herein. For example, and in another embodiment, the invention provides the following compounds, and pharmaceutically acceptable salt forms thereof, selected from: 'N-(4-((7-(methyloxy)-1,5-naphthyridin-4-yl)oxy)phenyl)-4-phenyl-1-phthalazinamine;

'N-(4-((7-(methyloxy)-1,5-naphthyridin-4-yl)oxy)phenyl)-4-(4-methyl-1,3-thiazol-2-yl)-1-phthalazinamine;

'4-ethyl-N-(6-((7-(methyloxy)-1,5-naphthyridin-4-yl)oxy)-3-pyridinyl)-6-phenyl-3-pyridazinamine;

'4-((4-((4-(4-methyl-1,3-thiazol-2-yl)-1-phthalazinyl)amino)phenyl)oxy)-7-quinolinecarbonitrile;

'N-(3-fluoro-4-((7-(methyloxy)-1,5-naphthyridin-4-yl)oxy)phenyl)-4-phenyl-1-phthalazinamine;

'N-(4-((7-(methyloxy)-1,6-naphthyridin-4-yl)oxy)phenyl)-4-phenyl-1-phthalazinamine;

'N-(4-((6,7-bis(methyloxy)-4-quinazolinyl)oxy)phenyl)-4-phenyl-1-phthalazinamine;

'N-(4-((7-(methyloxy)-1,5-naphthyridin-4-yl)oxy)phenyl)-4-(4-methyl-2-pyridinyl)-1-phthalazinamine;

'N-(7-(methyloxy)-1,6-naphthyridin-4-yl)-N'-(4-phenyl-1-phthalazinyl)-1,4-benzenediamine;

'N-3-(methyloxy)-8-((4-((4-(4-methylphenyl)-1-phthalazinyl)methyl)phenyl)oxy)-1,5-naphthyridine;

'N-(6-((7-(methyloxy)-1,5-naphthyridin-4-yl)oxy)-3-pyridinyl)-4-(6-methyl-2-pyridinyl)-1-phthalazinamine;

'4-(5-chloro-2-thienyl)-N-(4-((7-(methyloxy)-1,5-naphthyridin-4-yl)oxy)phenyl)-1-phthalazinamine;

'4-((4-((4-(4-(methyloxy)phenyl)-1-phthalazinyl)amino)phenyl)oxy)-7-quinolinecarbonitrile;

'4-(1-methyl-1H-indol-2-yl)-N-(4-((7-(methyloxy)-1,5-naphthyridin-4-yl)oxy)phenyl)-1-phthalazinamine;

'N-(4-((7-(methyloxy)-1,5-naphthyridin-4-yl)oxy)phenyl)-4-(4-(trifluoromethyl)phenyl)-1-phthalazinamine;

'4-((4-((4-(4-(trifluoromethyl)phenyl)-1-phthalazinyl)amino)phenyl)oxy)-7-quinolinecarbonitrile; and '4-(4-chlorophenyl)-N-(4-((7-(methyloxy)-1,5-naphthyridin-4-yl)oxy)phenyl)-1-phthalazinamine.

In another embodiment, the invention provides the following compounds, and pharmaceutically acceptable salt forms thereof, selected from '4-(1,3-benzodioxol-5-yl)-N-(4-((7-(methyloxy)-1,5-naphthyridin-4-yl)oxy)phenyl)-1-phthalazinamine;

'4-(2,3-dihydro-1-benzofuran-5-yl)-N-(4-((7-(methyloxy)-1,5-naphthyridin-4-yl)oxy)phenyl)-1-phthalazinamine;

'4-(3-chloro-4-(trifluoromethyl)phenyl)-N-(4-((7-(methyloxy)-1,5-naphthyridin-4-yl)oxy)phenyl)-1-phthalazinamine;

'4-(6-fluoro-3-pyridinyl)-N-(4-((7-(methyloxy)-1,5-naphthyridin-4-yl)oxy)phenyl)-1-phthalazinamine;

'4-(3-chloro-4-fluorophenyl)-N-(4-((7-(methyloxy)-1,5-naphthyridin-4-yl)oxy)phenyl)-1-phthalazinamine;

'4-(2-methyl-1,3-benzothiazol-5-yl)-N-(4-((7-(methyloxy)-1,5-naphthyridin-4-yl)oxy)phenyl)-1-phthalazinamine;

'4-(3,4-dichlorophenyl)-N-(4-((7-(methyloxy)-1,5-naphthyridin-4-yl)oxy)phenyl)-1-phthalazinamine;

'N-(4-((2-(1-methyl-1H-imidazol-5-yl)thieno[3,2-b]pyridin-7-yl)oxy)phenyl)-4-phenyl-1-phthalazinamine;

'4-(1-methyl-1H-indol-5-yl)-N-(4-((7-(methyloxy)-1,5-naphthyridin-4-yl)oxy)phenyl)-1-phthalazinamine;

'4-ethyl-N-(4-((7-(methyloxy)-1,5-naphthyridin-4-yl)oxy)phenyl)-6-(5-methyl-2-thienyl)-3-pyridazinamine; and 4-(1,3-benzodioxol-5-yl)-N-(4-((7-(methyloxy)-1,5-naphthyridin-4-yl)oxy)phenyl)-1-phthalazinamine.

In another embodiment, the invention provides the following compounds, and pharmaceutically acceptable salt forms thereof, selected from N-(4-((7-(methyloxy)-1,5-naphthyridin-4-yl)oxy)phenyl)-4-(5-pyrimidinyl)-1-phthalazinamine;

'N-(4-((7-(methyloxy)-1,5-naphthyridin-4-yl)oxy)phenyl)-4-phenylthieno[2,3-d]pyridazin-7-amine; '4-(4-fluorophenyl)-N-(4-((7-(methyloxy)-1,5-naphthyridin-4-yl)oxy)phenyl)-1-phthalazinamine;

'4-(4-chlorophenyl)-N-(6-((7-(methyloxy)-1,5-naphthyridin-4-yl)oxy)-3-pyridinyl)-1-phthalazinamine;

'4-(5-chloro-2-pyridinyl)-N-(4-((7-(methyloxy)-1,5-naphthyridin-4-yl)oxy)phenyl)-1-phthalazinamine;

'4-(6-chloro-3-pyridinyl)-N-(4-((7-(methyloxy)-1,5-naphthyridin-4-yl)oxy)phenyl)-1-phthalazinamine;

'4-(4-fluoro-3-methylphenyl)-N-(4-((7-(methyloxy)-1,5-naphthyridin-4-yl)oxy)phenyl)-1-phthalazinamine;

'4-((4-((4-(4-chlorophenyl)-1-phthalazinyl)amino)phenyl)thio)-7-quinolinecarbonitrile;

'4-(4-chlorophenyl)-N-(4-(thieno[3,2-b]pyridin-7-yloxy)phenyl)-1-phthalazinamine;

'8-((4-((4-(4-chlorophenyl)-1-phthalazinyl)amino)phenyl)oxy)-1,5-naphthyridine-3-carbonitrile;

N-(4-((7-(methyloxy)-1,5-naphthyridin-4-yl)thio)phenyl)-4-phenyl-1-phthalazinamine;

N-(4-(7-methoxy-1,5-naphthyridin-4-ylthio)phenyl)-4-(4-methylthiophen-2-yl)phthalazin-1-amine;

4-ethyl-N-(4-(7-methoxy-1,5-naphthyridin-4-ylthio)phenyl)-6-phenylpyridazin-3-amine;

6-(4-chlorophenyl)-4-ethyl-N-(6-(7-methoxy-1,5-naphthyridin-4-yloxy)pyridin-3-yl)pyridazin-3-amine;

6-(4-chlorophenyl)-4-ethyl-N-(6-(7-methoxy-1,5-naphthyridin-4-yloxy)pyridin-3-yl)pyridazin-3-amine;

'N-(4-((6-(methyloxy)-4-quinolinyl)thio)phenyl)-4-phenyl-1-phthalazinamine;

'N-(4-((2-(3-methyl-1,2,4-oxadiazol-5-yl)thieno[3,2-b]pyridin-7-yl)thio)phenyl)-4-phenyl-1-phthalazinamine; and '4-(5-chloro-2-pyridinyl)-N-(4-((7-(methyloxy)-1,5-naphthyridin-4-yl)thio)phenyl)-1-phthalazinamine.

DEFINITIONS

The following definitions should further assist in understanding the scope of the invention described herein.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Aurora kinase(s) in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human.

A "pharmaceutically-acceptable derivative" denotes any salt (also referred to as "pharmaceutically-acceptable salt"), any prodrug such as a phospshate or an ester of a compound of this invention, or any other compound which upon administration to a patient is capable of providing (directly or indirectly) a compound of this invention, or a metabolite or residue thereof, characterized by the ability to inhibit Aurora kinase.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies.

The terms "ring" and "ring system" refer to a one or more rings, typically fused together where more than one ring, comprising the delineated number of atoms, said atoms being carbon or, where indicated, a heteroatom such as nitrogen, oxygen or sulfur. The ring itself, as well as any substituents thereon, may be attached at any atom that allows a stable compound to be formed. The term "nonaromatic" ring or ring system refers to the fact that at least one, but not necessarily all, rings in a bicyclic or tricyclic ring system is not fully unsaturated.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

Where the term "alkyl" is used, either alone or within other terms such as "haloalkyl" and "alkylamino", it embraces linear or branched radicals preferably having alpha to beta number of carbon atoms. For example a $C_1$-$C_{10}$alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated.

The term "alkenyl", alone or in combination, embraces linear or branched radicals having at least one carbon-carbon double bond and having two or more carbon atoms. Examples of alkenyl radicals include, without limitation, ethenyl, propenyl, allyl, propenyl, butenyl and 4-methylbutenyl. The term "alkenyl" embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of alkynyl radicals include, without limitation, ethynyl, propynyl (propargyl), butynyl, and the like. It is contemplated herein that alkynyl radicals may be optionally substituted with various substituents, where indicated.

The term "halo", alone or in combination, means halogens such as fluorine, chlorine, bromine or iodine atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "alkoxy", alone or in combination, embraces linear or branched oxy-containing radicals each having alkyl portions of alpha to beta number of carbon atoms. For example, a $C_{1-10}$ alkoxy radical indicates an alkoxide having one to ten carbon atoms, arranged in a linear or branched fashion, attached to an oxygen atom. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "partially or fully saturated" as used herein, refers to a moiety, linear, branched or cyclic in nature, having no atom-atom double or triple bonds (fully saturated) or having one or more atom-atom double or triple bonds which are arranged such that where the structural moiety is cyclic, the cycle is not fully unsaturated (non-aromatic), as appreciated by those skilled in the art.

The term "fully unsaturated" as used herein, refers to a moiety having double or triple bonds, arranged in a manner such that the structure is aromatic in nature, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 or more substituents such as lower alkyl, hydroxyl, halo, haloalkyl, nitro, cyano, alkoxy and lower alkylamino, and the like. Phenyl substituted with —O—$CH_2$—O— forms an aryl benzodioxolyl substituent. Aryl as used herein, implies a fully unsaturated ring.

The term "heterocycles" or "heterocyclic radicals", alone or in combination, embraces saturated, partially saturated and partially unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 or more substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated (or partially unsaturated) heterocyclyl radicals include dihydrothienyl, dihydropyranyl, dihydrofuryl and dihydrothiazolyl.

The term "heteroaryl" radicals, alone or in combination, embraces fully unsaturated heteroatom-containing ring radicals, where the heteroatoms may be selected from nitrogen, sulfur and oxygen. Examples of heteroaryl radicals include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The terms "heterocycle" and "heteroaryl" also embraces radicals which are fused/condensed with aryl radicals: unsaturated condensed heterocyclic or heteroaryl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals. Further examples of beteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially and fully saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isotbiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The term "carbonyl", whether used alone or with other terms, such as "aminocarbonyl", denotes —(C=O)—.

The term "alkylthio" or "thioalkyl" embraces radicals containing a linear or branched alkyl radical, of one to ten carbon atoms, attached to a divalent sulfur atom. An example of "alkylthio" is methylthio, ($CH_3S$—).

The term "aminoalkyl" and "diaminoalkyl" embraces "N-alkylamino" and "N,N-dialkylamino", respectively, where amino groups are independently substituted with one alkyl radical and with two alkyl radicals, respectively. Examples of alkylamino radicals include "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "$C_{1-10}$alkyl-amino-" denotes amino groups, which have been substituted with one or two alkyl radicals, such as N-methylamino. The alkylamino radicals may be further substituted on the alkyl portion of the radical.

The term "aryl-alkyl-amino-" or "aralkylamino" denotes amino groups, which have been substituted with one or two aryl-substituted-alkyl radicals, such as benzyl-amino. The aralkyl-amino radicals may be further substituted on the aryl or alkyl portion of the radical.

The term "heterocyclyl-alkyl-amino-" denotes amino groups, which have been substituted with one or two heterocyclyl-substituted-alkyl radicals, such as piperidyl-methylamino. The heterocyclyl-alkyl-amino radicals may be further substituted on the heterocycle or alkyl portion of the radical.

The term "heteroaryl-alkyl-amino-" or "heteroaralkylamino" denotes amino groups, which have been substituted with one or two heteroaryl-substituted-alkyl radicals, such as pyrimidyl-amino. The heteroaralkyl-amino radicals may be further substituted on the heteroaryl or alkyl portion of the radical.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

The term "comprising" is meant to be open ended, including the indicated component(s) but not excluding other elements.

The terms "Formula I", "Formula II", "Formula III" and "Formula IV" include any sub formulas.

The present invention comprises processes for the preparation of a compound of Formulae I, II, III and IV.

Also included in the family of compounds of Formulas I-IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-IV may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-IV include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound of Formulas I-IV. When a basic group and an acid group are present in the same molecule, a compound of Formulas I-IV may also form internal salts.

General Synthetic Procedures

The compounds of the invention can be synthesized according to the following procedures of Schemes 1-8, wherein the substituents are as defined for Formulas I-IV, above, except where further noted. The synthetic methods described below are merely exemplary, and the compounds of the invention may be synthesized by alternate routes as appreciated by persons of ordinary skill in the art.

The following list of abbreviations, used throughout the specification represent the following:
ACN, AcCN, MeCN—acetonitrile
BSA—bovine serum albumin
$Cs_2CO_3$—cesium carbonate
$CHCl_3$—chloroform
$CH_2Cl_2$, DCM—dichloromethane, methylene chloride
DIBAL—diisobutylaluminum hydride
DIEA, ($iPr_2Net$)—diisopropylethylamine
DME—dimethoxyethane
DMF—dimethylformamide
DMAP—4-dimethylaminopyridine
DMSO—dimethylsulfoxide
dppa—diphenylphosphoryl azide
EDC—1-(3-dimethylaminopropyl)-3-ethylcarbodiimide hydrochloride
$Et_2O$—diethyl ether
EtOAc ethyl acetate
FBS—fetal bovine serum
g, gm—gram
h, hr—hour
HBr—hydrobromic acid
HCl—hydrochloric acid
HOBt—1-hydroxybenzotriazole hydrate
$H_2$—hydrogen
$H_2O_2$—hydrogen peroxide HATU—O-(7-azabenzotriazol-1-yl)-N,N,N',N'-tetramethyluroniumhexafluorophosphate
HPLC—high pressure liquid chromatography
IPA, IpOH—isopropyl alcohol
$K_2CO_3$—potassium carbonate
MCPBA—meta-chloroperbenzoic acid
$MgSO_4$— magnesium sulfate
MeOH—methanol
$N_2$— nitrogen
$NaHCO_3$-sodium bicarbonate
NaOH—sodium hydroxide
NaH—sodium hydride
$Na_2SO_4$— sodium sulfate
$NH_4Cl$—ammonium chloride
$NH_4OH$—ammonium chloride
NMP—N-methylpyrrolidinone
$P(t-bu)_3$—tri(tert-butyl)phosphine
PBS—phospate buffered saline
Pd/C—palladium on carbon
$Pd(PPh_3)_4$—palladium(0)triphenylphosphine tetrakis
$Pd(PhCN)_2Cl_2$—palladium di-cyanophenyl dichloride
$Pd(OAc)_2$— palladium acetate
$Pd_2(dba)_3$—bis(dibenzylideneacetone) palladium
PyBop—benzotriazol-1-yl-oxy-tripyrrolidino-phosphonium hexafluorophosphate
RT, rt—room temperature
RBF—round bottom flask
rac-BINAP—2,2'-Bis(diphenylphosphine)-1,1'-binaphthyl
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran

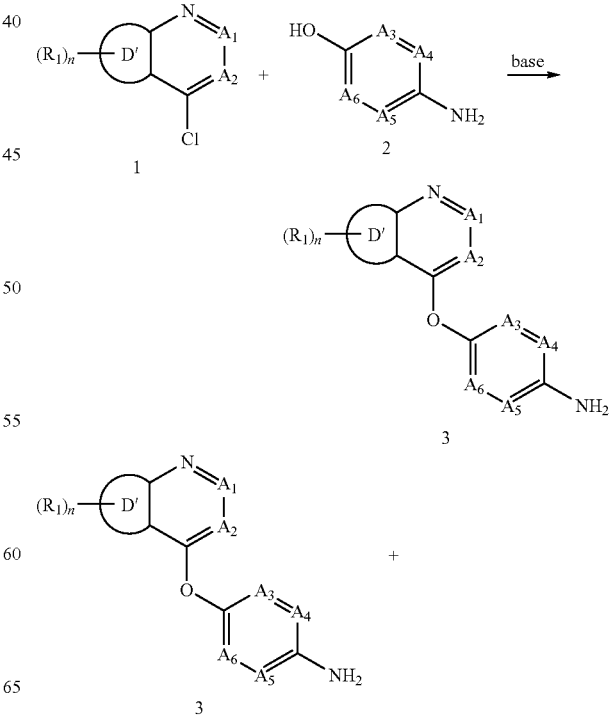

Scheme 1

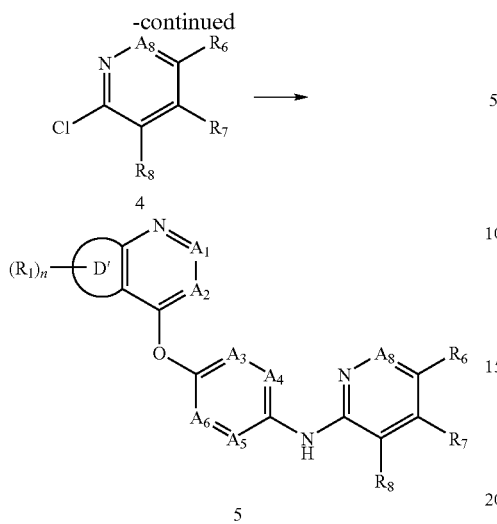

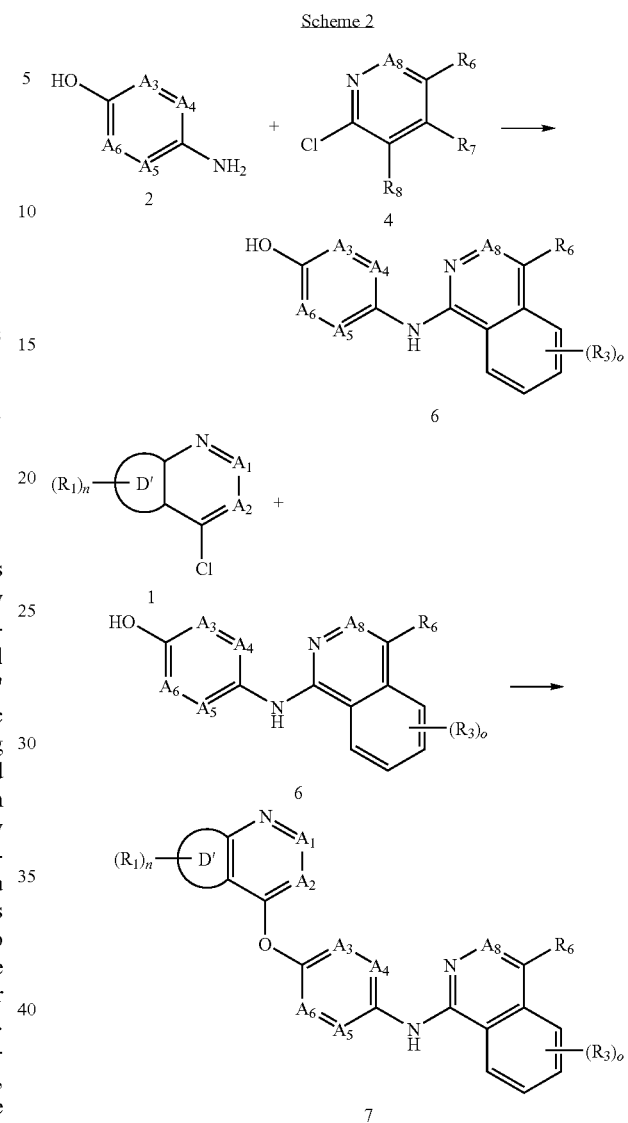

Compounds 5 of Formula I-IV (where L1 is O and L2 is NH), can be prepared according to the method generally described in Scheme 1. As shown, a base assisted nucleophilic displacement reaction by a compound 2 of an aryl halide 1 (where the halide as shown is chloride, and where D' may be an optionally substituted 5- or 6-membered aromatic ring) should generally afford amino intermediate 3. Starting compounds 1 may be commercially available or prepared using methods described in the Examples below or by known techniques in the art. The alcohol 2 is generally sufficiently nucleophilic, under suitable conditions, to displace the chloride of compound 1. Compound 2 may also be a thiol, a primary or secondary amine or a nucleophilic carbon species (all of which are not shown) to effect the transformation to compound 3, as appreciated by those skilled in the art. The amine group on compound 2 may be protected as necessary or left unprotected, as appreciated by those skilled in the art. Suitable bases to yield compound 3 include, without limitation, carbonate bases such as cesium carbonate ($Cs_2CO_3$), $Na_2CO_3$, $K_2CO_3$ and the like in a suitable solvent, whose properties will generally depend upon the solubility of the starting materials, polarity, and other factors readily appreciated in the art. Amine 3, if protected may generally first be deprotected, and then reacted with an optionally substituted chloro-pyridine, chloro-pyridazine (where $A^8$ is N), chloro-phthalazine (where $R^7$ and $R^8$ taken together form a phenyl ring) and the like under suitable conditions, including without limitation, under basic conditions (Method B4), acidic conditions (Method B1 (TFA) or Method B2 (pTsOH and HCl) and heated conditions (Method B3), in suitable solvent or combination of solvents to afford compound 5, of Formula I. It should be understood that compound 5 may also be a compound with formulas II, III and IV described herein. Representative examples of such reactions are further described hereinbelow.

The strategy for preparing compounds 5, as exemplified in scheme 1, may generally be approached by building and/or broken down 2 primary linking bonds, i.e., the connections of both $L^1$ and $L^2$. Thus, compounds 7 (similar to compounds 5 but having $R^7$ and $R^8$ taken together to form a phenyl ring, as in Formula IV herein) may alternatively be prepared according to the method shown in scheme 2 below.

Compounds 7 of Formulas I-IV (where $L^1$ is O and $L^2$ is NH), can be prepared according to the method generally described in Scheme 2. As shown, a nucleophilic displacement reaction by a compound 2 of an aryl halide 4 (where the halide as shown is chloride) should generally afford hydroxy intermediates 6. Such reaction may optionally be run in the presence of acid to afford compounds 6. Starting compounds 1 may be reacted with alcohols 6, under suitable conditions such as those conditions described in scheme I above or the Examples herein (Methods C1-C7), to afford compounds 7. As mentioned in scheme 1, compound 2 may also be a thiol, a primary or secondary amine or a nucleophilic carbon species (all of which are not shown) to effect the transformation to compound 7, as appreciated by those skilled in the art. In the event compound 2 is a thiol, the reaction may be accomplished without the need for acidic or basic conditions, and may also be accomplished at ambient temperatures, as appreciated by those skilled in the art. Representative examples of such reactions are further described hereinbelow. Suitable transformation methods are known to those skilled in the art, and are generally described in Jerry March's Advanced Organic Chemistry, 4th edition (1992), which disclosure is hereby incorporated by reference in its entirety.

Scheme 3 (Methods A1-A3)

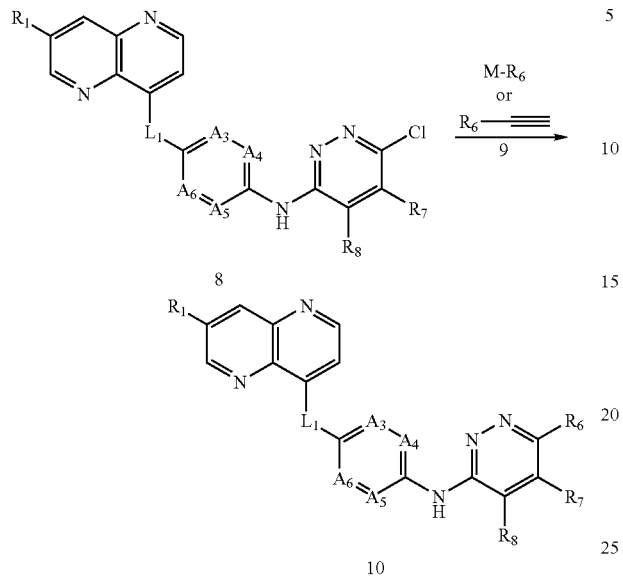

Compounds 10 can be made by treating compounds 8 (where $L^1$ is as defined herein) with either of reagents 9 in a Suzuki (Method A1), Stille (Method A2) or Sonagashira (Method A3) type reaction, under conditions suitable for each reaction, respectively, as shown in scheme 3 (also referred to herein as General Method A). Such reactions work well where $R^6$ is an aromatic group. Each reaction method is known in the art and generally appreciated by those skilled in the art. Examples of such reactions are described in further detail hereinbelow. In addition, methods for Sonagashira reactions may be found in *Angew. Chem. Int. Ed.* 2003, 42, 5993-5996. Ether linked $R^6$ groups may also be installed onto chloro-phthtalazines 8 using a base, such as cesium carbonate (Method A4) under suitable light conditions, such as irradiation, to afford compounds 10. Amine linked $R^6$ groups may also be afforded onto phthalazines 8 using heat (Method A5) in the presence of a suitable amine, such as piperidine, to provide compounds 10.

The method of scheme 3 allows desired $R^6$ groups to be the final step of synthesis of compounds 10. Care must be taken to restrict the $R^1$, $R^7$ and $R^8$ in this method to those groups, which would not interfere with or react under suitable reaction method and/or conditions to form compounds 10, as appreciated by persons of ordinary skill in the art.

Scheme 4 (Methods D1-D3)

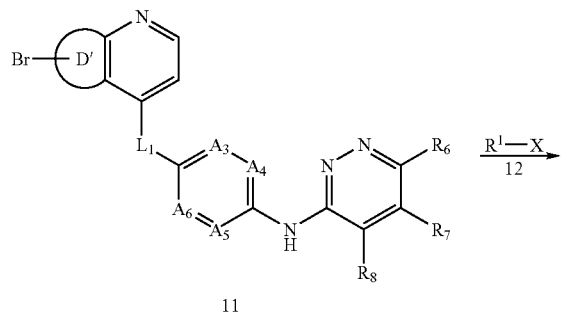

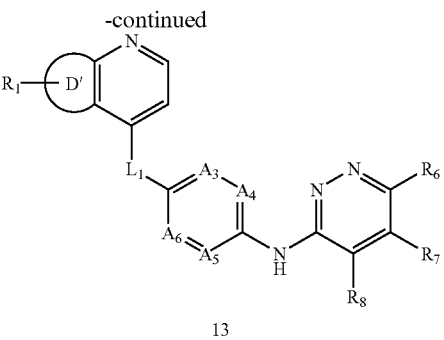

Compounds 13 may be prepared by a single reaction between a bromo-substituted compound 11 and a desired $R^1$ group appropriately substituted with a nucleophile or other suitable group to prepare compound 13. Such transformations may be accomplished using a variety of different methods, as appreciated by those skilled in the art. For example, desirable amino-$R^1$ groups can be installed at a suitable position on a D' ring by treating bromide 11 in the presence of a suitable palladium species and a suitable $R^1$-halide, $R^1$-amine or other desired $R^1$-reagent under suitable conditions. For example, modified Suzuki conditions involving the use of a Pd(0) mediated-coupling with an aryl boronate in the presence of mild base, such as sodium or potassium carbonate or bicarbonate, in toluene may also afford compounds 13. Compounds 13 can also be prepared using corresponding stannanes or zincates, as is known in the art. Alternatively, desired $R^1$ groups may be installed onto the D'-ring using conventional methods (not shown), as appreciated by those skilled in the art.

The Examples described hereinafter represent exemplary methods of synthesizing or preparing desired compounds of Formulas I-IV, intermediates and various starting materials and/or building blocks thereof. It should be appreciated that these methods are merely representative examples and other conventional, known or developed alternative methods may also be utilized. It should also be appreciated that the exemplary compounds are merely for illustrative purposes only and are not to be construed as limiting the scope of the present invention in any manner.

Analytical Methods:

Unless otherwise indicated, all HPLC analyses were run on a Agilent Model 1100 system with an Agilent Technologies Zorbax SB—$C_8$(5μ) reverse phase column (4.6×150 mm; Part no. 883975-906) run at 30° C. with a flow rate of about 1.50 mL/min. The mobile phase used solvent A ($H_2O$/0.1% TFA) and solvent B (AcCN/0.1% TFA) with a 11 min gradient from 5% to 100% AcCN. The gradient was followed by a 2 min return to 5% AcCN and about a 2.5 minute re-equilibration (flush).

LC-MS Method:

Samples were run on a Agilent model-1100 LC-MSD system with an Agilent Technologies XDB-$C_8$(3.5 p) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation with a 30×50 mm column at 40 mL/min. The mobile phase used a mixture of solvent A ($H_2O$/0.1% TFA) and solvent B (AcCN/0.1% TFA) with a 15 min gradient from 10% to 95% solvent B. The gradient is followed by a 2 min return to 10% AcCN.

Proton NMR Spectra:

Unless otherwise indicated, all $^1H$ NMR spectra were run on a Varian series Mercury 300 MHz or on a Bruker 400 MHz instrument. Where so characterized, all observed protons are reported as parts-per-million (ppm) downfield from tetramethylsilane (TMS) or other internal reference in the appropriate solvent indicated.

EXAMPLE 1

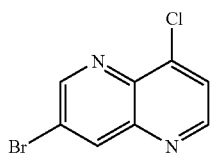

Synthesis of 3-bromo-8-chloro-1,5-naphthyridine

Step 1: Diethyl 2-((5-bromonyridin-3-ylamino)methylene)malonate

To a 500 mL RBF containing 5-bromopyridin-3-amine (60.0 g, 347 mmol) was added diethyl 2-(ethoxymethylene)malonate (71.0 mL, 354 mmol) and 121 mL of toluene. The reaction mixture was heated to reflux for 3 h. The reaction mixture was allowed to cool RT overnight, and the resulting precipitate was collected by filtration and dried to give the desired product as a white crystalline solid.

Step 2: Ethyl 7-bromo-4-oxo-1,4-dihydro-1,5-naphthyridine-3-carboxylate

In a RBF fitted with a reflux condenser a mixture of diethyl 2-((5-bromopyridin-3-ylamino)methylene)malonate (1 g, 3 mmol) and 1-phenoxybenzene (10 mL, 63 mmol) was heated to reflux for 1 h. The reaction mixture was allowed to cool to RT and $CH_3CN$ was added. The resulting solids were filtered and dried to provide the desired product as a light brown solid.

Step 3: 7-bromo-4-hydroxy-1,5-naphthyridine-3-carboxylic acid

Ethyl 7-bromo-4-oxo-1,4-dihydro-1,5-naphtyridine-3-carboxylate (1 g, 3 mmol) and 2.5 M NaOH (10 mL) were refluxed for 1 h in a RBF fitted with a reflux condenser. The hot, heterogeneous mixture was diluted with boiling water at which point a tan precipitate dissolved. Charcoal was added to the solution, which was swirled for 2 min and then the mixture was filtered. Glacial acetic acid was added to the filtrate and a white precipitate started to form (pH adjusted to 4). The precipitate was filtered off upon cooling, washed with water and dried to provide the desired product as a white solid.

Step 4: 7-bromo-1,5-naphthyridin-4-ol

In a RBF fitted with a reflux condenser, 7-bromo-4-hydroxy-1,5-naphthyridine-3-carboxylic acid (1 g, 4 mmol) was added in portions over 10 minutes to stirred refluxing quinoline (50 mL), and the resulting mixture was refluxed for 1 h. The mixture was cooled and diluted with acetone. The precipitate was filtered, washed with water and dried to give 0.8 g of a grey-brown powder. The product was reprecipitated from aq. NaOH with glacial acetic acid to give a white solid.

Step 5: 3-bromo-8-chloro-1,5-naphthyridine

7-Bromo-1,5-naphthyridin-4-ol (7.0 g) and phosphoryl chloride (200 mL) were refluxed for 5 h in a RBF fitted with a reflux condenser. Excess $POCl_3$ was distilled off under reduced pressure and the residue poured onto ice. This cold mixture was carefully neutralized with aq. ammonia, which caused an exotherm. The resulting solid was filtered, washed with water and dried. The product was recrystallized from n-heptane to give white needles of 3-bromo-8-chloro-1,5-naphthyridine.

EXAMPLE 2

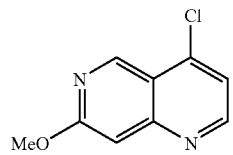

Synthesis of 7-Methoxy-1H-[1,6]naphthyridin-4-one

Step 1: 4-amino-3-bromo-2-chloropyridine

4-Amino-2-chloropyridine (50 g, 388 mmol) was dissolved in glacial acetic acid (500 mL). To this solution was added NBS (75 g, 426 mmol) portionwise at RT (water bath cooling was provided to control the exothermicity). The reaction mixture was stirred at RT for 1 h at which point the reaction was found complete (as monitored by TLC). Solvent was removed under reduced pressure followed by azeotropic distillation with ethanol. The crude product was purified by column chromatography on silica gel (230-400 mesh) eluting with ethyl acetate hexane mixture.

Step 2: 4-amino-3-bromo-2-methoxypyridine

Methanol (350 mL) was charged in a two-neck RBF equipped with a guard tube and septum and cooled to 0° C. Sodium metal (23 g) was added to it slowly in pieces. After all sodium metal had dissolved, 4-amino-3-bromo-2-chloro pyridine (23 g, 178 mmol) was added and the solution was heated at 180° C. in a pressure vessel for 5-6 h. The reaction mixture was then cooled to 0° C. and adjusted to pH 8 by addition of conc. HCl. Solvent was removed under reduced pressure and the residue was suspended in ethyl acetate. Undissolved impurities were removed by filtration and the filtrate was concentrated under reduced pressure to obtain pure product.

Step 3: 5-[(3-Bromo-2-methoxy-pyridin-4-ylamino)-methylene]-2,2-dimethyl-[1,3]dioxane-4,6-dione A two necked RBF equipped with a reflux condenser was charged with Meldrum's acid (15.6 g, 108 mmol) and trimethyl orthoformate (143 mL). The reaction mixture was heated 100° C. for 2 h. 4-amino-3-bromo-2-methoxypyridine (22 g, 108 mmol) was added and heating was continued for an additional 4 h at 100° C. The reaction mixture was allowed to cool to RT, diluted with hexane and filtered to obtain the product as a yellow solid.

Step 4: 8-Bromo-7-methoxy-1H-[1,6]naphthyridin-4-one

A two neck RBF equipped with an air condenser was charged with 5-[(3-Bromo-2-methoxy-pyridin-4-ylamino)-methylene]-2,2-dimethyl-[1,3]dioxane-4,6-dione (23 g, 64 mmol) and diphenyl ether (230 mL). The reaction mixture was heated at 250° C. for 30 min under nitrogen atmosphere after which it was cooled to RT, diluted with hexane and filtered to obtain a dark solid. The crude product was refluxed in hexane for 30 min and filtered to obtained 8-Bromo-7-methoxy-1H-[1,6]naphthyridin-4-one as a brown solid.

Step 5: 7-Methoxy-1H-[116]naphthyridin-4-one

8-Bromo-7-methoxy-1H-[1,6]naphthyridin-4-one (12 g, 33.5 mmol) was dissolved in anhydrous methanol (240 mL) and 10% Dry Pd/C (2.4 g) was added carefully in portions. This was followed by portionwise addition of ammonium formate (24 g) which caused an exotherm. The reaction mixture was heated to reflux for 1 h. The reaction mixture was cooled to RT, filtered through Celite, and washed with hot MeOH. The filtrate was concentrated and the residue purified by column chromatography on silica gel (230-400 mesh) eluting with ethyl acetate-methanol.

Step 6: 4-Chloro-7-methoxy-[1,6]naphthyridine

A two neck RBF equipped with $CaCl_2$ guard tube was charged with 7-Methoxy-1H-[1,6]naphthyridin-4-one (28 g, 159 mmol) and $POCl_3$ (280 mL). The reaction mixture was stirred at RT for 3 h. The reaction mixture was poured into ice water and the pH was carefully adjusted to 8 with solid sodium carbonate (highly exothermic reaction). The product was extracted with EtOAc. The combined organic layer was washed with water, dried over $Na_2SO_4$ and concentrated. The crude product was purified by column chromatography on silica gel (230-400 mesh) eluting with ethyl acetate hexane mixture.

EXAMPLE 3

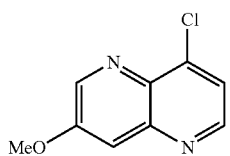

Synthesis of 8-chloro-3-methoxy-1,5-naphthyridine

Step 1: 3-Bromo-5-methoxypyridine

Sodium (12 g) was dissolved in methanol (150 mL) while cooling, and excess MeOH was removed under reduced pressure to obtain NaOMe, which was azeotroped with toluene (2×100 mL). A solution of 3,5-dibromopyridine (100 g) in DMSO (500 mL) was added to sodium methoxide and the mixture was stirred at 90° C. for 2 h. After cooling to RT, aqueous NaOH solution (3 M, 300 mL) was added and the mixture was extracted with $Et_2O$. The ethereal layer was washed with brine and dried over $Na_2SO_4$. After concentration the crude product obtained was purified by flash column chromatography (Hexane:EtOAc 85:15) to afford pure product 3-bromo-5-methoxy pyidine.

Step 2: 3-amino-5-methoxypyridine

3-Bromo-5-methoxypyridine (15 g) was added to a pressure vessel, and $CuSO_4$ (3.9 g) and 25% aq. ammonia (150 mL) were added. The reaction mixture was stirred for 4 h at 135° C., then cooled to RT, basified with aqueous NaOH solution, and extracted with $CH_2Cl_2$. After evaporation of volatiles, 3-amino-5-methoxypyridine was obtained as yellow solid.

Step 3: 5-[(5-Methoxy-pyridin-3-ylamino)-methylene]-2,2-dimethyl-[1,3]dioxane-4,6-dione A two-necked RBF equipped with a reflux condenser was charged with Meldrum's acid (14.4 g, 100 mmol) and trimethylorthoformate (100 mL). The reaction mixture was heated at 100-105° C. for 2 h. 5-amino-3-methoxy pyridine (12.5 g, 100 mmol) was added to the reaction mixture and heating was continued for an additional 4 h at the same temperature. The reaction mixture was allowed to cool to RT, diluted with hexane and filtered to obtain the product as light yellow solid.

Step 4: -Methoxy-1H-[1,5]naphthyridin-4-one

A two-necked RBF equipped with an air condenser was charged with 5-[(5-Methoxy-pyridin-3-ylamino)-methylene]-2,2-dimethyl-[1,3]dioxane-4,6-dione (18 g) and diphenyl ether (180 mL). The reaction mixture was heated at 240-250° C. for 5 min under $N_2$ atmosphere after which it was cooled to RT, diluted with hexane and filtered to obtain a dark solid. The crude product was refluxed in hexane for 30 min and filtered to obtain product as a brown solid.

Step 5: 8-chloro-3-methoxy-1,5-naphthyridine

A two-necked RBF equipped with an air condenser (protected with $CaCl_2$ guard tube) was charged with 7-Methoxy-1H-[1,5]naphthyridin-4-one (13 g) and $POCl_3$ (65 mL). The reaction mixture was allowed to reflux at 120° C. for 12 h. The $POCl_3$ was removed in vacuo and azeotroped twice with toluene. EtOAc (75 mL) was added and the reaction mixture was stirred at 50-60° C. for 15-20 min. EtOAc removed separated by decantation. The organic layers were combined and concentrated. The obtained crude was dissolved in EtOAc (50 ml) and a washed with satd. aqueous sodium bicarbonate. The organic layer was dried over $Na_2SO_4$ and concentrated. The resulting solids were suspended in hexane, stirred for 15 min, filtered and dried under vacuum.

EXAMPLE 4

Synthesis of 8-Chloro-2-methoxy-1,5-naphthyridine

Step 1: 5-((6-Methoxypyridin-3-ylamino)methylene)-2,2-dimethyl-1,3-dioxane-4,6-dione A mixture of Meldrum's acid (34.8 g, 0.242 mol) and trimethyl orthoformate (285 mL, 2.05 mol) was heated to 105° C. for 2 h. To the solution 6-methoxypyridin-3-amine (30 g, 0.242 mol) was added and continued the stirring overnight at the same temperature. The mixture was allowed to cool to RT and diluted with hexane. The solid precipitated was filtered and washed with hexane to afford 5-((6-methoxypyridin-3-ylamino)methylene)-2,2-dimethyl-1,3-dioxane-4,6-dione as a pale yellow solid.

Step 2: 6-Methoxy-1,5-naphthyridin-4(1H)-one

A suspension of 5-((6-methoxypyridin-3-ylamino)methylene)-2,2-dimethyl-1,3-dioxane-4,6-dione (51.3 g, 0.185 mol) in diphenylether (1275 mL) was heated to 250° C. under nitrogen atmosphere for 20 min. The reaction mixture was cooled to RT and diluted with hexane. The gummy solid was then triturated with hexane to obtain 6-methoxy-1,5-naphthyridin-4(1H)-one as a pale brown color solid.

Step 3: 8-Chloro-2-methoxy-1,5-naphthyridine

To the intermediate 6-methoxy-1,5-naphthyridin-4(1H)-one (15.0 g, 0.085 mol) was added $POCl_3$ (300 mL) dropwise under nitrogen atmosphere at RT. The reaction mixture was heated to 110° C. with constant stirring. After 12 h, the mixture was concentrated in vacuo and azeotroped with toluene (2×100 mL). The residue was dissolved in ice-water (100 mL) and adjusted pH of the solution to 7 using 10% $NaHCO_3$ solution, and extracted with EtOAc (4×100 mL). The combined organic extracts were washed with water (2×100 mL), saturated NaCl solution (100 mL), dried ($Na_2SO_4$), filtered and concentrated in vacuo.

EXAMPLE 5

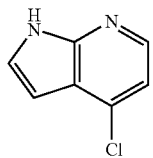

Synthesis of 4-Chloro-1H-pyrrolo[2,3-b]pyridine

Step 1: 1H-Pyrrolo[2,3-b]pyridine

The title compound was prepared according to a procedure described in WO2003082289A1. A solution of 1H-pyrrolo[2,3-b]pyridine (10.0 g, 84.6 mmol) in ethyl acetate (846 ml, 84.6 mmol) was cooled to 0° C. To the cold solution was added a solution of mCPBA (103 mmol, 23.1 g, 77% pure) in 53 mL of EtOAc over a period of 1.5 h. Halfway into the reaction, 100 mL of EtOAc was added to the reaction to ease stirring of the thick mixture. The residual mCPBA was washed into the reaction mixture by an additional portion of EtOAc (25 mL). Solid precipitated out of the solution, and the resulting mixture was warmed to rt, and allowed to stir at this temp until the starting azaindole had been consumed as judged by RPLC. After 3 h at rt, the reaction was completed. The reaction mixture was cooled back to 0° C. The resulting slurry was filtered to collect the N-oxide as the meta-chlorobenzoic acid salt. The solid was washed with additional EtOAc and dried under vacuum. The product, 1H-pyrrolo[2,3-b]pyridine 1-oxide salt of mCBA was obtained as light yellow solid.

The mCBA salt was treated with aqueous base to liberate the N-oxide. A slurry of the N-oxide mCBA salt (35.5 g, 265 mmol) in 149 mL of deionized water at 15° C. was treated with sufficient amount of aqueous solution containing 30% by weight of potassium carbonate (11.0 g, 79.4 mmol) to raise the pH of the slurry between 9.5 to 10.5. Additional water (74 mL) was added to the mixture while the temperature was maintained between 15° C. to rt for 2 h. The slurry was cooled to 0° C. for 5 h, and then filtered to recover the precipitate. The precipitate was washed with water and dried to afford the white N-oxide product, 1H-pyrrolo[2,3-b]pyridine 1-oxide. $^1$H NMR (Bruker, 400 MHz, DMSO-d6) 12.0 (br s, 1H), 8.19 (d, J=5.4 Hz, 1H), 7.60 (t, J=3.0 Hz, 1H), 7.20 (d, J=5.0 Hz, 1H), 6.52 (d, J=3.0 Hz, 1H).

Step 2: 4-Chloro-1H-pyrrolo[2,3-b]pyridine

The title compound was prepared according to a procedure described WO03/082289 A1. A solution of azaindole N-oxide (6.82 g, 51.0 mmol) in DMF (36.0 ml, 470 mmol) was heated to 50° C. Methanesulfonyl chloride (11.0 ml, 137 mmol) was added to the heated solution at such a rate as to maintain the reaction temperature at 65 to 75° C. The resulting mixture was heated at 68-77° C. until the reaction was judged complete by RPLC. The total reaction time was 4 h. The reaction was cooled to rt and quenched with water (10 mL). The mixture was cooled to 5° C. 10 N NaOH solution was added to raise the pH of the solution to 7. The resulting slurry was warmed to rt, agitated for 1 h, and then filtered to collect the product. The product was washed with additional water and dried under vacuum. Rusty solid, 4-chloro-1H-pyrrolo[2,3-b]pyridine was collected. $^1$H NMR (Bruker, 400 MHz, DMSO-d6) 12.0 (br s, 1H), 8.19 (d, J=5.4 Hz, 1H), 7.60 (t, J=3.0 Hz, 1H), 7.20 (d, J=5.0 Hz, 1H), 6.52 (d, J=3.0 Hz, 1H).

EXAMPLE 6

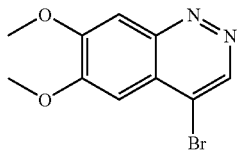

Synthesis of 4-Bromo-6,7-dimethoxycinnoline

Step 1: 6,7-Dimethoxycinnolin-4-ol 1-(2-Amino-4,5-dimethoxyphenyl)ethanone (105 g, 0.538 mol) was dissolved in concentrated HCl (2000 mL, 20 mol) at ambient temperature. The solution was then cooled to 0-4° C., and sodium nitrite (37.5 g, 0.543 mol) was added dropwise over 45 minutes as a solution in water (200 mL). The reaction mixture was stirred at 0-4° C. for one hour during which time it turned dark brown and became homogenous. The reaction mixture was then heated to 60-70° C. for four hours, and a yellow solid formed. After cooling the reaction mixture to 10° C., the solid was collected by filtration. The wet solid was suspended in 1500 mL of water, and the pH was adjusted to 12 with 4N NaOH to give a brown solution, followed by adjusting the pH to 7 with concentrated hydrochloric acid (78 mL). 6,7-Dimethoxycinnolin-4-ol precipitated as an off-white solid, which was filtered, washed with water (3×300 mL), and dried in a vacuum overnight at 50° C.

Step 2: 4-Bromo-6,7-dimethoxycinnoline

Phosphorus oxybromide (125 g, 0.436 mol) was added to a suspension of 6,7-dimethoxycinnolin-4-ol (65 g, 0.32 mol) in chloroform (550 mL, 6.9 mol). The reaction mixture was stirred at 65° C. for 18 hours. Formation of a fine yellow solid was observed. The reaction mixture was poured onto crushed ice (200 g), and the pH was adjusted to 6-7 with sodium acetate (285 g) and sat. NaHCO$_3$. The organic layer was separated, and the aqueous layer was extracted with dichloromethane (2×200 mL). The combined organic extracts were washed with brine (2×100 mL), dried over Na$_2$SO$_4$, filtered, and concentrated in vacuo to provide a light tan oil. DCM (40 mL) and hexanes (250 mL) were added, and the resulting solid was filtered to provide 4-bromo-6,7-dimethoxycinnoline as an off-white solid.

EXAMPLE 7

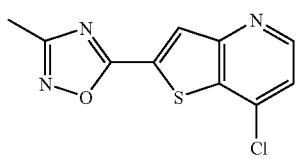

Synthesis of 7-chloro-2-(3-methyl-1,2,4-oxadiazol-5-yl)thieno[3,2-b]pyridine

To a mixture of lithium 7-chlorothieno[3,2-b]pyridine-2-carboxylate (2.125 g, 9.7 mmol) and DMF (20 drops) in CH$_2$Cl$_2$(35 mL), oxalyl dichloride (1.3 ml, 15 mmol) was added dropwise. The mixture was stirred at RT for 2.5 h and then was concentrated to give a yellow solid. The resultant crude acid chloride and (Z)-N'-hydroxyacetamidine (1.4 g, 19 mmol) were heated at 140° C. in xylene/pyridine (6/1, 35 mL) for 1 h. The mixture was diluted with CH$_2$Cl$_2$, and then washed with water, then sat. NaHCO$_3$ and brine. The crude product was purified via column chromatography on silica gel (RediSep 120 g column, gradient elution with 0-50% EtOAc in Hexane) to afford 7-chloro-2-(3-methyl-1,2,4-oxadiazol-5-yl)thieno[3,2-b]pyridine as a white solid.

EXAMPLE 8

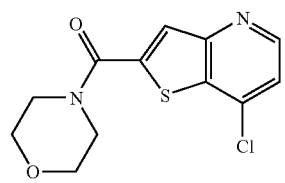

Synthesis of (7-chlorothieno[3,2-b]pyridin-2-yl)(morpholino)methanone

[Lithium 7-chlorothieno[3,2-b]pyridine-2-carboxylate (100 mg, 455 µmol) was dissolved in CH$_2$Cl$_2$(5 mL) with one drop of DMF and oxalyl chloride (2 mL) was added. The mixture was stirred at RT for one hour then concentrated and dried under high vacuum. Morpholine (60 µl, 683 µmol) was then added to the mixture with N-ethyl-N-isopropylpropan-2-amine (238 µl, 1366 µmol) and the mixture was stirred for 20 hours. The mix was then concentrated and purified using 0 to 100% 90/10/1 CH$_2$Cl$_2$/MeOH/ammonium hydroxide in CH$_2$Cl$_2$ to afford (7-chlorothieno[3,2-b]pyridin-2-yl)(morpholino)methanone.

EXAMPLE 9

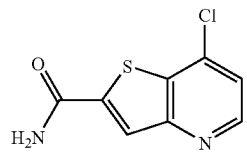

Synthesis of 7-chlorothieno[3,2-b]pyridine-2-carboxamide

A 250 mL flask was charged with lithium 7-chlorothieno[3,2-b]pyridine-2-carboxylate (3.00 g, 13.7 mmol) and CH$_2$Cl$_2$(100 ml) under nitrogen. DMF (cat)(0.100 ml) and oxalyl dichloride (1.49 ml, 17.1 mmol) were added dropwise, and the reaction mixture was stirred for 3 hours, and concentrated in vacuo. The brown solid was redissolved in CH$_2$Cl$_2$ (100 ml) and ammonia (gas)(0.233 g, 13.7 mmol) was gently bubbled through the reaction mixture for 5 minutes. The flask was then capped and stirred at room temperature overnight under closed atmosphere. The brown suspension was concentrated in vacuo and the resulting solid was taken up in water (to dissolve the starting material), then collected by filtration to give 7-chlorothieno[3,2-b]pyridine-2-carboxamide. MS m/z=213 [M+H]+. Calc'd for $C_8H_5ClN_2OS$: 212.66.

EXAMPLE 10

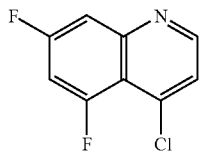

Synthesis of 4-Chloro-6,8-difluoro-quinoline

Step 1: 5-[(3,5-Difluoro-phenylamino)-methylene]-2,2-dimethyl-[1,3] dioxane-4,6-dione In a oven dried 2-neck RBF equipped with reflux condenser and inert atmosphere, meldrum's acid (30 g, 0.208 mole) was dissolved in triethylorthoformate (185 g, 1.25 mole) and the reaction mixture was refluxed at 100° C. under nitrogen for 1 h. On complete consumption of starting material (tic), 3,5-difluoroaniline (26.8 g, 0.208 mol) was added and the heating continued for 4 h. After completion of the reaction (tic), reaction mixture was brought to RT and diluted with hexane (300 ml) when yellow solid precipitated. The solid was filtered, washed thoroughly with hexane and dried to furnish the product.

Step 2: 4-Hydroxy-6,8-difluoro-quinoline (5-[(3,5-Difluoro-phenylamino)-methylene]-2,2-dimethyl-[1,3] dioxane-4,6-dione, (52 g, 0.1837 mol) was dissolved in diphenyl ether and refluxed for 20 min at 200° C. On complete consumption of starting material (tic), reaction mixture was cooled and diluted by hexane. Solid obtained was filtered and washed with sufficient quantities of hexane to furnish product. Mass: 182.09 (M+1).

Step 3: 4-Chloro-6,8-difluoro-quinoline (4-Hydroxy-6,8-difluoro-quinoline, 29.1 g, 0.160 mol) was dissolved in POCl$_3$(183 mL) and heated at reflux for 12 h. On complete consumption of starting material (tic) the contents were brought to RT and excess POCl$_3$ was removed under reduced pressure. Crude mass was azeotroped with toluene and product was diluted with ethyl acetate, organics were washed with sodium bicarbonate and solvent removed under reduced pressure. Crude product was purified by column chromatography at 100-200 mesh size silica in 0-2% EtOAc-hexane. Mass: 199.99 (M+1).

EXAMPLE 11

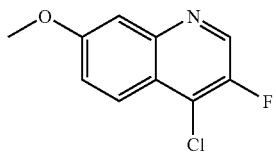

The title compound was prepared in accordance with a procedure described in PCT patent publication WO 2005047279, titled "Preparation of quinoxazolines and related derivatives vanilloid-1 receptor antagonists for treating pain."

EXAMPLE 12-a

Method A4

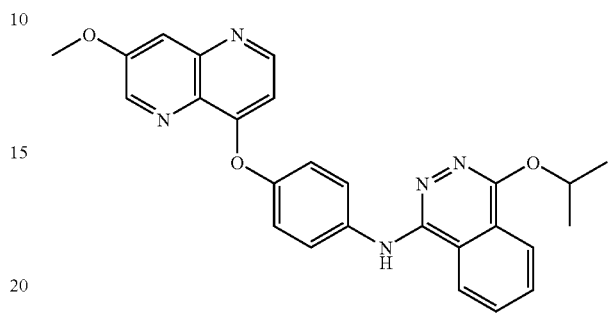

4-Isopropoxy-N-(4-(7-methoxy-1,5-naphthyridin-4-yloxy)phenyl)phthalazin-1-amine

In a 5 mL sealed tube, was dissolved 4-chloro-N-(4-(7-methoxy-1,5-naphthyridin-4-ylthio)phenyl)phthalazin-1-amine (0.100 g, 0.224 mmol) in iPrOH (0.500 mL). To this was added cesium carbonate (0.110 g, 0.336 mmol) and the mixture was irradiated for 30 min at 140° C. in the microwave. When the reaction was determined to be complete by LC/MS, it was concentrated. The mixture concentrate was purified using Isco silica gel chromatography, using 0-100% CH$_2$Cl$_2$:MeOH(90:10)/CH$_2$Cl$_2$, followed by reverse phase chromatography (Gilson, 10-90% TFA/acetonitrile in water over 15 min). The product-containing fractions were extracted into DCM, washed 1× sodium carbonate, 1×H$_2$O, dried with Na$_2$SO$_4$, filtered through fritted funnel, and concentrated to yield 4-isopropoxy-N-(4-(7-methoxy-1,5-naphthyridin-4-ylthio)phenyl)phthalazin-1-amine as a light yellow solid. MS [M+H]+=470.0; Calc'd=469.6 for $C_{26}H_{23}N_5O_2S$

EXAMPLE 12-b

Method A5

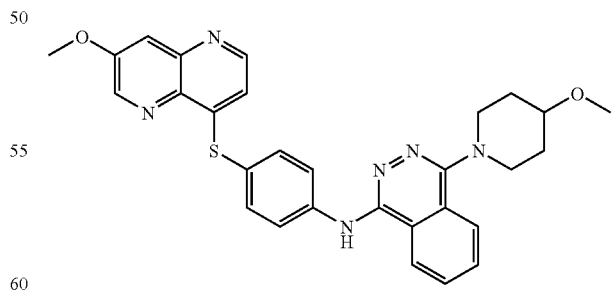

N-(4-(7-methoxy-1,5-naphthyridin-4-ylthio)phenyl)-4-(4-methoxypiperidin-1-yl)phthalazin-1-amine A 15 ml sealed pressure tube was charged with 4-chloro-N-(4-(7-methoxy-1,5-naphthyridin-4-ylthio)phenyl)phthalazin-1-amine (120 mg, 0.269 mmol) and 4-methoxypiperidine (620 mg, 5.382 mmol), in 0.3 ml of DMSO. The sealed tube was placed in a preheated oil bath at 100° C. where it was stirred for 16 hours. The reaction was cooled to ambient temperature, diluted with 2 ml of MeOH, and the solution purified using Gilson Reverse Phase HPLC. The fractions containing the desired product was neutralized with saturated sodium bicarbonate and extracted with 10 ml of DCM (3×). The organics were dried over $Na_2SO_4$, filtered and the filtrate was concentrated in vacuo to afford N-(4-(7-methoxy-1,5-naphthyridin-4-ylthio)phenyl)-4-(4-methoxypiperidin-1-yl)phthalazin-1-amine as a yellow solid. MS $[M+H]^+$= 525.

EXAMPLE 13

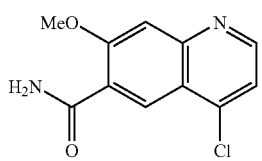

The title compound, 4-chloro-7-methoxyquinoline-6-carboxamide, was prepared by a method described WO 00/050405, Application No. WO 2000-GB579.

EXAMPLE 14

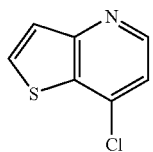

The title compound, 7-chlorothieno[3,2-b]pyridine, was prepared by a method described in Ragan, J. A.; Raggon, J. W.; Hill, P. D.; Jones, B. P.; McDermott, R. E.; Munchhof, M. J.; Marx, M. A.; Casavant, J. M.; Cooper, B. A.; Doty, J. L.; Lu, Y. Org. Process Res. Dev. 2003, 7, 676-683, and related references cited therein.

EXAMPLE 15

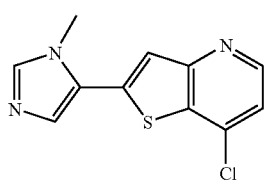

The title compound, 7-chloro-2-(1-methyl-1H-imidazol-5-yl)thieno[3,2-b]pyridine, was prepared by a method described in Ragan, J. A.; Raggon, J. W.; Hill, P. D.; Jones, B. P.; McDermott, R. E.; Munchhof, M. J.; Marx, M. A.; Casavant, J. M.; Cooper, B. A.; Doty, J. L.; Lu, Y. Org. Process Res. Dev. 2003, 7, 676-683.

EXAMPLE 16

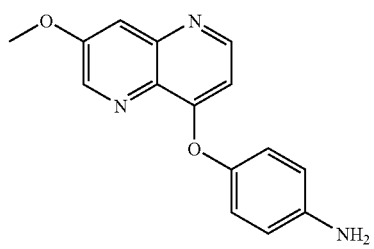

Synthesis of 4-(7-methoxy-1,5-naphthyridin-4-yloxy)benzenamine

Five 20 mL microwave vials were each charged with 4-aminophenol (0.700 mg, 33 mmol) and 3 equivalents of cesium carbonate in 6.0 ml of DMF. The mixture was stirred at RT for 10 minutes. Following addition of 8-chloro-3-methoxy-1,5-naphthyridine (1 g, 26 mmol), the reaction vessels were capped and irradiated at 150° C. for 15 min in the microwave, at which time the reaction was determined complete by LCMS. The mixture was allowed to cool to ambient temperature and material from the five vessels was combined. A deep brown solid crashed out with addition of water. Filtered solids, washed with water and dried overnight in the vacuum oven to afford 4-(7-methoxy-1,5-naphthyridin-4-yloxy)benzenamine as a brown solid.

Alternatively, the title compound may be prepared by the following method: In a nitrogen purged sealed pressure vessel, dissolved 4-aminophenol (0.617 g, 5.65 mmol) in DMF (0.030 L). Cesium carbonate (3.68 g, 11.3 mmol) was added and the mixture was stirred at RT for 5 min. Added 8-chloro-3-methoxy-1,5-naphthyridine (1.00 g, 5.14 mmol), heated to 90° C., stirred for 17 h. The mixture was allowed to cool to RT and was concentrated. The crude material was triturated with methanol, filtered, washed with methanol followed by water, and air dried to yield 4-(7-methoxy-1,5-naphthyridin-4-yloxy)benzenamine as brown solid. MS [M+H]=268.1; Calc'd 267.3 for $C_{15}H_{13}N_3O_2$.

EXAMPLE 17

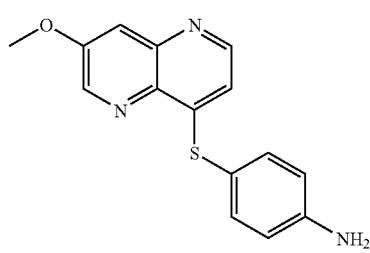

Synthesis of 4(7-methoxy-1,5-naphthyridin-4-ylthio)benzenamine

A RBF was charged with 4-aminothiophenol (161 mg, 1.285 mmol), 8-chloro-3-methoxy-1,5-naphthyridine (250 mg, 1.285 mmol) and 5.2 mL of DMF, and the mixture was stirred at RT for 45 min. The orange, heterogeneous mixture was diluted with EtOAc and washed with 1N NaHCO$_3$. The aqueous portion was extracted two additional times with EtOAc and the combined organics were dried with MgSO$_4$, filtered and concentrated. The crude oil was concentrated twice from toluene to remove DMF and the resulting solids were dried under high vacuum to provide 4-(7-methoxy-1,5-naphthyridin-4-ylthio)benzenamine as a tan solid. MS m/z=284 [M+H]$^+$. Calc'd for C$_{15}$H$_{13}$N$_3$OS: 283.35.

EXAMPLE 18

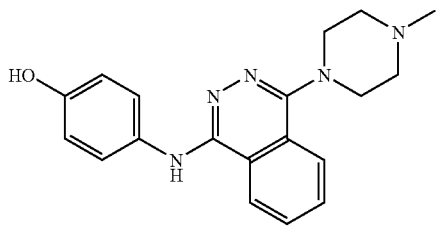

Synthesis of 4(4(4-methylpiperazin-1-yl)phthalazin-1-ylamino)phenol

A mixture of 4-aminophenol (42 mg, 0.38 mmol), 1-chloro-4-(4-methylpiperazin-1-yl)phthalazine (100 mg, 0.381 mmol), and TFA (29 μl, 0.38 mmol) was heated in 2-butanol (3 mL) in a sealed tube at 90° C. overnight. Next day LC/MS shows completion of reaction. The reaction was cooled and diluted with DCM. Aqueous sodium bicarbonate was added and the organic layer was collected. The aqueous layer was neutralized with 1N HCl and the product was extracted with DCM. The organic layers were combined, dried over sodium sulfate, and concentrated to afford 4-(4-(4-methylpiperazin-1-yl)phthalazin-1-ylamino)phenol as solid brown material. MS [M+H]=336.2. Calc'd for C$_{19}$H$_{21}$N$_5$O: 335.4.

EXAMPLE 19

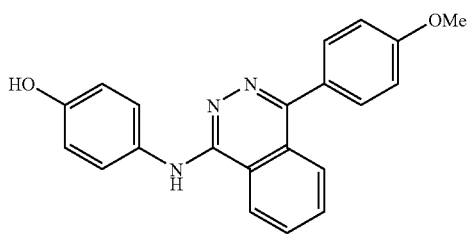

Synthesis of 4(4(4-methoxyphenyl)phthalazin-1-ylamino)phenol hydrochloride

4-Aminophenol (340 mg, 3.1 mmol), 1-chloro-4-(4-methoxyphenyl)phthalazine (837 mg, 3.1 mmol), and sec-butanol (12 mL, 3.1 mmol) were combined in a resealable tube and heated to 100° C. overnight. The reaction progress was monitored by LCMS, and upon completion, the orange reaction was cooled diluted with diethyl ether. The resulting precipitate was filtered and washed with diethyl ether, and the solid was dried in vacuo to provide 4-(4-(4-methoxyphenyl)phthalazin-1-ylamino)phenol hydrochloride (1.17 g, 100% yield) as an orange solid. MS [M+H]=344.0. Calc'd for C$_{19}$H$_{21}$N$_5$O: 343.13.

EXAMPLE 20

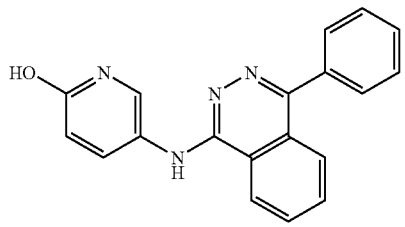

Synthesis of 5(4-phenylphthalazin-1-ylamino)pyridin-2-ol

Step 1: A RBF was charged with 6-methoxypyridin-3-amine (155 mg, 1.25 mmol), 1-chloro-4-phenylphthalazine (300 mg, 1.25 mmol), and 2-butanol (4 mL). The vessel was sealed and the mixture was stirred overnight at 90° C. LC/MS shows completion of reaction. Reaction cooled to RT and purified by silica gel chromatography (1-5% MeOH/DCM) to afford N-(6-methoxypyridin-3-yl)-4-phenylphthalazin-1-amine as tan solid. MS [M+H]=329.1. Calc'd for C$_{20}$H$_6$N$_4$O: 328.4.

Step 2: In a 25 RBF was added N-(6-methoxypyridin-3-yl)-4-phenylphthalazin-1-amine (290 mg, 0.88 mmol), hydrobromic acid (2.4 mL, 44.2 mmol) and acetic acid (2.5 mL, 43.3 mmol), and a reflux condenser open to air was fitted and the RBF was heated to 130° C., while stirring, for 2 h. The reaction was cooled to RT, the mixture neutralized with 6N NaOH, upon which a yellow solid crashed out. The yellow solid was filtered, washed with water, placed in vacuum oven at 30° C. to dry, to afford 5-(4-phenylphthalazin-1-ylamino)pyridin-2-ol, as light yellow solid. MS [M+H]=315.2. Calc'd for C$_{19}$H$_{14}$N$_4$O: 314.3.

EXAMPLE 21

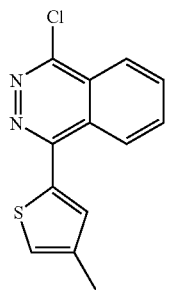

Synthesis of 1-Chloro-4-(4-methylthiophen-2-yl)phthalazine 1,4-Dichlorophthalazine (1.40 g, 7.03 mmol), 4-methylthiophen-2-ylboronic acid (999 mg, 7.03 mmol), and PdCl$_2$ (DPPF)(721 mg, 985 μmol) were added into a sealed tube. The tube was purged with Argon. Then sodium carbonate (2.0 M in water)(7.74 ml, 15.5 mmol) and 1,4-dioxane (35.2 ml, 7.03 mmol) were added. The tube was sealed, stirred at RT for 5 min, and placed in a preheated oil bath at 110° C. After 1 h, LC-MS showed product and byproduct (double coupling), and SM dichlorophthalazine. The reaction was cooled to RT, filtered through a pad of celite with an aid of EtOAc, concentrated, and loaded onto column. The product was purified by column chromatography using Hex to remove the top spot, then 80:20 Hex:EtOAc to collect the product. The product, 1-chloro-4-(4-methylthiophen-2-yl)phthalazine was obtained as yellow solid. LC-MS showed that the product was contaminated with a small amount of SM dichlorophthalazine and biscoupling byproduct. MS m/z=261 [M+1]$^+$. Calcd for $C_{13}H_9ClN_2S$: 260.12.

EXAMPLE 22

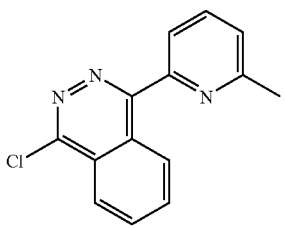

Synthesis of 1-Chloros(6-methylpyridin-2-yl)phthalazine

Step 1: 2-(Dimethylamino)isoindoline-1,3-dione

The title compound was prepared according to methods described in the following papers: (a) Deniau, E.; Enders. D.; Couture, A.; Grandclaudon, P. *Tetrahedron: Asymmetry* 2003, 14, 2253. (b) Saito, Y.; Sakamoto, T.; Kikugawa, Y. *Synthesis* 2001, 221. (c) Deniau, E.; Enders, D. *Tetrahedron Lett.* 2000, 41, 2347. To a solution of isobenzofuran-1,3-dione (5.00 g, 34 mmol) and N,N-dimethylhydrazine (2.9 ml, 37 mmol) in toluene (75 ml, 34 mmol) in a RBF was added p-TsOH.H$_2$O (0.32 g, 1.7 mmol). A Dean-Stark apparatus and a condenser were attached to the RBF. The mixture was refluxed. After 4 h, LCMS showed mainly product. The reaction was cooled to RT. Toluene was removed under reduced pressure, and the crude was dissolved in CH$_2$Cl$_2$, washed with sat NaHCO$_3$, water, and brine. The organic was dried over MgSO$_4$, filtered, and concentrated. Light yellow solid was obtained. $^1$H NMR showed mainly product, 2-(dimethylamino)isoindoline-1,3-dione. MS Calcd for $C_{10}H_{10}N_2O_2$: [M]$^+$=190. Found: [M+H]$^+$=191.

Step 2: 2-(Dimethylamino)-3-hydroxy-3-(6-methylpyridin-2-yl)isoindolin-1-one

In a dry RBF, 2-bromo-6-methylpyridine (66 μl, 581 μmol) and THF (1211 μl, 581 μmol) were added. The reaction was purged with argon, and cooled to −78° C. BuLi (244 μl, 610 μmol) was added via syringe. After 30 min, the anion was cannulated into a solution of 2-(dimethylamino)isoindoline-1,3-dione (166 mg, 872 μmol) in 2 mL of THF previously submerged in a cold bath at −78° C. for 2 min (the starting material precipitated out of the solution at low temp). After 15 min at −78° C., the temperature was warmed to −30° C. After 1 h, LCMS showed mainly product at 1.535 min. The reaction was quenched slowly with sat. NH$_4$Cl. The product was extracted with CH$_2$Cl$_2$. The organic layer was washed with brine, dried over MgSO$_4$, filtered, and concentrated to give a yellow oil. The product was purified using 85:15 CH$_2$Cl$_2$:(90:10:1 CH$_2$Cl$_2$:MeOH:NH$_4$OH). Viscous yellow oil was obtained. $^1$H NMR showed mainly product, 2-(dimethylamino)-3-hydroxy-3-(6-methylpyridin-2-yl)isoindolin-1-one. MS Calcd for $C_{16}H_{17}N_3O_2$: [M]$^+$=283. Found: [M+H]$^+$=284.

Step 3: 4-(6-Methylpyridin-2-yl)phthalazin-1(2H)-one

The title compound was prepared according to a method described in Saito, Y.; Sakamoto, T.; Kikugawa, Y. *Synthesis* 2001, 2, 221. 2-(Dimethylamino)-3-hydroxy-3-(6-methylpyridin-2-yl)isoindolin-1-one (3.18 g, 11.0 mmol), EtOH (11.0 ml, 11.0 mmol), and hydrazine (5.30 ml, 168 mmol) were added into a RBF fitted with a reflux condenser. A nitrogen balloon was attached on top of the condenser. The reaction was refluxed overnight. LCMS showed that the reaction was completed. The reaction was cooled to rt. Off-white solid precipitated out of the solution. Water was added and the mixture was cooled to 0° C. The solid was filtered off with an aid of water and dried under vacuum. White solid was obtained. LCMS of the solid showed product, 4-(6-methylpyridin-2-yl)phthalazin-1(2H)-one. MS Calcd for $C_{14}H_{11}N_3O$: [M]$^+$=237. Found: [M+H]$^+$=238.

Step 4: 1-Chloro-4-(6-methylpyridin-2-yl)phthalazine

A dry RBF set up with stirring bar and reflux condenser was charged with 4-(6-methylpyridin-2-yl)phthalazin-1(2H)-one (780 mg, 3.29 mmol) and POCl$_3$(10.7 ml, 115 mmol). This was stirred under reflux for 18 h. Excess POCl$_3$ was removed under vacuum with an aid of toluene. The residue was cooled to 0° C. and basified with cold 6 N NaOH until pH=9. Occasionally, ice was added to keep the mixture cold to prevent the hydrolysis. Stirring, agitation, and sonication eventually provided a solid material at basic pH. The solids were filtered, washed with ample amount of water and dried under vacuum to afford a white solid. MS Calcd for $C_{14}H_{10}ClN_3$: [M]$^+$=255. Found: [M+H]$^+$=256.

EXAMPLE 23

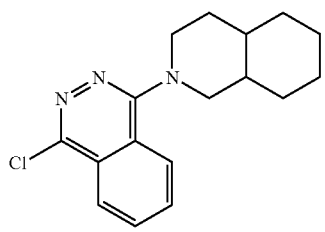

Synthesis of 1-chloro-(octahydroisoquinolin-2(1H)-yl)phthalazine

A resealable pressure bottle was charged with 1,4-dichlorophthalazine (1258 mg, 6.28 mmol), decahydroisoquinoline (588 μl, 3.95 mmol), potassium carbonate (546 mg, 3.95 mmol) and DMSO (20 mL, 0.2 M). Reaction was stirred at 80° C. for 16 h, then cooled to RT and diluted with 5 mL of DMSO. The solution was purified by Gilson HPLC (10% to 90% CH$_3$CN/H$_2$O/0.1% TFA) to afford 1-chloro-4-(octahydroisoquinolin-2(1H)-yl)phthalazine. MS [M+H]=302.1. Calcd for C$_{17}$H$_{20}$ClN$_3$: 301.8.

EXAMPLE 24

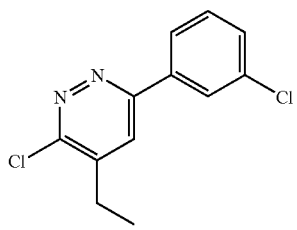

Synthesis of
3-chloro-6-(3-chlorophenyl)-4-ethylpyridazine

Step 1:
4-(3-chlorophenyl)-2-ethyl-2-hydroxy-4-oxobutanoic acid

A RBF was charged with 2-oxobutanoic acid (2.50 g, 24.5 mmol) and 3.2 mL of water and the mixture was cooled to 0° C. The acid was neutralized by slow addition of 20% aqueous KOH. 3'-chloroacetophenone (3.79 g, 24.5 mmol) was added, followed by a 1.3 M solution of KOH (2.20 g, 39.2 mmol) in MeOH. The reaction mixture was stirred at 0° C. for 48 h. The mixture was brought to pH 2 by dropwise addition of conc. H$_2$SO$_4$. The MeOH was removed in vacuo, and 25 mL of water was added. The heterogeneous mixture was filtered through Celite, and the filter cake was washed with water and CH$_2$Cl$_2$. The layers of the filtrate were separated, and the aqueous portion was extracted with additional CH$_2$Cl$_2$. The combined organics were dried with MgSO$_4$, filtered and concentrated to a volume of 25 mL. Hexane was added until the mixture became cloudy, and upon standing a white crystalline solid formed. The mother liquor was decanted and the solids were washed with hexane and dried to provide 4-(3-chlorophenyl)-2-ethyl-2-hydroxy-4-oxobutanoic acid as a white crystalline solid. MS m/z=279 [M+Na]$^+$. Calc'd for C$_{12}$H$_{13}$ClO$_4$: 256.69.

Step 2:
6-(3-chlorophenyl)-4-ethylpyridazin-3(2H)-one

A RBF was charged with 4-(3-chlorophenyl)-2-ethyl-2-hydroxy-4-oxobutanoic acid (2.78 g, 10.8 mmol), hydrazine (0.510 ml, 16.2 mmol) and 11 mL of n-BuOH. A Dean-Stark apparatus fitted with a reflux condenser was attached, and the mixture was heated under nitrogen at 130° C. for 15 h. Upon cooling a precipitate formed, which was filtered, washed with cold EtOH, and dried. 6-(3-chlorophenyl)-4-ethylpyridazin-3(2H)-one was isolated as a white solid. MS m/z=235 [M+H]$^+$. Calc'd for C$_{12}$H$_{11}$ClN$_2$O: 234.68.

Step 3:
3-chloro-6-(3-chlorophenyl)-4-ethylpyridazine

A RBF was charged with 6-(3-chlorophenyl)-4-ethylpyridazin-3(2H)-one (1.50 g, 6.4 mmol) and phosphorus oxychloride (6.0 ml, 64 mmol). Hunig's base (1.2 ml, 7.0 mmol) was added to the mixture dropwise (slightly exothermic). The flask was fitted with a reflux condenser and a nitrogen inlet and the mixture was heated at 110° C. for 3 h. Upon cooling the reaction mixture was poured onto ice. 6N NaOH was added dropwise until pH 9 while keeping the mixture cold by gradual addition of ice. The solids were filtered, washed with water and dried to provide 3-chloro-6-(3-chlorophenyl)-4-ethylpyridazine as a peach colored solid. MS m/z=253 [M]$^+$. Calc'd for C$_{12}$H$_{10}$Cl$_2$N$_2$: 253.13.

EXAMPLE 25

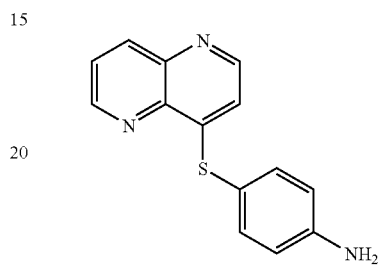

Synthesis of
4(1,5-naphthyridin-4-ylthio)benzenamine

To a mixture of tetrakis(triphenylphosphine)palladium (188 mg, 163 μmol) and sodium methoxide (176 mg, 3251 μmol) was added a solution of 4-(7-bromo-1,5-naphthyridin-4-ylthio)benzenamine (540 mg, 1625 μmol) in DMF (2 mL). The resealable tube was purged with argon, and the mixture was heated to 100° for 1.5 h. The mix was diluted with ethyl acetate, washed with brine twice, dried with sodium sulfate, and concentrated. The residue was purified by silica gel chromatography using 1-10% MeOH:CH$_2$Cl$_2$ w/1% NH$_4$OH to provide 4-(1,5-naphthyridin-4-ylthio)benzenamine. MS m/z=254 [M]$^+$. Calc'd for C$_{14}$H$_{11}$N$_3$S: 253.32.

EXAMPLE 26

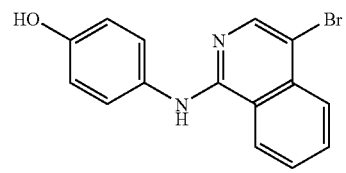

Synthesis of
4-(4-bromoisoquinolin-1-ylamino)phenol
hydrochloride

A mixture of 4-aminophenol (225 mg, 2062 μmol) and 4-bromo-1-chloroisoquinoline (500 mg, 2062 μmol) was heated in sec-butanol (15 mL) in a sealed tube at 100° C. for 2 hours. TFA (477 μl, 6186 μmol) was added and the reaction mixture was allowed to stir at 100° C. overnight. LCMS analysis showed conversion to 4-(4-bromoisoquinolin-1-ylamino)phenol hydrochloride. The dark red reaction mixture was cooled, and diethyl ether was added. The resulting precipitate was filtered and washed with diethyl ether, and the solid was dried in vacuo to provide 4-(4-bromoisoquinolin-1-ylamino)phenol hydrochloride as a purple solid.

EXAMPLE 27

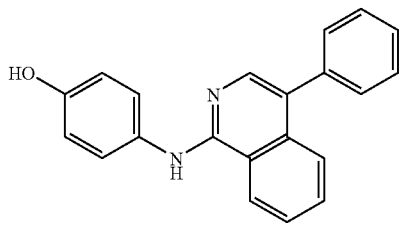

Synthesis of
4-(4-phenylisoquinolin-1-ylamino)phenol

To a solution of 4-(4-bromoisoquinolin-1-ylamino)phenol (578 mg, 1834 µmol), phenylboronic acid (335 mg, 2751 µmol), and tetrakis (triphenylphosphine) palladium (0) (212 mg, 183 µmol) in toluene (10480 µl, 1834 µmol) and ethanol (2620 µl, 1834 µmol) was added sodium carbonate (6281 µl, 12563 µmol) in water (2M). The reaction mixture was heated to 100° C. overnight. The reaction progress was monitored by LCMS, which showed conversion to 4-(4-phenylisoquinolin-1-ylamino)phenol. The product was purified by silica gel chromatography (eluent: hexanes:EtOAc 0-50%) to yield 4-(4-phenylisoquinolin-1-ylamino)phenol.

EXAMPLE 28

Synthesis of N-(4-(7-methoxy-1,5-naphthyridin-4-yloxy)phenyl)-4-(chloro)phthalazin-1-amine In a 150 mL pressure tube was dissolved 4-(7-methoxy-1,5-naphthyridin-4-yloxy)benzenamine (6.1 g, 23 mmol) in tBuOH (75 mL). To this solution was added 1,4-dichlorophthalazine (10.0 g, 50 mmol) and the mixture was placed in pre-heated oil bath at 100° C. A thick clay formed at the bottom of the tube after 20 minutes. LCMS on solid at the bottom of the tube showed mainly desired product with trace amounts of starting material. This solid material was dissolved and transferred to a flask using hot 90/10/1 (CH$_2$Cl$_2$/MeOH/ammonium hydroxide), and evaporated to dryness. The crude was dissolved in CH$_2$Cl$_2$ and washed with sat. sodium bicarbonate. The organic layer was separated and dried over sodium sulfate, and then concentrated. The mixture was then dissolved in approx. 30/70 MeOH/CH$_2$Cl$_2$, silica was added and the mix was concentrated to dryness. This silica pre-absorbed material was purified using 0 to 100% 90/10/1 (CH$_2$Cl$_2$/MeOH/ammonium hydroxide) to afford the title compound. MS Found: [M+H]=430.0. Calc'd for C$_{23}$H$_{16}$ClN$_5$O$_2$: 429.9.

EXAMPLE 29

Method A1

Synthesis of 3-(4-(4-(7-methoxy-1,5-naphthyridin-4-yloxy)phenylamino)phthalazin-1-yl)benzonitrile In a nitrogen purged sealed tube, 1,4-dioxane (1.4 mL) was added and the tube was purged with nitrogen for 5 min and sealed. 3-Cyanophenylboronic acid (0.056 g, 0.384 mmol), 4-chloro-N-(4-(7-methoxy-1,5-naphthyridin-4-yloxy)phenyl)phthalazin-1-amine (0.150 g, 0.349 mmol), and 2.0 M sodium carbonate (0.349 mL, 0.698 mmol) were added to the tube, followed by 1,1'-bis(diphenylphosphino)ferrocene-palladium dichloride (0.013 g, 0.017 mmol). The tube was purged with nitrogen, sealed, and the mixture was heated to 100° C. for 17 h. The mixture was allowed to cool to RT and was concentrated in vacuo. The crude material was purified by silica gel chromatography using 0-100% CH$_2$Cl$_2$:MeOH (90:10)/CH$_2$Cl$_2$. The remaining impurities were removed by diluting the crude with methanol causing a light yellow solid to precipitate, which were filtered and air dried to yield 3-(4-(4-(7-methoxy-1,5-naphthyridin-4-yloxy)phenylamino)phthalazin-1-yl)benzonitrile. MS [M+H]=497.0; Calc'd 496.5 for C$_{30}$H$_{20}$N$_6$O$_2$.

EXAMPLE 30

Method A2

Synthesis of N-(4-(7-methoxy-1,5-naphthyridin-4-yloxy)phenyl)-4-(1-methyl-1H-imidazol-2-yl)phthalazin-1-amine In a nitrogen purged sealed tube was added 1,4-dioxane (1.35 mL), and the solution was purged with nitrogen for 5 minutes, then sealed. 1-Methyl-2-(tributylstannyl)-1H-imidazole (0.311 g, 0.837 mmol), 4-chloro-N-(4-(7-methoxy-1,5-naphthyridin-4-yloxy)phenyl)phthalazin-1-amine (0.120 g, 0.279 mmol) were added to the tube, which was then purged with nitrogen and sealed. To the tube was added 1,1'-bis(diphenylphosphino)ferrocene-palladium dichloride (0.102 mg, 0.140 mmol), and the tube was purged with nitrogen, sealed, and heated to 100° C., while stirring the reaction for 17 hours. The reaction was cooled to RT, and concentrated. The concentrate was purified using reverse phase chromatography, the product fractions were concentrated, extracted into DCM, washed once with sodium carbonate and once with water, upon which the title compound precipiated. The solids were filtered, washed with water, air dried to yield N-(4-(7-methoxy-1,5-naphthyridin-4-yloxy)phenyl)-4-(1-methyl-1H-imidazol-2-yl)phthalazin-1-amine (0.039 g) as light yellow solid. MS [M+H]=476.0; Calc'd 475.5 for C$_{27}$H$_{21}$N$_7$O$_2$.

EXAMPLE 31

Method A3

Synthesis of 4(3,3-dimethylbut-1-ynyl)-N-(4-(7-methoxy-1,5-naphthyridin-4-yloxy)phenyl)phthalazin-1-amine A resealable pressure bottle, purged with argon, was charged with 4-chloro-N-(4-(7-methoxy-1,5-naphthyridin-4-yloxy)phenyl)phthalazin-1-amine (120 mg, 0.28 mmol), bis(triphenylphosphine)palladium(ii) chloride (24 mg, 0.03 mmol), copper(I) iodide (6.4 mg, 0.03 mmol), 3,3-dimethyl-1-butyne (86 µl, 0.70 mmol), and ACN (2.8 mL, 0.1 M). To the mixture was added TEA (0.785 mL, 5.6 mmol). The reaction vessel was sealed and the mixture was heated to 90° C. for 16 h. The reaction mixture was cooled to RT, diluted with DCM and filtered over Celite. The filtrate was concentrated under reduced pressure to give a brown residue, which was purified by Gilson HPLC {5-65% (0.1% TFA in CH$_3$CN) in H$_2$O over 20 min}. The product-containing fractions were combined, basified by addition of aq. NaHCO$_3$ and extracted with DCM. The organic portion was dried with Na$_2$SO$_4$, filtered, and concentrated to afford pure 4-(3,3-dimethylbut-1-ynyl)-N-(4-(7-methoxy-1,5-naphthyridin-4-yloxy)phenyl)phthalazin-1-amine MS [M+H]=476.1 Calc'd for C$_{29}$H$_{25}$N$_5$O$_2$: 475.5.

EXAMPLE 32

Method B1

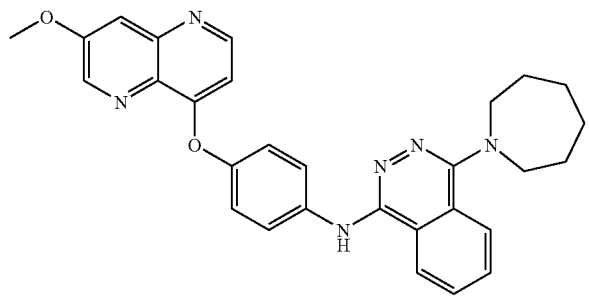

Synthesis of 4-(azepan-1-yl)-N-(4-(7-methoxy-1,5-naphthyridin-4-yloxy)phenyl)phthalazin-1-amine A pyrex reaction tube was charged with 4-(7-methoxy-1,5-naphthyridin-4-yloxy)benzenamine (128 mg, 0.478 mmol), 1-(azepan-1-yl)-4-chlorophthalazine (125 mg, 0.478 mmol), TFA (0.029 ml, 0.382 mmol) and 2.4 mL of 2-BuOH. The tube was sealed and the reaction mixture was heated at 100° C. for 1.5 h. Upon cooling, EtOAc was added, and the resulting precipitate was filtered and washed with EtOAc. The solid was dissolved in 90/10/1 CH$_2$Cl$_2$/MeOH/NH$_4$OH and purified by silica gel chromatography with 90/10/1 CH$_2$Cl$_2$/MeOH/NH$_4$OH. The material was further purified by reverse phase chromatography (Gilson, 5-95% ACN over 15 min) to provide 4-(azepan-1-yl)-N-(4-(7-methoxy-1,5-naphthyridin-4-yloxy)phenyl)phthalazin-1-amine as a tan solid. MS m/z=493 [M+H]$^+$. Calc'd for C$_{29}$H$_{28}$N$_6$O$_2$: 492.57.

EXAMPLE 33

Method B2

Synthesis of N-(4-(1,5-naphthyridin-4-ylthio)phenyl)-4-(4-chlorophenyl)phthalazin-1-amine 1-Chloro-4-(4-chlorophenyl)phthalazine (30 mg, 109 μmol), p-toluenesulfonic acid monohydrate (10 mg, 55 μmol) and 4-(1,5-naphthyridin-4-ylthio)benzenamine (33 mg, 131 μmol) were combined in t-butanol in a sealed tube and the reaction mixture was stirred at 100° C. for 2 h. The mixture was concentrated in vacuo and the crude material was purified by silica gel chromatography (0 to 100% 90/10/1 CH$_2$Cl$_2$/MeOH/NH$_4$OH) in CH$_2$Cl$_2$. The material was further purified by silica gel chromatography (0 to 100% EtOAc/hexane) to afford N-(4-(1,5-naphthyridin-4-ylthio)phenyl)-4-(4-chlorophenyl)phthalazin-1-amine. MS [M+H]=492; Calc'd 491.99 for C$_{28}$H$_{18}$ClN$_5$S.

EXAMPLE 34

Method B3

Synthesis of 4-(4,5-dimethylthiophen-2-yl)-N-(4-(7-methoxy-1,5-naphthyridin-4-yloxy)phenyl)phthalazin-1-amine In a nitrogen purged sealed tube, 1-chloro-4-(4,5-dimethylthiophen-2-yl)phthalazine (0.040 g, 0.146 mmol) was dissolved in tert-butanol (1.00 mL). 4-(7-Methoxy-1,5-naphthyridin-4-yloxy)benzenamine (0.039 g, 0.146 mmol) was added, and the reaction mixture in the tube was stirred at 100° C. for 3 h. The mixture was concentrated in vacuo, and the crude material was purified by silica gel chromatography using 0-100% CH$_2$Cl$_2$:MeOH(90:10)/CH$_2$Cl$_2$. Product-containing fractions were concentrated to yield 4-(4,5-dimethylthiophen-2-yl)-N-(4-(7-methoxy-1,5-naphthyridin-4-yloxy)phenyl)phthalazin-1-amine as light yellow solid. MS [N+H]=506.0; Calc'd 505.6 for C$_{29}$H$_{23}$N$_5$O$_2$S.

EXAMPLE 35

Method B4

Synthesis of 4-ethyl-N-(4-(7-methoxy-1,5-naphthyridin-4-ylthio)phenyl)-6-p-tolylpyridazin-3-amine A pyrex reaction tube was charged with tris(dibenzylideneacetone)dipalladium (20 mg, 0.021 mmol), 4-(7-methoxy-1,5-naphthyridin-4-ylthio)benzenamine (122 mg, 0.430 mmol), sodium tert-butoxide (99 mg, 1.031 mmol), S-Phos (35 mg, 0.086 mmol), and 3-chloro-4-ethyl-6-p-tolylpyridazine (100 mg, 0.430 mmol). The reaction tube was purged with nitrogen. 1.3 mL of toluene was added, and the tube was sealed. The reaction mixture was heated at 100° C. for 3 h. Upon cooling, the mixture was diluted with 5% iPrOH/EtOAc and washed with water. The organic portion was dried with MgSO$_4$, filtered and concentrated. The crude material was purified by silica gel chromatography (90/10/1 CH$_2$Cl$_2$/MeOH/NH$_4$OH) and reverse phase chromatography (Gilson, 10-95% CH$_3$CN over 15 min) to provide 4-ethyl-N-(4-(7-methoxy-1,5-naphthyridin-4-ylthio)phenyl)-6-p-tolylpyridazin-3-amine as a light yellow solid. MS m/z=480 [M+H]$^+$. Calc'd for C$_{28}$H$_{25}$N$_5$OS: 479.60.

EXAMPLE 36

Method B5)

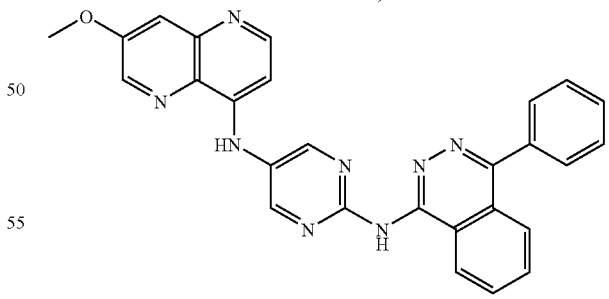

Synthesis of N$^5$-(7-Methoxy-1,5-naphthyridin-4-yl)-N$^2$-(4-phenylphthalazin-1-yl)pyrimidine-2,5-diamine N$^5$-(7-methoxy-1,5-naphthyridin-4-yl)pyrimidine-2,5-diamine (90 mg, 335 μmol), 1-chloro-4-phenylphthalazine (97 mg, 403 μmol), THF (1677 μl, 335 μmol), and LiHMDS (1006 μl, 1006 μmol) were added into a pressure tube. The mixture was stirred at RT for 10 min. A red solution was formed. The tube was placed in a preheated oil bath at 100° C. After 1 h, LCMS showed complete conversion of SM to product. The reaction was cooled to rt. Hexane was added to induce the product to precipitate out of the reaction mixture. The resulting red solid was filtered with an aid of hexane. LCMS confirmed that the solid was the product. The product was purified by performing a column chromatography on silica gel using 60:40 CH$_2$Cl$_2$:(90:10:1 CH$_2$Cl$_2$:MeOH:NH$_4$OH). Yellow solid was obtained. LCMS confirmed product. HPLC showed 96% pure. $^1$H NMR showed rotamers. Note: this cmpd was slightly soluble in DMSO at rt. MS Calcd for C$_{27}$H$_{20}$N$_8$O: [M]$^+$=472. Found: [M+H]$^+$=473.

EXAMPLE 37

Method C1

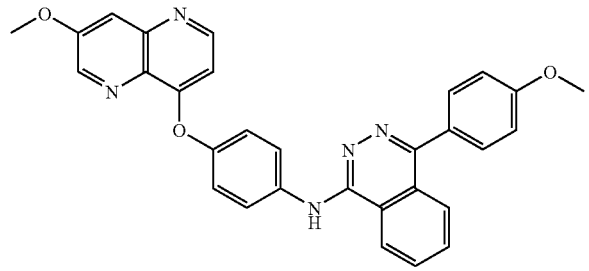

Synthesis of N-(4-(7-methoxy-1,5-naphthyridin-4-yloxy)phenyl)-4-(4-methoxyphenyl)phthalazin-1-amine A 5 mL microwave tube was charged with 4-(4-(4-methoxyphenyl)phthalazin-1-ylamino)phenol and 3 equivalents of cesium carbonate (342 mg, 1.048 mmol) in 1.8 mL of DMF. The mixture was stirred at RT for 10 min. Following addition of 8-chloro-3-methoxy-1,5-naphthyridine (88 mg, 0.454 mmol), the vessel was capped and irradiated at 150° C. for 15 min in the microwave, at which time the reaction was determined complete by LC/MS. The mixture was cooled to ambient temperature and diluted with water. The solids were filtered and washed with water. The solids were triturated with methanol, filtered to remove remaining impurities, washed with additional methanol and dried under vacuum to afford N-(4-(7-methoxy-1,5-naphthyridin-4-yloxy)phenyl)-4-(4-methoxyphenyl)phthalazin-1-amine as a light orange solid. MS [M+H]=502; Calc'd 501.54 for C$_{30}$H$_{25}$N$_5$O$_3$.

EXAMPLE 38

Method C2

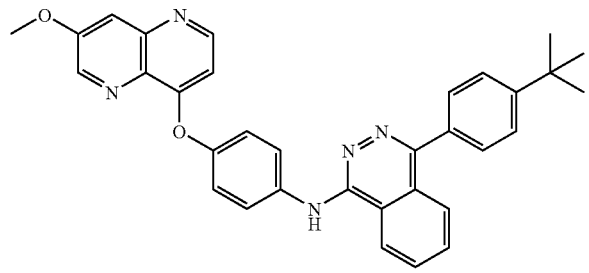

Synthesis of 4(4-tert-butylphenyl)N-(4-(7-methoxy-1,5-naphthyridin-4-yloxy)phenyl)phthalazin-1-amine In a nitrogen purged sealed tube, 8-chloro-3-methoxy-1,5-naphthyridine (0.053 g, 0.271 mmol) was dissolved in DMF (2.00 mL). 4-(4-(4-Tert-butylphenyl)phthalazin-1-ylamino)phenol (0.100 g, 0.271 mmol) and cesium carbonate (0.176 g, 0.541 mol) were added, and the mixture in the tube was stirred at 90° C. for 17 h. Upon cooling to RT, the mixture was concentrated in vacuo, and purified by silica gel chromatography using 0-100% CH$_2$Cl$_2$:MeOH(90:10)/CH$_2$Cl$_2$ to yield 4-(4-tert-butylphenyl)-N-(4-(7-methoxy-1,5-naphthyridin-4-yloxy)phenyl)phthalazin-1-amine as off-white solid. MS [M+H]=528.1; Calc'd 527.6 for C$_{33}$H$_{29}$N$_5$O$_2$.

EXAMPLE 39

Method C3

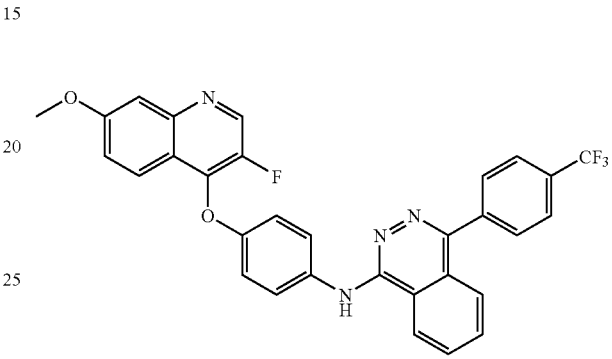

Synthesis of N-(4-(3-fluoro-7-methoxyquinolin-4-yloxy)phenyl)-4-(4-(trifluoromethyl)phenyl)phthalazin-1-amine Racemic-2-(di-t-butylphosphino)-1,1'-binaphthyl (84 mg, 210 μmol), 4-chloro-3-fluoro-7-methoxyquinoline (67 mg, 315 μmol), 4-(4-(4-(trifluoromethyl)phenyl)phthalazin-1-ylamino)phenol (80 mg, 210 μmol), cesium carbonate (137 mg, 420 μmol), and Pd$_2$ dba$_3$ (96 mg, 105 μmol) were combined in a resealable tube, and the tube was purged with nitrogen. Toluene (1049 μl, 210 μmol) was added and the tube was sealed and heated to 100° C. overnight. Analysis by LCMS showed incomplete conversion to product. The reaction mixture was diluted with water and DCM, and the water layer was separated and extracted first with DCM followed by ethyl acetate. The combined organic extracts were dried over MgSO$_4$, filtered, and concentrated in vacuo. The dark residue was taken up in DCM and hexanes, and a precipitate formed. The solid was filtered and purified by preparative HPLC. The crude reaction mixture was taken up in minimal DMSO and methanol and purified on the Gilson {15-85% (0.1% TFA in CH$_3$CN) in H$_2$O over 20 min}. Clean product containing fractions were combined and neutralized with saturated aqueous NaHCO$_3$ then extracted with ethyl acetate, dried over MgSO$_4$, filtered and concentrated in vacuo to afford N-(4-(3-fluoro-7-methoxyquinolin-4-yloxy)phenyl)-4-(4-(trifluoromethyl)phenyl) phthalazin-1-amine as a tan solid. Further purification was accomplished by silica gel chromatography (90:10 CH$_2$Cl$_2$:MeOH). N-(4-(3-fluoro-7-methoxyquinolin-4-yloxy)phenyl)-4-(4-(trifluoromethyl)phenyl) phthalazin-1-amine was afforded as a tan solid. MS [M+H]=557.0. Calc'd for C$_{19}$H$_{21}$N$_5$O: 556.15.

EXAMPLE 40

Method C4

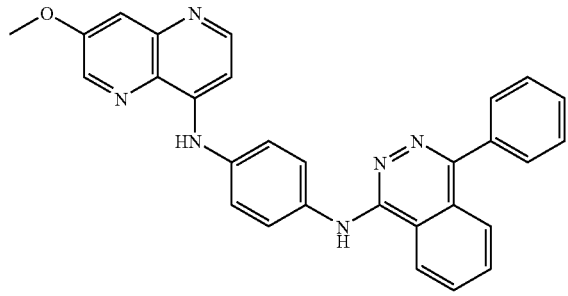

Synthesis of N$^1$-(7-methoxy-1,5-naphthyridin-4-yl) N$^4$-(4-phenylphthalazin-1-yl)benzene-1,4-diamine In a 20 mL sealed tube was dissolved 8-chloro-3-methoxy-1,5-naphthyridine (70 mg, 360 μmol) in DMF (2.00 mL). To this was added N1-(4-phenylphthalazin-1-yl)benzene-1,4-diamine (124 mg, 396 μmol) and the reaction mixture was stirred at 70° C. for 17 h. Upon cooling to RT, the mixture was dissolved in DMF and purified using Gilson reverse phase chromatography. The product fractions were combined, concentrated and the resulting crude was extracted into DCM, washed 1× sodium carbonate, 1×H$_2$O, dried with Na$_2$SO$_4$, filtered through fritted funnel, concentrated to yield N1-(7-methoxy-1,5-naphthyridin-4-yl)-N4-(4-phenylphthalazin-1-yl)benzene-1,4-diamine as light yellow solid. MS [M+H]= 471.0; Calc'd 470.5 for C$_{29}$H$_{22}$N$_6$O.

EXAMPLE 41

Method C5

Synthesis of N-(6-(7-methoxy-1,5-naphthyridin-4-yloxy)pyridin-3-yl)-4-phenylphthalazin-1-amine A pyrex reaction tube was charged with 8-chloro-3-methoxy-1,5-naphthyridine (50 mg, 0.26 mmol), 5-(4-phenylphthalazin-1-ylamino)pyridin-2-ol (80 mg, 0.26 mmol), cesium carbonate (249 mg, 0.76 mmol) and DMSO (2 mL). The tube was sealed and the reaction mixture was heated to 130° C. After 3.5 h, an aliquot was analyzed by LCMS, and the desired product was determined to be the major peak. The reaction mixture was diluted with DMSO and purified by Gilson HPLC {5-65% (0.1% TFA in CH$_3$CN) in H$_2$O over 20 min}. The product-containing fractions were combined, basified by addition of aq. NaHCO$_3$ and extracted with DCM. The organic portion was dried with Na$_2$SO$_4$, filtered, and concentrated to afford material that was further purified by silica gel chromatography, 90/10/1 CH$_2$Cl$_2$/MeOH/NH$_4$OH. This provided N-(6-(7-methoxy-1,5-naphthyridin-4-yloxy)pyridin-3-yl)-4-phenylphthalazin-1-amine as pure material. MS [M+H]=473.0@1.48 minutes. Calc'd for C$_{28}$H$_{20}$N$_6$O$_2$: 472.5.

EXAMPLE 42

Method D1a

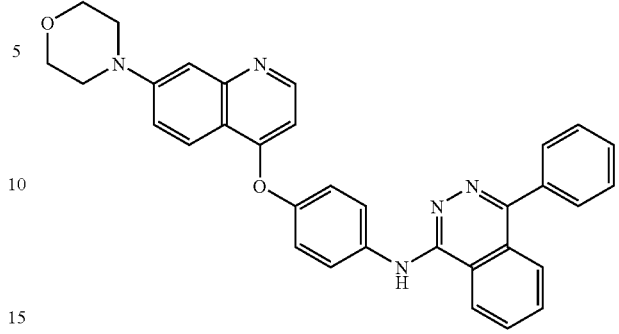

Synthesis of N-(4-(7-Morpholinoquinolin-4-yloxy)phenyl)-4-phenylphthalazin-1-amine The title compound was prepared according to a method described in Ali, M. H.; Buchwald, S. L. *J. Org. Chem.* 2001, 66, 2560. Pd$_2$(dba)$_3$ (21 mg, 23 μmol), DavePhos (18 mg, 46 μmol), and sodium tert-butoxide (110 mg, 1141 μmol) were added into a screw-capped tube equipped with a stir bar. The tube was purged with argon. N-(4-(7-Bromoquinolin-4-yloxy)phenyl)-4-phenylphthalazin-1-amine (237 mg, 456 μmol) was added to the purged tube, followed by morpholine (159 μl, 1825 μmol), 1,4-dioxane (2074 μl, 456 μmol), and tert-butanol (1037 μl, 456 μmol). The tube was sealed and heated to 100° C. in an oil bath for 1 h. The reaction was cooled to rt, and 22 mg of Pd$_2$(dba)$_3$, 20 mg of DavePhos, and 80 mg of NaOt-Bu were added. The tube was resealed and placed in a preheated oil bath at 100° C. After another 3.5 h, LCMS showed mainly product at 1.434 min as [M+H]$^+$=526. The mixture was passed through a pad of celite with an aid of CH$_2$Cl$_2$. The filtrate was concentrated. The product was purified by column chromatography on silica gel eluting with 70:30 to obtain top spot, then washing with 60:40 CH$_2$Cl$_2$:(90:10:1 CH$_2$Cl$_2$:MeOH:NOH) to collect the product. Fractions containing the product were concentrated. A yellow solid was obtained and dried in the vacuum oven. The yellow solid was further purified by RPLC on the acidic Gilson workstation. Fractions containing the product were diluted with CH$_2$Cl$_2$ and neutralized with sat. NaHCO$_3$. The organic layer was separated, dried over MgSO$_4$, filtered, and concentrated. Yellow solid was obtained. HPLC showed 100% pure. LCMS confirmed product. MS Calcd for C$_{33}$H$_{27}$N$_5$O$_2$: [M]$^+$=525. Found: [M+H]$^+$=526.

EXAMPLE 43

Method D1b

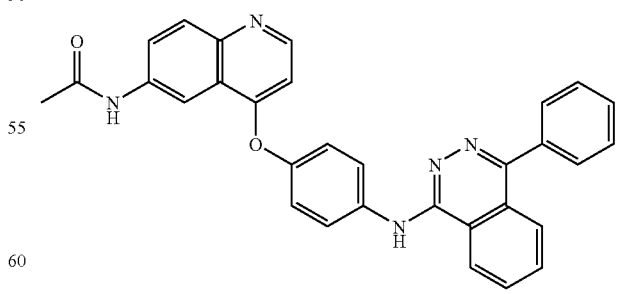

Synthesis of N-(4-(4-(4-Phenylphthalazin-1-ylamino)phenoxy)quinolin-6-yl)acetamide The title compound was prepared according to a method described in Garnier, E.; Andoux, J.; Pasquinet, E.; Suzenet, F.; Poullain, D.; Lebret, B.; Guillaumet, G. *J. Org. Chem.* 2004, 69, 7809. Xantphos (22 mg, 39 µmol) and 1,4-Dioxane (963 µl, 193 µmol) were added into a sealed tube. The tube was purged with argon, Palladium(II) acetate (4 mg, 19 µmol) was added, and the mixture was stirred under argon for 10 min. In a separate sealed tube, N-(4-(6-bromoquinolin-4-yloxy)phenyl)-4-phenylphthalazin-1-amine (100 mg, 193 µmol), acetamide (57 mg, 963 µmol), potassium carbonate (798 mg, 5776 µmol), and 1,4-dioxane (963 µl, 193 µmol) were added. Then the Pd(OAc)$_2$/Xantphos solution from the first tube was added with via syringe to the second tube. The resulting mixture was heated to 110° C. under an argon atmosphere with vigorous stirring until the halide disappeared. After 16 h, LCMS showed product at 1.324 as [M+H]$^+$=498. The reaction was cooled to rt, quenched with water, extracted with CH$_2$Cl$_2$. The organic portions were combined, washed with brine, dried over MgSO$_4$, filtered, and concentrated. The product was purified by RPLC on the acidic Gilson workstation. To provide N-(4-(4-(4-phenylphthalazin-1-ylamino)phenoxy)quinolin-6-yl)acetamide. MS Calcd for C$_{31}$H$_{23}$N$_5$O$_2$: [M]$^+$=497. Found: [M+H]$^+$=498.

EXAMPLE 44

Method D2

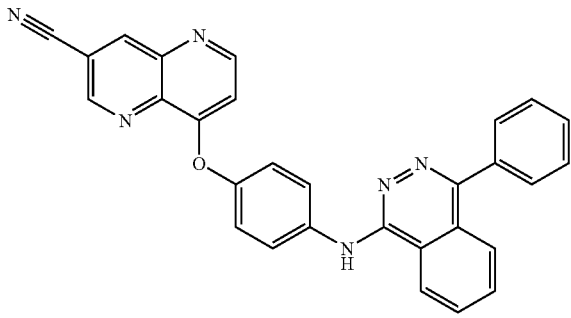

Synthesis of 8(4-(4-phenylphthalazin-1-ylamino)phenoxy)-1,5-naphthyridine-3-carbonitrile A pyrex reaction tube was charged with N-(4-(7-bromo-1,5-naphthyridin-4-yloxy)phenyl)-4-phenylphthalazin-1-amine (200 mg, 0.384 mmol), ZnCN$_2$(54.2 mg, 0.461 mmol), and palladium tetrakis (22.2 mg, 0.019 mmol) and was purged with nitrogen. 1.2 mL of DMF was added and the tube was purged with nitrogen for several minutes and then sealed. The reaction mixture was heated at 85° C. for 4 h. Upon cooling the mixture was poured into water, and the solids were filtered and washed with water. The crude material was dissolved in a mixture of MeOH and DMSO and purified by reverse phase chromatography (Gilson, 10-95% ACN over 15 min) to provide 8-(4-(4-phenylphthalazin-1-ylamino)phenoxy)-1,5-naphthyridine-3-carbonitrile as a light yellow solid. MS m/z=467 [M+H]$^+$. Calc'd for C$_{29}$H$_{18}$N$_6$O: 466.49.

EXAMPLE 45

Method D3

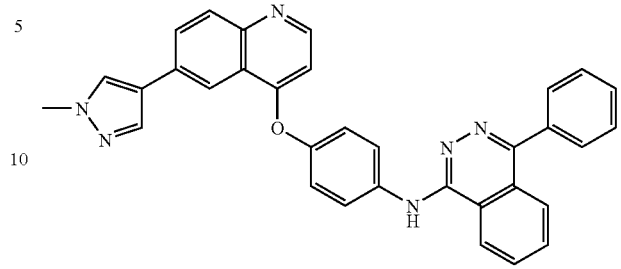

Synthesis of N-(4-(6-(1-Methyl-1H-pyrazol-4-yl)quinolin-4-yloxy)phenyl)-4-phenylphthalazin-1-amine A sealed tube was charged with N-(4-(6-bromoquinolin-4-yloxy)phenyl)-4-phenylphthalazin-1-amine (110 mg, 212 µmol), sodium carbonate (2.0 M aqueous)(424 µl, 847 µmol), and 1,4-dioxane (1059 µl, 212 µmol) under an argon atmosphere. After stirring for 5 min, 1-methyl-4-(4,4,5,5-tetramethyl-1,3,2-dioxaborolan-2-yl)-1H-pyrazole (75 mg, 360 µmol) and 1,1'-bis(diphenylphosphino)ferrocene-palladium dichloride (15 mg, 21 µmol) were added, and the tube was sealed and heated to 100° C. After 2 h, LCMS showed mainly product. The product was extracted with CH$_2$Cl$_2$, washed with brine, dried over MgSO$_4$, filtered, and concentrated. The crude residue was purified by RPLC on the acidic Gilson workstation. Fractions containing the product were diluted with CH$_2$Cl$_2$ and neutralized with sat. NaHCO$_3$. The organic layer was separated, dried over MgSO$_4$, filtered, and concentrated. Yellow solid was obtained. N-(4-(6-(1-methyl-1H-pyrazol-4-yl)quinolin-4-yloxy)phenyl)-4-phenylphthalazin-1-amine. MS Calcd for C$_{33}$H$_{24}$N$_6$O: [M]$^+$=520. Found: [M+H]$^+$=521.

EXAMPLE 46

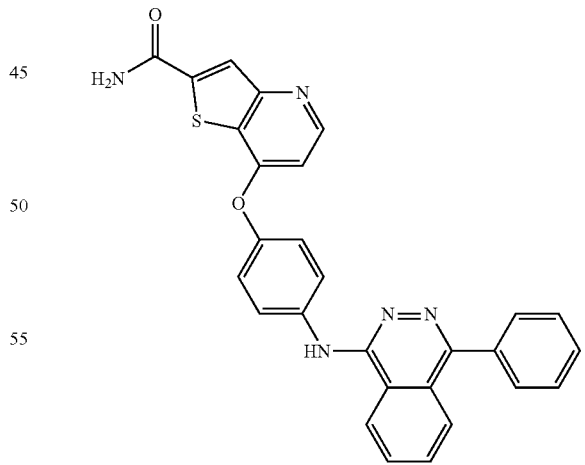

Synthesis of 7-(4(4-phenylphthalazin-1-ylamino)phenoxy)thieno[3,2-b]pyridine-2-carboxamide A 5 ml microwave tube was charged with 7-(4-aminophenoxy)thieno[3,2-b]pyridine-2-carboxamide (85 mg, 0.300 mmol) and 1-chloro-4-phenylphthalazine (60 mg, 0.250 mmol) in 2.0 ml of tert-butanol. The vessel was capped and irradiated at 140° C. for 15 minutes in the microwave. Analysis of an aliquot of the crude mixture by LCMS showed remaining starting material and approximately 20% conversion to desired product. Irradiated at 150° C. for an additional 20 minutes, at which time reaction was deemed complete by LCMS analysis. Cooled to ambient temperature and diluted reaction mixture with methanol. Filtered solids, washed with additional methanol and concentrated in vacuo to afford 7-(4-(4-phenylphthalazin-1-ylamino)phenoxy)thieno[3,2-b]pyridine-2-carboxamide. MS m/z=490 [M+H]$^+$. Calc'd for $C_{28}H_{19}N_5O_2S$: 489.55.

EXAMPLE 47

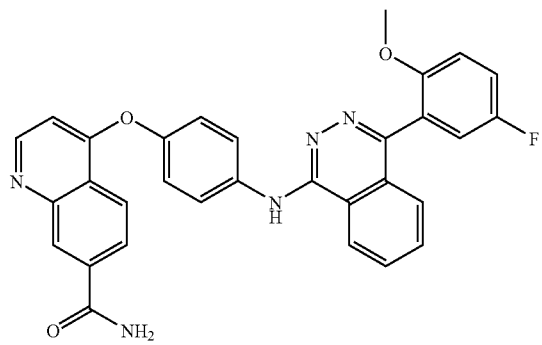

Synthesis of 4-(4-(4(5-fluoro-2-methoxyphenyl)phthalazin-1-ylamino)phenoxy)quinoline-7-carboxamide A sealed tube was charged with 4-(4-(4-(5-fluoro-2-methoxyphenyl)phthalazin-1-ylamino)phenoxy)quinoline-7-carbonitrile (150 mg, 0.529 mmol) in neat concentrated sulfuric acid (3 mL). The tube was sealed and placed in a preheated oil bath at 80° C. for 1 h, at which point the reaction was determined complete by LCMS. The reaction was cooled to RT and added drop-wise to sat. sodium bicarbonate in an ice bath. Neutralized the mixture with 2N NaOH to a pH of 7 and extracted with ethyl acetate (3×). Organic layers were dried over magnesium sulfate, filtered and concentrated. The crude was purified via silica gel chromatography using a slow gradient of 90:10:1 (DCM:methanol:ammonium hydroxide) in DCM. Fractions contained the desired material were pooled and concentrated in vacuo to afford 4-(4-(4-(5-fluoro-2-methoxyphenyl)phthalazin-1-ylamino)phenoxy)quinoline-7-carboxamide as a tan solid. MS m/z=532 [M+H]$^+$. Calc'd for $C_{31}H_{22}FN_5O_3$: 531.54.

EXAMPLE 48

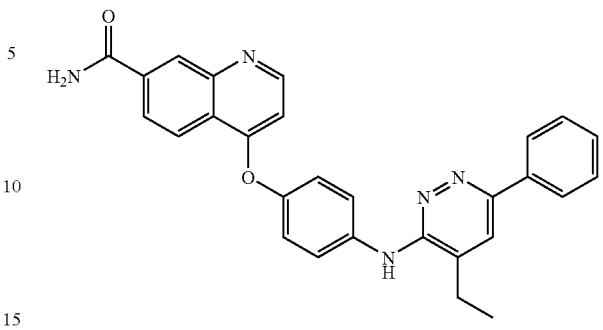

Synthesis of 4-(4-(4-ethyl-6-phenylpyridazin-3-ylamino)phenoxy)quinoline-7-carboxamide A microwave reaction vial was charged with 4-chloroquinoline-7-carbonitrile (97.1 mg, 0.515 mmol), 4-(4-ethyl-6-phenylpyridazin-3-ylamino)phenol (150 mg, 0.515 mmol), cesium carbonate (252 mg, 0.772 mmol) and 2.6 mL of DMSO. The vial was sealed, and the reaction mixture was irradiated in the microwave at 150° C. for 15 min. Upon cooling the mixture was poured into water and the resulting solids were filtered and washed with water. The crude solids were dissolved in 90/10/1 $CH_2Cl_2$/MeOH/$NH_4OH$ and purified by silica gel chromatography, 5-100% 90/10/1: $CH_2Cl_2$ over 25 min which provided 4-(4-(4-ethyl-6-phenylpyridazin-3-ylamino)phenoxy)quinoline-7-carboxamide as a tan solid. MS m/z=462 [M+H]$^+$. Calc'd for $C_{28}H_{23}N_3O_2$: 461.52.

EXAMPLE 49

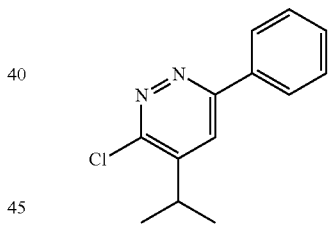

Synthesis of 3-chloro-4-isopropyl-6-phenylpyridazine

A RBF was charged with 3-chloro-4-ethyl-6-phenylpyridazine (250 mg, 1.143 mmol) and 5.7 mL of THF, and the mixture was cooled to –78° C. under nitrogen. Lithium diisopropylamide, 2.0 M solution in heptane/tetrahydrofuran/ethylbenzene (0.686 mL, 1.372 mmol) was added, and the mixture was stirred for 5 min at –78° C., followed by 1 h at room temperature. The mixture was cooled back down to –78° C., and methyl iodide (195 mg, 1.372 mmol) that had been passed through a plug of basic alumina prior to use was added dropwise. The reaction was stirred at this temperature for 5 min, followed by RT for 0.5 h. After quenching with water, the solution was diluted with $CH_2Cl_2$ and the layers were separated. The aqueous portion was extracted with additional $CH_2Cl_2$ and the combined organics were dried with $MgSO_4$, filtered and concentrated. The crude material was purified by silica gel chromatography ($CH_2Cl_2$— 10% MeOH/$CH_2Cl_2$) to provide 3-chloro-4-isopropyl-6-phenylpyridazine as a col-

EXAMPLE 50

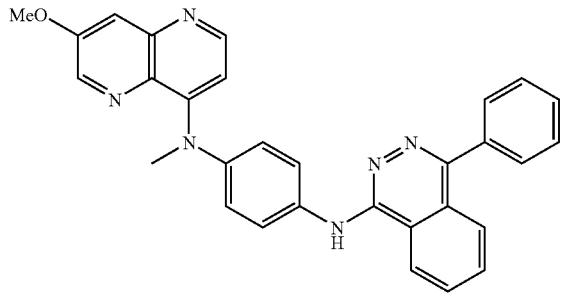

Synthesis of N1-(7-methoxy-1,5-naphthyridin-4-yl)-N-1-methyl-N4-(4-phenylphthalazin-1-yl)benzene-1,4-diamine

Step 1: 7-methoxy-N-methyl-N-(4-nitrophenyl)-1,5-naphthyridin-4-amine

To a resealable pressure vessel was added n-methyl-4-nitroaniline (0.911 ml, 7.19 mmol), pyridinium p-toluenesulfonate (1.81 g, 7.19 mmol), 8-chloro-3-methoxy-1,5-naphthyridine (1.000 g, 5.14 mmol), and n-BuOH (15 mL). The vessel was sealed and heated to 100° C. After 4 h, the mixture was cooled to RT, diluted with 1 N NaOH, and extracted with EtOAc. The organic fraction was dried with $Na_2SO_4$, concentrated in vacuo, and purified by silica gel chromatography using 50-100% Hexanes:EtOAc to afford 7-methoxy-N-methyl-N-(4-nitrophenyl)-1,5-naphthyridin-4-amine as a yellow solid. MH+=311.2@1.51 min.

Step 2: N1-(7-methoxy-1,5-naphthyridin-4-yl)-N1-methylbenzene-1,4-diamine

To a mixture of 7-methoxy-N-methyl-N-(4-nitrophenyl)-1,5-naphthyridin-4-amine (0.233 g, 0.751 mmol) in MeOH (10 mL) at RT was added a suspension of 10% palladium on carbon (0.0799 g, 0.751 mmol) in EtOAc (10 mL). The mixture was exposed to an atmosphere of hydrogen (balloon). After 4 h, the mixture was filtered over celite and concentrated in vacuo. The crude yellow foam, N1-(7-methoxy-1,5-naphthyridin-4-yl)-NI-methylbenzene-1,4-diamine, was advanced without further purification. MH+=281.2@1.21 min.

Step 3: N1-(7-methox-10,5-naphthyridin-4-yl)-N1-methyl-N4-(4-phenylphthalazin-1-yl)benzene-1,4-diamine A mixture of N1-(7-methoxy-1,5-naphthyridin-4-yl)-N1-methylbenzene-1,4-diamine (0.061 g, 0.22 mmol) and 1-chloro-4-phenylphthalazine (0.052 g, 0.22 mmol) was heated at 100° C. for 48 h. The solvent was removed in vacuo and the residue was purified by silica gel chromatography using 1-10% MeOH:$CH_2Cl_2$ containing 1% $NH_4OH$ to afford N1-(7-methoxy-1,5-naphthyridin-4-yl)-N1-methyl-N4-(4-phenylphthalazin-1-yl)benzene-1,4-diamine as a yellow solid.

EXAMPLE 51

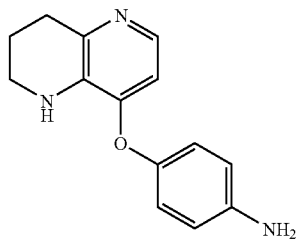

Synthesis of 4(5,6,7,8-tetrahydro-1,5-naphthyridin-4-yloxy)benzenamine

To a solution of 4-(7-bromo-1,5-naphthyridin-4-yloxy)benzenamine (0.150 g, 0.474 mmol) in MeOH (7 mL) at RT was added a suspension of 10% palladium on carbon (0.0505 g, 0.474 mmol) in EtOAc (2 mL). The mixture was subjected to an atmosphere of hydrogen (balloon) and stirred overnight. After 18 hrs, the mixture was filtered over celite and concentrated in vacuo. The resulting tan foam, crude 4-(5,6,7,8-tetrahydro-1,5-naphthyridin-4-yloxy)benzenamine, was advanced without further purification. MH+=242.2@0.49 min

EXAMPLE 52

Synthesis of N-(4-(1,5-naphthyridin-4-yloxy)phenyl-4-phenylphthalazin-1-amine

To a mixture of tetrakis(triphenylphosphine)palladium (9 mg, 0.0079 mmol) and sodium methoxide (9 mg, 0.16 mmol) was added a solution of N-(4-(7-bromo-1,5-naphthyridin-4-yloxy)phenyl)-4-phenylphthalazin-1-amine (0.041 g, 0.079 mmol) in DMF (2 mL). The mixture was heated to 100° C. in an Argon purged, resealable tube. After 3 hrs, the solvent was removed in vacuo and the residue was purified by silica gel chromatography using 1-10% MeOH:$CH_2Cl_2$ containing 1% $NH_4OH$ to afford N-(4-(1,5-naphthyridin-4-yloxy)phenyl)-4-phenylphthalazin-1-amine as a tan solid. MH+=442.1@1.51 min.

EXAMPLE 53

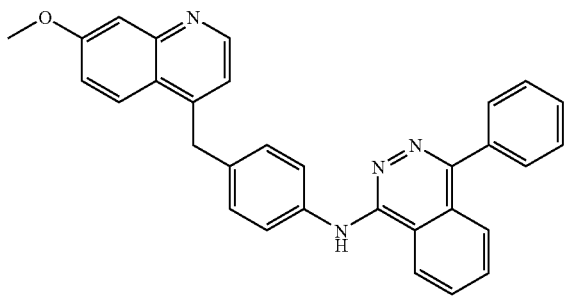

Synthesis of N-(4-((7-methoxyquinolin-4-yl)methyl)phenyl)-4-phenylphthalazin-1-amine

Step 1: 7-Methoxy-4-(phenylthio)quinoline

A resealable tube under $N_2$ was charged with 4-chloro-7-methoxyquinoline (1.00 g, 5.16 mmol), thiophenol (0.528 ml, 5.16 mmol), cesium carbonate (2.52 g, 7.75 mmol) and DMSO (5 mL). The mixture was heated at 100° C. for 2 hrs. The crude reaction mixture was directly purified by silica gel chromatography using 0-10% CH$_2$Cl$_2$:MeOH to afford 7-methoxy-4-(phenylthio)quinoline as a off-white solid. MH+=268.0.

Step 2: 7-Methox-4-(phenylsulfinyl)quinoline

To 7-methoxy-4-(phenylthio)quinoline (1.38 g, 5.16 mmol) in CH$_2$Cl$_2$(50 mL) at −78° C. was added m-CPBA (77%)(1.25 g, 7.23 mmol) portionwise. The mixture was allowed to slowly warm to RT (3 hrs). The reaction mixture was diluted with CH$_2$Cl$_2$ then neutralized with NaHCO$_3$ (sat.). The aqueous phase was extracted three times with CH$_2$Cl$_2$ then the organic layer was dried over Na$_2$SO$_4$, filtered, and concentrated in vacuo. The crude mixture was purified by silica gel chromatography using 0-10% CH$_2$Cl$_2$:MeOH to afford 7-methoxy-4-(phenylsulfinyl)quinoline (1.37 g, 94% yield) as a off-white foam. MH+=284.0.

Step 3:
(7-Methoxyquinolin-4-yl)(4-nitrophenyl)methanol

To a solution of 7-methoxy-4-(phenylsulfinyl)quinoline (0.232 g, 0.819 mmol) in THF (6 mL) at −78° C. was added phenylmagnesium chloride (2.0 M in THF)(0.819 ml, 1.64 mmol). After 5 min, the solution was warmed to RT for 15 minutes. The solution was then cooled to −78° C. and 4-nitrobenzaldehyde (0.371 g, 2.46 mmol) was added in one portion. After 5 min, the solution was warmed to RT. After 1 hr at RT, the reaction was quenched with saturated NH$_4$Cl. The mixture was diluted with CH$_2$Cl$_2$ and washed with water and brine. The organic fraction was dried with Na$_2$SO$_4$ and concentrated in vacuo. The yellow residue was purified by silica gel chromatography using 20-100% Hexanes:EtOAc to afford (7-methoxyquinolin-4-yl)(4-nitrophenyl)methanol as a white solid. MH+=311.2@1.44 min Step 4:
4-((7-Methoxyquinolin-4-yl)methyl)benzenamine A mixture of (7-methoxyquinolin-4-yl)(4-nitrophenyl) methanol (0.187 g, 0.603 mmol) and tin(II) chloride dihydrate (0.823 g, 3.62 mmol) in MeOH (10 mL) was heated to 60° C. After 1 hr, an additional 5 eq of tin(II) chloride dihydrate was added. After 3 hrs, the mixture was concentrated in vacuo and diluted with EtOAc and water. Saturated NaHCO$_3$ was added until the aqueous layer was basic. The resulting suspension was filtered and the solids washed with EtOAc. The organic fraction was washed with water and brine. After drying with Na$_2$SO$_4$ and concentrating in vacuo, the crude yellow solid, 4-((7-methoxyquinolin-4-yl)methyl)benzenamine was advanced without further purification. MH+=265.1@0.99 min.

Step 5: N-(4-((7-Methoxyquinolin-4-yl)methyl)phenyl)-4-phenylphthalazin-1-amine

A mixture of 1-chloro-4-phenylphthalazine (0.082 g, 0.34 mmol) and 4-((7-methoxyquinolin-4-yl)methyl)benzenamine (0.090 g, 0.34 mmol) in tBuOH (2.5 mL) was heated to 105° C. in a resealable tube. After 3 hrs, the mixture was cooled to RT, diluted with CH$_2$Cl$_2$ and washed with saturated NaHCO$_3$ and brine. The organic fraction was dried with Na$_2$SO$_4$, concentrated in vacuo, and purified by silica gel chromatography using 50-100% Hexanes:EtOAc to afford N-(4-((7-methoxyquinolin-4-yl)methyl)phenyl)-4-phenylphthalazin-1-amine as a light yellow solid. MH+=469.2@1.47 min

EXAMPLE 54

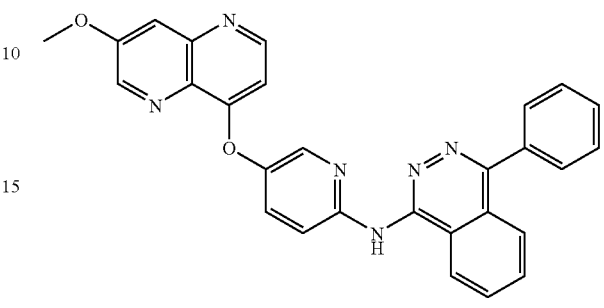

Synthesis of N-(5-(7-methoxy-1,5-naphthyridin-4-yloxy)pyridin-2-yl)-4-phenylphthalazin-1-amine Step 1.
N-(2,4-dimethoxybenzyl)-4-phenylphthalazin-1-amine In a nitrogen purged 75 mL sealed tube, dissolved 2,4-dimethoxybenzylamine hydrochloride (2.54 g, 12.5 mmol), cesium carbonate (4.06 g, 12.5 mmol) in tBuOH (15 mL). Added 1-chloro-4-phenylphthalazine (2.0 g, 8.31 mmol)and the tube was stirred at 100° C. for 17 h. The tube was cooled to RT, and the mixture was concentrated in vacuo. Dissolved the crude material in DCM, and filtered the solution to remove cesium carbonate. Performed silica gel chromatography using 0-100% EtOAc/Hex and concentrated to yield N-(2,4-dimethoxybenzyl)-4-phenylphthalazin-1-amine as orange oil. MS [M+H]=372; Calc'd 371.4 for C$_{23}$H$_{21}$N$_3$O$_2$.

Step 2. 4-phenylphthalazin-1-amine

In a 150 mL sealed tube, dissolved N-(2,4-dimethoxybenzyl)-4-phenylphthalazin-1-amine (3.00 g, 8.1 mmol) in acetic acid (40 mL). Hydrobromic acid (48% aqueous)(2.6 mL, 24 mmol) was added and the tube was stirred at 90° C. for 3 h. The solution was cooled to RT, and slowly poured into water, which caused a pink solid to crash out. The solid was filtered and rinsed with water. The product containing filtrate was slowly poured into saturated sodium carbonate. The aqueous phase was extracted with DCM, washed twice with water, dried with Na$_2$SO$_4$, filtered through fritted funnel, and concentrated to yield 4-phenylphthalazin-1-amine as light yellow solid. MS [M+H]=222; Calc'd 221.3 for C$_{14}$H$_{11}$N$_3$.

Step 3. N-(5-(7-methoxy-1,5-naphthyridin-4-yloxyy) pridin-2-yl)-4-phenylphthalazin-1-amine In a nitrogen purged sealed tube was added toluene (1.5 mL), purged the solvent with nitrogen for 5 minutes and sealed the tube. To the tube was added 8-(6-bromopyridin-3-yloxy)-3-methoxy-1,5-naphthyridine (0.100 g, 0.301 mmol), 4-phenylphthalazin-1-amine (0.080 g, 0.361 mmol), sodium tert-butoxide (0.072 g, 0.753 mmol), and the tube was again purged with nitrogen and sealed. Added tBu X-phos (0.013 g, 0.030 mmol), tris(dibenzylideneacetone)dipalladium (o)(0.007 g, 0.008 mmol), purged the reaction with nitrogen, sealed, heated the tube to 100° C., stirring for 24 h. The reaction was cooled to RT, filtered through pad of silica gel, washed with 100% $CH_2Cl_2$:MeOH(90:110)/$CH_2Cl_2$ and concentrated. The crude was purified using reverse phase chromatography, extracted the concentrated product fractions into DCM, washed the organic layer 1× with sodium carbonate, 1×$H_2O$, dried with Na2SO4, filtered solution through fritted funnel, and concentrated the filtrate to afford N-(5-(7-methoxy-1,5-naphthyridin-4-yloxy)pyridin-2-yl)-4-phenylphthalazin-1-amine as light yellow solid. MS [M+H]=473; Calc'd 472.5 for $C_{28}H_{20}N_6O_2$.

EXAMPLE 55

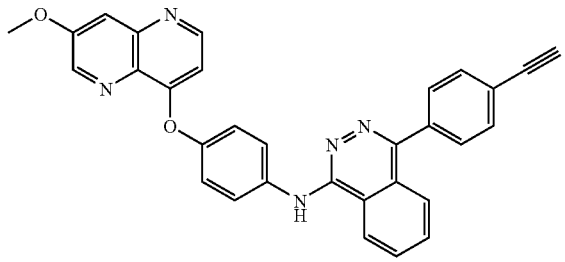

Synthesis of 4-(4-ethynylphenyl)-N-(4-(7-methoxy-1,5-naphthyridin-4-yloxy)phenyl)phthalazin-1-amine Step 1. N-(4-(7-Methox-1,5-naphthyridin-4-yloxy) phenyl)-4-(4-(2-(triethylsilyl)ethynyl)phenyl)ph-thalazin-1-amine In an argon purged sealed pressure vessel was added 4-(4-chlorophenyl)-N-(4-(7-methoxy-1,5-naphthyridin-4-yloxy) phenyl)phthalazin-1-amine (0.120 g, 0.237 mmol), cesium carbonate (0.201 g, 0.617 mmol), X-phos (0.017 g, 0.0356 mmol), dichloropalladium bisacetonitrile (0.003 mg, 0.011 mmol), and acetonitrile (0.50 mL). Starting material was not soluble in acetonitrile, so added 0.5 mL 1,4 dioxane. Purged the reaction with argon, then added (triethylsilyl)acetylene (0.055 mL, 0.308 mmol), and again purged with vessel with argon, sealed, heated it to 90° C. The reaction was stirred for 1 h. Reaction complete by LC/MS. The reaction was cooled to RT, passed through pad of silica, washed with 100% $CH_2Cl_2$: MeOH(90:10)/$CH_2Cl_2$ and the organics were concentrated. The crude material was purified by silica gel chromatography eluting with 0-100% $CH_2Cl_2$:MeOH(90:10)/$CH_2Cl_2$. The product fractions were concentrated to yield N-(4-(7-methoxy-1,5-naphthyridin-4-yloxy)phenyl)-4-(4-(2-(triethylsilyl)ethynyl)phenyl)phthalazin-1-amine as light yellow solid. MS [M+H]=610.2; Calc'd 609.8 for $C_{37}H_{35}N_5O_2Si$.

Step 2. 4-(4-Ethypylphenyl)-N-(4-(7-methoxn-1,5-naphtpyridin-4-yloxy)phenyl)phthalazin-1-amine In a nitrogen purged sealed tube was dissolved N-(4-(7-methoxy-1,5-naphthyridin-4-yloxy)phenyl)-4-(4-(2-(triethylsilyl)ethynyl)phenyl)phthalazin-1-amine (0.100 g, 0.164 mmol) in MeOH (2.00 mL). Potassium carbonate (0.068 g, 0.492 mmol) was added and the reaction was stirred at 20° C. for 24 h and then concentrated. The crude was extracted into DCM, washed 1× with water, 1× with brine, dried over $Na_2SO_4$, filtered through fritted funnel, concentrated. The resulting crude material was purified by silica gel chromatography eluting with 0-100% $CH_2Cl_2$:MeOH(90:10)/$CH_2Cl_2$. The product fractions were concentrated to afford 4-(4-ethynylphenyl)-N-(4-(7-methoxy-1,5-naphthyridin-4-yloxy) phenyl)phthalazin-1-amine as light yellow solid. MS [M+H]=496; Calc'd 495.5 for $C_{31}H_{21}N_5O_2$.

EXAMPLE 56

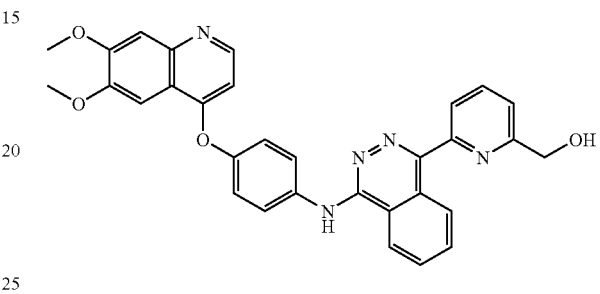

Synthesis of (6-(4-(4-(6,7-Dimethoxyquinolin-4-yloxy)phenylamino)phthalazin-1-yl)pyridin-2-yl) methanol (6-(4-(4-(6,7-dimethoxyquinolin-4-yloxy)phenylamino) phthalazin-1-yl)pyridin-2-yl)methyl acetate (45 mg, 78 mmol) was saponified in 0.5 mL of THF:MeOH:$H_2O$ (3:1:1) in a screw-capped tube. Lithium hydroxide hydrate (26 mg, 620 µmol) was added. After 1 h at rt, LCMS showed mainly product at 1.237 min as [M+H]$^+$=532. The product was extracted with $CH_2Cl_2$, washed with brine, dried over $MgSO_4$, filtered, and concentrated. The product was purified by performing column chromatography on silica gel using 40:60 $CH_2Cl_2$:(90:10:1 $CH_2Cl_2$:MeOH:$NH_4OH$). Yellow glass was obtained and dried in the vacuum oven overnight. Yellow solid was obtained. LCMS confirmed product (6-(4-(4-(6,7-dimethoxyquinolin-4-yloxy)phenylamino)ph-thalazin-1-yl)pyridin-2-yl)methanol. MS Calcd for $C_{31}H_{25}N_5O_4$: [M]$^+$=531. Found: [M+H]$^+$=532.

EXAMPLE 57

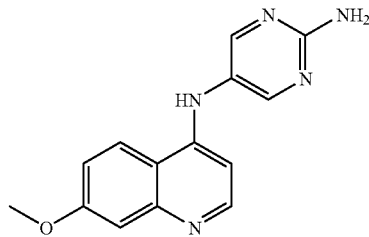

Synthesis of N$^5$-(7-Methoxyquinolin-4-yl)pyrimi-dine-2,5-diamine

Step 1: N-(5-(7-Methoxyquinolin-4-ylamino)pyrimi-din-2-yl)benzamide

In a screw cap test tube were dissolved 8-chloro-3-methoxy-1,5-naphthyridine (281 mg, 1443 mmol), N-(5-aminopyrimidin-2-yl)benzamide (281 mg, 1312 μmol) and pyridinium p-toluenesulfonate (494 mg, 1968 mmol) in butan-2-ol (2623 μl, 1312 μmol) then heated at 100° C. The reaction turned black in a minute. After 1 h, the reaction mixture showed full conversion to product according to LCMS. The reaction mixture was diluted with CH$_2$Cl$_2$, neutralized with sat. NaHCO$_3$. An emulsion was formed but the two layers eventually separated. The aqueous phase was extracted 3 times with CH$_2$Cl$_2$, washed with brine, dried over MgSO$_4$, filtered and evaporated under reduce pressure to give a tan solid. The solid was triturated with hexane, filtered, and dried under vacuo. Brown solid was collected. LCMS confirmed the presence of the product, N-(5-(7-methoxy-1,5-naphthyridin-4-ylamino)pyrimidin-2-yl)benzamide. MS Calcd for C$_{20}$H$_{16}$N$_6$O$_2$: [M]$^+$=372. Found: [M+H]$^+$=373.

Step 2: N$^5$-(7-Methoxyquinolin-4-yl)pyrimidine-2,5-diamine

In 25 mL sealed tube, N-(5-(7-methoxyquinolin-4-ylamino)pyrimidin-2-yl)benzamide (400 mg, 1077 μmol) was added into 6 ml of MeOH followed by addition of 2 mL of HCl (conc.). The reaction was heated at 80° C. After 1.5 h the reaction mixture based on LCMS showed full conversion to desired product [M+H]$^+$+1=269 @ 0.8 min—protonated form. The reaction was cooled to 0° C., 50 mL of CH$_2$Cl$_2$ was added, and the mixture was neutralized with 6N NaOH. Solid precipitated out of the solution in the aqueous layer. The whole mixture was concentrated under reduced pressure. The solid was filtered off with an aid of water to yield a sticky solid. The solid was transferred into a flask with an aid of MeOH. The solvent was evaporated under reduced pressure to afford N5-(7-methoxyquinolin-4-yl)pyrimidine-2,5-diamine as a gray solid.

EXAMPLE 58

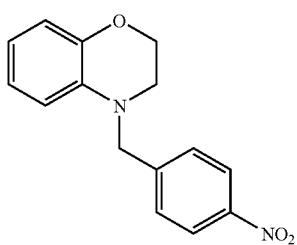

Synthesis of 4-(4-nitrobenzyl)-3,4-dihydro-2H-benzo[b][1,4]oxazine

To a mixture of 3,4-dihydro-2H-benzo[b][1,4]oxazine (0.500 g, 3.70 mmol) and potassium carbonate (2.56 g, 18.5 mmol) in acetone (25 mL) was added 1-(bromomethyl)-4-nitrobenzene (0.959 g, 4.44 mmol). The mixture was heated to reflux and stirred overnight. After 16 hrs the mixture was concentrated in vacuo, diluted with EtOAc, and washed with water and brine. The organic fraction was dried over Na$_2$SO$_4$, concentrated in vacuo, and the crude residue was purified by silica gel chromatography using 100% Hexanes to 30% Hexanes:EtOAc to afford 4-(4-nitrobenzyl)-3,4-dihydro-2H-benzo[b][1,4]oxazine as an orange oil. MS found: M+H+= 271.1.

EXAMPLE 59

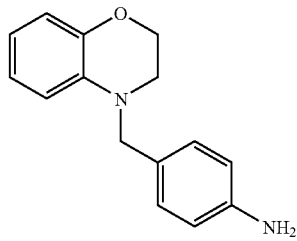

Synthesis of 4-((2,3-dihydrobenzo[b][1,4]oxazin-4-yl)methyl)benzenamine

A mixture of 4-(4-nitrobenzyl)-3,4-dihydro-2H-benzo[b][1,4]oxazine (0.432 g, 1.6 mmol) and tin(II) chloride dihydrate (1.8 g, 8.0 mmol) in MeOH (10 mL) was heated to 50° C. After 3 hrs the mixture was concentrated in vacuo and the residue taken up in EtOAc. Saturated NaHCO$_3$ was added and the mixture was filtered. The filtrate was washed with brine, dried with Na$_2$SO$_4$, concentrated in vacuo, and purified by silica gel chromatography using 20-100% Hexanes:EtOAc to afford 4-((2,3-dihydrobenzo[b][1,4]oxazin-4-yl)methyl)benzenamine as an orange oil. MS found: M+H+=241.1.

EXAMPLE 60

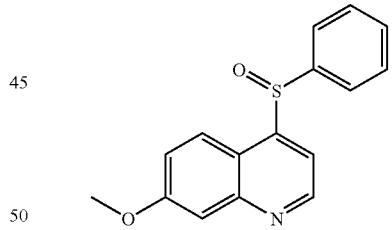

Synthesis of 7-methoxy-4(phenylsulfinyl)quinoline

To a mixture of 7-methoxy-4-(phenylthio)quinoline (1.38 g, 5.16 mmol) in CH$_2$Cl$_2$(50 mL) at −78° C. was added m-CPBA (77%)(1.25 g, 7.23 mmol) and the mixture was allowed to slowly warm to RT (ca. 1 h). The mixture was diluted with CH$_2$Cl$_2$ and washed with saturated NaHCO$_3$. The organic layer was dried over Na$_2$SO$_4$, filtered and concentrated under reduced pressure. The crude mixture was purified by silica gel chromatography using CH$_2$Cl$_2$:MeOH 100:0 to 90:10 to afford 7-methoxy-4-(phenylsulfinyl)quinoline as a off-white solid. MS found: M+H+=284.0.

EXAMPLE 61

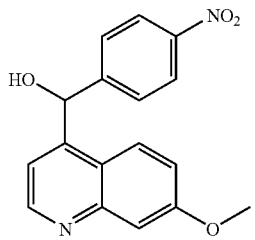

Synthesis of
(7-methoxyquinolin-4-yl)(4-nitrophenyl)methanol

To a solution of 7-methoxy-4-(phenylsulfinyl)quinoline (0.232 g, 0.819 mmol) in THF (6 mL) at −78° C. was added phenylmagnesium chloride, 2.0 M in THF (0.819 ml, 1.64 mmol). After 5 min, the solution was warmed to RT for 15 minutes. The solution was cooled to −78° C. and treated with 4-nitrobenzaldehyde (0.371 g, 2.46 mmol). After 5 min, the solution was warmed to RT. After 1 hr, the reaction was quenched with saturated NH$_4$Cl. The mixture was diluted with CH$_2$Cl$_2$ and washed with water and brine. The organic fraction was dried with Na$_2$SO$_4$ and concentrated in vacuo. The yellow residue was purified by silica gel chromatography using 20-100% Hexanes:EtOAc to afford (7-methoxyquinolin-4-yl)(4-nitrophenyl)methanol as a white solid. MS found M+H+=311.2.

EXAMPLE 62

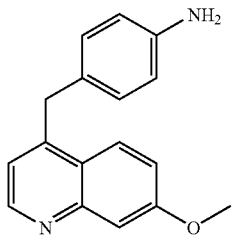

Synthesis of
4-((7-methoxyquinolin-4-yl)methyl)benzenamine

A mixture of (7-methoxyquinolin-4-yl)(4-nitrophenyl)methanol (0.187 g, 0.603 mmol) and tin(II) chloride dihydrate (0.823 g, 3.62 mmol) in MeOH (10 mL) was heated to 60° C. After 1 hr an additional 5 eq of tin(II) chloride dihydrate was added. After 3 hrs, the mixture was concentrated in vacuo and diluted with EtOAc and water. Saturated NaHCO$_3$ was added until the aqueous layer was basic. The resulting suspension was filtered and the solids washed with EtOAc. The organic fraction was washed with water, brine, and dried with Na$_2$SO$_4$. After concentrating in vacuo, the crude, yellow solid, 4-((7-methoxyquinolin-4-yl)methyl)benzenamine was advanced without further purification. MS found: M+H+=265.1.

EXAMPLE 63

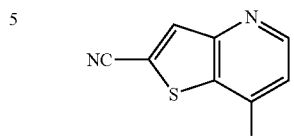

Synthesis of
7-chlorothieno[3,2-b]pyridine-2-carbonitrile

4-Chloro-7-methoxyquinoline-6-carboxamide was prepared in accordance to a procedure described in WO 01/94353.

EXAMPLE 64

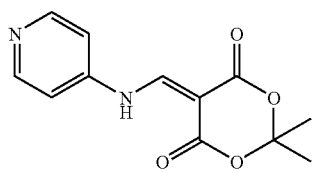

Synthesis of 2,2-dimethyl-5-((pyridin-4-ylamino)methylene)-1,3-dioxane-4,6-dione In a dried 2-necked RBF equipped with reflux condenser and inert atmosphere, 2,2-dimethyl-1,3-dioxane-4,6-dione (2.33 g, 16 mmol) was dissolved in triethyl orthoformate (16 ml, 97 mmol) and the mixture was stirred at 100° C. under nitrogen for 1.5 h. On complete consumption of starting material (tlc), pyridin-4-amine (1.5 g, 16 mmol) was added and heating continued for 4.5 h. The reaction mixture was cooled down to RT and poured into hexane (50 mL). The solid was filtered off and washed with hexane to afford 2,2-dimethyl-5-((pyridin-4-ylamino)methylene)-1,3-dioxane-4,6-dione as an orange solid.

EXAMPLE 65

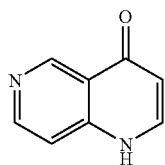

Synthesis of 1,6-naphthyridin-4-ol

A solution of 2,2-dimethyl-5-((pyridin-4-ylamino)methylene)-1,3-dioxane-4,6-dione (1.149 g, 4.63 mmol) in diphenyl ether was heated at 200° C. for 20 min, then cooled to RT. Hexane was added and the mixture was stirred at RT for 30 mins. The solid was filtered off and washed with hexane to furnish 1,6-naphthyridin-4-ol as an off-brown solid.

EXAMPLE 66

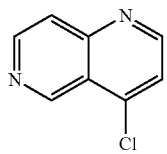

Synthesis of 4-chloro-1,6-naphthyridine 1,6-naphthyridin-4-ol (0.530 g, 3.63 mmol) was dissolved in phosphorus oxychloride (4.06 ml, 43.5 mmol) and heated at reflux for 14 h. Excess POCl$_3$ was removed under reduced pressure and the mixture was azeotroped with toluene. The resultant gum was treated with sat. NaHCO$_3$ until no gas was generated. The mixture was extracted with EtOAc, the combined extracts were washed with sodium bicarbonate and the solvent was removed under reduced pressure. The crude product was purified via column chromatography on silica gel (RediSep 40 g column, gradient elution with 0-90% EtOAc/DCM) to afford 4-chloro-1,6-naphthyridine as a white solid.

EXAMPLE 67

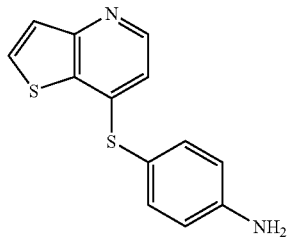

Synthesis of 4(thieno[3,2-b]pyridin-7-ylthio)aniline 4-(Thieno[3,2-b]pyridin-7-ylthio)aniline was prepared using the procedure described in Example 17. MS m/z=259 [M+H]$^+$. Calc'd for C$_{13}$H$_{10}$N$_2$S$_2$: 258.36.

EXAMPLE 68

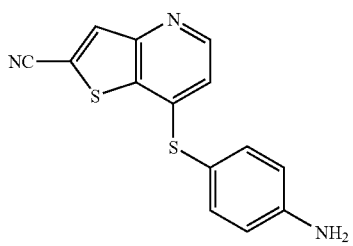

Synthesis of 7-(4-aminophenylthio)thieno[3,2-b]pyridine-2-carbonitrile 7-(4-Aminophenylthio)thieno[3,2-b]pyridine-2-was prepared using the procedure described in Example 17. MS m/z=284 [M+H]$^+$. Calc'd for C$_{14}$H$_9$N$_3$S$_2$: 283.37.

EXAMPLE 69

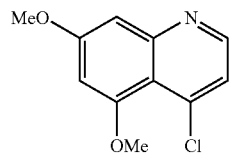

Synthesis of 4-chloro-5,7-dimethoxyquinoline

Step 1: 5-((3,5-Dimethoxyphenylamino)methylene)-2,2-dimethyl-1,3-dioxane-4,6-dione In a dried 2-necked round bottom flask equipped with reflux condenser and inert atmosphere, 2,2-dimethyl-1,3-dioxane-4,6-dione (5.3 g, 37 mmol) was dissolved in triethyl orthoformate (37 ml, 221 mmol) and the mixture was stirred at 100° C. under nitrogen for 1.5 h. 3,5-Dimethoxybenzenamine (5.6 g, 37 mmol) was added and heating continued for 4.5 h. The reaction mixture was cooled down to RT and poured into hexane (50 mL). The solid was filtered off and washed with hexane to afford 5-((3,5-dimethoxyphenylamino)methylene)-2,2-dimethyl-1,3-dioxane-4,6-dione as a light yellow solid. MS Found m/z=[M+H]$^+$. 308.1 Calc'd for C$_{15}$H$_{17}$NO$_6$: 307.3.

Step 2: 5,7-Dimethoxyquinolin-4-ol

A solution of 5-((3,5-dimethoxyphenylamino)methylene)-2,2-dimethyl-1,3-dioxane-4,6-dione (9.23 g, 30.0 mmol) in diphenyl ether was heated at 200° C. for 20 min., then cooled down to RT. Hexane was added and the mixture was stirred at RT for 30 mins. The solvent was removed to furnish 5,7-dimethoxyquinolin-4-ol as a light brown solid, which was used for next step without further purification. MS Found m/z=[M+H]$^+$. 206.2 Calc'd for C$_{11}$H$_{11}$NO$_3$: 205.2.

Step 3: 4-Chloro-5,7-dimethoxiyquinoline

To a mixture of crude 5,7-dimethoxyquinolin-4-ol (5.36 g, 26 mmol) and Hunig'sBase (9.1 ml, 52 mmol) in toluene, was added POCl$_3$(29 ml, 313 mmol). The mixture was refluxed for 5 h. Excess POCl$_3$ was removed under reduced pressure and azeotroped with toluene. The resultant gum was treated with sat. NaHCO$_3$ until no gas generated. The mixture was extracted with EtOAc, the organic extracts were combined and washed with sodium bicarbonate and solvent removed under reduced pressure. The crude product was purified via column chromatography on silica gel (RediSep 120 g column, gradient elution with 0-50% EtOAc/DCM) to afford 4-chloro-5,7-dimethoxyquinoline as a yellow solid. MS Found m/z=[M+H]⁺. 224.2 Calc'd for $C_{11}H_{10}ClN$: 223.7.

EXAMPLE 70

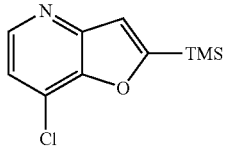

Synthisis of 7-chloro-2-(trimethylsilyl)furo[3,2-b]pyridine

Step 1: 2-(Trimethylsilyl)furo[3,2-b]pyridine

A sealed pressure flask was charged with 2-bromopyridin-3-ol (10.0 g, 57.5 mmol), ethynyltrimethylsilane (15.9 ml, 115 mmol), copper (I) iodide (1.09 g, 5.75 mmol), bis(triphenylphosphine)palladium(II) chloride (2.02 g, 2.87 mmol) and 7.5 mL of dioxane. Ethynyltrimethylsilane (15.9 ml, 115 mmol) and TEA (40.0 ml, 287 mmol) were added, the vial was flushed with nitrogen, and the reaction was stirred at 50° C. for 18 h. The reaction was concentrated and purified via column chromatography (gradient elution 0-40% EtOAc:Hex) to afford 2-(trimethylsilyl)furo[3,2-b]pyridine as a brown oil. MS Found M+H+=192.3

Step 2: 2-(Trimethylsilyl)furo[3,2-b]pyridine N-oxide 2-(Trimethylsilyl)furo[3,2-b]pyridine (14.68 g, 76.7 mmol) was dissolved in 80 mL DCM and cooled to 0° C. m-CPBA (33.1 g, 192 mmol) was dissolved in 160 mL DCM and slowly added to the reaction vessel. Upon complete addition, the reaction was warmed to RT and stirred for three hours. Reaction was diluted with DCM and washed twice with saturated sodium bicarbonate solution. 30 g of carbonate scavenger beads (—30 mmol) were added to the organic layer and the solution was stirred for 30 minutes. The reaction was filtered, washed with brine, dried with sodium sulfate, filtered, and concentrated. The material was purified via column chromatography (gradient elution 0-10% MeOH:DCM) to afford 2-(trimethylsilyl)furo[3,2-b]pyridine N-oxide as a light brown oil that solidified under high vacuum. MS: M+H+=208.2

Step 3: 7-Chloro-2-(trimethylsilyl)furo[3,2-b]pyridine 2-(Trimethylsilyl)furo[3,2-b]pyridine N-oxide (10.51 g, 50.7 mmol) dissolved in POCl₃ (47.3 ml, 507 mmol) in a sealed flask and heated at 100° C. for one hour. The reaction was cooled to RT, poured into a beaker washing with minimal DCM, and cooled in a brine bath. Saturated sodium bicarbonate solution was added very slowly and then solid sodium bicarbonate was added portion wise until the solution was at about pH=8. The solution was extracted twice with DCM, and the combined organic layers were dried with sodium sulfate, filtered, and concentrated. The material was purified via column chromatography (gradient elution 5-40% EtOAc:Hex) to afford 7-chloro-2-(trimethylsilyl)furo[3,2-b]pyridine as a pale yellow oil. MS: M+H+=226.2

EXAMPLE 71

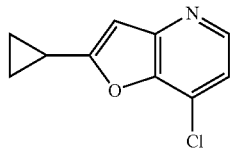

Synthesis of 7-chloro-2-cyclopropylfuro[3,2-b]pyridine

Step 1: 7-Chloro-2-iodofuro[3,2-b]pyridine

7-Chloro-2-(trimethylsilyl)furo[3,2-b]pyridine (0.250 g, 1.11 mmol) and NIS (2.49 g, 11.1 mmol) were dissolved in 3 mL of ACN and stirred for 5 minutes. Potassium fluoride (0.0708 g, 1.22 mmol) was added and the reaction was stirred at 50° C. for one hour. The reaction was concentrated, redissolved in ethyl acetate, and washed with saturated sodium thiosulfate, water and brine. The organic layer was dried with sodium sulfate, filtered, and concentrated. The crude material was purified via column chromatography (gradient elution 0-100% EtOAc:Hex) to afford 7-chloro-2-iodofuro[3,2-b]pyridine as a white solid. MS: M+H+=280.2.

Step 2: 7-Chloro-2-cyclopropylfuro[3,2-b]pyridine

7-Chloro-2-iodofuro[3,2-b]pyridine (0.130 g, 0.47 mmol), cyclopropylboronic acid (0.080 g, 0.93 mmol), and tricyclohexylphosphine (0.026 g, 0.093 mmol) were dissolved in 3 mL toluene and 1 mL water. Potassium phosphate (0.30 g, 1.4 mmol) was added followed by PdOAc2 (0.010 g, 0.047 mmol), the reaction was flushed with argon, and the reaction stirred at 100° C. for 48 h. The reaction was cooled to RT and partitioned between DCM and water. The layers were separated and the aqueous layer was extracted with DCM. The combined organic layers were dried with sodium sulfate, filtered, and concentrated. The crude material was purified via column chromatography (gradient elution 0-50% EtOAc:Hex) to afford 7-chloro-2-cyclopropylfuro[3,2-b]pyridine as an orange oil. MS: M+H+=194.4.

EXAMPLE 72

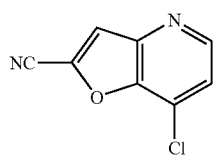

Synthesis of 7-chlorofuro[3,2-b]pyridine-2-carbonitrile

In a sealed tube 7-chloro-2-iodofuro[3,2-b]pyridine (0.200 g, 0.72 mmol), KCN (0.093 g, 1.4 mmol), and copper (I) iodide (0.014 g, 0.072 mmol) were dissolved in 2 mL DMF.

Pd(Ph3P)₄ (0.041 g, 0.036 mmol) was added, the tube was flushed with nitrogen, and the reaction in the tube was stirred overnight at 100° C. The reaction was cooled to RT, diluted with DCM, and washed with water. The aqueous layer was extracted with DCM, and the combined organic layers were washed with brine, dried with sodium sulfate, filtered, and concentrated. The material was purified via column chromatography (gradient elution 0-50% EtOAc:Hex) to afford 7-chlorofuro[3,2-b]pyridine-2-carbonitrile as a white solid. MS: M+H+=179.4.

EXAMPLE 73

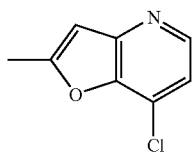

Synthesis of 7-chloro-2-methylfuro[3,2-b]pyridine

In an oven-dried round bottom flask, 7-chloro-2-iodofuro[3,2-b]pyridine (0.200 g, 0.72 mmol) was dissolved in 3 mL THF and cooled to –78° C. nBuLi (0.43 ml, 1.1 mmol) was slowly added and the reaction was stirred for one hour. Meanwhile, a vial was filled with MeI and warmed to RT. Magnesium sulfate was added and the mixture was stirred for 5 minutes and filtered into another vial. Immediately from this vial, MeI (0.11 ml, 1.8 mmol) was added to the reaction which was stirred at –78° C. for 3 hours. The reaction was quenched with saturated ammonium chloride solution and warmed to RT. DCM was added, the layers were separated, and the aqueous layer was extracted twice with DCM. The combined organic layers were dried with sodium sulfate, filtered, and concentrated. The material was purified via column chromatography (gradient elution 0-50% EtOAc:Hex) to afford 7-chloro-2-methylfuro[3,2-b]pyridine as a light brown oil. MS: M+H+=168.3.

The Examples disclosed in Table I below are additional representative examples, of the present invention. These Examples were made by the methods indicated in Table I, which generally correlate to Methods A1-3, B1-5, C1-5 and D1a, D1b, D2 and D3 of Examples 29-45 herein. The MS data is the M+H⁺ ion value found for the example. Biological data is provided for a majority of those compounds exemplified in Table I. It should be understood and appreciated by those of ordinary skill in the art that the data for compound examples 39, 174, 230, 248, 282, 311, 318, 323, 333, 340-341, 347, 360 and 369 may not be completely accurate, as presented herein, likely due to poor sample solubility, or other possible solution related issues, causing a decreased calculated activity. It is believed that these examples should be more active than recorded herein.

TABLE 1

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 74 | N-(4-((6,7-bis(methyloxy)-4-quinolinyl)oxy)phenyl)-4-(3,4-dimethylphenyl)-1-phthalazinamine | 529 | B3 | 0.014 | 0.032 | 0.018 |
| 75 | N-(4-((6,7-bis(methyloxy)-4-quinolinyl)oxy)phenyl)-4-(1-piperidinyl)-1-phthalazinamine | 508 | B3 | 0.023 | 0.042 | 0.025 |
| 76 | N-(4-((6,7-bis(methyloxy)-4-quinolinyl)oxy)-3-fluorophenyl)-4-(2-thienyl)-1-phthalazinamine | 525.1 | B3 | 0.034 | 0.106 | 0.060 |
| 77 | N-(4-((6,7-bis(methyloxy)-4-quinolinyl)oxy)-3-fluorophenyl)-4-(3,5-dimethyl-1H-pyrazol-1-yl)-1-phthalazinamine | 537.1 | B3 | 0.701 | 0.079 | 3.087 |
| 78 | 7-((2-fluoro-4-((4-phenyl-1-phthalazinyl)amino)phenyl)oxy)-thieno[3,2-b]pyridine-2-carboxamide | 508 | B3 | 0.022 | 0.004 | 0.031 |
| 79 | N-(4-((7-(methyloxy)-1,5-naphthyridin-4-yl)oxy)phenyl)-4-phenyl-1-phthalazinamine | 472 | B3 | 0.028 | 0.008 | 0.041 |
| 40 | N-(7-(methyloxy)-1,5-naphthyridin-4-yl)-N'-(4-phenyl-1-phthalazinyl)-1,4-benzenediamine | 471 | C4 | 0.044 | 0.007 | 0.070 |
| 80 | 4-(5-fluoro-2-(methyloxy)phenyl)-N-(4-((7-(methyloxy)-1,5-naphthyridin-4-yl)oxy)phenyl)-1-phthalazinamine | 520 | B3 | 0.414 | 0.041 | 0.487 |
| 81 | N-(4-((7-(methyloxy)-1,5-naphthyridin-4-yl)oxy)phenyl)-4-(4-methylphenyl)-1-phthalazinamine | 486 | B3 | 0.012 | 0.006 | 0.008 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 82 | N-(4-((7-(methyloxy)-1,5-naphthyridin-4-yl)oxy)phenyl)-4-(4-methyl-1,3-thiazol-2-yl)-1-phthalazinamine | 493 | B3 | 0.013 | 0.006 | 0.061 |
| 83 | 4-ethyl-N-(6-((7-(methyloxy)-1,5-naphthyridin-4-yl)oxy)-3-pyridinyl)-6-phenyl-3-pyridazinamine | 451 | C2 | 0.080 | 0.010 | 0.349 |
| 84 | N-(5-((7-(methyloxy)-1,5-naphthyridin-4-yl)oxy)-2-pyrimidinyl)-4-phenyl-1-phthalazinamine | 474 | unique | 0.160 | 0.002 | 0.485 |
| 46 | 7-((4-((4-phenyl-1-phthalazinyl)amino)phenyl)oxy)-thieno[3,2-b]pyridine-2-carboxamide | 490 | unique | 0.015 | 0.001 | 0.171 |
| 85 | N-(4-((7-(methyloxy)-1,5-naphthyridin-4-yl)oxy)phenyl)-4-(4-methyl-1-piperazinyl)-1-phthalazinamine | 494 | B1 | 0.066 | 0.004 | 0.085 |
| 86 | 4-((4-((4-(4-methyl-1,3-thiazol-2-yl)-1-phthalazinyl)amino)phenyl)oxy)-7-quinolinecarbonitrile | 487 | B3 | 0.031 | 0.014 | 0.097 |
| 87 | 4-((4-((4-(5-fluoro-2-(methyloxy)phenyl)-1-phthalazinyl)amino)phenyl)oxy)-7-quinolinecarbonitrile | 514 | B3 | 0.142 | 0.013 | |
| 88 | 4-((4-((4-(4-methylphenyl)-1-phthalazinyl)amino)phenyl)oxy)-7-quinolinecarbonitrile | 480 | B3 | 0.006 | 0.003 | 0.006 |
| 89 | N-(3-fluoro-4-((7-(methyloxy)-1,5-naphthyridin-4-yl)oxy)phenyl)-4-phenyl-1-phthalazinamine | 490.1 | B3 | 0.012 | 0.007 | 0.052 |
| 90 | N-(4-((6,7-bis(methyloxy)-4-quinolinyl)oxy)phenyl)-4-phenyl-1-phthalazinamine | 501 | B3 | 0.019 | 0.025 | 0.013 |
| 36 | N~5~-(7-(methyloxy)-1,5-naphthyridin-4-yl)-N~2~-(4-phenyl-1-phthalazinyl)-2,5-pyrimidinediamine | 473 | B5 | 0.038 | 0.004 | 0.326 |
| 91 | N-(4-((7-(methyloxy)-4-quinolinyl)oxy)phenyl)-4-phenyl-1-phthalazinamine | 471 | B3 | 0.054 | 0.012 | 0.030 |
| 92 | 4-(hexahydropyrrolo[1,2-a]pyrazin-2(1H)-yl)-N-(4-((7-(methyloxy)-1,5-naphthyridin-4-yl)oxy)phenyl)-1-phthalazinamine | 520 | B1 | 0.007 | 0.003 | 0.054 |
| 93 | 4-((4-((4-(3-hydroxyphenyl)-1-phthalazinyl)amino)phenyl)oxy)-7-quinolinecarbonitrile | 482 | B3 | 0.008 | 0.001 | 0.025 |
| 94 | 4-((4-((4-(4-methyl-1-piperazinyl)-1-phthalazinyl)amino)phenyl)oxy)-7-quinolinecarbonitrile | 488 | B1 | 0.027 | 0.001 | 0.090 |
| 95 | 4-((4-((4-(4-methyl-1,3-thiazol-2-yl)-1-phthalazinyl)amino)phenyl)oxy)-7-quinolinecarboxamide | 505 | Example 47 | 0.027 | 0.002 | 0.167 |
| 47 | 4-((4-((4-(5-fluoro-2-(methyloxy)phenyl)-1-phthalazinyl)amino)phenyl)oxy)-7-quinolinecarboxamide | 532 | unique | 5.000 | 0.138 | 1.200 |
| 96 | N-(4-((7-(methyloxy)-1,6-naphthyridin-4-yl)oxy)phenyl)-4-phenyl-1-phthalazinamine | 472.1 | C1 | 0.026 | 0.005 | 0.063 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 97 | 4-((8aS)-hexahydropyrrolo[1,2-a]pyrazin-2(1H)-yl)-N-(4-((7-(methyloxy)-1,5-naphthyridin-4-yl)oxy)phenyl)-1-phthalazinamine | 520 | B1 | 0.010 | 0.002 | 0.026 |
| 98 | N-(4-((6,7-bis(methyloxy)-4-quinazolinyl)oxy)phenyl)-4-phenyl-1-phthalazinamine | 502.1 | C1 | 0.016 | 0.007 | 0.019 |
| 99 | N-(4-((7-(methyloxy)-1,5-naphthyridin-4-yl)oxy)phenyl)-4-(6-(methyloxy)-2-pyridinyl)-1-phthalazinamine | 503 | C2 | 0.010 | 0.002 | 0.023 |
| 100 | 4-(6-(methyloxy)-2-pyridinyl)-N-(4-((7-(methyloxy)-4-quinolinyl)oxy)phenyl)-1-phthalazinamine | 502 | C2 | 0.038 | 0.006 | 0.020 |
| 101 | N-(4-((6,7-bis(methyloxy)-4-quinolinyl)oxy)phenyl)-4-(6-(methyloxy)-2-pyridinyl)-1-phthalazinamine | 532 | B3 | 0.010 | 0.010 | 0.009 |
| 102 | 4-((4-((4-(6-(methyloxy)-2-pyridinyl)-1-phthalazinyl)amino)phenyl)oxy)-7-quinolinecarbonitrile | 497 | B3 | 0.028 | 0.003 | 0.028 |
| 103 | N-(4-((7-(methyloxy)-1,6-naphthyridin-4-yl)oxy)phenyl)-4-(5-methyl-2-pyridinyl)-1-phthalazinamine | 487 | C2 | 0.035 | 0.004 | 0.030 |
| 104 | N-(4-((6,7-bis(methyloxy)-4-quinolinyl)thio)phenyl)-4-phenyl-1-phthalazinamine | 517 | B3 | 0.036 | 0.042 | 0.020 |
| 105 | 4-((4-((4-phenyl-1-phthalazinyl)amino)phenyl)oxy)-7-quinolinecarbonitrile | 466 | C1 | 0.039 | 0.003 | 0.036 |
| 106 | N-(4-((6,7-bis(methyloxy)-4-quinolinyl)oxy)phenyl)-4-(4-(1,1-dimethylethyl)phenyl)-1-phthalazinamine | 557 | B3 | 0.010 | 0.038 | 0.033 |
| 38 | 4-(4-(1,1-dimethylethyl)phenyl)-N-(4-((7-(methyloxy)-1,5-naphthyridin-4-yl)oxy)phenyl)-1-phthalazinamine | 528 | C2 | 0.023 | 0.017 | 0.080 |
| 107 | 4-methyl-N-(4-((7-(methyloxy)-1,5-naphthyridin-4-yl)oxy)phenyl)-6-phenyl-3-pyridazinamine | 436 | C2 | 0.018 | 0.005 | 0.390 |
| 108 | 4-ethyl-N-(4-((7-(methyloxy)-1,5-naphthyridin-4-yl)oxy)phenyl)-6-phenyl-3-pyridazinamine | 450 | C2 | 0.016 | 0.004 | 0.083 |
| 109 | N-(4-((7-(methyloxy)-1,6-naphthyridin-4-yl)oxy)phenyl)-4-(4-methyl-1-piperazinyl)-1-phthalazinamine | 494 | C2 | 0.060 | 0.001 | 0.297 |
| 110 | N-(4-((7-(methyloxy)-1,6-naphthyridin-4-yl)oxy)phenyl)-4-(6-methyl-2-pyridinyl)-1-phthalazinamine | 487.1 | C2 | 0.043 | 0.002 | 0.124 |
| 111 | N-(4-((7-(methyloxy)-1,5-naphthyridin-4-yl)oxy)phenyl)-4-(6-methyl-2-pyridinyl)-1-phthalazinamine | 487.1 | C2 | 0.040 | 0.005 | 0.109 |
| 112 | (6-(4-((4-((6,7-bis(methyloxy)-4-quinolinyl)oxy)phenyl)amino)-1-phthalazinyl)-2-pyridinyl)methanol | 532 | B3 followed by hydrolysis | 0.015 | 0.003 | 0.020 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 113 | (6-(4-((4-((6,7-bis(methyloxy)-4-quinolinyl)oxy)phenyl)amino)-1-phthalazinyl)-2-pyridinyl)methyl acetate | 573 | B3 | 0.014 | 0.011 | 0.048 |
| 114 | (6-(4-((4-((7-(methyloxy)-1,5-naphthyridin-4-yl)oxy)phenyl)amino)-1-phthalazinyl)-2-pyridinyl)methanol | 503 | B3 followed by hydrolysis | 0.036 | 0.005 | 0.390 |
| 115 | N-(3-fluoro-4-(4-quinolinyloxy)phenyl)-4-phenyl-1-phthalazinamine | 459 | B3 | 0.163 | 0.006 | 0.116 |
| 116 | N-(4-((7-(methyloxy)-1,5-naphthyridin-4-yl)oxy)phenyl)-4-(4-methyl-2-pyridinyl)-1-phthalazinamine | 487 | B3 | 0.062 | 0.011 | 0.179 |
| 117 | N-(4-((6,7-bis(methyloxy)-4-quinolinyl)oxy)phenyl)-4-(4-methyl-2-pyridinyl)-1-phthalazinamine | 516 | B3 | 0.057 | 0.043 | 0.066 |
| 118 | N-(4-((7-(methyloxy)-4-quinolinyl)oxy)phenyl)-4-(4-methyl-2-pyridinyl)-1-phthalazinamine | 486 | B3 | 0.136 | 0.009 | 0.110 |
| 119 | 4-((4-((4-(2-(methyloxy)phenyl)-1-phthalazinyl)amino)phenyl)oxy)-7-quinolinecarbonitrile | 496 | B3 | 0.175 | 0.007 | 1.200 |
| 120 | 4-(6-((methyloxy)methyl)-2-pyridinyl)-N-(4-((7-(methyloxy)-1,5-naphthyridin-4-yl)oxy)phenyl)-1-phthalazinamine | 517 | B3 | 0.019 | 0.003 | 0.305 |
| 121 | N-(4-((7-(methyloxy)-1,6-naphthyridin-4-yl)oxy)phenyl)-4-(4-methyl-2-pyridinyl)-1-phthalazinamine | 487 | C2 | 0.041 | 0.007 | 0.132 |
| 122 | 4-((4-((4-(5-methyl-2-pyridinyl)-1-phthalazinyl)amino)phenyl)oxy)-7-quinolinecarbonitrile | 481 | B3 | 0.022 | 0.003 | 0.053 |
| 123 | N-(4-((6,7-bis(methyloxy)-4-quinazolinyl)oxy)phenyl)-4-(4-methyl-2-pyridinyl)-1-phthalazinamine | 517 | C2 | 0.132 | 0.015 | 0.077 |
| 124 | N-(7-(methyloxy)-1,6-naphthyridin-4-yl)-N'-(4-phenyl-1-phthalazinyl)-1,4-benzenediamine | 471 | | 0.042 | 0.002 | 0.025 |
| 125 | N-(4-((7-(methyloxy)-1,5-naphthyridin-4-yl)oxy)phenyl)-4-(5-methyl-2-pyridinyl)-1-phthalazinamine | 487 | B3 | 0.018 | 0.003 | 0.059 |
| 126 | 3-(methyloxy)-8-((4-((4-(4-methylphenyl)-1-phthalazinyl)methyl)phenyl)oxy)-1,5-naphthyridine | 485 | C2 | 0.388 | 0.017 | 1.200 |
| 127 | N-(6-((7-(methyloxy)-1,6-naphthyridin-4-yl)oxy)-3-pyridinyl)-4-(6-methyl-2-pyridinyl)-1-phthalazinamine | 488.1 | C2 | 0.241 | 0.009 | 1.200 |
| 128 | N-(6-((7-(methyloxy)-1,5-naphthyridin-4-yl)oxy)-3-pyridinyl)-4-(6-methyl-2-pyridinyl)-1-phthalazinamine | 488 | C2 | 0.099 | 0.018 | 1.200 |
| 129 | N-(4-((7-(methyloxy)-1,5-naphthyridin-4-yl)oxy)phenyl)-4-(5-(methyloxy)-3-pyridinyl)-1-phthalazinamine | 503 | B3 | 0.165 | 0.014 | 0.181 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 130 | N-(4-((7-(methyloxy)-1,5-naphthyridin-4-yl)oxy)phenyl)-4-(3-(methyloxy)-4-pyridinyl)-1-phthalazinamine | 503 | B3 | 0.654 | 0.100 | 1.200 |
| 131 | N-(4-((7-(methyloxy)-1,6-naphthyridin-4-yl)oxy)phenyl)-4-(6-(methyloxy)-2-pyridinyl)-1-phthalazinamine | 503 | C2 | 0.019 | 0.003 | |
| 132 | (6-(4-((4-((7-(methyloxy)-1,5-naphthyridin-4-yl)oxy)phenyl)amino)-1-phthalazinyl)-2-pyridinyl)methyl acetate | 545 | B3 | 0.022 | 0.005 | 0.323 |
| 133 | N-(4-((7-bromo-4-quinolinyl)oxy)phenyl)-4-phenyl-1-phthalazinamine | 519, 521 | C2 | 0.494 | 0.028 | 0.116 |
| 134 | N-(4-((6-bromo-4-quinolinyl)oxy)phenyl)-4-phenyl-1-phthalazinamine | 519, 521 | C2 | 0.176 | 0.024 | 0.091 |
| 135 | N-(5-((7-(methyloxy)-1,5-naphthyridin-4-yl)oxy)-2-pyridinyl)-4-phenyl-1-phthalazinamine | 473 | | 0.063 | 0.012 | 0.449 |
| 136 | 4-(2,2-dimethyl-2,3-dihydro-1-benzofuran-5-yl)-N-(4-((7-(methyloxy)-1,5-naphthyridin-4-yl)oxy)phenyl)-1-phthalazinamine | 542 | A1 | 0.037 | 0.016 | 0.099 |
| 137 | 4-(4-((1-methylethyl)oxy)phenyl)-N-(4-((7-(methyloxy)-1,5-naphthyridin-4-yl)oxy)phenyl)-1-phthalazinamine | 530 | A1 | 0.091 | 0.018 | 0.850 |
| 138 | N-(4-((7-(methyloxy)-1,5-naphthyridin-4-yl)oxy)phenyl)-4-(5-methyl-2-thienyl)-1-phthalazinamine | 492 | B3 | 0.018 | 0.013 | 0.030 |
| 139 | N-(4-((7-(methyloxy)-1,5-naphthyridin-4-yl)oxy)phenyl)-4-(3-(methyloxy)phenyl)-1-phthalazinamine | 502 | A1 | 0.018 | 0.006 | 0.057 |
| 140 | 4-(5-chloro-2-thienyl)-N-(4-((7-(methyloxy)-1,5-naphthyridin-4-yl)oxy)phenyl)-1-phthalazinamine | 512 | A1 | 0.022 | 0.008 | 0.022 |
| 141 | 4-((4-((4-(4-(methyloxy)phenyl)-1-phthalazinyl)amino)phenyl)oxy)-7-quinolinecarbonitrile | 496 | C1 | 0.019 | 0.004 | 0.025 |
| 142 | 4-(1-benzothien-5-yl)-N-(4-((7-(methyloxy)-1,5-naphthyridin-4-yl)oxy)phenyl)-1-phthalazinamine | 528 | A1 | 0.008 | 0.007 | 0.007 |
| 143 | 4-(1-methyl-1H-indol-2-yl)-N-(4-((7-(methyloxy)-1,5-naphthyridin-4-yl)oxy)phenyl)-1-phthalazinamine | 525 | A1 | 0.012 | 0.009 | 0.094 |
| 144 | N-(4-((7-(methyloxy)-1,5-naphthyridin-4-yl)oxy)phenyl)-4-phenyl-1-isoquinolinamine | 471.1 | C1 | 0.061 | 0.020 | 0.155 |
| 145 | N-(4-((7-(methyloxy)-1,6-naphthyridin-4-yl)oxy)phenyl)-4-phenyl-1-isoquinolinamine | 471.1 | C1 | 0.326 | 0.096 | 1.200 |
| 146 | N-(4-((7-(methyloxy)-1,5-naphthyridin-4-yl)oxy)phenyl)-4-(4-(trifluoromethyl)phenyl)-1-phthalazinamine | 540.1 | C1 | 0.026 | 0.008 | 0.057 |
| 147 | 4-((4-((4-(4-(trifluoromethyl)phenyl)-1-phthalazinyl)amino)phenyl)oxy)-7-quinolinecarbonitrile | 534.2 | C1 | 0.025 | 0.011 | 0.020 |
| 148 | N-(4-((6,7-bis(methyloxy)-4-quinazolinyl)oxy)phenyl)-4- | 480 | C1 | 0.062 | 0.016 | 0.039 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| | ethyl-6-phenyl-3-pyridazinamine | | | | | |
| 29 | 3-(4-((4-((7-(methyloxy)-1,5-naphthyridin-4-yl)oxy)phenyl)amino)-1-phthalazinyl)benzonitrile | 497 | A1 | 0.139 | 0.018 | 0.442 |
| 149 | 4-((4-((4-ethyl-6-phenyl-3-pyridazinyl)amino)phenyl)oxy)-7-quinolinecarbonitrile | 444 | C1 | 0.146 | 0.014 | 0.420 |
| 150 | N-(4-((6,7-bis(methyloxy)-4-quinolinyl)oxy)phenyl)-4-(6-methyl-2-pyridinyl)-1-phthalazinamine | 516.2 | B3 | 0.014 | 0.007 | 0.017 |
| 37 | N-(4-((7-(methyloxy)-1,5-naphthyridin-4-yl)oxy)phenyl)-4-(4-(methyloxy)phenyl)-1-phthalazinamine | 502 | C1 | 0.020 | 0.004 | 0.052 |
| 151 | N-(4-((7-(methyloxy)-1,5-naphthyridin-4-yl)oxy)phenyl)-4-(1-piperidinyl)-1-phthalazinamine | 479 | B1 | 0.022 | 0.005 | 0.128 |
| 152 | N-(4-((7-(methyloxy)-1,5-naphthyridin-4-yl)oxy)phenyl)-4-(4-methyl-2-thienyl)-1-phthalazinamine | 492 | C2 | 0.006 | 0.006 | 0.009 |
| 153 | N-(4-((6,7-bis(methyloxy)-4-quinazolinyl)oxy)phenyl)-4-(4-methyl-2-thienyl)-1-phthalazinamine | 522 | C2 | 0.009 | 0.012 | 0.001 |
| 154 | 2-chloro-5-(4-((4-((7-(methyloxy)-1,5-naphthyridin-4-yl)oxy)phenyl)amino)-1-phthalazinyl)benzonitrile | 531 | A1 | 0.018 | 0.004 | 0.061 |
| 155 | 4-(4-(1-methylethyl)phenyl)-N-(4-((7-(methyloxy)-1,5-naphthyridin-4-yl)oxy)phenyl)-1-phthalazinamine | 514 | B1 | 0.029 | 0.011 | 0.068 |
| 49 | 4-((4-((4-ethyl-6-phenyl-3-pyridazinyl)amino)phenyl)oxy)-7-quinolinecarboxamide | 462 | unique | 0.021 | 0.001 | 0.028 |
| 156 | N-(4-((7-(methyloxy)-1,5-naphthyridin-4-yl)oxy)phenyl)-6-phenyl-4-propyl-3-pyridazinamine | 464 | C2 | 0.047 | 0.005 | 0.061 |
| 32 | 4-(1-azepanyl)-N-(4-((7-(methyloxy)-1,5-naphthyridin-4-yl)oxy)phenyl)-1-phthalazinamine | 493 | B1 | 0.016 | 0.009 | 0.036 |
| 157 | 4-(4-methyl-3,4-dihydro-2H-1,4-benzoxazin-7-yl)-N-(4-((7-(methyloxy)-1,5-naphthyridin-4-yl)oxy)phenyl)-1-phthalazinamine | 543.1 | A1 | 0.012 | 0.005 | 0.028 |
| 158 | N-(4-((7-(methyloxy)-1,5-naphthyridin-4-yl)oxy)phenyl)-4-(6-(methyloxy)-3-pyridinyl)-1-phthalazinamine | 503 | A1 | 0.037 | 0.005 | 0.075 |
| 159 | 4-(1-benzofuran-5-yl)-N-(4-((7-(methyloxy)-1,5-naphthyridin-4-yl)oxy)phenyl)-1-phthalazinamine | 512 | A1 | 0.010 | 0.007 | 0.007 |
| 160 | 4-(4-chlorophenyl)-N-(4-((7-(methyloxy)-1,5-naphthyridin-4-yl)oxy)phenyl)-1-phthalazinamine | 506 | A1 | 0.007 | 0.003 | 0.005 |
| 161 | N-(3-fluoro-4-(4-quinolinyloxy)phenyl)-4-(4-methylphenyl)-1-phthalazinamine | 473 | B3 | 0.027 | 0.005 | 0.010 |
| 162 | 4-((4-((4-(5-methyl-2-thienyl)-1-phthalazinyl)amino)phenyl)oxy)-7-quinolinecarbonitrile | 486 | B3 | 0.012 | 0.004 | 0.004 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 163 | N-(4-((7-(methyloxy)-1,5-naphthyridin-4-yl)oxy)phenyl)-4-(4-((trifluoromethyl)oxy)phenyl)-1-phthalazinamine | 556 | A1 | 0.072 | 0.009 | 1.200 |
| 164 | N-(4-((3-fluoro-7-(methyloxy)-4-quinolinyl)oxy)phenyl)-4-phenyl-1-phthalazinamine | 489.1 | C1 | 0.040 | 0.003 | 0.076 |
| 165 | 4-(1,3-benzodioxol-5-yl)-N-(4-((7-(methyloxy)-1,5-naphthyridin-4-yl)oxy)phenyl)-1-phthalazinamine | 516.1 | A1 | 0.009 | 0.007 | 0.006 |
| 166 | 4-(2,3-dihydro-1,4-benzodioxin-6-yl)-N-(4-((7-(methyloxy)-1,5-naphthyridin-4-yl)oxy)phenyl)-1-phthatazinamine | 530 | A1 | 0.023 | 0.006 | 0.087 |
| 167 | 4-(1H-indol-5-yl)-N-(4-((7-(methyloxy)-1,5-naphthyridin-4-yl)oxy)phenyl)-1-phthalazinamine | 511 | A1 | 0.013 | 0.004 | 0.027 |
| 168 | 4-(2,3-dihydro-1-benzofuran-5-yl)-N-(4-((7-(methyloxy)-1,5-naphthyridin-4-yl)oxy)phenyl)-1-phthalazinamine | 514 | A1 | 0.008 | 0.005 | 0.007 |
| 169 | 4-(1-benzothien-3-yl)-N-(4-((7-(methyloxy)-1,5-naphthyridin-4-yl)oxy)phenyl)-1-phthalazinamine | 528 | A1 | 0.010 | 0.009 | 0.027 |
| 170 | 4-((4-((4-(4-methyl-2-thienyl)-1-phthalazinyl)amino)phenyl)oxy)-7-quinolinecarbonitrile | 486 | B3 | 0.016 | 0.009 | 0.007 |
| 171 | 4-(1-benzothien-2-yl)-N-(4-((7-(methyloxy)-1,5-naphthyridin-4-yl)oxy)phenyl)-1-phthalazinamine | 528 | A1 | 0.013 | 0.015 | 0.004 |
| 172 | 4-(3-chloro-4-(trifluoromethyl)phenyl)-N-(4-((7-(methyloxy)-1,5-naphthyridin-4-yl)oxy)phenyl)-1-phthalazinamine | 574 | A1 | 0.039 | 0.017 | 0.034 |
| 41 | N-(6-((7-(methyloxy)-1,5-naphthyridin-4-yl)oxy)-3-pyridinyl)-4-phenyl-1-phthalazinamine | 473 | C5 | 0.079 | 0.009 | 0.195 |
| 173 | N-(4-((7-(methyloxy)-1,5-naphthyridin-4-yl)oxy)phenyl)-4-((4aR,8aR)-octahydro-2(1H)-isoquinolinyl)-1-phthalazinamine | 533 | C2 | 0.019 | 0.019 | 0.006 |
| 174 | 4-(5-(4-phenylphthalazin-1-ylamino)pyridin-2-yloxy)quinoline-7-carbonitrile | 467 | C5 | 25.000 | 5.000 | 1.200 |
| 175 | 4-(2-(ethyloxy)-1,3-thiazol-4-yl)-N-(4-((7-(methyloxy)-1,5-naphthyridin-4-yl)oxy)phenyl)-1-phthalazinamine | 523 | A2 | 0.013 | 0.003 | 0.059 |
| 176 | 4-(1-benzofuran-2-yl)-N-(4-((7-(methyloxy)-1,5-naphthyridin-4-yl)oxy)phenyl)-1-phthalazinamine | 512.2 | A1 | 0.007 | 0.002 | 0.008 |
| 177 | 4-(4-((4-((7-(methyloxy)-1,5-naphthyridin-4-yl)oxy)phenyl)amino)-1-phthalazinyl)benzamide | 515.2 | A1 | 0.206 | 0.004 | 1.200 |
| 178 | 4-(2-fluoro-6-methyl-3-pyridinyl)-N-(4-((7-(methyloxy)-1,5-naphthyridin-4-yl)oxy)phenyl)-1-phthalazinamine | 505.1 | A1 | 0.035 | 0.002 | 0.027 |
| 179 | N-(4-((2-fluoro-4-((4-phenyl-1-phthalazinyl)amino)phenyl)oxy)- | 537 | unique | 0.180 | 0.043 | 0.226 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| | 2-pyridinyl)-4-morpholinecarboxamide | | | | | |
| 180 | 4-(4-fluoro-3-(methyloxy)phenyl)-N-(4-((7-(methyloxy)-1,5-naphthyridin-4-yl)oxy)phenyl)-1-phthalazinamine | 520 | A1 | 0.027 | 0.004 | 0.025 |
| 181 | 4-(4-((4-((7-(methyloxy)-1,5-naphthyridin-4-yl)oxy)phenyl)amino)-1-phthalazinyl)benzonitrile | 497 | A1 | 0.171 | 0.007 | 0.104 |
| 182 | N-(4-((7-(methyloxy)-1,5-naphthyridin-4-yl)oxy)phenyl)-4-(3-quinolinyl)-1-phthalazinamine | 523 | A1 | 0.023 | 0.002 | 0.032 |
| 183 | 4-(1H-indol-4-yl)-N-(4-((7-(methyloxy)-1,5-naphthyridin-4-yl)oxy)phenyl)-1-phthalazinamine | 511 | A1 | 0.033 | 0.003 | 0.052 |
| 184 | 4-((4-((4-(3-methyl-2-thienyl)-1-phthalazinyl)amino)phenyl)oxy)-7-quinolinecarbonitrile | 486 | B3 | 0.201 | 0.003 | 0.130 |
| 185 | N-(4-((7-(methyloxy)-1,5-naphthyridin-4-yl)oxy)phenyl)-4-(3-methyl-2-thienyl)-1-phthalazinamine | 492 | C2 | 0.231 | 0.006 | 0.241 |
| 186 | N-(3-fluoro-4-(4-quinolinyloxy)phenyl)-4-(6-(methyloxy)-2-pyridinyl)-1-phthalazinamine | 490 | B3 | 0.059 | 0.002 | 0.031 |
| 187 | N-(3-fluoro-4-((7-(methyloxy)-1,5-naphthyridin-4-yl)oxy)phenyl)-4-(4-methylphenyl)-1-phthalazinamine | 504 | B3 | 0.006 | 0.004 | 0.006 |
| 39 | N-(4-((3-fluoro-7-(methyloxy)-4-quinolinyl)oxy)phenyl)-4-(4-(trifluoromethyl)phenyl)-1-phthalazinamine | 557 | C3 | 25.000 | 1.000 | 1.200 |
| 42 | N-(4-((7-(4-morpholinyl)-4-quinolinyl)oxy)phenyl)-4-phenyl-1-phthalazinamine | 526 | D1 | 0.011 | 0.002 | 0.007 |
| 188 | 4-(3,5-dimethylphenyl)-N-(4-((7-(methyloxy)-1,5-naphthyridin-4-yl)oxy)phenyl)-1-phthalazinamine | 500 | A1 | 0.017 | 0.006 | 0.051 |
| 189 | N-(4-((7-(methyloxy)-1,5-naphthyridin-4-yl)oxy)phenyl)-4-(5-methyl-1,3-thiazol-2-yl)-1-phthalazinamine | 493 | A2 | 0.022 | 0.009 | 0.191 |
| 190 | 4-(6-fluoro-3-pyridinyl)-N-(4-((7-(methyloxy)-1,5-naphthyridin-4-yl)oxy)phenyl)-1-phthalazinamine | 491.1 | A1 | 0.052 | 0.005 | 0.129 |
| 191 | 4-(2-fluoro-3-pyridinyl)-N-(4-((7-(methyloxy)-1,5-naphthyridin-4-yl)oxy)phenyl)-1-phthalazinamine | 491.1 | A1 | 0.104 | 0.009 | 1.200 |
| 192 | 4-(3,4-dimethylphenyl)-N-(4-((7-(methyloxy)-1,5-naphthyridin-4-yl)oxy)phenyl)-1-phthalazinamine | 500.1 | A1 | 0.005 | 0.005 | 0.005 |
| 193 | 4-(3-chloro-4-fluorophenyl)-N-(4-((7-(methyloxy)-1,5-naphthyridin-4-yl)oxy)phenyl)-1-phthalazinamine | 524.1 | A1 | 0.023 | 0.005 | 0.027 |
| 194 | 4-(4-(dimethylamino)phenyl)-N-(4-((7-(methyloxy)-1,5-naphthyridin-4-yl)oxy)phenyl)-1-phthalazinamine | 515 | A1 | 0.023 | 0.010 | 0.033 |
| 195 | 4-(2-methyl-1,3-benzothiazol-5-yl)-N-(4-((7-(methyloxy)-1,5- | 543 | A1 | 0.088 | 0.005 | 0.197 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| | naphthyridin-4-yl)oxy)phenyl)-1-phthalazinamine | | | | | |
| 196 | 4-((4-((6-phenyl-4-propyl-3-pyridazinyl)amino)phenyl)oxy)-7-quinolinecarbonitrile | 458 | C1 | 0.672 | 0.006 | 0.342 |
| 197 | N-(4-((7-(methyloxy)-1,5-naphthyridin-4-yl)oxy)phenyl)-4-(3-(1-piperidinyl)phenyl)-1-phthalazinamine | 555 | A1 | 0.034 | | 0.021 |
| 198 | N-(4-((7-(methyloxy)-1,5-naphthyridin-4-yl)oxy)phenyl)-4-(4-(1-piperidinyl)phenyl)-1-phthalazinamine | 555 | A1 | 0.128 | 0.004 | 0.399 |
| 199 | 4-ethyl-N-(4-((7-(methyloxy)-1,5-naphthyridin-4-yl)oxy)phenyl)-6-(4-methylphenyl)-3-pyridazinamine | 464 | B4 | 0.027 | 0.002 | 0.018 |
| 200 | N-(4-((7-(methyloxy)-1,5-naphthyridin-4-yl)oxy)phenyl)-4-(1,3-oxazol-2-yl)-1-phthalazinamine | 463 | A2 | 0.087 | 0.003 | 0.314 |
| 201 | 4-(3,4-dichlorophenyl)-N-(4-((7-(methyloxy)-1,5-naphthyridin-4-yl)oxy)phenyl)-1-phthalazinamine | 540 | A1 | 0.035 | 0.006 | 0.022 |
| 202 | N-(4-((2-(1-methyl-1H-imidazol-5-yl)thieno[3,2-b]pyridin-7-yl)oxy)phenyl)-4-phenyl-1-phthalazinamine | 527 | B3 | 0.020 | 0.002 | 0.011 |
| 203 | N-(4-((2-(1-methyl-1H-imidazol-5-yl)thieno[3,2-b]pyridin-7-yl)oxy)phenyl)-4-(4-methylphenyl)-1-phthalazinamine | 541.2 | B3 | 0.008 | 0.002 | 0.002 |
| 204 | 4-(1-methyl-1H-indol-5-yl)-N-(4-((7-(methyloxy)-1,5-naphthyridin-4-yl)oxy)phenyl)-1-phthalazinamine | 525 | A1 | 0.026 | 0.003 | 0.021 |
| 205 | 4-ethyl-N-(4-((7-(methyloxy)-1,5-naphthyridin-4-yl)oxy)phenyl)-6-(5-methyl-2-thienyl)-3-pyridazinamine | 470 | B4 | 0.060 | 0.004 | 0.074 |
| 30 | 4-(1-methyl-1H-imidazol-2-yl)-N-(4-((7-(methyloxy)-1,5-naphthyridin-4-yl)oxy)phenyl)-1-phthalazinamine | 476 | A2 | 1.387 | | 1.200 |
| 206 | 4-(1H-indol-6-yl)-N-(4-(7-methoxy-1,5-naphthyridin-4-yloxy)phenyl)phthalazin-1-amine | 511 | A1 | 0.017 | 0.003 | 0.002 |
| 207 | N-(4-((7-(methyloxy)-1,5-naphthyridin-4-yl)thio)phenyl)-4-phenyl-1-phthalazinamine | 488 | B3 | 0.060 | 0.009 | 0.005 |
| 208 | 4-((4-((4-phenyl-1-phthalazinyl)amino)phenyl)thio)-7-quinolinecarbonitrile | 482 | B3 | 0.180 | 0.007 | 0.023 |
| 209 | 4-(3-amino-4-methylphenyl)-N-(4-((7-(methyloxy)-1,5-naphthyridin-4-yl)oxy)phenyl)-1-phthalazinamine | 500 | A1 | 0.012 | 0.001 | 0.004 |
| 210 | 4-ethyl-N-(4-((7-(methyloxy)-1,5-naphthyridin-4-yl)oxy)phenyl)-6-(4-methyl-2-thienyl)-3-pyridazinamine | 470 | B4 | 0.031 | 0.002 | 0.056 |
| 211 | 7-(methyloxy)-4-((4-((4-(4-methylphenyl)-1-phthalazinyl)amino)phenyl)oxy)-6-quinolinecarboxamide | 528.1 | B3 | 0.006 | 0.001 | 0.002 |
| 212 | N-(4-((7-(methyloxy)-1,5-naphthyridin-4-yl)oxy)phenyl)-4-(1H-pyrazol-4-yl)-1-phthalazinamine | 462 | A1 | 0.478 | 0.018 | 0.501 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 213 | 4-(3-methyl-4-(methyloxy)phenyl)-N-(4-((7-(methyloxy)-1,5-naphthyridin-4-yl)oxy)phenyl)-1-phthalazinamine | 516 | A1 | 0.079 | 0.011 | 0.044 |
| 214 | 4-(3,4-difluorophenyl)-N-(4-((7-(methyloxy)-1,5-naphthyridin-4-yl)oxy)phenyl)-1-phthalazinamine | 508 | A1 | 0.085 | 0.007 | 0.033 |
| 215 | N-(4-((7-(methyloxy)-1,5-naphthyridin-4-yl)oxy)phenyl)-4-(5-pyrimidinyl)-1-phthalazinamine | 474 | A1 | 0.743 | 0.024 | 1.200 |
| 216 | N-(4-((7-(methyloxy)-1,5-naphthyridin-4-yl)oxy)phenyl)-4-(1-methyl-1H-pyrazol-4-yl)-1-phthalazinamine | 476 | A1 | 0.160 | 0.006 | 0.074 |
| 217 | 4-((4-((4-(4-cyanophenyl)-1-phthalazinyl)amino)phenyl)oxy)-7-quinolinecarbonitrile | 491 | A1 | 0.454 | 0.016 | 0.369 |
| 218 | N-(4-((7-(methyloxy)-1,5-naphthyridin-4-yl)oxy)phenyl)-4-phenylthieno[2,3-d]pyridazin-7-amine | 478 | B4 | 0.027 | 0.003 | 0.061 |
| 219 | 4-(3-chlorophenyl)-N-(4-((7-(methyloxy)-1,5-naphthyridin-4-yl)oxy)phenyl)-1-phthalazinamine | 506.1 | A1 | 0.051 | 0.010 | 0.031 |
| 220 | 4-(4-fluorophenyl)-N-(4-((7-(methyloxy)-1,5-naphthyridin-4-yl)oxy)phenyl)-1-phthalazinamine | 490.1 | A1 | 0.047 | 0.004 | 0.036 |
| 221 | 4-(4-ethylphenyl)-N-(4-((7-(methyloxy)-1,5-naphthyridin-4-yl)oxy)phenyl)-1-phthalazinamine | 500.1 | A1 | 0.026 | 0.007 | 0.015 |
| 222 | 4-(4-chlorophenyl)-N-(6-((7-(methyloxy)-1,5-naphthyridin-4-yl)oxy)-3-pyridinyl)-1-phthalazinamine | 507 | C5 | 0.047 | 0.006 | 0.026 |
| 223 | N-(4-((7-(methyloxy)-1,5-naphthyridin-4-yl)oxy)phenyl)-4-(1-methyl-1H-pyrazol-5-yl)-1-phthalazinamine | 476 | A1 | 1.327 | 0.039 | 1.200 |
| 224 | 4-(3-chloro-4-methylphenyl)-N-(4-((7-(methyloxy)-1,5-naphthyridin-4-yl)oxy)phenyl)-1-phthalazinamine | 520 | A1 | 0.034 | 0.011 | 0.007 |
| 225 | 7-(methyloxy)-4-((4-((4-phenyl-1-phthalazinyl)amino)phenyl)oxy)-6-quinolinecarboxamide | 513.5 | B3 | 0.023 | 0.004 | 0.004 |
| 226 | N,N-dimethyl-3-(4-(4-((7-(methyloxy)-1,5-naphthyridin-4-yl)oxy)phenyl)amino)-1-phthalazinyl)benzamide | 543 | A1 | 0.187 | 0.014 | 1.200 |
| 227 | 4-(3-fluoro-4-(methyloxy)phenyl)-N-(4-((7-(methyloxy)-1,5-naphthyridin-4-yl)oxy)phenyl)-1-phthalazinamine | 520 | A1 | 0.051 | 0.003 | 0.061 |
| 228 | 4-(5-chloro-2-pyridinyl)-N-(4-((7-(methyloxy)-1,5-naphthyridin-4-yl)oxy)phenyl)-1-phthalazinamine | 507 | B3 | 0.034 | 0.004 | 0.035 |
| 229 | 4-(5-ethyl-2-thienyl)-N-(4-((7-(methyloxy)-1,5-naphthyridin-4-yl)oxy)phenyl)-1-phthalazinamine | 506 | B3 | 0.024 | 0.007 | 0.026 |
| 230 | 4-phenyl-N-(4-(5,6,7,8-tetrahydro-1,5-naphthyridin-4-yloxy)phenyl)-1-phthalazinamine | 446.2 | B3 | 5.000 | 0.031 | |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 231 | 4-((4-((4-(4-chloro-3-cyanophenyl)-1-phthalazinyl)amino)phenyl)oxy)-7-quinolinecarbonitrile | 525 | A1 | 0.379 | 0.032 | 0.067 |
| 232 | 4-(4-chlorophenyl)-N-(4-((7-(methyloxy)-1,5-naphthyridin-4-yl)thio)phenyl)-1-phthalazinamine | 522 | B3 | 0.036 | 0.015 | 0.004 |
| 233 | 4-(4-chloro-2-methylphenyl)-N-(4-((7-(methyloxy)-1,5-naphthyridin-4-yl)oxy)phenyl)-1-phthalazinamine | 520 | A1 | 0.845 | 0.021 | 0.600 |
| 234 | 4-(1-methylethyl)-N-(4-((7-(methyloxy)-1,5-naphthyridin-4-yl)oxy)phenyl)-6-phenyl-3-pyridazinamine | 464 | B4 | 0.173 | 0.006 | 0.196 |
| 235 | 4-(6-chloro-3-pyridinyl)-N-(4-((7-(methyloxy)-1,5-naphthyridin-4-yl)oxy)phenyl)-1-phthalazinamine | 507.2 | A1 | 0.123 | 0.003 | 0.058 |
| 236 | 4-(4-chloro-3-methylphenyl)-N-(4-((7-(methyloxy)-1,5-naphthyridin-4-yl)oxy)phenyl)-1-phthalazinamine | 520.1 | A1 | 0.027 | 0.008 | 0.011 |
| 237 | N-(4-((7-(methyloxy)-1,5-naphthyridin-4-yl)oxy)phenyl)-4-(4-(methylthio)phenyl)-1-phthalazinamine | 518 | A1 | 0.038 | 0.005 | 0.030 |
| 238 | N-(4-((6-(methyloxy)-4-quinolinyl)oxy)phenyl)-4-phenyl-1-phthalazinamine | 471 | B3 | 0.265 | 0.005 | 0.053 |
| 239 | 4-(4-chlorophenyl)-N-(4-((6-(methyloxy)-4-quinolinyl)oxy)phenyl)-1-phthalazinamine | 505 | B3 | 0.120 | 0.008 | 0.001 |
| 31 | 4-(3,3-dimethyl-1-butyn-1-yl)-N-(4-((7-(methyloxy)-1,5-naphthyridin-4-yl)oxy)phenyl)-1-phthalazinamine | 476 | A3 | 0.033 | 0.008 | 0.045 |
| 240 | N-(4-((2-(1-methyl-1H-imidazol-5-yl)thieno[3,2-b]pyridin-7-yl)oxy)phenyl)-4-(6-(methyloxy)-2-pyridinyl)-1-phthalazinamine | 558 | B3 | 0.006 | 0.001 | 0.010 |
| 241 | 4-(4-chlorophenyl)-N-(4-(1H-pyrrolo[2,3-b]pyridin-4-yloxy)phenyl)-1-phthalazinamine | 464 | B3 | 0.089 | 0.001 | 0.101 |
| 242 | 4-((4-((4-(4-chlorophenyl)-1-phthalazinyl)amino)phenyl)oxy)-7-quinolinecarbonitrile | 500 | A1 | 0.173 | 0.022 | 0.019 |
| 243 | 4-(3-fluoro-4-methylphenyl)-N-(4-((7-(methyloxy)-1,5-naphthyridin-4-yl)oxy)phenyl)-1-phthalazinamine | 504 | A1 | 0.014 | 0.005 | 0.006 |
| 244 | 4-(4-chlorophenyl)-N-(3-fluoro-4-(4-quinolinyloxy)phenyl)-1-phthalazinamine | 492 | B3 | 0.048 | 0.003 | 0.040 |
| 245 | N-(4-((7-bromo-1,5-naphthyridin-4-yl)oxy)phenyl)-4-phenyl-1-phthalazinamine | 522.1 | B3 | 0.153 | 0.006 | 0.381 |
| 51 | N-methyl-N-(7-(methyloxy)-1,5-naphthyridin-4-yl)-N'-(4-phenyl-1-phthalazinyl)-1,4-benzenediamine | 485.2 | unique | 0.860 | 0.023 | 0.372 |
| 246 | 4-(4-fluoro-3-methylphenyl)-N-(4-((7-(methyloxy)-1,5-naphthyridin-4-yl)oxy)phenyl)-1-phthalazinamine | 504 | A1 | 0.032 | 0.008 | 0.030 |
| 247 | N-methyl-N-(7-(methyloxy)-1,5-naphthyridin-4-yl)-N'-(4-(4-methyl-2-thienyl)-1- | 505.1 | Example 51 | 0.219 | 0.032 | 0.112 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| | phthalazinyl)-1,4-benzenediamine | | | | | |
| 53 | N-(4-(1,5-naphthyridin-4-yloxy)phenyl)-4-phenyl-1-phthalazinamine | 442.1 | unique | 0.153 | 0.003 | 0.105 |
| 248 | 4-((4-((4-(4-chlorophenyl)-1-phthalazinyl)amino)phenyl)thio)-7-quinolinecarbonitrile | 517 | B3 | 25.000 | 25.000 | 0.022 |
| 249 | 4-(4-chlorophenyl)-N-(4-((2-(1-methyl-1H-imidazol-5-yl)thieno[3,2-b]pyridin-7-yl)oxy)phenyl)-1-phthalazinamine | 561 | B3 | 0.004 | 0.001 | 0.008 |
| 250 | 4-(4-chlorophenyl)-N-(4-(thieno[3,2-b]pyridin-7-yloxy)phenyl)-1-phthalazinamine | 481 | B3 | 0.094 | 0.003 | 0.031 |
| 251 | 4-phenyl-N-(4-(thieno[3,2-b]pyridin-7-yloxy)phenyl)-1-phthalazinamine | 447.1 | B3 | 0.376 | 0.004 | 0.227 |
| 252 | 4-(4-methylphenyl)-N-(4-(thieno[3,2-b]pyridin-7-yloxy)phenyl)-1-phthalazinamine | 461 | B3 | 0.077 | 0.005 | 0.027 |
| 253 | 4-(4-chloro-2-(methyloxy)phenyl)-N-(4-((7-(methyloxy)-1,5-naphthyridin-4-yl)oxy)phenyl)-1-phthalazinamine | 536 | A1 | 0.173 | 0.009 | 0.835 |
| 44 | 8-((4-((4-phenyl-1-phthalazinyl)amino)phenyl)oxy)-1,5-naphthyridine-3-carbonitrile | 467 | D2 | 0.332 | 0.015 | 1.200 |
| 254 | N-(4-((6,7-bis(methyloxy)-4-cinnolinyl)oxy)phenyl)-4-phenyl-1-phthalazinamine | 502.1 | C1 | 1.641 | 0.253 | 1.200 |
| 255 | N-(4-((2-(1-methyl-1H-imidazol-5-yl)thieno[3,2-b]pyridin-7-yl)oxy)phenyl)-4-(5-methyl-2-pyridinyl)-1-phthalazinamine | 542 | B3 | 0.005 | 0.000 | 0.014 |
| 256 | 6-(4-chlorophenyl)-4-ethyl-N-(4-((7-(methyloxy)-1,5-naphthyridin-4-yl)oxy)phenyl)-3-pyridazinamine | 484 | C1 | 0.012 | 0.003 | 0.049 |
| 257 | 4-phenyl-N-(4-(7H-purin-6-yloxy)phenyl)-1-phthalazinamine | 432 | B3 | 0.868 | 0.129 | 1.200 |
| 258 | 4-(3-(dimethylamino)phenyl)-N-(4-((7-(methyloxy)-1,5-naphthyridin-4-yl)oxy)phenyl)-1-phthalazinamine | 515 | A1 | 0.005 | 0.002 | 0.004 |
| 259 | 4-(4-chlorophenyl)-N-(4-((2-(4-morpholinylcarbonyl)thieno[3,2-b]pyridin-7-yl)oxy)phenyl)-1-phthalazinamine | 594 | C1 | 0.023 | 0.006 | 0.051 |
| 34 | 4-(4,5-dimethyl-1,3-thiazol-2-yl)-N-(4-((7-(methyloxy)-1,5-naphthyridin-4-yl)oxy)phenyl)-1-phthalazinamine | 507 | B3 | 0.013 | 0.010 | 0.062 |
| 260 | 4-(4,5-dimethyl-2-thienyl)-N-(4-((7-(methyloxy)-1,5-naphthyridin-4-yl)oxy)phenyl)-1-phthalazinamine | 506 | B3 | 0.008 | 0.009 | 0.002 |
| 261 | N-(4-((7-(methyloxy)-1,5-naphthyridin-4-yl)oxy)phenyl)-4-(1,3,5-trimethyl-1H-pyrazol-4-yl)-1-phthalazinamine | 504 | A1 | 1.605 | 0.156 | 1.200 |
| 262 | N-(4-((7-(methyloxy)-1,5-naphthyridin-4-yl)oxy)phenyl)-4-(4-(methylsulfinyl)phenyl)-1-phthalazinamine | 534.2 | A1 | 0.102 | 0.006 | 1.200 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 263 | N-(4-((7-(methyloxy)-1,5-naphthyridin-4-yl)oxy)phenyl)-4-(4-(methylsulfonyl)phenyl)-1-phthalazinamine | 550 | A1 | 0.036 | 0.002 | 0.138 |
| 264 | N-(4-((6-(4-morpholinyl)-4-quinolinyl)oxy)phenyl)-4-phenyl-1-phthalazinamine | 526 | D1 | 0.139 | 0.016 | 0.387 |
| 265 | 8-((4-((4-(4-chlorophenyl)-1-phthalazinyl)amino)phenyl)oxy)-1,5-naphthyridine-3-carbonitrile | 501 | D2 | 0.113 | 0.009 | 0.056 |
| 266 | 4-(4-chlorophenyl)-N-(4-(9H-purin-6-yloxy)phenyl)-1-phthalazinamine | 466 | B3 | 0.679 | 0.045 | 1.200 |
| 267 | 4-(4-chlorophenyl)-N-(6-((2-(1-methyl-1H-imidazol-5-yl)thieno[3,2-b]pyridin-7-yl)oxy)-3-pyridinyl)-1-phthalazinamine | 562 | C5 | 0.011 | 0.000 | 0.013 |
| 268 | N-(4-((7-(methyloxy)-1,5-naphthyridin-4-yl)oxy)phenyl)-4-(6-methyl-3-pyridinyl)-1-phthalazinamine | 487 | A1 | 0.064 | 0.003 | 0.066 |
| 269 | N-(4-((6-(methyloxy)-4-quinolinyl)oxy)phenyl)-4-(4-methyl-2-thienyl)-1-phthalazinamine | 491 | B3 | 0.049 | 0.006 | 0.016 |
| 270 | 7-((4-((4-(4-chlorophenyl)-1-phthalazinyl)amino)phenyl)oxy)-N,N-diethylthieno[3,2-b]pyridine-2-carboxamide | 580 | C1 | 0.084 | 0.010 | 0.082 |
| 271 | N-(4-(7-methoxy-1,5-naphthyridin-4-ylthio)phenyl)-4-(4-methylthiophen-2-yl)phthalazin-1-amine | 508 | B3 | 0.066 | 0.024 | 0.004 |
| 272 | 4-(2,3-dihydrobenzofuran-5-yl)-N-(4-(thieno[3,2-b]pyridin-7-yloxy)phenyl)phthalazin-1-amine | 489.1 | A1 | 0.033 | 0.001 | 0.006 |
| 273 | N-(4-(7H-pyrrolo[2,3-d]pyrimidin-4-yloxy)phenyl)-4-phenylphthalazin-1-amine | 431 | B3 | 1.660 | 0.039 | 1.200 |
| 274 | 4-ethyl-N-(4-(7-methoxy-1,5-naphthyridin-4-ylthio)phenyl)-6-phenylpyridazin-3-amine | 466 | B4 | 0.066 | 0.004 | 0.029 |
| 275 | 6-(4-chlorophenyl)-4-ethyl-N-(6-(7-methoxy-1,5-naphthyridin-4-yloxy)pyridin-3-yl)pyridazin-3-amine | 485 | C1 | 0.156 | 0.011 | 0.161 |
| 276 | N-(4-(5,7-difluoroquinolin-4-yloxy)phenyl)-4-phenylphthalazin-1-amine | 477.1 | B3 | 0.670 | 0.018 | 0.054 |
| 277 | 4-((4-((4-(4,5-dimethyl-1,3-thiazol-2-yl)-1-phthalazinyl)amino)phenyl)oxy)-7-quinolinecarbonitrile | 501 | B3 | 0.065 | 0.007 | 0.035 |
| 278 | 4-(5-chloro-2-pyridinyl)-N-(4-((6-(methyloxy)-4-quinolinyl)oxy)phenyl)-1-phthalazinamine | 506 | B3 | 0.082 | 0.004 | 0.011 |
| 279 | 4-(1,3-benzodioxol-5-yl)-N-(4-(thieno[3,2-b]pyridin-7-yloxy)phenyl)-1-phthalazinamine | 491 | A1 | 0.078 | 0.001 | 0.011 |
| 280 | N-(4-((7-(methyloxy)-1,5-naphthyridin-4-yl)oxy)phenyl)-4-(1H-pyrrolo[2,3-b]pyridin-5-yl)-1-phthalazinamine | 512.2 | A1 | 0.062 | 0.002 | 0.080 |
| 281 | 4,5-dimethyl-N-(4-((7-(methyloxy)-1,5-naphthyridin-4-yl)oxy)phenyl)-6-phenyl-3-pyridazinamine | 450 | C2 | 0.696 | 0.019 | 0.378 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 33 | 4-(4-chlorophenyl)-N-(4-(1,5-naphthyridin-4-ylthio)phenyl)-1-phthalazinamine | 492 | B2 | 0.022 | 0.003 | 0.002 |
| 282 | N-(4-((6,7-bis(methyloxy)-4-cinnolinyl)oxy)phenyl)-4-(4-chlorophenyl)-1-phthalazinamine | 536 | C1 | 25.000 | 0.189 | 1.200 |
| 283 | 4-(2-chloro-4-pyridinyl)-N-(4-((7-(methyloxy)-1,5-naphthyridin-4-yl)oxy)phenyl)-1-phthalazinamine | 507.2 | A1 | 0.100 | 0.010 | 0.343 |
| 284 | 4-(4-chlorophenyl)-N-(3-fluoro-4-((7-(methyloxy)-1,5-naphthyridin-4-yl)oxy)phenyl)-1-phthalazinamine | 524 | B3 | 0.019 | 0.007 | 0.011 |
| 285 | N-(4-(1,5-naphthyridin-4-ylthio)phenyl)-4-phenyl-1-phthalazinamine | 458 | B2 | 0.029 | 0.002 | 0.009 |
| 286 | 4-(4-chlorophenyl)-N-(4-((2-(3-methyl-1,2,4-oxadiazol-5-yl)thieno[3,2-b]pyridin-7-yl)oxy)phenyl)-1-phthalazinamine | 563 | B3 | 0.087 | 0.022 | 0.088 |
| 287 | 4-(4-ethynylphenyl)-N-(4-((7-(methyloxy)-1,5-naphthyridin-4-yl)oxy)phenyl)-1-phthalazinamine | 496 | | 0.061 | 0.013 | 0.060 |
| 288 | N-(4-((2-(3-methyl-1,2,4-oxadiazol-5-yl)thieno[3,2-b]pyridin-7-yl)oxy)phenyl)-4-phenyl-1-phthalazinamine | 529 | B3 | 0.302 | 0.039 | 0.828 |
| 289 | 4-(4-methyl-2-thienyl)-N-(4-(thieno[3,2-b]pyridin-7-yloxy)phenyl)-1-phthalazinamine | 467 | B3 | 0.068 | 0.011 | 0.073 |
| 290 | 4-(4-chlorophenyl)-N-(4-(7H-pyrrolo[2,3-d]pyrimidin-4-yloxy)phenyl)-1-phthalazinamine | 465 | B3 | 0.350 | 0.009 | 0.397 |
| 291 | 4-(2,2-difluoro-1,3-benzodioxol-5-yl)-N-(4-((7-(methyloxy)-1,5-naphthyridin-4-yl)oxy)phenyl)-1-phthalazinamine | 552 | A1 | 0.031 | 0.010 | 0.045 |
| 292 | N-(4-((6-(methyloxy)-4-quinolinyl)thio)phenyl)-4-phenyl-1-phthalazinamine | 487 | B3 | 0.144 | 0.011 | 0.012 |
| 293 | 4-(2,2-difluoro-1,3-benzodioxol-5-yl)-N-(4-(thieno[3,2-b]pyridin-7-yloxy)phenyl)-1-phthalazinamine | 527 | A1 | 0.266 | 0.006 | 0.045 |
| 45 | N-(4-((6-(1-methyl-1H-pyrazol-4-yl)-4-quinolinyl)oxy)phenyl)-4-phenyl-1-phthalazinamine | 521 | D3 | 0.079 | 0.030 | 0.056 |
| 43 | N-(4-((4-((4-phenyl-1-phthalazinyl)amino)phenyl)oxy)-6-quinolinyl)acetamide | 498 | D1 | 0.112 | 0.008 | 0.025 |
| 294 | 4-phenyl-N-(4-(4-quinolinylthio)phenyl)-1-phthalazinamine | 457 | B3 | +++ | +++ | +++ |
| 295 | N-(4-((5,7-difluoro-4-quinolinyl)thio)phenyl)-4-phenyl-1-phthalazinamine | 493 | B2 | 25.000 | +++ | +++ |
| 296 | (7-(4-(4-(4-methylthiophen-2-yl)phthalazin-1-ylamino)phenylthio)thieno[3,2-b]pyridin-2-yl)(morpholino)methanone | 594 | C1 | +++ | +++ | +++ |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 297 | 4-(4-chlorophenyl)-N-(4-(6-methoxyquinolin-4-ylthio)phenyl)phthalazin-1-amine | 522 | B3 | 0.036 | 0.031 | 0.014 |
| 298 | 4-(4-chloro-2-thienyl)-N-(4-((7-(methyloxy)-1,5-naphthyridin-4-yl)oxy)phenyl)-1-phthalazinamine | 513 | B3 | 0.014 | 0.023 | 0.027 |
| 299 | N-(4-((7-(methyloxy)-1,5-naphthyridin-4-yl)oxy)phenyl)-4-(3-methylphenyl)-1-phthalazinamine | 486 | B3 | 0.018 | 0.015 | 0.033 |
| 54 | N-(4-((7-(methyloxy)-4-quinolinyl)methyl)phenyl)-4-phenyl-1-phthalazinamine | 469 | | 0.176 | 0.020 | 0.028 |
| 300 | 4-ethyl-N-(4-((7-(methyloxy)-1,5-naphthyridin-4-yl)oxy)phenyl)-6-((4aR,8aS)-octahydro-2(1H)-isoquinolinyl)-3-pyridazinamine | 511 | B4 | 0.112 | 0.067 | 0.120 |
| 301 | N-(4-((7-bromo-1,5-naphthyridin-4-yl)thio)phenyl)-4-(4-chlorophenyl)-1-phthalazinamine | 570 | B3 | 0.035 | 0.063 | 0.029 |
| 302 | 4-(4-chlorophenyl)-N-(4-((2-(3-methyl-1,2,4-oxadiazol-5-yl)thieno[3,2-b]pyridin-7-yl)thio)phenyl)-1-phthalazinamine | 580 | B3 | | | |
| 303 | N-(4-((2-(3-methyl-1,2,4-oxadiazol-5-yl)thieno[3,2-b]pyridin-7-yl)thio)phenyl)-4-phenyl-1-phthalazinamine | 545 | B3 | 25.000 | 0.070 | 0.250 |
| 304 | 4-(5-chloro-2-pyridinyl)-N-(4-((7-(methyloxy)-1,5-naphthyridin-4-yl)thio)phenyl)-1-phthalazinamine | 523 | B3 | 0.013 | 0.019 | 0.008 |
| 305 | N-(4-((7-(methyloxy)-1,5-naphthyridin-4-yl)oxy)phenyl)-4-(4-methylphenyl)-1-phthalazinamine | 486 | B3 | | | |
| 306 | 4-(1,3-benzodioxol-5-yl)-N-(4-((7-(methyloxy)-1,5-naphthyridin-4-yl)oxy)phenyl)-1-phthalazinamine | 516.1 | A1 | 0.011 | 0.030 | 0.006 |
| 307 | 4-ethyl-N-(4-((7-(methyloxy)-1,5-naphthyridin-4-yl)oxy)phenyl)-6-(4-methylphenyl)-3-pyridazinamine | 464 | C1 | 0.022 | 0.006 | 0.023 |
| 308 | 4-(4-chlorophenyl)-N-(4-(1,5-naphthyridin-4-ylthio)phenyl)-1-phthalazinamine | 492 | B3 | 0.029 | 0.004 | 0.006 |
| 309 | N-(4-(1,5-naphthyridin-4-ylthio)phenyl)-4-phenyl-1-phthalazinamine | 458 | B3 | 0.054 | 0.003 | 0.021 |
| 310 | 4-phenyl-N-(4-(4-quinolinylthio)phenyl)-1-phthalazinamine | 457 | B3 | 0.209 | 0.017 | 0.011 |
| 311 | N-(4-((5,7-difluoro-4-quinolinyl)thio)phenyl)-4-phenyl-1-phthalazinamine | 493 | B2 | 25.000 | 0.093 | 0.055 |
| 312 | (7-(4-(4-(4-methylthiophen-2-yl)phthalazin-1-ylamino)phenylthio)thieno[3,2-b]pyridin-2-yl)(morpholino)methanone | 596 | B3 | 0.022 | 0.030 | 0.032 |
| 313 | morpholino(7-(4-(4-phenylphthalazin-1-ylamino)phenylthio)thieno[3,2-b]pyridin-2-yl)methanone | 576 | B3 | 0.091 | 0.056 | 0.076 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 314 | (7-(4-(4-(4-chlorophenyl)phthalazin-1-ylamino)phenylthio)thieno[3,2-b]pyridin-2-yl)(morpholino)methanone | 610 | B3 | 0.058 | 0.057 | 0.030 |
| 315 | 4-(4-chlorophenyl)-N-(4-(6-methoxyquinolin-4-ylthio)phenyl)phthalazin-1-amine | 521 | B3 | 0.036 | 0.031 | 0.014 |
| 316 | 4-(4-chloro-2-thienyl)-N-(4-((7-(methyloxy)-1,5-naphthyridin-4-yl)oxy)phenyl)-1-phthalazinamine | 512 | B3 | 0.014 | 0.023 | 0.027 |
| 317 | N-(4-((7-(methyloxy)-1,5-naphthyridin-4-yl)oxy)phenyl)-4-(3-methylphenyl)-1-phthalazinamine | 486 | A1 | 0.018 | 0.015 | 0.033 |
| 318 | N-(4-((2-(3-methyl-1,2,4-oxadiazol-5-yl)thieno[3,2-b]pyridin-7-yl)thio)phenyl)-4-phenyl-1-phthalazinamine | 545 | B3 | 25.000 | 0.070 | 0.250 |
| 319 | N-(4-((7-(methyloxy)-4-quinolinyl)methyl)phenyl)-4-phenyl-1-phthalazinamine | 469.2 | unique | 0.176 | 0.020 | 0.028 |
| 320 | 4-ethyl-N-(4-((7-(methyloxy)-1,5-naphthyridin-4-yl)oxy)phenyl)-6-((4aR,8aS)-octahydro-2(1H)-isoquinolinyl)-3-pyridazinamine | 511 | B4 | 0.112 | 0.067 | 0.120 |
| 321 | 4-ethyl-N-(4-((7-(methyloxy)-1,5-naphthyridin-4-yl)oxy)phenyl)-6-(1-piperidinyl)-3-pyridazinamine | 457 | B4 | 0.304 | 0.051 | 1.200 |
| 322 | 4-ethyl-N-(4-((7-(methyloxy)-1,5-naphthyridin-4-yl)thio)phenyl)-6-(4-methylphenyl)-3-pyridazinamine | 480 | B4 | 0.033 | 0.032 | 0.017 |
| 323 | 4-(4-chlorophenyl)-N-(4-((2-(3-methyl-1,2,4-oxadiazol-5-yl)thieno[3,2-b]pyridin-7-yl)thio)phenyl)-1-phthalazinamine | 579.1 | B3 | 25.000 | 25.000 | 0.131 |
| 324 | N-(4-((7-bromo-1,5-naphthyridin-4-yl)thio)phenyl)-4-(4-chlorophenyl)-1-phthalazinamine | 570 | B3 | 0.035 | 0.063 | 0.029 |
| 325 | 4-(5-chloro-2-pyridinyl)-N-(4-((7-(methyloxy)-1,5-naphthyridin-4-yl)thio)phenyl)-1-phthalazinamine | 523 | B3 | 0.013 | 0.019 | 0.008 |
| 326 | N-(4-((6-(methyloxy)-7-((phenylmethyl)oxy)-4-quinolinyl)oxy)phenyl)-4-phenyl-1-phthalazinamine | 577 | C2 | 0.026 | 0.039 | 0.060 |
| 327 | 4-(6-(methyloxy)-2-pyridinyl)-N-(4-(4-quinolinylthio)phenyl)-1-phthalazinamine | 488 | B3 | 0.118 | 0.014 | 0.017 |
| 328 | 4-(4-chlorophenyl)-N-(4-((7-(methyloxy)-4-quinolinyl)methyl)phenyl)-1-phthalazinamine | 503.2 | unique | 0.047 | 0.032 | 0.006 |
| 329 | 4-phenyl-N-(4-(1H-pyrrolo[2,3-b]pyridin-4-ylthio)phenyl)-1-phthalazinamine | 446 | B3 | 0.114 | 0.009 | 0.057 |
| 330 | 4-(4-chlorophenyl)-N-(4-(1H-pyrrolo[2,3-b]pyridin-4-ylthio)phenyl)-1-phthalazinamine | 480 | B3 | 0.038 | 0.009 | 0.016 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 331 | N-(4-((7-(methyloxy)-4-quinolinyl)thio)phenyl)-4-phenyl-1-phthalazinamine | 487 | B3 | 0.192 | 0.155 | 0.021 |
| 332 | 4-(4-chlorophenyl)-N-(4-(thieno[3,2-b]pyridin-7-ylthio)phenyl)-1-phthalazinamine | 497 | B3 | 0.016 | 0.003 | 0.001 |
| 333 | 4-(4-chlorophenyl)-N-(4-(quinolin-4-ylthio)phenyl)phthalazin-1-amine | 491 | B3 | 25.000 | 0.036 | 1.200 |
| 334 | 4-(4-chlorophenyl)-N-(4-(7-methoxyquinolin-4-ylthio)phenyl)phthalazin-1-amine | 521 | B3 | 0.049 | 0.067 | 0.018 |
| 335 | 6-(3-chlorophenyl)-4-ethyl-N-(4-(7-methoxy-1,5-naphthyridin-4-yloxy)phenyl)pyridazin-3-amine | 484 | C1 | 0.062 | 0.021 | 0.191 |
| 336 | N-(4-(1,5-naphthyridin-4-ylthio)phenyl)-4-(4-methylthiophen-2-yl)phthalazin-1-amine | 478 | B2 | 0.019 | 0.010 | 0.001 |
| 337 | N-(4-(7-methoxy-1,5-naphthyridin-4-yloxy)phenyl)-4-thiomorpholinophthalazin-1-amine | 497.1 | B3 | 0.076 | 0.015 | 0.229 |
| 338 | N-(4-(7-(1-methyl-1H-pyrazol-4-yl)quinolin-4-yloxy)phenyl)-4-phenylphthalazin-1-amine | 5212 | D3 | 0.005 | 0.009 | 0.005 |
| 339 | 4-phenyl-N-(4-(7-(thiophen-3-yl)quinolin-4-yloxy)phenyl)phthalazin-1-amine | 523.1 | D3 | 0.021 | 0.028 | 0.027 |
| 340 | N-(4-((1H-benzo[d]imidazol-1-yl)methyl)phenyl)-4-phenylphthalazin-1-amine | 428 | B3 | 25.000 | 25.000 | 1.200 |
| 341 | N-(4-((1H-benzo[d]imidazol-1-yl)methyl)phenyl)-4-(4-chlorophenyl)phthalazin-1-amine | 462 | B3 | 25.000 | 25.000 | 1.200 |
| 342 | 4-(4-chlorophenyl)-N-(4-(5,7-difluoroquinolin-4-ylthio)phenyl)phthalazin-1-amine | 527 | B2 | 0.189 | 0.045 | 0.044 |
| 343 | N-(4-(7-(furan-3-yl)quinolin-4-yloxy)phenyl)-4-phenylphthalazin-1-amine | 507.2 | D3 | 0.024 | 0.008 | 0.025 |
| 344 | N-(4-(7-(5-methylfuran-2-yl)quinolin-4-yloxy)phenyl)-4-phenylphthalazin-1-amine | 521.2 | D3 | 0.057 | 0.022 | 0.044 |
| 345 | 4-(4-chlorophenyl)-N-(4-(7-methoxyquinolin-4-yloxy)phenyl)phthalazin-1-amine | 505 | B2 | 0.040 | 0.024 | 0.013 |
| 346 | N-(4-(7-methoxy-1,5-naphthyridin-4-ylthio)phenyl)-4-(piperidin-1-yl)phthalazin-1-amine | 495 | B1 | 0.044 | 0.024 | 0.016 |
| 347 | N-(4-(6-methoxy-1,5-naphthyridin-4-yloxy)phenyl)-4-phenylphthalazin-1-amine | 472 | C2 | 0.067 | 0.010 | 0.039 |
| 348 | 4-(4-chlorophenyl)-N-(4-(6-methoxy-1,5-naphthyridin-4-ylthio)phenyl)phthalazin-1-amine | 522 | B2 | 0.057 | 0.023 | 0.012 |
| 349 | 4-(4-chlorophenyl)-N-(4-((2,3-dihydrobenzo[b][1,4]oxazin-4-yl)methyl)phenyl)phthalazin-1-amine | 479.2 | | 25.000 | 0.045 | 1.200 |
| 350 | N-(4-(7-methoxy-1,5-naphthyridin-4-yloxy)phenyl)- | 477 | A2 | 0.040 | 0.007 | 0.077 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| | 4-(3-methylisoxazol-5-yl)phthalazin-1-amine | | | | | |
| 351 | 7-(4-(4-(4-chlorophenyl)phthalazin-1-ylamino)phenylthio)thieno[3,2-b]pyridine-2-carbonitrile | 522.0, 524.0 | B3 | 0.008 | 0.003 | 0.053 |
| 352 | N-(4-(1H-pyrazolo[3,4-b]pyridin-4-ylthio)phenyl)-4-phenylphthalazin-1-amine | 447.1 | B3 | 0.074 | 0.001 | 0.055 |
| 353 | N-(4-(7-methoxy-1,6-naphthyridin-4-ylthio)phenyl)-4-phenylphthalazin-1-amine | 488 | B3 | 0.058 | 0.008 | 0.007 |
| 354 | 4-(4-chlorophenyl)-N-(4-(7-methoxy-1,6-naphthyridin-4-ylthio)phenyl)phthalazin-1-amine | 522 | B3 | 0.025 | 0.009 | 0.007 |
| 355 | 4-phenyl-N-(4-(thieno[3,2-b]pyridin-7-ylthio)phenyl)phthalazin-1-amine | 463 | B3 | 0.241 | 0.006 | 0.015 |
| 356 | 4-(4-fluorophenyl)-N-(4-(7-methoxy-1,5-naphthyridin-4-ylthio)phenyl)phthalazin-1-amine | 506 | A1 | 0.036 | 0.012 | 0.007 |
| 357 | N-(4-(7-methoxy-1,5-naphthyridin-4-ylthio)phenyl)-4-(4-methoxyphenyl)phthalazin-1-amine | 518 | A1 | 0.029 | 0.012 | 0.007 |
| 358 | N-(4-(1,5-naphthyridin-4-ylthio)phenyl)-4-ethyl-6-p-tolylpyridazin-3-amine | 450 | B4 | 0.049 | 0.006 | 0.035 |
| 359 | N-(4-(1H-pyrazolo[3,4-b]pyridin-4-ylthio)phenyl)-4-(4-chlorophenyl)phthalazin-1-amine | 481.1 | B3 | 0.012 | 0.017 | 0.013 |
| 360 | 4-(4-(4-(4-chlorophenyl)phthalazin-1-ylamino)phenylthio)-N-methylpicolinamide | 498.1 | B3 | 25.000 | 0.345 | 0.413 |
| 361 | 4-(4-(4-(4-chlorophenyl)phthalazin-1-ylamino)phenoxy)-N-methylpicolinamide | 482 | B3 | 0.245 | 0.173 | 0.220 |
| 362 | N-(4-(3H-imidazo[4,5-b]pyridin-7-ylthio)phenyl)-4-phenylphthalazin-1-amine | 447 | B3 | 0.066 | 0.092 | 0.105 |
| 363 | N-(4-(3H-imidazo[4,5-b]pyridin-7-ylthio)phenyl)-4-(4-chlorophenyl)phthalazin-1-amine | 481 | B3 | 0.019 | 0.036 | 0.032 |
| 364 | 4-(5-chloropyridin-2-yl)-N-(4-(7-methoxyquinolin-4-ylthio)phenyl)phthalazin-1-amine | 522 | B3 | 0.036 | 0.073 | 0.005 |
| 365 | 4-(5-chloropyridin-2-yl)-N-(4-(quinolin-4-ylthio)phenyl)phthalazin-1-amine | 492 | B3 | 0.016 | 0.011 | 0.003 |
| 366 | 4-(4-methylthiophen-2-yl)-N-(4-(thieno[3,2-b]pyridin-7-ylthio)phenyl)phthalazin-1-amine | 483 | B3 | 0.037 | 0.051 | 0.002 |
| 367 | N-(4-(7-methoxy-1,5-naphthyridin-4-yloxy)phenyl)-4-phenyl-6,7-dihydro-5H-cyclopenta[d]pyridazin-1-amine | 462.1 | C1 | 0.028 | 0.057 | 0.039 |
| 368 | N-(4-(7-methoxyquinolin-4-yloxy)phenyl)-4-phenyl-6,7-dihydro-5H-cyclopenta[d]pyridazin-1-amine | 461.2 | C1 | 0.040 | 0.063 | 0.021 |

TABLE 1-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 369 | N-(4-(6-bromocinnolin-4-yloxy)phenyl)-4-(4-chlorophenyl)phthalazin-1-amine | 556 | C1 | 25.000 | 3.003 | >1.200000 |
| 370 | 4-phenyl-N-(4-(pyrazolo[1,5-a]pyrimidin-7-yloxy)phenyl)phthalazin-1-amine | 431.2 | B3 | 0.505 | 0.594 | 0.757 |

EXAMPLE 371

Synthesis of 4-chloro-5,7-dimethoxyquinoline

Step 1: 5-((3,5-Dimethoxyphenylamino)methylene)-2,2-dimethyl-1,3-dioxane-4,6-dione In a dried 2-necked round bottom flask equipped with reflux condenser and inert atmosphere, 2,2-dimethyl-1,3-dioxane-4,6-dione (5.3 g, 37 mmol) was dissolved in triethyl orthoformate (37 ml, 221 mmol) and the mixture was stirred at 100° C. under nitrogen for 1.5 h. 3,5-dimethoxybenzenamine (5.6 g, 37 mmol) was added and heating continued for 4.5 h. The reaction mixture was cooled down to RT and poured into hexane (50 mL). The solid was filtered off and washed with hexane to afford 5-((3,5-dimethoxyphenylamino)methylene)-2,2-dimethyl-1,3-dioxane-4,6-dione as a light yellow solid. MS: W/z=[M+H]$^+$. 308.1 Calc'd for $C_{15}H_{17}NO_6$: 307.3.

Step 2: 5,7-Dimethoxyquinolin-4-ol

A solution of 5-((3,5-dimethoxyphenylamino)methylene)-2,2-dimethyl-1,3-dioxane-4,6-dione (9.23 g, 30.0 mmol) in diphenyl ether was heated at 200° C. for 20 min. It was cooled down to RT. Hexane was added and the mixture was stirred at RT for 30 mins. The solvent was removed to furnish 5,7-dimethoxyquinolin-4-ol as a light brown solid, which was used for next step without further purification. MS: m/z=[M+H]$^+$. 206.2 Calc'd for $C_{11}H_{11}NO_3$: 205.2.

Step 3: 4-Chloro-5,7-dimethoxyquinoline

To a mixture of crude 5,7-dimethoxyquinolin-4-ol (5.36 g, 26 mmol) and Hunig'sBase (9.1 ml, 52 mmol) in toluene, was added $POCl_3$ (29 ml, 313 mmol). The mixture was refluxed for 5 h. Excess $POCl_3$ was removed under reduced pressure and the mixture was azeotroped with toluene. The resultant gum was treated with sat. $NaHCO_3$ until no gas generated. The mixture was extracted with EtOAc, the organic extracts were combined and washed with sodium bicarbonate and solvent removed under reduced pressure. The crude product was purified via column chromatography on silica gel (RediSep 120 g column, gradient elution with 0-50% EtOAc/DCM) to afford 4-chloro-5,7-dimethoxyquinoline as a yellow solid. MS: m/z=[M+H]$^+$. 224.2 Calc'd for $C_{11}H_{10}ClN$: 223.7.

EXAMPLE 372

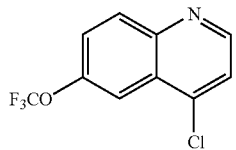

Synthesis of 4-Chloro-6(trifluoromethoxy)quinoline

Step 1: 2,2-Dimethyl-5-((4-(trifluoromethoxy)phenylamino)methylene)-1,3-dioxane-4,6-dione In a 48 mL sealed tube was dissolved 2,2-dimethyl-1,3-dioxane-4,6-dione (0.81 g, 5.6 mmol) in trimethyl orthoformate (5.6 mL). The mixture was heated to 100° C. and stirred for 2 h. To the mixture was added 4-(trifluoromethoxy)aniline (0.76 mL, 5.6 mmol) and it was stirred at 100° C. for 3 hours. The reaction was cooled to RT, diluted with hexane, filtered, and the filtered solids were air dried to yield 2,2-dimethyl-5-((4-(trifluoromethoxy)phenylamino)methylene)-1,3-dioxane-4,6-dione as a light yellow solid. MS [M+H]=332.0; Calc'd 331.2 for $C_{14}H_{12}F_3NO_5$.

Step 2: 6-(Trifluoromethoxy)quinolin-4(1H)-one

In a 50 mL round bottom flask with a reflux condenser attached was dissolved 2,2-dimethyl-5-((4-(trifluoromethoxy)phenylamino)methylene)-1,3-dioxane-4,6-dione (1.00 g, 3.02 mmol) in Ph2O (8.63 mL, 0.35 M). The mixture was heated to 250° C. in a heating mantle. At about 180° C., the reaction turned from a light yellow and homogeneous to an orange, then to a dark brown color and began to bubble, slowly at first and then more violently. Internal temperature of reaction went up to 230° C., although heating ceased at 180° C. Heating at 250° C. while stirring was continued for five minutes, and the reaction was cooled to RT, diluted with hexane, and the precipitate was filtered to yield 6-(trifluoromethoxy)quinolin-4(1H)-one as a crude brown solid. MS [M+H]=230.1; Calc'd 229.2 for $C_{10}H_6F_3NO_2$.

Step 3: 4-Chloro-6-(trifluoromethoxy)quinoline

In a 25 mL round bottom flask was dissolved 6-(trifluoromethoxy)quinolin-4(1H)-one (0.50 g, 2.18 mmol) in $POCl_3$(3.05 mL). A reflux condenser was attached and the reaction mixture was stirred at 130° C. for 3 hours. The reaction turned dark brown and became homogeneous. The reaction was cooled to RT, poured slowly into ice bath while stirring. A thick gum resulted, which was basified with 6N NaOH to give a dark brown solution. The solution was extracted into ethyl acetate, washed 1× water, 1× NaCl, dried with Na2SO4, filtered through fritted funnel, concentrated down. The curde material was purified using an Isco silica gel chromatography system eluting with a solvent gradient of 0-100% $CH_2Cl_2$:MeOH(90:10)/$CH_2Cl_2$. The product fractions were concentrated down to yield 4-chloro-6-(trifluoromethoxy)quinoline as an orange oil. MS [M+H]=248.0; Calc'd 247.6 for $C_{10}H_5ClF_3NO$.

EXAMPLE 373

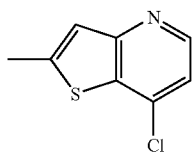

Synthesis of 7-Chloro-2-methylthieno[3,2-b]pyridine

A solution of n-butyllithium (0.71 ml, 1.77 mmol) in THF (20.0 mL) was cooled to −78° C. and 7-chlorothieno[3,2-b]pyridine (200 mg, 1.18 mmol) was added dropwise. The mixture stirred at −78° C. for 1 h to afford a yellow suspension. A solution of iodomethane (0.22 ml, 3.54 mmol) in THF (1.0 mL) was added dropwise via syringe, and the mixture stirred at −78° C. for 3 h.; LCMS showed completion of the reaction. The reaction was quenched with water and warmed to RT. The layers were separated, and the aqueous phase was extracted with DCM. The combined organic phases were washed with brine, dried over anhydrous sodium sulfate, filtered, and concentrated to afford a tan solid. This material was purified via column chromatography (RediSep 40 g column, gradient elution with 10-50% ethyl acetate-hexane) to afford 7-chloro-2-methylthieno[3,2-b]pyridine as white solid. MS [M+H]=184.1; Calc'd for $C_8H_6ClNS$: 183.7.

EXAMPLE 374

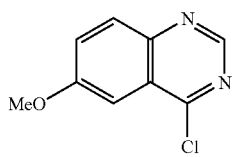

Synthesis of 4-Chloro-6-methoxyquinazoline

Step 1: 6-Methoxnquinazolin-4(3H)-one

Formamidine acetate (12.5 g, 119.6 mmol) was added to a stirred solution of 2-amino-5-methoxybenzoic acid (2.0 g, 119.6 mmol) in methoxy ethanol (40 mL) at RT. The reaction mixture was stirred at 140° C. (T oil bath) for ~17 h. LC/MS showed completion of the reaction. The reaction cooled to RT and concentrated in vacuo. Aq. $NaHCO_3$ solution was added to the concentrate and the precipitated solids were filtered (rinsing with water) to afford 6-methoxyquinazolin-4(3H)-one as off-white solid. MS [M+H]=177.1; Calc'd for $C_9H_8N_2O_2$: 176.2.

Step 2: 4-Chloro-6-methoxyquinazoline

A pressure resistant bottle was charged with 6-methoxyquinazolin-4(3H)-one (1.0 g, 5.68 mmol) and $POCl_3$(17.5 ml, 187.3 mmol). The resulting mixture was heated at 105° C. for 18 hours. The reaction mixture was cooled to RT and poured onto ice slurry while stirring heavily. The solution was quickly neutralized with 6N NaOH, and product extracted with DCM. The organic layer was collected, dried over sodium sulfate and concentrated to afford 4-chloro-6-methoxyquinazoline as tan solid. MS: [M+H]=194.9; Calc'd for $C_9H_7ClN_2O$: 194.6.

EXAMPLE 375

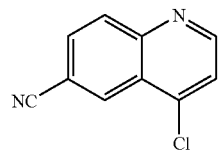

Synthesis of 4-Chloroquinoline-6-carbonitrile

A pyrex reaction tube was charged with $Pd(PPh_3)_4$(200 mg, 173 μmol), 4-chloro-6-iodoquinoline (1.00 g, 3454 μmol), zinc cyanide (406 mg, 3454 μmol) and DMF. The tube was purged with argon, sealed, and the heterogeneous mixture was stirred at 50° C. for 17 h. The mixture was poured into water and the resulting solids were filtered, washed with water, and dried. The crude material was purified by silica gel chromatography, 0-5% MeOH/DCM to provide 4-chloroquinoline-6-carbonitrile as a white solid. MS: [M+H]=189.

EXAMPLE 376

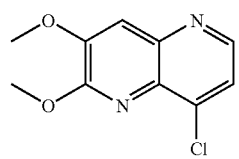

Synthesis of 8-Chloro-2,3-dimethoxy-1,5-naphthyridine

Step 1: 2,3-Dimethoxy-5-nitropyridine

A round bottom flask was charged with methanol under nitrogen. Freshly cut sodium (91 mg, 3977 μmol) was added, and the mixture was stirred at RT under nitrogen until the sodium had dissolved. 2-Chloro-3-methoxy-5-nitropyridine (500 mg, 2652 μmol) was added and the reaction mixture was stirred under nitrogen at RT. After ~15 min the mixture became heterogeneous and thick, and GC/MS analysis of a sample taken at 0.5 h indicated complete conversion to the desired product. The mixture was diluted with DCM and water and the layers were separated. The aqueous portion was extracted with additional DCM and the combined organics were dried, filtered and concentrated. The crude solid was passed through a silica plug using 5% MeOH/DCM. The filtrate was concentrated to provide 2,3-dimethoxy-5-nitropyridine as a light yellow solid. MS [M+H]=185.

Step 2: 2,3-Dimethoxy-5-nitropyridine

A stainless steel bomb was charged with 2,3-dimethoxy-5-nitropyridine (430 mg, 2335 μmol), 10% Pd/C (124 mg, 1168 μmol) and 4.7 mL EtOAc. The vessel was sealed and was purged with hydrogen once, before filling with hydrogen at a pressure of 2 attn. The reaction mixture was heated at 50° C. for 3 h. Upon cooling, the mixture was filtered through a pad of Celite, rinsing with EtOAc. The filtrate was concentrated and passed through a silica plug using 5% MeOH/DCM. The filtrate was concentrated to provide 5,6-dimethoxypyridin-3-amine as a peach colored oil that crystallized upon standing. GC/MS confirmed the correct mass to be [M+H]=155.

Step 3: (E)-5-((5,6-dimethoxapyridin-3-ylimino)methyl)-2,2-dimethyl-1,3-dioxane-4,6-dione A round bottom flask was charged with 2-methoxyacetaldehyde dimethyl acetal (2076 μl, 2076 μmol) and 2,2-dimethyl-1,3-dioxane-4,6-dione (299 mg, 2076 μmol). The flask was fitted with a reflux condenser and the mixture was heated at 100° C. for 2 h under nitrogen. 5,6-Dimethoxypyridin-3-amine (320 mg, 2076 μmol) was added, and within a minute a solid had precipitated out of solution. The heterogeneous mixture was heated at 100° C. for 10 min. The mixture was cooled to RT and the solids were filtered and washed with hexanes. (E)-5-((5,6-dimethoxypyridin-3-ylimino)methyl)-2,2-dimethyl-1,3-dioxane-4,6-dione was isolated as a yellow/orange solid. MS [M+H]=309.

Step 4: 6,7-dimethoxy-1,5-naphthyridin-4(1H)-one

A round bottom flask was charged with (E)-5-((5,6-dimethoxypyridin-3-ylimino)methyl)-2,2-dimethyl-1,3-dioxane-4,6-dione (450 mg, 1460 μmol) and 4.2 mL diphenyl ether. A reflux condenser was attached, and the solution was heated at 200° C. for 0.5 h. Upon cooling, hexane was added and the solids were filtered and washed with hexane. 6,7-dimethoxy-1,5-naphthyridin-4(1H)-one was isolated as a tan solid. MS [M+H]=207

Step 5: 8-chloro-2,3-dimethoxy-1,5-naphthynidine

A pyrex reaction tube was charged with 6,7-dimethoxy-1,5-naphthyridin-4(1H)-one (1.80 g, 8729 μmol) phosphorus oxychloride (8137 μl, 87295 μmol). The tube was sealed and the mixture was heated at 110° C. for 2 h. Upon cooling the mixture was poured onto ice and brought to pH 10 with dropwise addition of 6N NaOH. The aqueous portion was extracted with EtOAc three times. The extracts were combined, dried with MgSO₄, filtered and concentrated. The solids were triturated in hexane, filtered and dried to provide 8-chloro-2,3-dimethoxy-1,5-naphthyridine as a white solid. MS [M+H]=225.

EXAMPLE 377

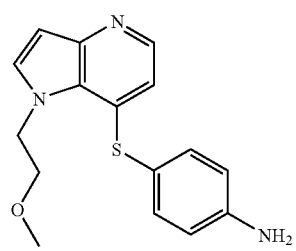

Synthesis of 4(1-(2-methoxyethyl)-1H-pyrrolo[3,2-b]pyridin-7-ylthio)benzenamine

Step 1: 1-(2-methoxyethyl)-7-(4-nitrophenylthio)-1H-pyrrolo[3,2-b]pyridine

A sealed vial was charged with potassium hydroxide (0.124 g, 2.21 mmol) and DMSO (5 mL). 7-(4-nitrophenylthio)-1H-pyrrolo[3,2-b]pyridine (0.150 g, 0.553 mmol) was added and the reaction was stirred for 45 minutes. 1-Bromo-2-methoxyethane (0.104 ml, 1.11 mmol) was added, the system was flushed with argon, and the reaction was stirred at RT for 2 hours. LC-MS indicated starting material remaining, so 1 eq. bromoether was added and the reaction stirred for two more hours. The reaction was diluted with water and extracted four times with DCM and twice with ethyl acetate. The combined organic layers were dried with sodium sulfate, filtered, and concentrated. The material was purified via column chromatography (gradient elution 0-5% MeOH:DCM) to afford 1-(2-methoxyethyl)-7-(4-nitrophenylthio)-1H-pyrrolo[3,2-b]pyridine as an orange oil that solidified under high vacuum. MS: M+H+=330.1

Step 2: 4-(1-(2-methoxyethyl)-1H-pyrrolo[3,2-b]pyridin-7-ylthio)benzenamine

A sealed vial was charged with 1-(2-methoxyethyl)-7-(4-nitrophenylthio)-1H-pyrrolo[3,2-b]pyridine (0.147 g, 0.446 mmol) and methanol (5 mL). Tin (II) chloride dihydrate (0.504 g, 2.23 mmol) was added and the reaction was stirred at 50° C. for 3 hours. The reaction was concentrated and dissolved in DCM. The solution was washed with saturated sodium bicarbonate solution, which was extracted with DCM. The combined organic layers were washed with water, dried with sodium sulfate, filtered, and concentrated. The material was purified via column chromatography (gradient elution 0-10% DCM:MeOH) to afford 4-(1-(2-methoxyethyl)-1H-pyrrolo[3,2-b]pyridin-7-ylthio)benzenamine as an orange oil that solidified under high vacuum. MS: M+H+= 300.1.

EXAMPLE 378

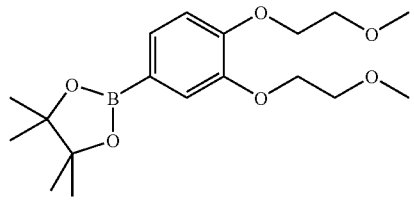

Synthesis of 2-(3,4-bis(2-methoxyethoxy)phenyl)-4,4,5,5-tetramethyl-1,3,2-dioxaborolane Step 1: 4-Bromo-1,2-bis(2-methoxyethoxy)benzene Potassium hydroxide (4.45 g, 79.4 mmol) was dissolved in DMSO (40 mL) and stirred for five minutes. 4-Bromobenzene-1,2-diol (3.00 g, 15.9 mmol) was added and the reaction was stirred for 45 minutes. 1-Bromo-2-methoxyethane (5.97 ml, 63.5 mmol) was added and the reaction stirred at RT for 18 hours. The reaction was diluted with water and extracted twice with ethyl acetate. The combined organic layers were dried with sodium sulfate, filtered, and concentrated. The material was purified via column chromatography (gradient elution 0-50% EtOAc:Hex) to afford 4-bromo-1,2-bis(2-methoxyethoxy)benzene as a clear oil. MS: M+H+=305.1.

Step 2: 2-(3,4-Bis(2-methoxyethoxy)phenyl)-4,4,5,5-tetramethyl-1,3,2-dioxaborolane A sealed tube was charged with 4-bromo-1,2-bis(2-methoxyethoxy)benzene (1.00 g, 3.28 mmol), bis(pinacolato)diboron (1.25 g, 4.92 mmol), potassium acetate (0.965 g, 9.83 mmol), and dioxane (10 mL). 1,1'-Bis(diphenylphosphino)ferrocene-palladium dichloride (0.240 g, 0.328 mmol) was added, the system was flushed with argon, and the tube was sealed. The reaction was stirred at 100° C. overnight. The reaction was filtered through celite and washed with DCM until solvent passing through was clear. The filtrate was concentrated, dissolved in hexanes and passed through a membrane filter. The filtrate was concentrated to afford 2-(3,4-bis(2-methoxyethoxy)phenyl)-4,4,5,5-tetramethyl-1,3,2-dioxaborolane as a brown oil. MS: M+H+=353.2.

EXAMPLE 379

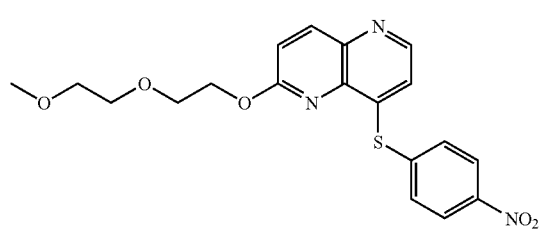

and

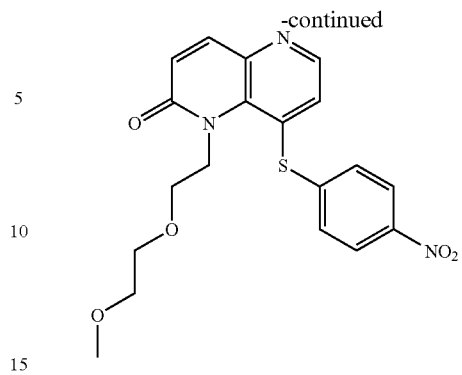

Synthesis of 2-(2-(2-Methoxyethoxy)ethoxy)-8-(4-nitrophenylthio)-1,5-naphthyridine and 1-(2-(2-Methoxyethoxy)ethyl)-8-(4-nitrophenylthio)-1,5-naphthyridin-2(1H)-one 8-(4-Nitrophenylthio)-1,5-naphthyridin-2(1H)-one (0.099 g, 0.33 mmol) and potassium carbonate (0.091 g, 0.66 mmol) were dissolved in ACN (5 mL) and stirred for 5 minutes. 1-Bromo-2-(2-methoxyethoxy)ethane (0.18 ml, 1.3 mmol) was added and the reaction was stirred overnight at 60° C. The reaction was cooled to RT, filtered, concentrated, dissolved in ethyl acetate, and washed with sat. sodium bicarbonate solution. The organic layer was dried with sodium sulfate, filtered, and concentrated to afford a mixture of 2-(2-(2-methoxyethoxy)ethoxy)-8-(4-nitrophenylthio)-1,5-naphthyridine and 1-(2-(2-methoxyethoxy)ethyl)-8-(4-nitrophenylthio)-1,5-naphthyridin-2(H1H)-one as a dark brown oil. MS: M+H+= 402.2.

EXAMPLE 380

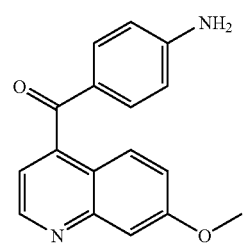

Synthesis of 4-aminophenyl)(7-methoxyquinolin-4-yl)methanone

Step 1: 7-Methoxy-4-(phenalthio)quinoline

A resealable tube under N₂ was charged with 4-chloro-7-methoxyquinoline (1.00 g, 5.16 mmol), thiophenol (0.528 ml, 5.16 mmol), cesium carbonate (2.52 g, 7.75 mmol) and DMSO (5 mL). The mixture was heated at 100° C. for 2 hrs. The crude reaction mixture was directly purified by silica gel chromatography using 0-10% CH₂Cl₂:MeOH to afford 7-methoxy-4-(phenylthio)quinoline as a off-white solid. MS: M+H+=268.0.

Step 2: 7-Methoxy-4-(phenylsulfinyl)quinoline

To 7-methoxy-4-(phenylthio)quinoline (1.38 g, 5.16 mmol) in CH$_2$Cl$_2$ (50 mL) at –78° C. was added m-CPBA (77%) (1.25 g, 7.23 mmol) portionwise. The mixture was allowed to slowly warm to RT (3 hrs). The reaction mixture was diluted with CH$_2$Cl$_2$ then neutralized with NaHCO$_3$ (sat.). The aqueous phase was extracted three times with DCM then the organic layer was dried over Na$_2$SO$_4$, filtered, and concentrated in vacuo. The crude mixture was purified by silica gel chromatography using 0-10% CH$_2$Cl$_2$:MeOH to afford 7-methoxy-4-(phenylsulfinyl)quinoline as a off-white foam. MS: M+H+=284.0.

Step 3: (7-Methoxyquinolin-4-yl)(4-nitrophenyl)methanol

To a solution of 7-methoxy-4-(phenylsulfinyl)quinoline (0.232 g, 0.819 mmol) in THF (6 mL) at –78° C. was added phenylmagnesium chloride (2.0 M in THF) (0.819 ml, 1.64 mmol). After 5 min, the solution was warmed to RT for 15 minutes. The solution was then cooled to –78° C. and 4-nitrobenzaldehyde (0.371 g, 2.46 mmol) was added in one portion. After 5 min, the solution was warmed to RT. After 1 hr at RT, the reaction was quenched with saturated NH$_4$Cl. The mixture was diluted with CH$_2$Cl$_2$ and washed with water and brine. The organic fraction was dried with Na$_2$SO$_4$ and concentrated in vacuo. The yellow residue was purified by silica gel chromatography using 20-100% Hexanes:EtOAc to afford (7-methoxyquinolin-4-yl)(4-nitrophenyl)methanol as a white solid. MS: M+H+=311.2.

Step 4: (7-Methoxyquinolin-4-yl)(4-nitrophenyl)methanone

A mixture of (7-methoxyquinolin-4-yl)(4-nitrophenyl)methanol (220 mg, 0.709 mmol) and manganese dioxide (247 mg, 2.84 mmol) in CHCl$_3$ (20 mL) was heated to 50° C. After 3 hrs, the mixture was cooled to RT and filtered over a silica plug to afford (7-methoxyquinolin-4-yl)(4-nitrophenyl)methanone as a yellow solid that was advanced without further purification. MS: M+H+=309.1.

Step 5: (4-aminophenyl)(7-methoxyquinolin-4-yl)methanone

A mixture of (7-methoxyquinolin-4-yl)(4-nitrophenyl)methanone (55 mg, 0.18 mmol) and palladium on carbon, 10% (57 mg, 0.54 mmol) in EtOAc (5 mL) and MeOH (0.5 mL) at RT was exposed to an atmosphere of Hydrogen (balloon). After 2 hrs, crude LCMS showed complete conversion to (4-aminophenyl)(7-methoxyquinolin-4-yl)methanone with a trace amount of corresponding alcohol. The material was filtered through a plug of celite, concentrated in vacuo, and advanced without further purification. MS: M+H+=279.1.

EXAMPLE 381

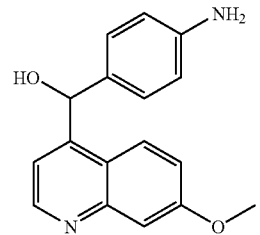

Synthesis of (4-aminophenyl)(7-methoxyquinolin-4-yl)methanol

A mixture of (7-methoxyquinolin-4-yl)(4-nitrophenyl)methanone (96 mg, 0.31 mmol) and palladium on carbon, 10% (99 mg, 0.93 mmol) in EtOAc (6 mL) and MeOH (2 mL) at RT was exposed to an atmosphere of hydrogen (balloon). Crude LCMS after 8 hrs showed complete conversion to (4-aminophenyl)(7-methoxyquinolin-4-yl)methanol with trace amounts of the corresponding keto-aniline. The material was filtered through a plug of celite and concentrated in vacuo to afford crude (4-aminophenyl)(7-methoxyquinolin-4-yl)methanol as a white foam that was advanced without further purification. MS: M+H+=281.1.

EXAMPLE 382

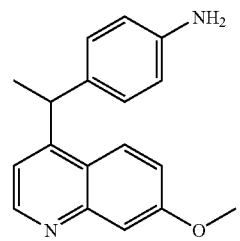

Synthesis of 4-(1-(7-methoxyquinolin-4-yl)ethyl)benzenamine

Step 1: 7-Methoxy-4-(1-(4-nitrophenyl)vinyl)quinoline

To a mixture of methyltriphenylphosphonium chloride (0.54 g, 1.7 mmol) in THF (10 mL) at –78° C. was added n-butyllithium, 2.5 M in hexanes (0.80 ml, 2.0 mmol). After 20 min, a mixture of (7-methoxyquinolin-4-yl)(4-nitrophenyl)methanone (0.177 g, 0.57 mmol) in THF (5 mL) was slowly added. After 10 min, the mixture was allowed to warm to RT. The reaction was quenched with saturated aqueous NH$_4$Cl. The mixture was diluted with EtOAc and washed with water and brine. After drying the organic fraction with Na$_2$SO$_4$, the solvent was removed in vacuo and the residue purified by silica gel chromatography using 40-100% hexanes:EtOAc to afford 7-methoxy-4-(1-(4-nitrophenyl)vinyl) quinoline as a yellow foam. MS: M+H+=307.1.

Step 2:
4-(1-(7-Methoxyquinolin-4-yl)ethyl)benzenamine

A mixture of 7-methoxy-4-(1-(4-nitrophenyl)vinyl)quinoline (0.146 g, 0.477 mmol) and Palladium on carbon, 10% (0.152 g, 1.43 mmol) in EtOAc (10 mL) and MeOH (1 mL) at RT was exposed to an atmosphere of Hydrogen (balloon). After 3 hrs, the mixture was filtered through celite and concentrated in vacuo to afford 4-(1-(7-methoxyquinolin-4-yl) ethyl)benzenamine as a white foam. MH+=279.1.

EXAMPLE 383

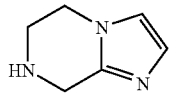

Synthesis of
5,6,7,8-Tetrahydroimidazo[1,2-a]pyrazine

Step 1: Imidazo[1,2-a]pyrazine

A round bottom set up with reflux condenser was charged with pyrazin-2-amine (1000 mg, 10.52 mmol), 2-chloroacetaldehyde (~50% wt) (2.03 ml, 31.55 mmol), and EtOH (23 mL) and heated under reflux overnight. Next day LC/MS showed completion. The mixture was concentrated and passed through a plug of silica (solvent used: 1% MeOH/DCM) to afford imidazo[1,2-a]pyrazine as off-white solid. MS [M+H]=120.1; Calc'd for $C_6H_5N_3$: 119.1

Step 2: 5,6,7,8-Tetrahydroimidazo[1,2-a]pyrazine

Imidazo[1,2-a]pyrazine (250 mg, 2.1 mmol) and palladium on carbon (10%) (55.8 mg, 0.53 mmol) were placed in a pressure resistant bottle and suspended under nitrogen in 0.5M HCl/EtOH. The mixture was stirred under at 45 psi $H_2$ for 16 hrs. LC/MS showed completion. The next day, the reaction mixture was passed through celite cake. The filtrate was concentrated under reduced pressure to afford a tan solid. This was used directly without further purification. MS: [N+H]=124.2; Calc'd for $C_6H_9N_3$: 123.2.

EXAMPLE 384

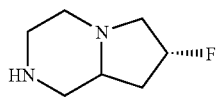

Synthesis of
(7R)-7-Fluoro-octahydropyrrolo[1,2-a]pyrazine

Step 1: (2S,4R)- and (2R,4R)
4-Fluoropyrrolidine-2-methyl ester

A round bottom flask was charged with (2S,4R)-4-fluoropyrrolidine-2-carboxylic acid (300 mg, 2254 µmol) and 22 mL MeOH. The heterogeneous mixture was cooled to 0° C. under nitrogen, and thionyl chloride (181 µl, 2479 µmol) was added dropwise. The reaction mixture was allowed to warm slowly to RT, and stirring was continued overnight at 65° C. The mixture was concentrated under high vacuum to provide methyl 4-fluoropyrrolidine-2-carboxylate hydrochloride as a mixture of the (2S,4R) and (2R,4R) diastereomers, confirmed by $^1H$ and $^{13}C$ NMR.

Step 2: (2S,4R)- and (2R,4R)-Methyl 1-(2-(((9H-fluoren-9-yl)methoxy)carbonyl)acetyl)-4-fluoropyrrolidine-2-carboxylate A pyrex reaction tube was charged with (2S,4R), (2R,4R)-methyl 4-fluoropyrrolidine-2-carboxylate hydrochloride (350 mg, 1906 µmol), 1H-benzo[d][1,2,3]triazol-1-ol (309 mg, 2287 µmol), 2-(((9H-fluoren-9-yl)methoxy)carbonyl) acetic acid (567 mg, 1906 µmol), N-ethyl-N-isopropylpropan-2-amine (996 µL, 5719 µmol) and 7.6 mL DMF. The mixture was stirred for 5 min at RT, and benzotriazole-1-yl-oxy-tris-(dimethylamino)-phosphonium hexafluorophosphate (1012 mg, 2287 µmol) was added, and the mixture was stirred at RT overnight. The mixture was diluted with DCM and washed with water. The organic portion was dried with $MgSO_4$, filtered, concentrated, and then was concentrated twice from toluene to remove DMF. The crude oil was purified by silica gel chromatography DCM to 5% MeOH/DCM to provide (2S,4R), (2R,4R)-methyl 1-(2-(((9H-fluoren-9-yl) methoxy)carbonyl)acetyl)-4-fluoropyrrolidine-2-carboxylate as a waxy solid. MS: [M+H]=427.

Step 3: (7R)-7-Fluoro-hexahydropyrrolo[1,2-a]pyrazine-1,4-dione

A scintillation vial was charged with (2S,4R), (2R,4R)-methyl 1-(2-(((9H-fluoren-9-yl)methoxy)carbonyl)acetyl)-4-fluoropyrrolidine-2-carboxylate (815 mg, 1911 µmol), 19 mL MeOH and piperidine (946 µl, 9556 µmol). The mixture was stirred at RT overnight The mixture was concentrated, dissolved in DCM/MeOH and purified by silica gel chromatography, 50-100% 90/10/1 DCM/MeOH/$NH_4OH$ in DCM. (7R)-7-fluoro-hexahydropyrrolo[1,2-a]pyrazine-1,4-dione was isolated as a white solid, and confirmed by $^1H$-NMR.

Step 4:
(7R)-7-Fluoro-octahydropyrrolo[1,2-a]pyrazine

A pressure bottle was charged with (7R)-7-fluoro-hexahydropyrrolo[1,2-a]pyrazine-1,4-dione (200 mg, 1162 µmol) and 4.6 mL THF, and the bottle was purged with nitrogen and cooled to 0° C. Lithium aluminum hydride (2323 µl, 2323 µmol) was added. The mixture was allowed to warm to RT, and was then heated at reflux for 4 h. The reaction was cooled to 0° C. and 1 mL water was added carefully, followed by 1 mL 6N NaOH. The mixture was stirred for 15 min, and was filtered through a pad of Celite, washing with EtOAc. The filtrate was concentrated and a sample was analyzed by H-NMR and GC/MS: [M+H]=145.

EXAMPLE 385

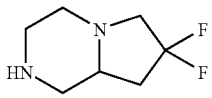

Synthesis of 7,7-Difluoro-octahydropyrrolo[1,2-a]pyrazine

Step 1: (R)-1-Tert-butyl 2-methyl 4,4-difluoropyrrolidine-1,2-dicarboxylate A pyrex reaction tube was charged with (R)-1-tert-butyl 2-methyl 4-oxopyrrolidine-1,2-dicarboxylate (750 mg, 3083 µmol) and 12.3 mL DCM, and the solution was cooled to 0° C. under nitrogen. DAST (1018 µl, 7708 µmol) was added dropwise, and the mixture was allowed to warm to RT. The reaction was quenched after 3 h by careful addition of saturated NaHCO₃. After 5 min, the layers were separated, the aqueous was extracted with DCM, and the combined organics were dried, filtered and concentrated. The crude oil was purified by silica gel chromatography, 10-50% EtOAc/hex, to provide (R)-1-tert-butyl 2-methyl 4,4-difluoropyrrolidine-1,2-dicarboxylate as a yellow oil. Mass was confirmed by GC/MS: [M+H]=266.

Step 2: Crude (S)-methyl-4,4-difluoronyrrolidine-2-carboxylate TFA salt

A round-bottom flask was charged with (R)-1-tert-butyl 2-methyl 4,4-difluoropyrrolidine-1,2-dicarboxylate (675 mg, 2545 µmol), 10.2 mL DCM and trifluoroacetic acid (980 µl, 12724 µmol). The mixture was stirred at RT. After 6 h, TLC (50% hex/EtOAc, KMnO4 stain) indicated complete conversion. The mixture was concentrated, and the crude (S)-methyl-4,4-difluoropyrrolidine-2-carboxylate TFA salt was use as is.

Step 3: (R)-Methyl 1-(2-(((9H-fluoren-9-yl)methoxy)carbonyl)acetyl)-4,4-difluoropyrrolidine-2-carboxylate A round bottom flask was charged with Fmoc-glycine (756 mg, 2543 µmol), 1H-benzo[d][1,2,3]triazol-1-ol (412 mg, 3052 µmol), (S)-methyl-4,4-difluoropyrrolidine-2-carboxylate TFA salt (710 mg, 2543 µmol), Hunig'sBase (2221 µl, 12717 µmol) and 10.2 mL DMF. The mixture was stirred for 5 min at RT, and benzotriazole-1-yl-oxy-tris-(dimethylamino)-phosphonium hexafluorophosphate (1350 mg, 3052 µmol) was added. The reaction mixture was stirred overnight at RT. The solution was diluted with DCM and washed with water. The organic layer was dried, filtered, and concentrated. The crude oil was purified by silica gel chromatography, 0-5% MeOH/DCM to provide (R)-methyl 1-(2-(((9H-fluoren-9-yl)methoxy)carbonyl)acetyl)-4,4-difluoropyrrolidine-2-carboxylate. MS: [M+H]=445.

Step 4: (S)-7,7-Difluoro-hexahydropyrrolo[1,2-a]pyrazine-1,4-dione

A round bottom flask was charged with (R)-methyl 1-(2-(((9H-fluoren-9-yl)methoxy)carbonyl)acetyl)-4,4-difluoropyrrolidine-2-carboxylate (1.10 g, 2475 µmol) and 25 mL MeOH. Piperidine (1225 µl, 12375 µmol) was added, and the mixture was stirred at RT overnight. The mixture was concentrated and purified by silica gel chromatography, DCM in 90/10 DCM/MeOH to provide (S)-7,7-difluoro-hexahydropyrrolo[1,2-a]pyrazine-1,4-dione as a white solid. GC/MS: [M+H]=191.

Step 5: 7,7-Difluoro-octahydropyrrolo[1,2-a]pyrazine

A pressure bottle was charged with (S)-7,7-difluoro-hexahydropyrrolo[1,2-a]pyrazine-1,4-dione (350 mg, 1841 µmol) and THF under nitrogen, and the solution was cooled to 0° C. under nitrogen. Lithium aluminum hydride (3681 µl, 3681 µmol) was added, the mixture was allowed to warm to RT, followed by heating at reflux for 3 h. 2 mL of water was carefully added, followed by 2 mL of 6N NaOH. After stirring for 10 min, the mixture was filtered through Celite and washed with EtOAc. The filtrate was concentrated. GC/MS: [M+H]=163.

EXAMPLE 386

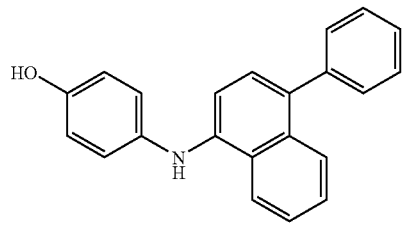

Synthesis of 4(4-Phenylnaphthalen-1-ylamino)phenol

Step 1: 4-phenylnaphthalen-1-amine

A pressure bottle was charged with 4-bromonaphthalen-1-amine (500 mg, 2251 µmol), phenylboronic acid (357 mg, 2927 µmol), PdCl₂(dppf)-CH₂Cl₂ adduct (91.9 mg, 113 µmol), 2.0 M sodium carbonate (2251 µl, 4503 µmol) and 9.0 mL of dioxane. The bottle was sealed and the mixture was heated at 85° C. for 2 h. LCMS showed desired product as the major component. The mixture was diluted with DCM and washed with water. The organic portion was dried, filtered and concentrated. The crude material was purified by silica gel chromatography, DCM to 2% MeOH/DCM to provide 4-phenylnaphthalen-1-amine. MS: [M+H]=220.

Step 2: N-(4-methoxyphenyl)-4-phenylnaphthalen-1-amine

A pyrex reaction tube was charged with sodium tert-butoxide (239 mg, 2490 µmol), Pd2(dba)₃(81.4 mg, 88.9 µmol), S-Phos (146 mg, 356 µmol), 1-bromo-4-methoxybenzene (333 mg, 1779 µmol), 4-phenylnaphthalen-1-amine (390 mg, 1779 µmol) and dioxane. The tube was sealed and the mixture was stirred at 100° C. for 2 h. LCMS showed complete conversion to product. The mixture was diluted with DCM and washed with water. The organic portion was dried, filtered and concentrated. The crude material was passed through a plug of silica gel using 50% EtOAc/hex and the filtrate was concentrated to provide the desired product. MS: [M+H]=326.

Step 3: 4-(4-phenylnaphthalen-1-ylamino)phenol

A round bottom flask was charged with N-(4-methoxyphenyl)-4-phenylnaphthalen-1-amine (600 mg, 1844 µmol) and 6 mL 1:1 HBr (100 µl, 1844 µmol) and HOAc (106 µl, 1844 µmol). The flask was fitted with a reflux condenser and the mixture was heated at 140° C. After 1 h, LCMS showed ~50% conversion to desired product. Heating was continued for another 5 h. Upon cooling, the mixture was brought to neutral pH by addition of 6 N NaOH and extracted with DCM. The organic portion was dried, filtered and concentrated. The crude material was purified by silica gel chromatography, 0-50% EtOAc/hex to provide 4-(4-phenylnaphthalen-1-ylamino)phenol. MS: [M+H]=312.

EXAMPLE 387

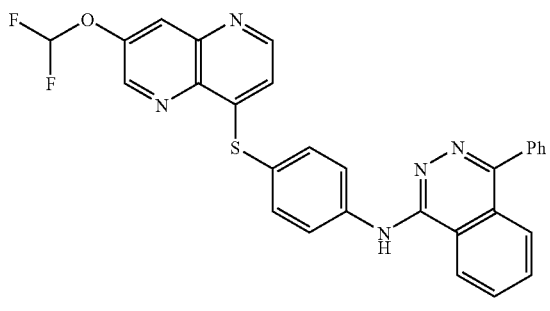

Synthesis of N-(4(7-(difluoromethoxy)-1,5-naphthyridin-4-ylthio)phenyls phenylphthalazin-1-amine

Step 1: 8-(4-(4-phenylphthalazin-1-ylamino)phenylthio)-1,5-naphthyridin-3-ol A reaction vial was charged with N-(4-(7-methoxy-1,5-naphthyridin-4-ylthio)phenyl)-4-phenylphthalazin-1-amine (40 mg, 82 µmol), HBr (891 µl, 16408 µmol), and acetic acid (939 µl, 16408 µmol). The vial was sealed, and the reaction mixture was stirred at 85° C. for 2 hrs. Upon cooling, LC/MS analysis showed a mass ion peak corresponding to N-(4-(7-methoxy-1,5-naphthyridin-4-ylthio)phenyl)-4-phenylphthalazin-1-amine (40 mg, 82 µmol). The reaction mixture was poured into an ice-cooled aqueous solution of sodium bicarbonate. Extraction of the product was attempted with DCM. However, the product seemed insoluble in DCM and was present in both the aqueous and organic layers, so all liquid was removed in vacuo. The resulting white solid was taken up in water and filtered. The filtrate was washed several times with water, and the resulting yellow solid was analyzed by LCMS. LCMS analysis showed clean 8-(4-(4-phenylphthalazin-1-ylamino)phenylthio)-1,5-naphthyridin-3-ol. The crude material was carried forward.

Step 2: N-(4-(7-(Difluoromethoxy)-1,5-naphthyridin-4-ylthio)phenyl)-4-phenylphthalazin-1-amine DMF (338 µl, 84 µmol) and water (68 µl, 84 µmol) were added to a mixture of cesium carbonate (39 mg, 118 µmol), sodium chlorodifluoroacetate (30 mg, 194 µmol), and 8-(4-(4-phenylphthalazin-1-ylamino)phenylthio)-1,5-naphthyridin-3-ol (40 mg, 84 µmol) in a resealable tube. The tube was sealed and heated to 100° C. for about 1.5 hrs, and then reaction progress was checked by LCMS. Conversion to N-(4-(7-(difluoromethoxy)-1,5-naphthyridin-4-ylthio)phenyl)-4-phenylphthalazin-1-amine was low, so the reaction mixture was heated to 100° C. for an additional 20 hours and again checked by LCMS. LCMS analysis showed mass peak corresponding to N-(4-(7-(difluoromethoxy)-1,5-naphthyridin-4-ylthio)phenyl)-4-phenylphthalazin-1-amine as the major peak. The reaction mixture was diluted with water. A light tan precipitate formed and was filtered through a 0.45 uM membrane filter. The precipitate was taken up in minimal DMSO and methanol and purified by preparative HPLC{Gilson; 15-85% (0.1% TFA in CH$_3$CN) in H$_2$O over 20 min}. Clean fractions were combined and neutralized with saturated aqueous NaHCO$_3$ then extracted with ethyl acetate, dried over MgSO$_4$, filtered and concentrated to dryness in vacuo to afford pure N-(4-(7-(difluoromethoxy)-1,5-naphthyridin-4-ylthio)phenyl)-4-phenylphthalazin-1-amine as a white solid.

EXAMPLE 388

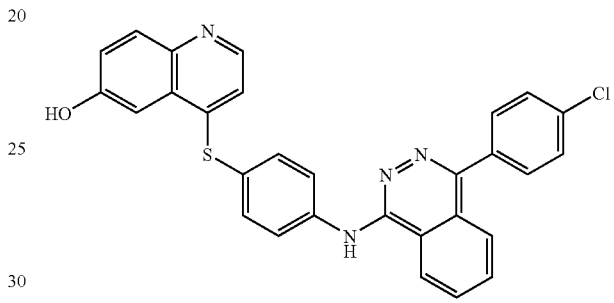

Synthesis of 4-(4-(4-(4-Chlorophenyl)phthalazin-1-ylamino)phenylthio)quinolin-6-ol A flask was charged with 4-(4-chlorophenyl)-N-(4-(6-methoxyquinolin-4-ylthio)phenyl)phthalazin-1-amine (0.325 g, 0.624 mmol), AcOH (5.71 ml, 99.8 mmol) and HBr (5.42 ml, 99.8 mmol). The mixture was stirred at 85° C. for 2 h, then cooled to RT and quenched with saturated aqueous NaHCO$_3$ to precipitate a solid. The solid was filtered, washed with water and dried to give 4-(4-(4-(4-chlorophenyl)phthalazin-1-ylamino)phenylthio)quinolin-6-ol as a light yellow solid. MS: m/z=[M+H]$^+$. 508.0 Calc'd for C$_{29}$H$_{19}$ClN$_4$OS: 507.0.

EXAMPLE 389

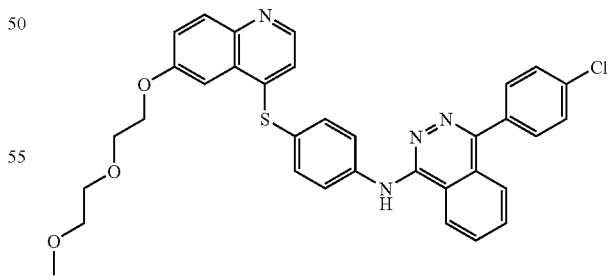

Synthesis of 4-(4-Chlorophenyl)-N-(4-(6-(2-(2-methoxyethoxy)ethoxy)quinolin-4-ylthio) phenyl) phthalazin-1-amine To a mixture of 4-(4-(4-(4-chlorophenyl)phthalazin-1-ylamino)phenylthio)quinolin-6-ol (0.054 g, 0.11 mmol) and potassium carbonate (0.059 g, 0.43 mmol) in DMF was added 1-bromo-2-(2-methoxyethoxy)ethane (0.057 ml, 0.43 mmol), the resulting mixture was stirred at 80° C. for 1 h. The crude product was purified via column chromatography on silica gel (RediSep 40 g column, gradient elution with 0-60% (EtOAc-DCM) to afford 4-(4-chlorophenyl)-N-(4-(6-(2-(2-methoxyethoxy)ethoxy)quinolin-4-ylthio)phenyl)phthalazin-1-amine as a light yellow solid. MS: m/z [M+H]⁺. 610.0 Calc'd for C$_{34}$H$_{29}$ClN$_4$O$_3$S: 609.1.

EXAMPLE 390

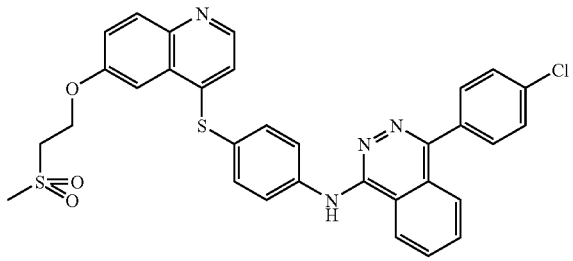

Synthesis of 4-(4-Chlorophenyl)-N-(4-(6-(2-(methylsulfonyl)ethoxy)quinolin-4-ylthio) phenyl)phthalazin-1-amine To a solution of 4-(4-(4-(4-chlorophenyl)phthalazin-1-ylamino)phenylthio)quinolin-6-ol (0.062 g, 0.12 mmol) in THF at 0° C., was added NaH (0.018 g, 0.73 mmol). The mixture was stirred at 0° C. for 30 minutes. 1-Chloro-2-(methylsulfonyl)ethane (0.035 g, 0.24 mmol) and trace amount of NaI were added. The mixture was stirred and warmed to RT for 15 h. The reaction was quenched with sat. NH$_4$Cl, and extracted with DCM. The combined organic layers were washed with brine, dried, filtered and concentrated. The crude product was purified via column chromatography on silica gel (RediSep 40 g column, gradient elution with 0-50% (90:10:1 DCM/MeOH/NH$_4$OH-DCM) to afford 4-(4-chlorophenyl)-N-(4-(6-(2-(methylsulfonyl)ethoxy)quinolin-4-ylthio)phenyl)phthalazin-1-amine as a light yellow solid. MS: m/z=[M+H]⁺. 614.0 Calc'd for C$_{32}$H$_{25}$ClN$_4$O$_3$S$_2$: 613.1.

EXAMPLE 391

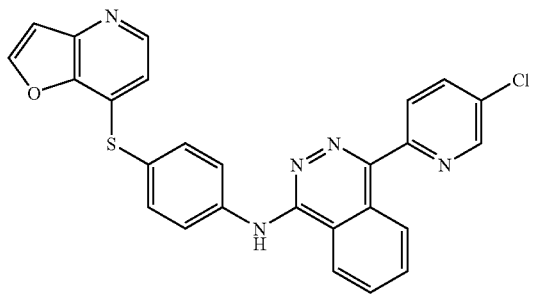

Synthesis of 4-(5-Chloropyridin-2-yl)-N-(4-(furo[3,2-b]pyridin-7-ylthio)phenyl)phthalazin-1-amine A resealable tube was charged with 1-chloro-4-(5-chloropyridin-2-yl)phthalazine (0.095 g, 0.34 mmol), 4-(2-(trimethylsilyl)furo[3,2-b]pyridin-7-ylthio)benzenamine (0.090 g, 0.29 mmol) and 2-butanol (3.0 mL). The system was flushed with argon, and the tube was sealed. The mixture stirred at 100° C. for 2 h. LC-MS showed starting aniline and hydrolyzed phthalazine, so 90 mg of chlorophthalazine was added and the reaction was stirred for 1 h at 100° C. The reaction was concentrated, re-dissolved in THF, and TBAF (1.0 M in THF) (0.29 ml, 0.29 mmol) was added. The reaction was stirred at 60° C. overnight. The reaction was concentrated and purified via Gilson HPLC (gradient elution 10-90% MeCN:H$_2$O). The clean fractions were partitioned between DCM and saturated sodium bicarbonate solution and the layers were separated. The aqueous layer was extracted with DCM and the combined organic layers were dried with sodium sulfate, filtered, and concentrated to afford 4-(5-chloropyridin-2-yl)-N-(4-(furo[3,2-b]pyridin-7-ylthio)phenyl)phthalazin-1-amine as a yellow solid. MS: M+H+=482.1.

EXAMPLE 392

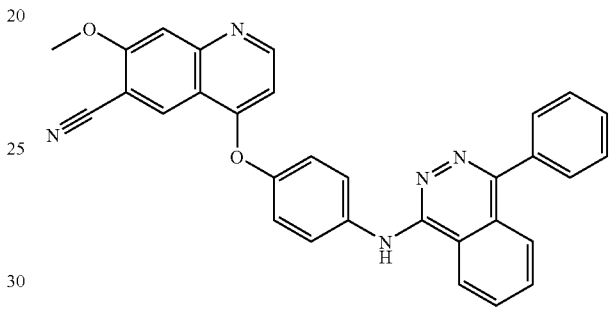

Synthesis of 7-Methoxy-4-(4-(4-phenylphthalazin-1-ylamino)phenoxy)quinoline-6-carbonitrile 7-Methoxy-4-(4-(4-phenylphthalazin-1-ylamino)phenoxy)quinoline-6-carboxamide (125 mg, 243 μmol) and thionyl chloride (10 ml, 24341 μmol) were combined and heated to 80° C. for 3 hours. Thionyl chloride was then removed under vacuum. The mixture was then made basic with sat. sodium bicarbonate and extracted with DCM. The organic extracts were combined, dried with sodium sulfate, filtered and concentrated. The product was purified by silica gel chromatography using a 0 to 70% gradient of 90/10/1 (DCM/methanol/ammonium hydroxide) in DCM. MS: M+H+=496.

EXAMPLE 393

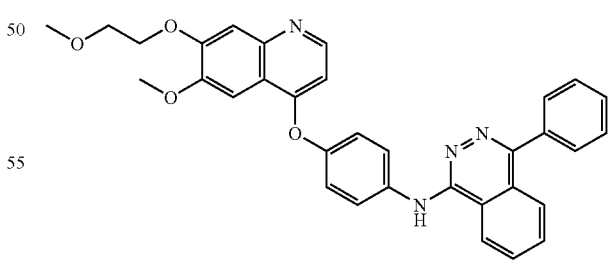

Synthesis of N-(4-(6-Methoxy-7-(2-methoxyethoxy)quinolin-4-yloxy)phenyl)-4-phenylphthalazin-1-amine 6-Methoxy-4-(4-(4-phenylphthalazin-1-ylamino)phenoxy)quinolin-7-ol (45 mg, 92 μmol) and cesium carbonate (33 mg, 102 μmol) were combined in DMF (2 Ml) and stirred for 5 min. 1-Bromo-2-methoxyethane (9.6 µl, 204 µmol) was added and the mixture was stirred at RT for 12 hours. DMF was then removed under vacuum overnight. The crude material was purified by silica gel chromatography using 0 to 100% ethyl acetate in hexane to afford the titled product. MS: M+H+=545.

EXAMPLE 394

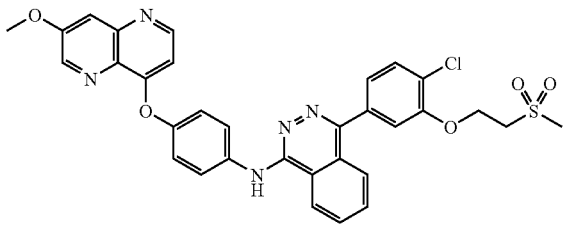

Synthesis of 4-(4-Chloro-3-(2-(methylsulfonyl)ethoxy)phenyl)-N-(4-(7-methoxy-1,5-naphthyridin-4-yloxy)phenyl)phthalazin-1-amine Step 1:
(2-(5-Bromo-2-chlorophenoxy)ethyl)(methyl)sulfane 5-Bromo-2-chlorophenol (500 mg, 2410 µmol) and (2-chloroethyl)(methyl)sulfane (262 µl, 2651 µmol) were combined with cesium carbonate (942 mg, 2892 µmol) in DMF and heated to 100° C. for 2 h. The mixture was then filtered and purified using reverse phase chromatography. This purified material was carried forward to the next step.

Step 2: 2-(4-Chloro-3-(2-(methylthio)ethoxy)phenyl)-4,4,5,5-tetramethyl-1,3,2-dioxaborolane 4,4,5,5-Tetramethyl-2-(4,4,5,5-tetramethyl-1,3,2-dioxaborolan-2-yl)-1,3,2-dioxaborolane (79 mg, 313 µmol), (2-(5-bromo-2-chlorophenoxy)ethyl)(methyl)sulfane (80 mg, 284 µmol), potassium acetate (84 mg, 852 µmol) and Pd(DPPF) were combined in dioxane and stirred for 4 hours at 100° C. The mixture was then filtered, concentrated, and purified on silica using 0 to 40% ethyl acetate in hexane. MS: M+Na+=351

Step 3: 4-(4-Chloro-3-(2-(methylsulfonyl)ethoxy)phenyl)-N-(4-(7-methoxy-1,5-naphthyridin-4-yloxy)phenyl)phthalazin-1-amine 4-(4-Chloro-3-(2-(methylthio)ethoxy)phenyl)-N-(4-(7-methoxy-1,5-naphthyridin-4-yloxy)phenyl)phthalazin-1-amine (150 mg, 252 µmol) and oxone (464 mg, 755 µmol) were combined in 3:1 MeOH/water (20 ml) and stirred for 3 h. The mixture was then concentrated to remove methanol, then extracted with DCM, dried with sat. sodium bicarb., and concentrated. The crude material was then purified by chromatography using 0 to 100% 90/10/1 in DCM, followed by reverse phase chromatography to provide the titled compound. MS: M+H+=628.

EXAMPLE 395

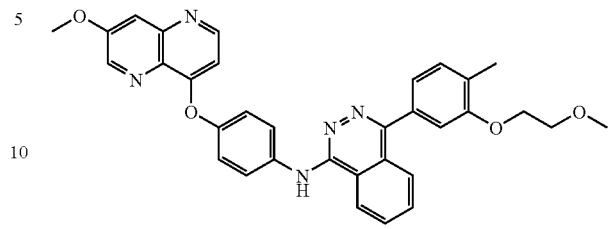

Synthesis of N-(4-(7-Methoxy-1,5-naphthyridin-4-yloxy)phenyl)-4-(3-(2-methoxyethoxy)-4-methylphenyl)phthalazin-1-amine 5-(4-(4-(7-Methoxy-1,5-naphthyridin-4-yloxy)phenylamino)phthalazin-1-yl)-2-methylphenol (120 mg, 239 µmol) and cesium carbonate (234 mg, 718 µmol) were combined in DMF and stirred for 5 min. 1-Bromo-2-methoxyethane (66.5 mg, 479 µmol) was added and the mixture was stirred for 1 h. The mixture was then filtered and purified using reverse phase chromatography to provide the titled product. MS: M+H+=560.

EXAMPLE 396

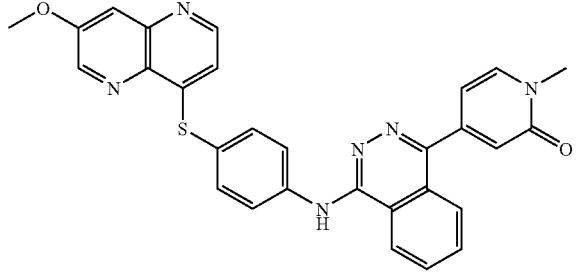

Synthesis of 4(4(4(7-Methoxy-1,5-naphthyridin-4-ylthio)phenylamino)phthalazin-1-yl)-1-methylpyridin-2(1H)-one Step 1:
1-Methyl-4-(trimethylstannyl)pyridin-2(1H)-one 4-Iodo-1-methylpyridin-2(1H)-one (110 mg, 468 µmol), 1,1,1,2,2,2-hexamethyldistannane (126 µl, 608 µmol), and the Pd catalyst were added to toluene and heated to 100° C. for 2 h. The mixture was concentrated and purified by silica gel chromatography using 0 to 30% MeOH in ethyl acetate.

Step 2: 4-(4-(4-(7-Methoxy-1,5-naphthyridin-4-ylthio)phenylamino)phthalazin-1-yl)-1-methylpyridin-2(1H)-one 4-Chloro-N-(4-(7-methoxy-1,5-naphthyridin-4-ylthio)phenyl)phthalazin-1-amine (148 mg, 331 µmol), 1-methyl-4-(trimethylstannyl)pyridin-2(1H)-one (90 mg, 331 µmol), and the Pd catalyst were added to toluene and heated to 100° C. for 2 h. The mixture was concentrated and purified by silica gel chromatography using 0 to 30% MeOH in ethyl acetate. MS: M+H+=519.

EXAMPLE 397

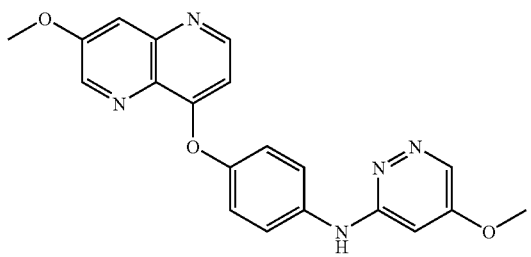

Synthesis of 5-Methoxy-N-(4(7-methoxy-1,5-naphthyridin-4-yloxy)phenyl)pyridazin-3-amine A pyrex reaction tube was charged with potassium phosphate (88 mg, 415 μmol), Pd$_2$dba$_3$ (16 mg, 17 mmol), Xantphos (22 mg, 38 mmol), 4-(7-methoxy-1,5-naphthyridin-4-yloxy)benzenamine (92 mg, 346 μmol), 3-chloro-5-methoxypyridazine (50 mg, 346 μmol), and toluene (1 mL). The tube was purged with argon, sealed, and the mixture was heated at 100° C. for 4 h. LCMS showed complete conversion to desired product. The mixture was then concentrated and purified by silica gel chromatography using 0 to 60% (90/10/1 DCM/MeOH/ammonium hydroxide) in DCM. MS: M+H+=376.

EXAMPLE 398

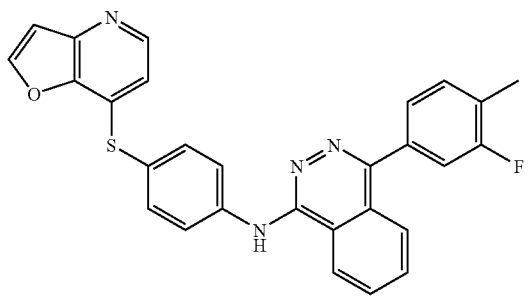

Synthesis of 4-(3-Fluoro-4-methylphenyl)-N-(4-(furo[3,2-b]pyridin-7-ylthio)phenyl)phthalazin-1-amine A microwave vial was charged with 3-fluoro-4-methylphenylboronic acid (0.058 g, 0.38 mmol), 4-chloro-N-(4-(2-(trimethylsilyl)furo[3,2-b]pyridin-7-ylthio)phenyl)phthalazin-1-amine (0.090 g, 0.19 mmol), and sodium carbonate (2.0 M in H$_2$O) (0.38 ml, 0.75 mmol) and dissolved in toluene (1.5 mL) and water (0.2 mL). Pd(Ph3P)$_4$(0.011 g, 0.0094 mmol) was added and the reaction was microwaved at 200° C. for 30 minutes. The reaction was partitioned between water and DCM. The layers were separated and the aqueous layer was extracted twice with DCM. The combined organic layers were dried with sodium sulfate, filtered, and concentrated. The material was redissolved in 2 mL THF and TBAF (0.23 ml, 0.23 mmol) was added. The reaction was stirred at RT overnight. The reaction was concentrated and purified via Gilson HPLC (10-90% ACN:H$_2$O). The clean fractions were partitioned between saturated sodium bicarbonate solution and DCM and the aqueous layer was extracted with DCM. The combined organic layers were dried with sodium sulfate, filtered, and concentrated to afford 4-(3-fluoro-4-methylphenyl)-N-(4-(furo[3,2-b]pyridin-7-ylthio)phenyl)phthalazin-1-amine as a light yellow solid. MS: M+H+=479.1

EXAMPLE 399

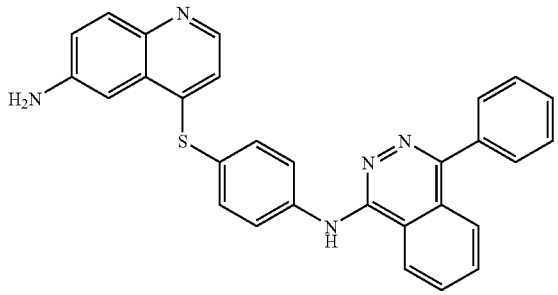

Synthesis of N-(4-(6-Aminoquinolin-4-ylthio)phenyl)-4-phenylphthalazin-1-amine

To a solution of N-(4-(6-nitroquinolin-4-ylthio)phenyl)-4-phenylphthalazin-1-amine (228 mg, 455 μmol) in 1 mL of DMF, was added tin (II) chloride (431 mg, 2273 μmol) and 115 uL of water. After 15 minutes of sonication, the reaction was stirred at rt. After 2 days, water was removed under vacuum azeotropically with benzene. DCM was added to the suspension. Yellow solids precipitated out of the solution and were filtered off with DCM. The filtrate was concentrated and purified by RPLC on an acidic Gilson column system. Fractions containing the product were washed with sat. NaHCO$_3$. The product was extracted with DCM. The organic was washed with brine, dried over MgSO$_4$, filtered, and concentrated. The product was purified further by performing a column chromatography using 60:40 DCM:(90:10:1 DCM:MeOH:NH$_4$OH). Yellow solid, N-(4-(6-aminoquinolin-4-ylthio)phenyl)-4-phenylphthalazin-1-amine was obtained.

EXAMPLE 400

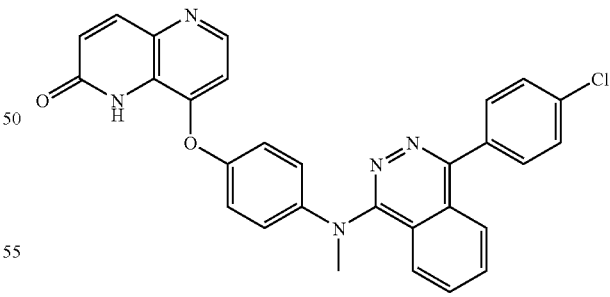

Synthesis of S(4-((4-(4-Chlorophenyl)phthalazin-1-yl)(methyl)amino)phenoxy)-1,5-naphthyridin-2(1H)-one Step 1: 8-(4-(4-(4-Chlorophenyl)phthalazin-1-ylamino)phenoxy)-1,5-naphthyridin-2(1H)-one In a 48 mL sealed pressure vessel, was added 4-(4-chlorophenyl)-N-(4-(6-methoxy-1,5-naphthyridin-4-yloxy)phenyl)phthalazin-1-amine (0.280 g, 0.553 mmol), HBr (6.01 mL, 11.1 mmol), and acetic acid (6.34 mL, 11.1 mmol). The mixture was stirred at 85° C. for 1 hour. The reaction was monitored and found complete by LC/MS. The reaction mixture was cooled to RT, carefully basified with 6 N NaOH. Light yellow solids crashed out, which were filtered, rinsed with water and dried in vacuum oven to yield 8-(4-(4-(4-chlorophenyl)phthalazin-1-ylamino)phenoxy)-1,5-naphthyridin-2(1H)-one. The product was used without further purification. MS:[M+H]=492.1; Calc'd 491.9 for $C_{28}H_{18}ClN_5O_2$.

Step 2: 8-(4-((4-(4-Chlorophenyl)phthalazin-1-yl)(methyl)amino)phenoxy)-1,5-naphthyridin-2(1H)-one In a 20 mL sealed tube, was dissolved 8-(4-(4-(4-chlorophenyl)phthalazin-1-ylamino)phenoxy)-1,5-naphthyridin-2(1H)-one (0.25 g, 0.508 mmol) in THF (2.2 mL), and the mixture was cooled to 0° C. Sodium Hydride, 60% in mineral oil (0.045 g, 1.12 mmol), was added and the mixture was stirred at 0° C. for 1 hour. Iodomethane (0.070 mL, 1.12 mmol), was added and the mixture was warmed to 60° C., and stirred for 3 hours. A mixture of products was revealed by LC/MS. The mixture was cooled to RT, quenched with water, extracted into ethyl acetate, washed 1× water, 1× NaCl, dried with $Na_2SO_4$, filtered through fritted funnel, and filtrate was concentrated. The crude concentrate was purified by reverse phase chromatography. The product containing fractions were extracted into DCM, washed 1× sodium carbonate, 1×$H_2O$, dried with $Na_2SO_4$, filtered through fritted funnel, and the filtrate was concentrated down to a light yellow solid containing two methylated products. The solids were suspended in methanol, filtered, rinsed with methanol, and air dried to yield 8-(4-((4-(4-chlorophenyl)phthalazin-1-yl)(methyl)amino)phenoxy)-1,5-naphthyridin-2(1H)-one. MS: [M+H]=506.0; Calc'd 505.9 for $C_{29}H_{20}ClN_5O_2$.

EXAMPLE 401

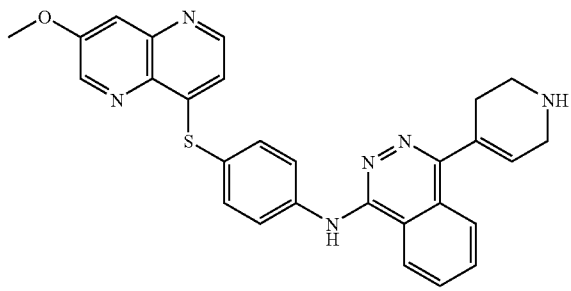

Synthesis of N-(4-(7-Methoxy-1,5-naphthyridin-4-ylthio)phenyl)-4-(1,2,3,6 tetrahydropyridin-4-yl)phthalazin-1-amine

Step 1: Tert-butyl 4-(4-(4-(7-methoxy-1,5-naphthyridin-4-ylthio)phenylamino)phthalazin-1-yl)-5,6-dihydropyridine-1(2H)-carboxylate In a 20 mL sealed tube, was added 1,4-dioxane (1.08 mL), purged the solvent with nitrogen for 5 minutes, and sealed the tube. To the tube was added 4-chloro-N-(4-(7-methoxy-1,5-naphthyridin-4-ylthio)phenyl)phthalazin-1-amine (0.150 g, 0.336 mmol), tert-butyl 4-(4,4,5,5-tetramethyl-1,3,2-dioxaborolan-2-yl)-5,6-dihydropyridine-1(2H)-carboxylate (0.125 g, 0.404 mmol) and sodium carbonate (2.0 M aqueous) (0.336 mL, 0.673 mmol). The mixture was purged with nitrogen, sealed, and then to it was added $PdCl_2(dppf)$ (0.012 g, 0.017 mmol). The mixture was again purged with nitrogen, sealed, and heated to 100° C., while stirring for 3 hours. The reaction was cooled to RT and concentrated. The crude material was purified by Isco silica gel chromatography using 0-100% $CH_2Cl_2$:MeOH(90:110)/$CH_2Cl_2$. The product containing fractions were concentrated to yield tert-butyl 4-(4-(4-(7-methoxy-1,5-naphthyridin-4-ylthio)phenylamino)phthalazin-1-yl)-5,6-dihydropyridine-1(2H)-carboxylate as light yellow solid. MS: [M+H]=593.0; Calc'd 592.7 for $C_{33}H_{32}N_6O_3S$.

Step 2: N-(4-(7-Methoxy-1,5-naphthyridin-4-ylthio)phenyl)-4-(1,2,3,6-tetrahydropyridin-4-yl)phthalazin-1-amine In a 20 mL sealed tube was dissolved tert-butyl 4-(4-(4-(7-methoxy-1,5-naphthyridin-4-ylthio)phenylamino)phthalazin-1-yl)-5,6-dihydropyridine-1(2H)-carboxylate (0.200 g, 0.337 mmol) in DCM (1.00 mL). To the mixture was added TFA (0.130 mL, 1.69 mmol). The mixture was stirred at 50° C. for 3 hours, then cooled to RT and concentrated. The crude material was purified on an Isco silica gel chromatography using 0-100% $CH_2Cl_2$:MeOH:$NH_4OH$ (90:10:1)/$CH_2Cl_2$. The product fractions were concentrated to yield N-(4-(7-methoxy-1,5-naphthyridin-4-ylthio)phenyl)-4-(1,2,3,6-tetrahydropyridin-4-yl)phthalazin-1-amine as a light yellow solid. MS: [N+H]=493.0; Calc'd 492.6 for $C_{28}H_{24}N_6OS$.

EXAMPLE 402

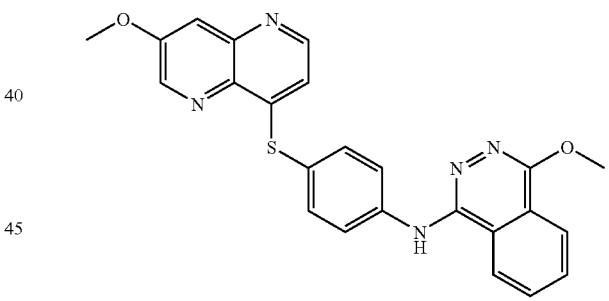

Synthesis of 4-Methoxy-N-(4-(7-methoxy-1,5-naphthyridin-4-ylthio)phenyl)phthalazin-1-amine In a 100 ml RBF was added 4-chloro-N-(4-(7-methoxy-1,5-naphthyridin-4-ylthio)phenyl)phthalazin-1-amine (158 mg, 0.354 mmol) to a solution of sodium methoxide (96 mg, 1.772 mmol) in MeOH. The mixture was heated to reflux with a water condenser attached. The solution was stirred for 16 hours. A white solid precipitated. The mixture was cooled to 0° C., quenched with excess methoxide, followed by saturated $NH_4Cl$, and the resulting solids were filtered and washed with water. The crude solids were purified by Gilson Reverse Phase HPLC eluting with a 15-70% gradient of ACN in water with 0.1% TFA. The product fractions were combined, neutralized with saturated sodium bicarbonate, extracted with 15 ml of methylene chloride (3×), dried organics over $Na_2SO_4$, filtered and concentrated filtrate in vacuo to afford 4-methoxy-N-(4-(7-methoxy-1,5-naphthyridin-4-ylthio)phenyl)phthalazin-1-amine as an off-white solid. MS: [M+H]=442.

EXAMPLE 403

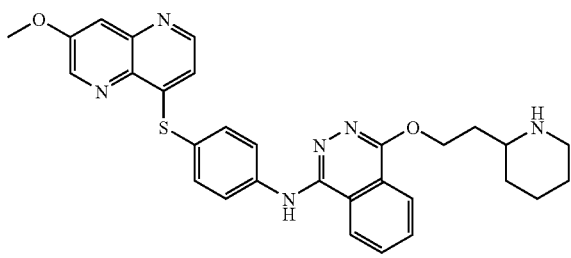

Synthesis of N-(4-(7-Methoxy-1,5-naphthyridin-4-ylthio)phenyl)-4-(2-(piperidin-2-yl)ethoxy)phthalazin-1-amine Sodium Hydride (11 mg, 449 µmol), 2-(piperidin-2-yl)ethanol (58 mg, 449 µmol), and benzene (2243 µl, 449 µmol) were combined in a resealable tube capped with a septum and heated to 40° C. for 30 minutes. 4-Chloro-N-(4-(7-methoxy-1,5-naphthyridin-4-ylthio)phenyl)phthalazin-1-amine (200 mg, 449 µmol) was added, and the reaction mixture was allowed to stir at 80° C. for 18 hours. The mixture was concentrated in vacuo and the crude material was partitioned between methylene chloride and water. The organic layers were combined and over $Na_2SO_4$ and concentrated. The crude material was purified via ISCO, 12 g RediSep column eluting with a 20-100% gradient of 90:10:1 (DCM:MeOH:$NH_4OH$) in DCM. The product fractions were combined and concentrated in vacuo to afford N-(4-(7-methoxy-1,5-naphthyridin-4-ylthio)phenyl)-4-(2-(piperidin-2-yl)ethoxy)phthalazin-1-amine. MS: [M+H]=539.

EXAMPLE 404

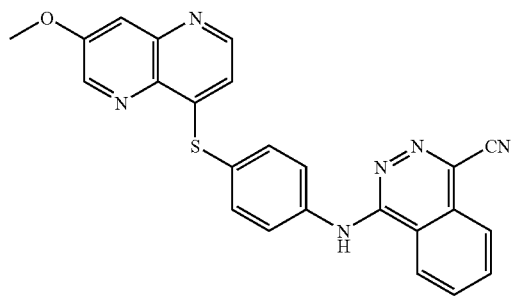

Synthesis of 4(4-(7-Methoxy-1,5-naphthyridin-4-ylthio)phenylamino)phthalazine-1-carbonitrile In a 15 ml sealed pressure tube, was dissolved 4-chloro-N-(4-(7-methoxy-1,5-naphthyridin-4-ylthio)phenyl)phthalazin-1-amine (150 mg, 490 µmol) in 0.8 ml of DMSO. Sodium cyanide (72 mg, 1469 µmol) was added and the reaction was capped and stirred at 130° C. for 3 hours. The reaction was cooled to RT and purified via Gilson Reverse Phase HPLC eluting with a 12-75% gradient of ACN in water with 0.1% TFA. The product fractions were basified with saturated sodium bicarbonate and extracted into DCM. The DCM layers were dried over $Na_2SO_4$, filtered and concentrated in vacuo to afford 4-(4-(7-methoxy-1,5-naphthyridin-4-ylthio)phenylamino)phthalazine 1-carbonitrile. MS: [M+H]=437.

EXAMPLE 405

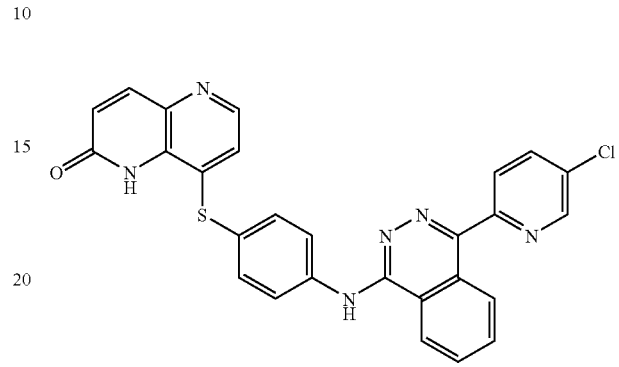

Synthesis of 8(4-(4-(5-Chloropyridin-2-yl)phthalazin-1-ylamino)phenylthio)-1,5-naphthyridin-2(1H)-one A small reaction vial was charged with 4-(5-chloropyridin-2-yl)-N-(4-(6-methoxy-1,5-naphthyridin-4-ylthio)phenyl)phthalazin-1-amine (50 mg, 0.096 mmol), HBr (1.04 mL, 19.12 mmol), and acetic acid (1.1 mL, 19.12 mmol). The mixture was stirred at 85° C. for 2 hrs. LC/MS showed completion of the reaction. The reaction mixture was poured onto an aqueous sodium bicarbonate solution ice bath and the product was extracted with DCM. The organic layer was dried over sodium sulfate and concentrated to afford 8-(4-(4-(5-chloropyridin-2-yl)phthalazin-1-ylamino)phenylthio)-1,5-naphthyridin-2(1H)-one as yellow solid. MS: [M+H]= 509.1; Calc'd for $C_{27}H_{17}ClN_6OS$: 509.

EXAMPLE 406

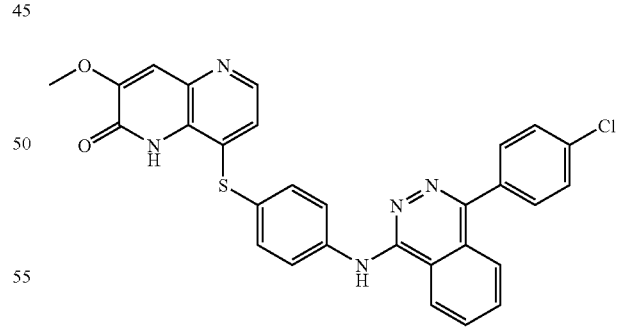

Synthesis of 8(4(4-(4-Chlorophenyl)phthalazin-1-ylamino)phenylthio)-3-methoxy-1,5-naphthyridin-2(1H)-one 4-(4-Chlorophenyl)-N-(4-(6,7-dimethoxy-1,5-naphthyridin-4-ylthio)phenyl)phthalazin-1-amine (40 mg, 72 µmol) was added to a pyrex reaction tube along with 2 mL of 1:1 HBr:AcOH. The tube was sealed and the mixture was heated at 85° C. for 1.5 h. Upon cooling the mixture was diluted with water and brought to basic pH by dropwise addition of 6N NaOH. The solids were filtered, washed with water, and dried. The crude material was purified by silica gel chromatography, 10-50% 90/10/1 DCM/MeOH/NH$_4$OH in DCM to provide 8-(4-(4-(4-chlorophenyl)phthalazin-1-ylamino)phenylthio)-3-methoxy-1,5-naphthyridin-2(1H)-one as a light yellow solid. MS: [M+H]=539.

EXAMPLE 407

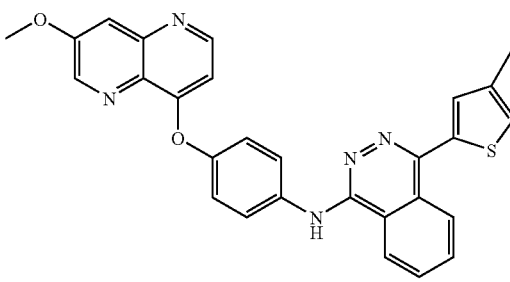

Synthesis of (5-(4-(4-(7-Methoxy-1,5-naphthyridin-4-yloxy)phenylamino)phthalazin-1-yl)thiophen-3-yl) methanol A scintillation vial was charged with (5-(4-(4-(7-methoxy-1,5-naphthyridin-4-yloxy)phenylamino)phthalazin-1-yl) thiophen-3-yl)methyl acetate (137 mg, 249 µmol), 1.0 mL 3:1:1 THF:MeOH:water and lithium hydroxide (47.8 mg, 1994 µmol). The homogeneous mixture was stirred at RT for 2 h. Water was added to the mixture, and the precipitated solids were filtered, washed with water, and dried. The crude solids were purified by reverse phase chromatography, Gilson, 10-90% 0.1% TFA/ACN in water to provide (5-(4-(4-(7-methoxy-1,5-naphthyridin-4-yloxy)phenylamino)phthalazin-1-yl)thiophen-3-yl)methanol. MS: [M+H]=508.

EXAMPLE 408

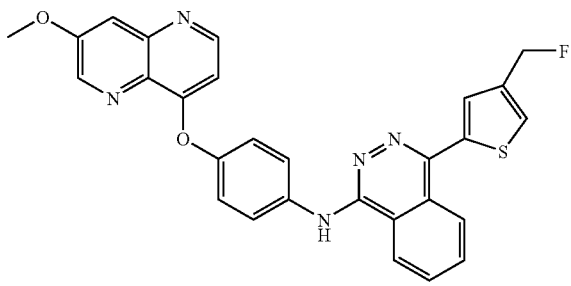

Synthesis of 4-(4-(Fluoromethyl)thiophen-2-yl)N-(4-(7-methoxy-1,5-naphthyridin-4-yloxy)phenyl)phthalazin-1-amine A round bottom flask was charged with (5-(4-(4-(7-methoxy-1,5-naphthyridin-4-yloxy)phenylamino)phthalazin-1-yl)thiophen-3-yl)methanol (71 mg, 140 µmol) and 2.8 mL DCM, and the mixture was cooled to 0° C. under nitrogen. (Diethylamino) trifluorosulfur (55 µl, 420 µmol) was added, and the mixture was stirred at 0° C. for 20 min and was then allowed to warm to RT. After another 0.5 h, saturated NaHCO$_3$ was added and the mixture was stirred for 10 min. The solids were filtered, and the crude material was purified by silica gel chromatography, 90/10/1 DCM/MeOH/NH$_4$OH in DCM, followed by reverse phase chromatography, Gilson, 10-90% 0.1% TFA/ACN in water, to provide the titled compound. MS: [M+H]=510.

EXAMPLE 409

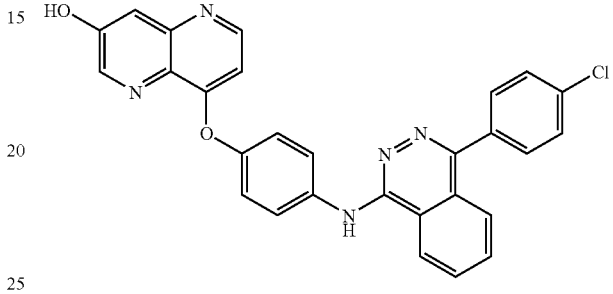

Synthesis of S(4-(4-(4-Chlorophenyl)phthalazin-1-ylamino)phenoxy)-1,5-naphthyridin-3-ol

Step 1: 8-Chloro-1,5-naphthyridin-3-ol

A pressure-resistant vial was charged with 8-chloro-3-methoxy-1,5-naphthyridine (1200 mg, 6166 mmol), boron tribromide (6412 µl, 67825 µmol) and dichloroethane (10277 µl, 6166 µmol). The vessel was sealed and the mixture was stirred at 60° C. for 16 h. The reaction mixture was carefully diluted with DCM, and the solids were filtered.

The crude material was purified by silica gel chromatography with 40-70% (90:10:1 DCM/MeOH/NH$_4$OH)/DCM to afford 8-chloro-1,5-naphthyridin-3-ol. MS:[M+H]=181.

Step 2: 3-(Benzyloxy)-8-chloro-1,5-naphthyridine (220 mg, 813 µmol)

A pyrex reaction tube was charged with 8-chloro-1,5-naphthyridin-3-ol (165 mg, 914 µmol), potassium carbonate (631 mg, 4568 µmol), 1-(chloromethyl)benzene (376 µl, 4568 µmol) and 3.7 mL DMF. The tube was sealed and the mixture was heated at 65° C. for 3 h. The reaction was diluted with DCM and washed with water. The organic portion was dried, filtered, and concentrated. The crude material was purified by silica gel chromatography, 0-25% EtOAc in DCM to provide product as a white solid. MS: [M+H]=271.

Step 3: N-(4-(7-(Benzyloxy)-1,5-naphthyridin-4-yloxy)phenyl)-4-(4-chlorophenyl)phthalazin-1-amine A pyrex reaction tube was charged with 4-(4-(4-chlorophenyl)phthalazin-1-ylamino)phenol hydrochloride (344 mg, 894 µmol), 3-(benzyloxy)-8-chloro-1,5-naphthyridine (220 mg, 813 µmol), cesium carbonate (662 mg, 2032 µmol) and 4.1 mL DMSO. The tube was sealed and the mixture was heated at 100° C. for 4 h. Water was added and the resulting precipitate was filtered, washed with water and dried. The crude material was purified by silica gel chromatography, 90/10/1 DCM/MeOH/NH4OH in DCM to provide N-(4-(7-(benzyloxy)-1,5-naphthyridin-4-yloxy)phenyl)-4-(4-chlorophenyl)phthalazin-1-amine. MS: [M+H]=583.

Step 4: 8-(4-(4-(4-Chlorophenyl)phthalazin-1-ylamino)phenoxy)-1,5-naphthyridin-3-ol A round bottom flask was charged with N-(4-(7-(benzyloxy)-1,5-naphthyridin-4-yloxy)phenyl)-4-(4-chlorophenyl)phthalazin-1-amine (400 mg, 687 μmol), 10% Pd/C (73.1 mg, 687 μmol) and 3.4 mL MeOH. The flask was fitted with a hydrogen-filled balloon and the mixture was stirred overnight. The mixture was diluted with DCM and filtered through Celite. The filtrate was concentrated and the crude material was purified by reverse phase chromatography, Gilson, 10-90% 0.1% TFA/ACN in water over 15 min to provide 8-(4-(4-(4-chlorophenyl)phthalazin-1-ylamino)phenoxy)-1,5-naphthyridin-3-ol as a light yellow solid. MS: [M+H]=492.

EXAMPLE 410

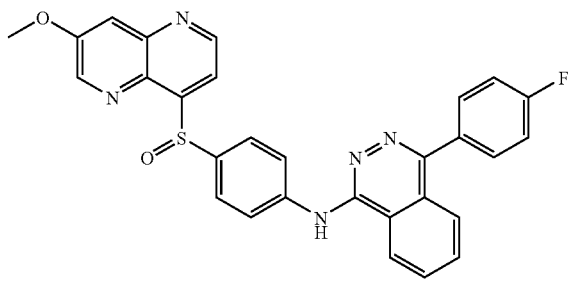

Synthesis of 4-(4-fluorophenyl)-N-(4-(7-methoxy-1,5-naphthyridin-4-ylsulfinyl)phenyl)phthalazin-1-amine To a solution of 4-(4-fluorophenyl)-N-(4-(7-methoxy-1,5-naphthyridin-4-ylthio)phenyl)phthalazin-1-amine (29 mg, 0.057 mmol) in $CH_2Cl_2$(2 mL) and $CHCl_3$(3 mL) at −78° C. was added mCPBA, 77% (14 mg, 0.080 mmol) in one portion. After 1 hr, the mixture was slowly warmed to 0° C. and stirred for an additional 15 min. The solution was diluted with $CH_2Cl_2$ and washed with 10% $Na_2S_2O_4$ and saturated aqueous $NaHCO_3$. After drying the organic fraction with $Na_2SO_4$, the solvent was removed in vacuo and the residue purified by silica gel chromatography using 100% $CH_2Cl_2$ to 8% MeOH:$CH_2Cl_2$ with 1% $NH_4OH$ to afford 4-(4-fluorophenyl)-N-(4-(7-methoxy-1,5-naphthyridin-4-ylsulfinyl)phenyl)phthalazin-1-amine (18 mg, 60% yield) as a light yellow solid. MS: M+H+=522. 1.

The Examples disclosed in Table 2 below are additional representative examples, of the present invention. These Examples were made by the methods indicated in Table 2, which generally correlate to Methods A1-5, B1-5, $C_{1-5}$ and D1a, D1b, D2 and D3 of Examples 12-A, 12-B and 29-45 herein. The MS data is the M+H$^+$ ion value found for the example. Biological data is provided for a majority of those compounds exemplified in Table 2. It should be understood and appreciated by those of ordinary skill in the art that where the data is missing for a particular example, that data was unavailable. Also, data for certain examples may not be completely accurate, as presented herein, likely due to poor sample solubility, or other possible solution related issues, causing a decreased calculated activity. It is believed that these examples may be more active than recorded herein.

TABLE 2

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 411 | 4-(4-chlorophenyl)-N-(4-((7-(methyloxy)-1,5-naphthyridin-4-yl)oxy)phenyl)-6,7-dihydro-5H-cyclopenta[d]pyridazin-1-amine | 496.1 | C1 | >25.000000 | >25.000000 | >1.200000 |
| 412 | 4-(4-chlorophenyl)-N-(4-((7-(methyloxy)-4-quinolinyl)oxy)phenyl)-6,7-dihydro-5H-cyclopenta[d]pyridazin-1-amine | 494.6 | C1 | >25.000000 | >25.000000 | >1.200000 |
| 413 | N-(6-((7-(methyloxy)-1,5-naphthyridin-4-yl)thio)-3-pyridinyl)-4-phenyl-1-phthalazinamine | 489.1 | B3 | 0.090 | 0.031 | 0.041 |
| 414 | 4-(4-chlorophenyl)-N-(6-((7-(methyloxy)-1,5-naphthyridin-4-yl)thio)-3-pyridinyl)-1-phthalazinamine | 522.5 | B3 | 0.023 | 0.026 | 0.011 |
| 415 | 8-((4-((4-phenyl-1-phthalazinyl)amino)phenyl)thio)-1,5-naphthyridin-3-ol | 474 | unique | 0.043 | 0.012 | 0.015 |
| 387 | N-(4-((7-((difluoromethyl)oxy)-1,5-naphthyridin-4-yl)thio)phenyl)-4-phenyl-1-phthalazinamine | 524 | unique | 0.135 | 0.048 | 0.120 |
| 416 | 4-(3-amino-4-methylphenyl)-N-(4-((1,5-naphthyridin-4-yloxy)phenyl)-1-phthalazinamine | 471.2 | C2 | 0.098 | 0.003 | 0.008 |
| 417 | 4-phenyl-N-(4-((7-(1H-pyrazol-4-yl)-4-quinolinyl)oxy)phenyl)-1-phthalazinamine | 507.2 | D3 | 0.009 | 0.002 | 0.001 |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 418 | N-(4-((6,7-bis(methyloxy)-4-quinazolinyl)thio)phenyl)-4-(4-chlorophenyl)-1-phthalazinamine | 552 | B3 | 0.028 | 0.012 | 0.004 |
| 419 | N-(4-((6-(methyloxy)-1,5-naphthyridin-4-yl)thio)phenyl)-4-(6-methyl-2-pyridinyl)-1-phthalazinamine | 502.8 | B3 | 0.309 | 0.026 | 0.124 |
| 420 | N-(4-((7-(methyloxy)-1,5-naphthyridin-4-yl)thio)phenyl)-4-(6-methyl-2-pyridinyl)-1-phthalazinamine | 503.1 | B3 | 0.072 | 0.015 | 0.029 |
| 421 | 4-(6-methyl-2-pyridinyl)-N-(4-(1,5-naphthyridin-4-ylthio)phenyl)-1-phthalazinamine | 473.1 | B3 | 0.142 | 0.008 | 0.051 |
| 422 | 6-(methyloxy)-4-((4-((4-phenyl-1-phthalazinyl)amino)phenyl)oxy)-7-quinolinol | 487 | C1 | 0.029 | 0.013 | 0.010 |
| 423 | 4-(4-chlorophenyl)-N-(4-(1,6-naphthyridin-4-yloxy)phenyl)-1-phthalazinamine | 476.2 | B3 | 0.047 | 0.003 | 0.031 |
| 424 | 4-(1,3-benzodioxol-5-yl)-N-(4-(1,6-naphthyridin-4-yloxy)phenyl)-1-phthalazinamine | 486.2 | B3 | 0.055 | 0.004 | 0.024 |
| 425 | N-(4-(1,6-naphthyridin-4-ylthio)phenyl)-4-phenyl-1-phthalazinamine | 458.2 | B3 | 0.171 | 0.003 | 0.024 |
| 426 | 4-(4-chlorophenyl)-N-(4-(1,6-naphthyridin-4-ylthio)phenyl)-1-phthalazinamine | 492.1 | B3 | 0.100 | 0.008 | 0.008 |
| 427 | 4-(1,3-benzodioxol-5-yl)-N-(4-(1,6-naphthyridin-4-ylthio)phenyl)-1-phthalazinamine | 502.1 | B3 | 0.055 | 0.007 | 0.002 |
| 428 | 4-(4-methyl-2-thienyl)-N-(4-(1,6-naphthyridin-4-ylthio)phenyl)-1-phthalazinamine | 478.1 | B3 | 0.032 | 0.013 | 0.016 |
| 429 | 4-(4-methyl-2-thienyl)-N-(4-(1,6-naphthyridin-4-yloxy)phenyl)-1-phthalazinamine | 462.1 | B3 | 0.046 | 0.012 | 0.034 |
| 430 | 4-(5-chloro-2-pyridinyl)-N-(4-(1,6-naphthyridin-4-ylthio)phenyl)-1-phthalazinamine | 493.1 | B3 | 0.084 | 0.007 | 0.007 |
| 431 | 4-(4-chlorophenyl)-N-(4-((7-((2-(methyloxy)ethyl)oxy)-4-quinolinyl)thio)phenyl)-1-phthalazinamine | 565.1 | B3 | 0.012 | 0.018 | 0.010 |
| 432 | 4-(5-methyl-2-pyridinyl)-N-(4-(1,6-naphthyridin-4-yloxy)phenyl)-1-phthalazinamine | 457.1 | B3 | 0.122 | 0.012 | 0.109 |
| 433 | 4-(5-methyl-2-pyridinyl)-N-(4-(1,6-naphthyridin-4-ylthio)phenyl)-1-phthalazinamine | 473.2 | B3 | 0.056 | 0.004 | 0.017 |
| 434 | 4-(4-chlorophenyl)-N-(4-((6-((2-(methyloxy)ethyl)oxy)-4-quinolinyl)thio)phenyl)-1-phthalazinamine | 565.2 | B3 | 0.109 | 0.109 | 0.027 |
| 388 | 4-((4-((4-(4-chlorophenyl)-1-phthalazinyl)amino)phenyl)thio)-6-quinolinol | 508 | unique | 0.020 | 0.003 | 0.013 |
| 389 | 4-(4-chlorophenyl)-N-(4-((6-((2-((2-(methyloxy)ethyl)oxy)ethyl)oxy)-4-quinolinyl)thio)phenyl)-1-phthalazinamine | 610 | C6 | 0.021 | 0.022 | 0.055 |
| 390 | 4-(4-chlorophenyl)-N-(4-((6-((2-(methylsulfonyl)ethyl)oxy)-4-quinolinyl)thio)phenyl)-1-phthalazinamine | 614 | C7 | >125.000000 | >125.000000 | >1.200000 |
| 435 | 4-(4-chlorophenyl)-N-(4-((5,7-dimethoxy-4-quinolinyl)oxy)phenyl)-1-phthalazinamine | 535 | B3 | 0.038 | 0.121 | 0.009 |
| 436 | 4-(4-chlorophenyl)-N-(4-((5,7-dimethoxy-4- | 551 | B1 | 0.401 | 0.675 | 0.049 |

TABLE 2-continued

| Ex. No | Compound Name | MS dataMS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| | quinolinyl)sulfanyl)phenyl)-1-phthalazinamine | | | | | |
| 437 | 4-(4-chlorophenyl)-N-(4-((7-fluoro-5-methoxy-4-quinolinyl)oxy)phenyl)-1-phthalazinamine | 523 | B3 | 0.042 | 0.035 | 0.005 |
| 438 | 4-(4-chlorophenyl)-N-(4-((7-fluoro-5-methoxy-4-quinolinyl)sulfanyl)phenyl)-1-phthalazinamine | 539 | B1 | 0.112 | 0.051 | 0.016 |
| 439 | N-(4-((5,7-dimethoxy-4-quinolinyl)sulfanyl)phenyl)-4-(4-methyl-2-thiophenyl)-1-phthalazinamine | 537.1 | B1 | 1.662 | 3.195 | 0.113 |
| 440 | N-(4-((7-fluoro-5-methoxy-4-quinolinyl)sulfanyl)phenyl)-4-(4-methyl-2-thiophenyl)-1-phthalazinamine | 525 | B1 | 0.585 | 0.596 | 0.029 |
| 441 | N-(4-((5,7-dimethoxy-4-quinolinyl)oxy)phenyl)-4-(4-methyl-2-thiophenyl)-1-phthalazinamine | 521.2 | B3 | 0.456 | 0.135 | 0.008 |
| 442 | N-(4-((7-fluoro-5-methoxy-4-quinolinyl)oxy)phenyl)-4-(4-methyl-2-thiophenyl)-1-phthalazinamine | 509.1 | B3 | 0.157 | 0.017 | <0.002300 |
| 443 | 4-(1,3-benzodioxol-5-yl)-N-(4-(1,5-naphthyridin-4-ylthio)phenyl)-1-phthalazinamine | 502 | B2 | 0.012 | 0.002 | 0.007 |
| 444 | 4-(2,2-difluoro-1,3-benzodioxol-5-yl)-N-(4-(1,5-naphthyridin-4-ylthio)phenyl)-1-phthalazinamine | 539 | A1 | 0.128 | 0.022 | 0.024 |
| 445 | 4-(2,3-dihydro-1-benzofuran-5-yl)-N-(4-(1,5-naphthyridin-4-ylthio)phenyl)-1-phthalazinamine | 500 | A1 | 0.030 | 0.013 | 0.001 |
| 446 | 4-(1-benzofuran-5-yl)-N-(4-(1,5-naphthyridin-4-ylthio)phenyl)-1-phthalazinamine | 498 | A1 | 0.035 | 0.011 | 0.000 |
| 392 | 7-(methyloxy)-4-(4-((4-phenyl-1-phthalazinyl)amino)phenyl)oxy)-6-quinolinecarbonitrile | 496 | unique | 0.159 | 0.260 | 0.085 |
| 447 | 4-(4-methyl-2-thienyl)-N-(4-(1,5-naphthyridin-4-yloxy)phenyl)-1-phthalazinamine | 462 | B3 | 0.027 | 0.013 | 0.012 |
| 448 | 4-(4-chlorophenyl)-N-(4-(1,5-naphthyridin-4-yloxy)phenyl)-1-phthalazinamine | 476 | B3 | 0.039 | 0.011 | 0.016 |
| 393 | N-(4-((6-(methyloxy)-7-((2-(methyloxy)ethyl)oxy)-4-quinolinyl)oxy)phenyl)-4-phenyl-1-phthalazinamine | 545 | unique | 0.013 | 0.017 | 0.001 |
| 394 | 4-(4-chloro-3-((2-(methylsulfonyl)ethyl)oxy)phenyl)-N-(4-((7-(methyloxy)-1,5-naphthyridin-4-yl)oxy)phenyl)-1-phthalazinamine | 628 | unique | 0.015 | 0.009 | 0.045 |
| 449 | 5-(4-((4-((7-methoxy-1,5-naphthyridin-4-yl)oxy)phenyl)amino)-1-phthalazinyl)-2-methylphenol | 502 | A1 | 0.026 | 0.006 | <0.002300 |
| 395 | 4-(3-(2-methoxyethoxy)-4-methylphenyl)-N-(4-((7-methoxy-1,5-naphthyridin-4-yl)oxy)phenyl)-1-phthalazinamine | 560 | unique | 0.047 | 0.012 | 0.023 |
| 450 | 4-(4-chloro-3-(2-methoxyethoxy)phenyl)-N-(4-((7-methoxy-1,5-naphthyridin-4-yl)sulfanyl)phenyl)-1-phthalazinamine | 596 | unique | 0.101 | 0.054 | 0.008 |
| 451 | 5-(4-((4-((7-methoxy-1,5-naphthyridin-4-yl)sulfanyl)phenyl)amino)-1-phthalazinyl)-2-methylphenol | 518 | A1 | 0.078 | 0.033 | <0.002300 |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 452 | 2-chloro-5-(4-((4-(1,5-naphthyridin-4-ylsulfanyl)phenyl)amino)-1-phthalazinyl)phenol | 508 | A1 | 0.058 | 0.003 | <0.002300 |
| 453 | 4-(1H-indazol-6-yl)-N-(4-((7-methoxy-1,5-naphthyridin-4-yl)sulfanyl)phenyl)-1-phthalazinamine | 528 | A1 | 0.028 | 0.032 | <0.002300 |
| 396 | 4-(4-((4-((7-methoxy-1,5-naphthyridin-4-yl)sulfanyl)phenyl)amino)-1-phthalazinyl)-1-methyl-2(1H)-pyridinone | 519 | unique | 0.050 | >125.000000 | 0.008 |
| 454 | 4-(4-chlorophenyl)-N-(3,5-difluoro-4-((7-methoxy-1,5-naphthyridin-4-yl)oxy)phenyl)-1-phthalazinamine | 542 | B3 | 0.050 | 0.010 | 0.008 |
| 455 | 4-(4-chlorophenyl)-N-(4-((7-fluoro-4-quinolinyl)oxy)phenyl)-1-phthalazinamine | 493 | C1 | >125.000000 | 0.013 | 0.008 |
| 456 | 5-methoxy-N-(4-((7-methoxy-1,5-naphthyridin-4-yl)oxy)phenyl)-3-pyridazinamine | 376 | unique | 1.003 | 0.058 | >1.200000 |
| 457 | 7-((4-((4-(1,3-benzodioxol-5-yl)-1-phthalazinyl)amino)phenyl)thio)thieno[3,2-b]pyridine-2-carbonitrile | 532 | B3 | 0.062 | 0.015 | 0.021 |
| 458 | 7-((4-((4-phenyl-1-phthalazinyl)amino)phenyl)thio)thieno[3,2-b]pyridine-2-carbonitrile | 488 | B3 | >25.000000 | 0.097 | 0.148 |
| 459 | 7-((4-((4-(4-methyl-2-thienyl)-1-phthalazinyl)amino)phenyl)thio)thieno[3,2-b]pyridine-2-carbonitrile | 508 | B3 | 0.210 | 0.150 | 0.048 |
| 460 | 7-((4-((4-(5-chloro-2-pyridinyl)-1-phthalazinyl)amino)phenyl)thio)thieno[3,2-b]pyridine-2-carbonitrile | 523 | B3 | 0.045 | 0.015 | 0.041 |
| 461 | 7-((4-((4-(6-methyl-3-pyridinyl)-1-phthalazinyl)amino)phenyl)thio)thieno[3,2-b]pyridine-2-carbonitrile | 503 | B3 | 0.044 | 0.009 | 0.019 |
| 462 | 4-phenyl-N-(4-(1H-pyrrolo[3,2-b]pyridin-7-ylthio)phenyl)-1-phthalazinamine | 446 | B1 | 0.557 | 0.010 | 0.043 |
| 463 | 4-(4-chlorophenyl)-N-(4-(1H-pyrrolo[3,2-b]pyridin-7-ylthio)phenyl)-1-phthalazinamine | 480 | B2 | 0.146 | 0.008 | 0.010 |
| 464 | 4-(4-methyl-2-thienyl)-N-(4-(1H-pyrrolo[3,2-b]pyridin-7-ylthio)phenyl)-1-phthalazinamine | 466 | B3 | 0.088 | 0.006 | 0.001 |
| 465 | 4-(4-chlorophenyl)-N-(4-(furo[3,2-b]pyridin-7-ylthio)phenyl)-1-phthalazinamine | 481 | unique | 0.093 | 0.012 | 0.020 |
| 466 | N-(4-(furo[3,2-b]pyridin-7-ylthio)phenyl)-4-phenyl-1-phthalazinamine | 447 | B3 | 0.431 | 0.013 | 0.086 |
| 467 | 4-(1,3-benzodioxol-5-yl)-N-(4-(furo[3,2-b]pyridin-7-ylthio)phenyl)-1-phthalazinamine | 491 | unique | 0.095 | 0.010 | 0.016 |
| 468 | N-(4-(furo[3,2-b]pyridin-7-ylthio)phenyl)-4-(4-methyl-2-thienyl)-1-phthalazinamine | 467 | unique | 0.129 | 0.029 | 0.014 |
| 469 | 4-(4-chlorophenyl)-N-(4-((1-(2-(methyloxy)ethyl)-1H-pyrrolo[3,2-b]pyridin-7-yl)thio)phenyl)-1-phthalazinamine | 538 | B3 | 0.110 | 0.053 | 0.003 |
| 470 | N-(4-((1-(2-(methyloxy)ethyl)-1H-pyrrolo[3,2-b]pyridin-7-yl)thio)phenyl)-4-(4-methyl-2-thienyl)-1-phthalazinamine | 524 | B2 | 0.041 | 0.051 | <0.002300 |
| 471 | 4-(4-chlorophenyl)-N-(4-((1-(1-methylethyl)-1H-pyrrolo[3,2-b]pyridin-7-yl)thio)phenyl)-1-phthalazinamine | 522 | B2 | 0.090 | 0.049 | 0.006 |

TABLE 2-continued

| Ex. No | Compound Name | MS dataMS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 472 | N-(4-((1-(1-methylethyl)-1H-pyrrolo[3,2-b]pyridin-7-yl)thio)phenyl-4-(4-methyl-2-thienyl)-1-phthalazinamine | 508 | B2 | 0.064 | 0.099 | 0.007 |
| 473 | 4-(3,4-bis((2-(methyloxy)ethyl)oxy)phenyl)-N-(4-((7-(methyloxy)-1,5-naphthyridin-4-yl)thio)phenyl)-1-phthalazinamine | 636 | A1 | 0.073 | 0.011 | 0.100 |
| 474 | 4-(4-((2-(methyloxy)ethyl)oxy)phenyl)-N-(4-((7-(methyloxy)-1,5-naphthyridin-4-yl)thio)phenyl)-1-phthalazinamine | 562 | A1 | 0.051 | 0.016 | 0.024 |
| 475 | 4-(4-chlorophenyl)-N-(4-((6-((2-((2-(methyloxy)ethyl)oxy)ethyl)oxy)-1,5-naphthyridin-4-yl)thio)phenyl)-1-phthalazinamine | 610 | B3 | 0.035 | 0.026 | 0.017 |
| 476 | 8-((4-((4-(4-chlorophenyl)-1-phthalazinyl)amino)phenyl)thio)-1-(2-((2-(methyloxy)ethyl)oxy)ethyl)-1,5-naphthyridin-2(1H)-one | 610 | B3 | 0.746 | 0.293 | 0.140 |
| 477 | 4-(3-amino-4-methylphenyl)-N-(4-((7-(methyloxy)-1,5-naphthyridin-4-yl)thio)phenyl)-1-phthalazinamine | 517 | A1 | 0.009 | 0.026 | 0.001 |
| 478 | N-(4-(furo[3,2-b]pyridin-7-yloxy)phenyl)-4-(4-(methyloxy)-1-piperidinyl)-1-phthalazinamine | 468 | B3 | 2.026 | 0.074 | 0.381 |
| 479 | 4-(3-amino-4-methylphenyl)-N-(4-(furo[3,2-b]pyridin-7-ylsulfanyl)phenyl)-1-phthalazinamine | 476 | B3 | >125.000000 | >125.000000 | 0.009 |
| 480 | 4-(3-amino-4-methylphenyl)-N-(4-(furo[3,2-b]pyridin-7-yloxy)phenyl)-1-phthalazinamine | 460 | B3 | 0.162 | 0.013 | 0.112 |
| 481 | N-(4-(furo[3,2-b]pyridin-7-ylsulfanyl)phenyl)-4-(6-methyl-3-pyridinyl)-1-phthalazinamine | 462 | B3 | 0.341 | 0.002 | 0.032 |
| 482 | N-(4-(furo[3,2-b]pyridin-7-ylsulfanyl)phenyl)-4-(5-methyl-2-pyridinyl)-1-phthalazinamine | 462 | B3 | 0.415 | 0.004 | 0.036 |
| 483 | 4-(4-chlorophenyl)-N-(4-(furo[3,2-b]pyridin-7-yloxy)phenyl)-1-phthalazinamine | 465 | B3 | 0.583 | 0.013 | 0.102 |
| 391 | 4-(5-chloro-2-pyridinyl)-N-(4-(furo[3,2-b]pyridin-7-ylsulfanyl)phenyl)-1-phthalazinamine | 482 | unique | 0.601 | 0.018 | 0.032 |
| 484 | 4-chloro-N-(4-((2-(trimethylsilyl)furo[3,2-b]pyridin-7-yl)sulfanyl)phenyl)-1-phthalazinamine | 477 | B3 | >125.000000 | 0.107 | >1.200000 |
| 485 | N-(4-(furo[3,2-b]pyridin-7-ylsulfanyl)phenyl)-4-(6-methoxy-3-pyridinyl)-1-phthalazinamine | 478 | unique | 0.479 | 0.005 | 0.069 |
| 398 | 4-(3-fluoro-4-methylphenyl)-N-(4-(furo[3,2-b]pyridin-7-ylsulfanyl)phenyl)-1-phthalazinamine | 479 | unique | 1.729 | 0.059 | 0.009 |
| 486 | 4-(4-chlorophenyl)-N-(4-((2-cyclopropylfuro[3,2-b]pyridin-7-yl)sulfanyl)phenyl)-1-phthalazinamine | 521 | B3 | 0.141 | 0.018 | 0.002 |
| 487 | 4-(3-amino-4-methylphenyl)-N-(4-((2-cyclopropylfuro[3,2-b]pyridin-7-yl)sulfanyl)phenyl)-1-phthalazinamine | 516 | B3 | | | 0.006 |
| 488 | N-(4-(furo[3,2-b]pyridin-7-ylsulfanyl)phenyl)-4-(6-methyl-2-pyridinyl)-1-phthalazinamine | 462 | B3 | 1.295 | 0.015 | 0.241 |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 489 | 7-((4-((4-(4-chlorophenyl)-1-phthalazinyl)amino)phenyl)sulfanyl)furo[3,2-b]pyridine-2-carbonitrile | 506 | B3 | 0.090 | 0.019 | 0.017 |
| 490 | 7-((4-((4-(3-amino-4-methylphenyl)-1-phthalazinyl)amino)phenyl)sulfanyl)furo[3,2-b]pyridine-2-carbonitrile | 501 | B3 | 0.090 | 0.013 | 0.009 |
| 491 | 4-(4-chlorophenyl)-N-(4-((2-methylfuro[3,2-b]pyridin-7-yl)sulfanyl)phenyl)-1-phthalazinamine | 495 | B3 | 0.150 | 0.039 | 0.037 |
| 492 | 4-(3-amino-4-methylphenyl)-N-(4-((2-methylfuro[3,2-b]pyridin-7-yl)sulfanyl)phenyl)-1-phthalazinamine | 490 | B3 | 0.142 | 0.046 | 0.021 |
| 493 | 4-(5-chloro-2-pyridinyl)-N-(4-(1,5-naphthyridin-4-ylthio)phenyl)-1-phthalazinamine | 493 | B3 | 0.020 | 0.002 | 0.016 |
| 494 | N-(4-((7-(methyloxy)-1,6-naphthyridin-4-yl)thio)phenyl)-4-(4-methyl-2-thienyl)-1-phthalazinamine | 508 | B3 | 0.026 | 0.017 | 0.009 |
| 495 | 4-(2-fluorophenyl)-N-(4-((7-(methyloxy)-1,5-naphthyridin-4-yl)thio)phenyl)-1-phthalazinamine | 506 | A1 | 0.150 | 0.026 | 0.024 |
| 399 | N-(4-((6-amino-4-quinolinyl)thio)phenyl)-4-phenyl-1-phthalazinamine | 472 | unique | 0.286 | 0.025 | 0.019 |
| 496 | 4-phenyl-N-(4-((7-((trifluoromethyl)oxy)-4-quinolinyl)oxy)phenyl)-1-phthalazinamine | 525 | C2 | 1.037 | 0.374 | 0.397 |
| 497 | 4-phenyl-N-(4-((7-((trifluoromethyl)oxy)-4-quinolinyl)thio)phenyl)-1-phthalazinamine | 541 | B3 | >25.000000 | 0.333 | 0.079 |
| 498 | 4-(4-chlorophenyl)-N-(4-((7-((trifluoromethyl)oxy)-4-quinolinyl)oxy)phenyl)-1-phthalazinamine | 559 | B3 | 0.183 | 0.165 | 0.078 |
| 499 | 4-(4-methyl-2-thienyl)-N-(4-((7-((trifluoromethyl)oxy)-4-quinolinyl)thio)phenyl)-1-phthalazinamine | 561 | B3 | 0.277 | 0.363 | 0.052 |
| 500 | 8-((4-((4-(4-chlorophenyl)-1-phthalazinyl)(methyl)amino)phenyl)oxy)-1,5-naphthyridin-2(1H)-one | 506 | unique | >25.000000 | 4.170 | >1.200000 |
| 501 | 4-(1-benzofuran-5-yl)-N-(4-((7-(methyloxy)-1,5-naphthyridin-4-yl)thio)phenyl)-1-phthalazinamine | 528 | A1 | 0.029 | 0.058 | 0.014 |
| 502 | 4-(2-methyl-2H-indazol-6-yl)-N-(4-((7-(methyloxy)-1,5-naphthyridin-4-yl)thio)phenyl)-1-phthalazinamine | 542 | A1 | 0.027 | 0.009 | 0.006 |
| 503 | N-(4-((7-(methyloxy)-1,5-naphthyridin-4-yl)thio)phenyl)-4-(4-methyl-1-piperazinyl)-1-phthalazinamine | 510 | A5 | 0.020 | 0.007 | 0.014 |
| 504 | 4-(2,1,3-benzoxadiazol-5-yl)-N-(4-((7-(methyloxy)-1,5-naphthyridin-4-yl)thio)phenyl)-1-phthalazinamine | 530 | A1 | 0.017 | 0.032 | 0.006 |
| 505 | 4-(2-(ethyloxy)-1,3-thiazol-4-yl)-N-(4-((7-(methyloxy)-1,5-naphthyridin-4-yl)thio)phenyl)-1-phthalazinamine | 539 | A2 | 0.016 | 0.014 | 0.022 |
| 506 | N-(4-((7-(methyloxy)-1,5-naphthyridin-4-yl)thio)phenyl)-4-(1,3-thiazol-4-yl)-1-phthalazinamine | 495 | A2 | 0.748 | 0.089 | 0.067 |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 507 | 4-(4-(2,2-difluoroethyl)-1-piperazinyl)-N-(4-((7-(methyloxy)-1,5-naphthyridin-4-yl)thio)phenyl)-1-phthalazinamine | 560 | A5 | 0.152 | 0.042 | 0.018 |
| 508 | N-(4-((7-methoxy-1,5-naphthyridin-4-yl)sulfanyl)phenyl)-N'-(3-(methylsulfanyl)propyl)-1,4-phthalazinediamine | 515 | A5 | 0.082 | 0.009 | 0.072 |
| 509 | 4-(6-methoxy-3-pyridinyl)-N-(4-(1,5-naphthyridin-4-ylsulfanyl)phenyl)-1-phthalazinamine | 489 | A1 | 0.317 | 0.013 | 0.008 |
| 510 | 6,7-difluoro-4-(4-methyl-2-thiophenyl)-N-(4-(1,5-naphthyridin-4-yloxy)phenyl)-1-phthalazinamine | 498 | A1 | 0.320 | 0.050 | 0.017 |
| 401 | N-(4-((7-methoxy-1,5-naphthyridin-4-yl)sulfanyl)phenyl)-4-(1,2,3,6-tetrahydro-4-pyridinyl)-1-phthalazinamine | 493 | unique | 0.847 | 0.052 | 0.187 |
| 511 | N-(4-((7-methoxy-1,5-naphthyridin-4-yl)sulfanyl)phenyl)-4-(1-methylethoxy)-1-phthalazinamine | 470 | A4 | 0.585 | 0.069 | 0.094 |
| 512 | 4-ethoxy-N-(4-((7-methoxy-1,5-naphthyridin-4-yl)sulfanyl)phenyl)-1-phthalazinamine | 456 | A4 | 0.501 | 0.120 | 0.033 |
| 513 | N-(4-((7-methoxy-1,5-naphthyridin-4-yl)sulfanyl)phenyl)-4-(2,2,2-trifluoroethoxy)-1-phthalazinamine | 510 | A4 | 0.231 | 0.030 | 0.059 |
| 514 | N-(4-((7-methoxy-1,5-naphthyridin-4-yl)sulfanyl)phenyl)-4-(methylsulfanyl)-1-phthalazinamine | 458 | A4 | 0.189 | 0.010 | 0.020 |
| 515 | 4-(2-methoxyethoxy)-N-(4-((7-methoxy-1,5-naphthyridin-4-yl)sulfanyl)phenyl)-1-phthalazinamine | 486 | A4 | 0.072 | 0.012 | 0.018 |
| 516 | 4-(3-chlorophenyl)-N-(4-((7-(methyloxy)-1,5-naphthyridin-4-yl)thio)phenyl)-1-phthalazinamine | 522 | B3 | 0.088 | 0.068 | 0.025 |
| 517 | 4-(1,3-benzodioxol-5-yl)-N-(4-(4-quinolinylthio)phenyl)-1-phthalazinamine | 501 | B3 | 0.150 | 0.017 | 0.011 |
| 518 | 4-(3-chlorophenyl)-N-(4-(thieno[3,2-b]pyridin-7-ylthio)phenyl)-1-phthalazinamine | 497 | A1 | 0.218 | 0.010 | 0.016 |
| 519 | N-(3-fluoro-4-((7-(methyloxy)-1,5-naphthyridin-4-yl)thio)phenyl)-4-phenyl-1-phthalazinamine | 506 | B3 | 0.083 | 0.053 | 0.009 |
| 520 | N-(4-((7-(methyloxy)-1,5-naphthyridin-4-yl)thio)phenyl)-4-(4-(methyloxy)-1-piperidinyl)-1-phthalazinamine | 524 | A5 | 0.027 | 0.017 | 0.004 |
| 521 | N-(4-((7-(methyloxy)-1,5-naphthyridin-4-yl)thio)phenyl)-4-(1-pyrrolidinyl)-1-phthalazinamine | 481 | A5 | 0.112 | 0.025 | 0.021 |
| 522 | 4-(1,3-benzodioxol-5-yl)-N-(3-fluoro-4-((7-(methyloxy)-1,5-naphthyridin-4-yl)thio)phenyl)-1-phthalazinamine | 550 | B3 | 0.009 | 0.022 | 0.001 |
| 523 | N-(4-((7-(methyloxy)-1,5-naphthyridin-4-yl)thio)phenyl)-4-(4-(trifluoromethyl)-1-piperidinyl)-1-phthalazinamine | 563 | A5 | 0.036 | 0.144 | 0.006 |
| 524 | N-methyl-N'-(4-((7-(methyloxy)-1,5-naphthyridin-4-yl)thio)phenyl)-N-propyl-1,4-phthalazinediamine | 482 | A5 | 0.093 | 0.099 | |
| 525 | 4-(4-methyl-3-(methyloxy)phenyl)-N-(4-((7-(methyloxy)-1,5-naphthyridin-4-yl)oxy)phenyl)-1-phthalazinamine | 516 | A1 | 0.013 | 0.028 | |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 526 | N-(4-((7-(methyloxy)-1,5-naphthyridin-4-yl)thio)phenyl)-4-(4-morpholinyl)-1-phthalazinamine | 496 | A5 | 0.294 | 0.032 | 0.025 |
| 527 | 4-(4-chloro-1-piperidinyl)-N-(4-((7-(methyloxy)-1,5-naphthyridin-4-yl)thio)phenyl)-1-phthalazinamine | 530 | A5 | 0.036 | 0.138 | 0.004 |
| 528 | N-(3-fluoro-4-((7-(methyloxy)-1,5-naphthyridin-4-yl)thio)phenyl)-4-(4-methyl-2-thienyl)-1-phthalazinamine | 526 | B3 | 0.064 | 0.293 | 0.009 |
| 529 | 4-(4-methyl-3-(methyloxy)phenyl)-N-(4-((7-(methyloxy)-1,5-naphthyridin-4-yl)thio)phenyl)-1-phthalazinamine | 532 | B3 | 0.020 | 0.037 | 0.006 |
| 530 | 4-(1,3-benzodioxol-5-yl)-N-(4-((7-(methyloxy)-1,5-naphthyridin-4-yl)thio)phenyl)-1-phthalazinamine | 532 | B3 | 0.014 | 0.014 | 0.001 |
| 531 | 4-(4,4-difluoro-1-piperidinyl)-N-(4-((7-(methyloxy)-1,5-naphthyridin-4-yl)thio)phenyl)-1-phthalazinamine | 531 | A5 | 0.089 | 0.024 | 0.049 |
| 532 | N-(4-((7-(methyloxy)-1,5-naphthyridin-4-yl)thio)phenyl)-4-((3R)-3-(methyloxy)-1-piperidinyl)-1-phthalazinamine | 525 | A5 | 0.061 | 0.019 | 0.020 |
| 533 | N-(2-(methyloxy)ethyl)-N'-(4-((7-(methyloxy)-1,5-naphthyridin-4-yl)thio)phenyl)-1,4-phthalazinediamine | 485 | A5 | 0.045 | 0.030 | 0.062 |
| 534 | 4-((4-((4-(4-(methyloxy)-1-piperidinyl)-1-phthalazinyl)amino)phenyl)thio)-7-quinolinecarbonitrile | 519 | A5 | 0.035 | 0.020 | 0.006 |
| 535 | N-(4-((7-(methyloxy)-1,5-naphthyridin-4-yl)thio)phenyl)-N'-(3-(methyloxy)propyl)-1,4-phthalazinediamine | 499 | A5 | 0.022 | 0.020 | 0.026 |
| 536 | 4-chloro-N-(4-((7-methoxy-1,5-naphthyridin-4-yl)sulfanyl)phenyl)-1-phthalazinamine | 446 | B3 | 0.812 | 0.031 | 0.031 |
| 537 | N-(4-((7-methoxy-1,5-naphthyridin-4-yl)sulfanyl)phenyl)-N'-(2-(2-pyridinyl)ethyl)-1,4-phthalazinediamine | 532 | A5 | 0.198 | 0.111 | 0.002 |
| 538 | N-(4-((7-methoxy-1,5-naphthyridin-4-yl)sulfanyl)phenyl)-4-(4-(1-pyrrolidinyl)-1-piperidinyl)-1-phthalazinamine | 564 | A5 | 3.432 | 0.045 | 0.178 |
| 539 | 4-(3,5-difluorophenyl)-N-(4-((7-methoxy-1,5-naphthyridin-4-yl)oxy)phenyl)-1-phthalazinamine | 508 | A1 | 0.133 | 0.020 | 0.081 |
| 540 | N-(4-((7-methoxy-1,5-naphthyridin-4-yl)sulfanyl)phenyl)-4-((3R)-3-methoxy-1-pyrrolidinyl)-1-phthalazinamine | 511 | A5 | | | 0.013 |
| 402 | 4-methoxy-N-(4-((7-methoxy-1,5-naphthyridin-4-yl)sulfanyl)phenyl)-1-phthalazinamine | 442 | unique | 0.167 | 0.015 | 0.066 |
| 403 | N-(4-((7-methoxy-1,5-naphthyridin-4-yl)sulfanyl)phenyl)-4-(2-(2-piperidinyl)ethoxy)-1-phthalazinamine | 539 | unique | 0.239 | 0.005 | 0.037 |
| 541 | 4-cyclopropyl-N-(4-((7-methoxy-1,5-naphthyridin-4-yl)sulfanyl)phenyl)-1-phthalazinamine | 452 | B3 | 0.393 | 0.025 | 0.038 |
| 542 | N-(4-((7-methoxy-1,5-naphthyridin-4-yl)oxy)phenyl)-1-phthalazinamine | 396 | B3 | 0.319 | 0.041 | 0.382 |
| 543 | 4-cyclopropyl-N-(4-((7-methoxy-1,5-naphthyridin-4-yl)oxy)phenyl)-1-phthalazinamine | 436 | B3 | 0.581 | 0.044 | 0.281 |

TABLE 2-continued

| Ex. No | Compound Name | MS dataMS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 404 | 4-((4-((7-methoxy-1,5-naphthyridin-4-yl)sulfanyl)phenyl)amino)-1-phthalazinecarbonitrile | 437 | unique | 0.447 | 0.009 | 0.063 |
| 544 | 4-(3-amino-4-methylphenyl)-N-(4-(4-quinolinyloxy)phenyl)-1-phthalazinamine | 470 | B3 | 0.126 | 0.012 | 0.008 |
| 544 | 4-(4-chlorophenyl)-6,7-difluoro-N-(4-((7-methoxy-1,5-naphthyridin-4-yl)oxy)phenyl)-1-phthalazinamine | 542 | A1 | 0.116 | 0.031 | 0.041 |
| 545 | 4-(3-amino-4-methylphenyl)-6,7-difluoro-N-(4-((7-methoxy-1,5-naphthyridin-4-yl)oxy)phenyl)-1-phthalazinamine | 537 | A1 | 0.085 | 0.020 | 0.012 |
| 546 | 4-(2-chlorophenyl)-N-(4-((7-methoxy-1,5-naphthyridin-4-yl)oxy)phenyl)-1-phthalazinamine | 507 | A1 | 0.723 | 0.135 | |
| 547 | N-(4-((7-methoxy-1,5-naphthyridin-4-yl)sulfanyl)phenyl)-1-phthalazinamine | 412 | B3 | 0.335 | 0.020 | |
| 548 | N-(4-((6-(methyloxy)-1,5-naphthyridin-4-yl)thio)phenyl)-4-(1-piperidinyl)-1-phthalazinamine | 495 | B3 | 0.270 | 0.031 | 0.036 |
| 549 | N-(4-((6-(methyloxy)-1,5-naphthyridin-4-yl)thio)phenyl)-4-(4-methyl-2-thienyl)-1-phthalazinamine | 508 | B3 | 0.098 | 0.064 | 0.009 |
| 550 | 4-(5-chloro-2-pyridinyl)-N-(4-((6-(methyloxy)-1,5-naphthyridin-4-yl)thio)phenyl)-1-phthalazinamine | 523 | B3 | 0.107 | 0.022 | 0.016 |
| 551 | 4-(1,3-benzodioxol-5-yl)-N-(4-((6-(methyloxy)-1,5-naphthyridin-4-yl)oxy)phenyl)-1-phthalazinamine | 516 | B3 | 0.096 | 0.017 | 0.002 |
| 552 | N-(4-((6-(methyloxy)-1,5-naphthyridin-4-yl)oxy)phenyl)-4-(4-methyl-2-thienyl)-1-phthalazinamine | 492 | B3 | 0.056 | 0.036 | 0.010 |
| 553 | 4-(6-methyl-3-pyridinyl)-N-(4-(1,5-naphthyridin-4-ylthio)phenyl)-1-phthalazinamine | 473 | A1 | 0.042 | 0.005 | 0.001 |
| 554 | N-(4-((6-(methyloxy)-4-quinolinyl)oxy)phenyl)-4-(5-methyl-2-pyridinyl)-1-phthalazinamine | 486 | B3 | 0.172 | 0.011 | 0.108 |
| 555 | 4-(3,3-dimethyl-1-piperidinyl)-N-(4-((7-(methyloxy)-1,5-naphthyridin-4-yl)thio)phenyl)-1-phthalazinamine | 523 | A5 | 0.102 | 0.105 | 0.064 |
| 556 | 4-(3,5-dimethyl-1-piperidinyl)-N-(4-((7-(methyloxy)-1,5-naphthyridin-4-yl)thio)phenyl)-1-phthalazinamine | 523 | A5 | 0.116 | 0.159 | 0.026 |
| 557 | 4-(4-fluoro-1-piperidinyl)-N-(4-((7-(methyloxy)-1,5-naphthyridin-4-yl)thio)phenyl)-1-phthalazinamine | 513 | A5 | 0.161 | 0.059 | 0.026 |
| 558 | 4-(1-methylethyl)-N-(4-((7-(methyloxy)-1,5-naphthyridin-4-yl)thio)phenyl)-1-phthalazinamine | 454 | B3 | 0.378 | 0.041 | 0.100 |
| 559 | 4-(4-chlorophenyl)-N-(4-((2-methylthieno[3,2-b]pyridin-7-yl)thio)phenyl)-1-phthalazinamine | 511 | B3 | 0.168 | 0.098 | 0.018 |
| 560 | 4-(5-chloro-2-pyridinyl)-N-(4-((2-methylthieno[3,2-b]pyridin-7-yl)thio)phenyl)-1-phthalazinamine | 512 | B3 | 0.416 | 0.081 | 0.023 |
| 561 | 4-phenyl-N-(4-(4-quinazolinylthio)phenyl)-1-phthalazinamine | 458 | B3 | >25.000000 | >5.000000 | >1.200000 |
| 562 | 4-(4-chlorophenyl)-N-(4-(4-quinazolinyloxy)phenyl)-1-phthalazinamine | 476 | C2 | 0.107 | 0.006 | 0.026 |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 563 | 4-((8aS)-hexahydropyrrolo[1,2-a]pyrazin-2(1H)-yl)-N-(4-((7-(methyloxy)-1,5-naphthyridin-4-yl)thio)phenyl)-1-phthalazinamine | 536 | A5 | 0.023 | 0.009 | <0.002300 |
| 405 | 8-((4-((4-(5-chloro-2-pyridinyl)-1-phthalazinyl)amino)phenyl)thio)-1,5-naphthyridin-2(1H)-one | 509 | unique | 0.042 | 0.007 | 0.036 |
| 564 | 4-(4-chlorophenyl)-N-(4-((6-(methyloxy)-4-quinazolinyl)oxy)phenyl)-1-phthalazinamine | 506 | C2 | >25.000000 | 0.129 | 0.043 |
| 565 | N-(4-((6-(methyloxy)-4-quinazolinyl)oxy)phenyl)-4-(4-methyl-2-thienyl)-1-phthalazinamine | 492 | C2 | 0.686 | 0.108 | 0.030 |
| 566 | 4-(4-chlorophenyl)-N-(3-(methyloxy)-4-((7-(methyloxy)-1,5-naphthyridin-4-yl)oxy)phenyl)-1-phthalazinamine | 536 | B3 | 0.093 | 0.043 | 0.191 |
| 567 | N-(3-(methyloxy)-4-((7-(methyloxy)-1,5-naphthyridin-4-yl)oxy)phenyl)-4-(4-methyl-2-thienyl)-1-phthalazinamine | 522 | B3 | 0.092 | 0.041 | 0.227 |
| 568 | 4-(4-methyl-2-thienyl)-N-(4-(4-quinazolinyloxy)phenyl)-1-phthalazinamine | 462 | C2 | 0.233 | 0.011 | 0.034 |
| 569 | 8-((4-((4-(4-chlorophenyl)-1-phthalazinyl)amino)phenyl)oxy)-1,5-naphthyridin-2(1H)-one | 492 | unique | 0.128 | 0.013 | 0.115 |
| 570 | 4-(4-chlorophenyl)-N-(4-(5,6,7,8-tetrahydro-1,8-naphthyridin-4-ylthio)phenyl)-1-phthalazinamine | 496 | B3 | 0.050 | 0.008 | 0.008 |
| 571 | 4-phenyl-N-(4-((6-((trifluoromethyl)oxy)-4-quinolinyl)thio)phenyl)-1-phthalazinamine | 541 | B3 | >25.000000 | >25.000000 | 0.060 |
| 572 | 4-(4-methyl-2-thienyl)-N-(4-((6-((trifluoromethyl)oxy)-4-quinolinyl)thio)phenyl)-1-phthalazinamine | 561 | B3 | >25.000000 | >25.000000 | 0.055 |
| 573 | N-(4-((5,7-bis(methyloxy)-4-quinazolinyl)oxy)phenyl)-4-(4-methyl-2-thienyl)-1-phthalazinamine | 522 | C2 | 0.042 | 0.114 | 0.011 |
| 574 | 4-(4-chlorophenyl)-N-(4-((6-((trifluoromethyl)oxy)-4-quinolinyl)oxy)phenyl)-1-phthalazinamine | 559 | B3 | 0.752 | 0.365 | 0.119 |
| 575 | 4-(4-methyl-2-thienyl)-N-(4-((6-((trifluoromethyl)oxy)-4-quinolinyl)oxy)phenyl)-1-phthalazinamine | 545 | B3 | 0.226 | 0.810 | 0.112 |
| 576 | 4-(5,6-dihydroimidazo[1,2-a]pyrazin-7(8H)-yl)-N-(4-((7-(methyloxy)-1,5-naphthyridin-4-yl)thio)phenyl)-1-phthalazinamine | 533 | A5 | 0.077 | 0.026 | 0.013 |
| 577 | 4-phenyl-N-(4-(5,6,7,8-tetrahydro-1,8-naphthyridin-4-ylthio)phenyl)-1-phthalazinamine | 462 | B3 | 0.428 | 0.021 | 0.025 |
| 578 | 4-(6,7-dihydrothieno[3,2-c]pyridin-5(4H)-yl)-N-(4-((7-(methyloxy)-1,5-naphthyridin-4-yl)thio)phenyl)-1-phthalazinamine | 549 | A5 | 0.033 | 0.081 | 0.007 |
| 579 | 4-(5,6-dihydro[1,2,4]triazolo[1,5-a]pyrazin-7(8H)-yl)-N-(4-((7-(methyloxy)-1,5-naphthyridin-4-yl)thio)phenyl)-1-phthalazinamine | 534 | A5 | 0.228 | 0.032 | 0.054 |
| 580 | N-(4-((7-(methyloxy)-1,5-naphthyridin-4-yl)thio)phenyl)-4-((9aR)-octahydro-2H-pyrido[1,2-a]pyrazin-2-yl)-1-phthalazinamine | 550 | A5 | 0.023 | 0.005 | 0.005 |

TABLE 2-continued

| Ex. No | Compound Name | MS data MS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 581 | N-(4-((5,7-bis(methyloxy)-4-quinazolinyl)thio)phenyl)-4-phenyl-1-phthalazinamine | 518 | B1 | 1.131 | 0.236 | 0.036 |
| 582 | 4-((8aR)-hexahydropyrrolo[1,2-a]pyrazin-2(1H)-yl)-N-(4-((7-(methyloxy)-1,5-naphthyridin-4-yl)thio)phenyl)-1-phthalazinamine | 536 | A5 | 0.029 | 0.006 | 0.006 |
| 583 | N-(4-((7-(methyloxy)-1,5-naphthyridin-4-yl)thio)phenyl)-4-(6-(methyloxy)-3-pyridinyl)-1-phthalazinamine | 519 | A1 | 0.028 | 0.008 | 0.005 |
| 584 | N-(4-((7-(methyloxy)-1,5-naphthyridin-4-yl)thio)phenyl)-4-((9aR)-octahydro-2H-pyrido[1,2-a]pyrazin-2-yl)-1-phthalazinamine | 550 | A5 | 0.009 | 0.005 | 0.005 |
| 585 | N-(4-((7-(methyloxy)-1,5-naphthyridin-4-yl)thio)phenyl)-4-((9aS)-octahydro-2H-pyrido[1,2-a]pyrazin-2-yl)-1-phthalazinamine | 550 | A5 | 0.036 | 0.006 | 0.018 |
| 586 | N-(4-((7-(methyloxy)-1,5-naphthyridin-4-yl)oxy)phenyl)-4-((4aR,8aS)-octahydro-2(1H)-isoquinolinyl)-1-phthalazinamine | 533 | C2 | 0.124 | 0.042 | 0.028 |
| 587 | N-(4-((7-(methyloxy)-1,5-naphthyridin-4-yl)oxy)phenyl)-4-((4aS,8aR)-octahydro-2(1H)-isoquinolinyl)-1-phthalazinamine | 533 | C2 | 0.217 | 0.033 | 0.140 |
| 588 | N-(4-((7-(methyloxy)-1,5-naphthyridin-4-yl)thio)phenyl)-4-(6-methyl-3-pyridinyl)-1-phthalazinamine | 503 | A1 | 0.051 | 0.017 | 0.004 |
| 589 | 8-((4-((4-(4-methyl-2-thienyl)-1-phthalazinyl)amino)phenyl)thio)-1,5-naphthyridin-2(1H)-one | 494 | unique | 0.019 | 0.008 | 0.007 |
| 590 | N-(4-((5,7-bis(methyloxy)-4-quinazolinyl)oxy)phenyl)-4-(4-chlorophenyl)-1-phthalazinamine | 536, 538 | B3 | 0.027 | 0.020 | 0.004 |
| 591 | 4-(4-chlorophenyl)-N-(4-(thieno[3,2-d]pyrimidin-4-yloxy)phenyl)-1-phthalazinamine | 482, 484 | C1 | 0.250 | 0.005 | 0.115 |
| 592 | 4-((4-((4-phenyl-1-phthalazinyl)amino)phenyl)oxy)-6-quinolinecarbonitrile | 466 | C1 | 0.338 | 0.022 | 0.147 |
| 593 | 4-((methyloxy)methyl)-N-(4-((7-(methyloxy)-1,5-naphthyridin-4-yl)oxy)phenyl)-6-phenyl-3-pyridazinamine | 466 | B4 | 0.526 | 0.082 | >1.200000 |
| 594 | 6-(1,3-benzodioxol-5-yl)-4-ethyl-N-(4-((7-(methyloxy)-1,5-naphthyridin-4-yl)oxy)phenyl)-3-pyridazinamine | 494 | B4 | 0.094 | 0.051 | 0.202 |
| 595 | N-(4-ethyl-6-(4-methylphenyl)-3-pyridazinyl)-N'-(7-(methyloxy)-1,5-naphthyridin-4-yl)-1,4-benzenediamine | 463 | C4 | 0.102 | 0.023 | 0.083 |
| 596 | 4-((4-((4-ethyl-6-(4-methylphenyl)-3-pyridazinyl)amino)phenyl)amino)-7-quinolinecarbonitrile | 457 | C4 | 0.160 | 0.058 | 0.084 |
| 597 | N-(4-((6,7-bis(methyloxy)-1,5-naphthyridin-4-yl)thio)phenyl)-4-phenyl-1-phthalazinamine | 518 | B1 | 0.246 | 0.681 | 0.061 |
| 598 | N-(4-((6,7-bis(methyloxy)-1,5-naphthyridin-4-yl)thio)phenyl)-4-(4-chlorophenyl)-1-phthalazinamine | 552, 554 | B3 | 0.135 | 0.595 | 0.028 |
| 599 | N-(4-((7-bromopyrido[3,2-d]pyrimidin-4-yl)oxy)phenyl)-4-phenyl-1-phthalazinamine | 521, 523 | C2 | 0.794 | 0.256 | >1.200000 |
| 406 | 8-((4-((4-(4-chlorophenyl)-1-phthalazinyl)amino)phenyl)thio)-3-(methyloxy)-1,5-naphthyridin-2(1H)-one | 538, 540 | unique | 0.034 | 0.186 | <0.002300 |

TABLE 2-continued

| Ex. No | Compound Name | MS dataMS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 600 | 4-((7R,8aS)-7-fluorohexahydropyrrolo[1,2-a]pyrazin-2(1H)-yl)-N-(4-((7-(methyloxy)-1,5-naphthyridin-4-yl)thio)phenyl)-1-phthalazinamine | 554 | A5 | 0.014 | 0.010 | 0.007 |
| 407 | (5-(4-((4-((7-(methyloxy)-1,5-naphthyridin-4-yl)oxy)phenyl)amino)-1-phthalazinyl)-3-thienyl)methanol | 508 | unique | 0.016 | 0.004 | 0.012 |
| 601 | 4-((8aS)-7,7-difluorohexahydropyrrolo[1,2-a]pyrazin-2(1H)-yl)-N-(4-((7-(methyloxy)-1,5-naphthyridin-4-yl)thio)phenyl)-1-phthalazinamine | 572 | A5 | 0.021 | 0.012 | 0.005 |
| 408 | 4-(4-(fluoromethyl)-2-thienyl)-N-(4-((7-(methyloxy)-1,5-naphthyridin-4-yl)oxy)phenyl)-1-phthalazinamine | 510 | unique | 0.024 | 0.009 | 0.025 |
| 602 | 4-((8aR)-7,7-difluorohexahydropyrrolo[1,2-a]pyrazin-2(1H)-yl)-N-(4-((7-(methyloxy)-1,5-naphthyridin-4-yl)oxy)phenyl)-1-phthalazinamine | 556 | B2 | 0.018 | 0.013 | 0.051 |
| 602 | N-(4-((7-(methyloxy)-1,5-naphthyridin-4-yl)thio)phenyl)-4-((10aR)-octahydropyrazino[1,2-a]azepin-2(1H)-yl)-1-phthalazinamine | 564 | A5 | 0.017 | 0.005 | 0.012 |
| 604 | N-(4-((7-(methyloxy)-1,5-naphthyridin-4-yl)oxy)phenyl)-4-((10aR)-octahydropyrazino[1,2-a]azepin-2(1H)-yl)-1-phthalazinamine | 548 | B2 | 0.027 | 0.013 | 0.087 |
| 605 | N-(4-((7-(methyloxy)-1,5-naphthyridin-4-yl)thio)phenyl)-4-(4-(methylsulfonyl)-1-piperazinyl)-1-phthalazinamine | 574 | A5 | 0.803 | 0.083 | 0.018 |
| 606 | N-(6-((5,7-bis(methyloxy)-4-quinazolinyl)oxy)-3-pyridinyl)-4-phenyl-1-phthalazinamine | 503 | B4 | >25.000000 | 0.035 | 0.292 |
| 607 | N-(4-((7-methoxy-1,5-naphthyridin-4-yl)oxy)phenyl)-4-(4-(methylsulfonyl)-1-piperazinyl)-1-phthalazinamine | 558 | B2 | 2.822 | 0.324 | 0.482 |
| 608 | 4-(4-acetyl-1-piperazinyl)-N-(4-((7-methoxy-1,5-naphthyridin-4-yl)sulfanyl)phenyl)-1-phthalazinamine | 538 | A5 | 0.352 | 0.022 | 0.016 |
| 609 | 4-ethyl-N-(4-((7-methoxy-1,5-naphthyridin-4-yl)sulfanyl)phenyl)-6-(2-methoxyphenyl)-3-pyridazinamine | 496 | B4 | 0.123 | 0.020 | 0.055 |
| 409 | 8-(4-((4-(4-chlorophenyl)-1-phthalazinyl)amino)phenoxy)-1,5-naphthyridin-3-ol | 492, 494 | unique | 0.020 | 0.005 | 0.032 |
| 610 | N-(4-((7-(benzyloxy)-1,5-naphthyridin-4-yl)oxy)phenyl)-4-(4-chlorophenyl)-1-phthalazinamine | 582, 584 | C2 | 0.047 | 0.033 | 0.014 |
| 611 | | 470 | A1 | >125.000 | 0.671 | >1.2000 |
| 612 | | 471 | C1 | 0.684 | 0.023 | |
| 410 | 4-(4-fluorophenyl)-N-(4-((7-(methyloxy)-1,5-naphthyridin-4-yl)sulfinyl)phenyl)-1-phthalazinamine | 522.1 | unique | 0.532 | 0.645 | 0.260 |
| 613 | 4-(4-chlorophenyl)-N-(4-(1-(7-(methyloxy)-4-quinolinyl)ethyl)phenyl)-1-phthalazinamine | 517.2 | B3 | >25.000000 | 0.243 | >1.200000 |
| 614 | (4-((4-(4-chlorophenyl)-1-phthalazinyl)amino)phenyl)(7-(methyloxy)-4-quinolinyl)methanol | 519.1 | B3 | 0.223 | 0.046 | 0.053 |

TABLE 2-continued

| Ex. No | Compound Name | MS dataMS Data [M + H]+ | Method | AurA_IC50_IP (uM Avg) | AurB_IC50_IP (uM Avg) | 24h_4 NPloidy EC50_IP (uM Avg) |
|---|---|---|---|---|---|---|
| 615 | (4-((4-(4-chlorophenyl)-1-phthalazinyl)amino)phenyl)(7-(methyloxy)-4-quinolinyl)methanone | 517.2 | B3 | 0.300 | 0.039 | 0.150 |

The invention further provides methods for making compounds of Formulas I-IV. For example, and in one embodiment, there is provided a method of making a compound of Formula I, the method comprising the step of reacting compound of Formula A

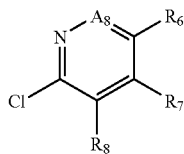

A with a compound of Formula B

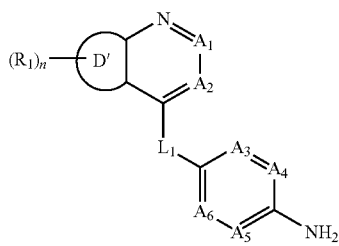

B wherein $A^8$ and $R^{6-8}$ of the compound of formula A and $A^1$, $A^2$, D', $L^1$, $R^1$, $A^{3-6}$ and n of the compound of formula B are as defined herein, to make a compound of Formula I. This method may also be used to make a compound of Formulas II, III and IV.

While the examples described above provide processes for synthesizing compounds of Formulas I-IV, other methods may be utilized to prepare such compounds. In the procedures described herein, the steps may be performed in an alternate order and may be preceded, or followed, by additional protection/deprotection steps as necessary.

Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. Those of ordinary skill in the art know, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like, many of which were utilized in the Examples above. Reactions conditions such as temperature, duration, pressure, and atmosphere (inert gas, ambient) are known in the art and may be adjusted as appropriate for the reaction.

All synthetic procedures described herein can be carried out either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H+ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further includes salt forms of compounds of Formulas I, II, III and IV. Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

The invention further encompasses pro-drugs of compounds of Formulas I, II, III and IV. For example, a phosphate group may be a pro-drug derivative of an alcohol group or an amine group, or an ester may be a pro-drug of a carboxylic acid functional group. Phosphate groups may be incorporated into desired compounds of Formulas I, II, III and IV in order to improve upon in-vivo bioavailability and/or other pharmacokinetic or pharmacodynamic properties of the compound.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with chiral reagents, such as an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The synthetic chemistry transformations, as well as protecting group methodologies (protection and deprotection) described above and useful in synthesizing the inhibitor compounds described herein, are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

BIOLOGICAL EVALUATION

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention. Briefly, representative compounds of the invention were found to inhibit the activity of Aurora kinase selectively or non-selectively, at doses less than 25 µM. This activity demonstrates the utility of the compounds in the prophylaxis and treatment of cellular proliferative disorders, including cancer as described herein.

Aurora Kinase HTRF Assays

AuroraA-TPX2-Homogeneous Time Resolved Fluorescent (HTRF) Kinase Assay:

The Aurora-A HTRF assay begins with Aurora-A in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The AuroraA HTRF assay comprises 1 µL of compound in 100% DMSO, 20 µL of ATP and biotinylated PLK, and 20 p-L of AuroraA-TPX2 KD GST for a final volume of about 41 µL. The final concentration of PLK is about 1 µM. The final concentration of ATP is about 1 µM (Km(app)=1 µM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

Many of the Examples described herein were tested, and fund to be active compounds. Table I includes related biological data, which may be interpreted using the activity gauge below. Selected Examples 29-45 and 74-370 exhibited an average activity in the Aurora kinase A HTRF assay as follows:

"+" represents an activity ($IC_{50}$) in the range of 2.5 uM-500 nM;

"++" represents an activity ($IC_{50}$) in the range of 500-100 nM; and

"+++" represents an activity ($IC_{50}$) of less than 100 nM.

AuroraB-Homogeneous Time Resolved Fluorescent (HTRF) Kinase Assay:

The AuroraB HTRF assay begins with AuroraB in the presence of ATP phosphorylating the biotinylated peptide Histone H3. The reaction incubates for about 90 min. the reaction is quentched by addition of detection reagents, which stop the reaction by diluting out the enzyme and chelating the metals due to the presence of EDTA. After addition, the assay is incubated for about 60 min to allow detection reagents to equilibrate.

The AuroraB HTRF assay comprises 1 µL of compound in 100% DMSO, 20 µL of ATP and biotinylated Histone H3, and 20 µL of AuroraB FL His for a final volume of 41 µL. The final concentration of Histone H3 is 0.1 µM. The final concentration of ATP is 23 µM (Km(app)=23 µM+/−2.6) and the final concentration of AuroraB is 400 µM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-His H3) at a final conc of 0.064 nM.

The assay plate is read in either a Discovery or a RubyStar. The eu-anti-His H3 is excited at 320 nm and emits at 615 nm to excite the SA-APC which in turn emits at 655 nm. The ratio of SA-APC at 655 nm (excited due to close proximity to the Eu-anti-HisH3 because of phosphorylation of the peptide) to free Eu-anti-His H3 at 615 nm will give substrate phosphorylation.

Many of the Examples described herein were tested, and fund to be active compounds. Table I includes related biological data, which may be interpreted using the activity gauge below. Selected Examples 2945 and 74-370 exhibited an average activity in the Aurora kinase B HTRF assay as follows:

"+" represents an activity ($IC_{50}$) in the range of 2.5 uM-500 nM;

"++" represents an activity ($IC_{50}$) in the range of 500-100 nM; and

"+++" represents an activity ($IC_{50}$) of less than 100 nM.

Aurora Kinase Cell-based Assay

HeLa Cell 24 Hr Ploidy Assay Protocol

The purpose of this assay is to evaluate the ability of selected individual compounds to induce Deoxyribonucleic acid (DNA) content (ploidy) in cells through failed cell division. Cell cycle analysis is a rapid and efficient way to evaluate the status of DNA content (ploidy) of a given cell. HeLa cells ($1 \times 10^4$ HeLa cells/well) in 100 ul of media (MEM+10% FBS) were plated in 96-well plates (Packard View) and cultured for 24 hrs at 37° C. maintained in a 5% $CO_2$ atmosphere.

The following day, cells were treated for 24 hrs with inhibitor compounds (10 pt. Dose ranging from 0.0024-1.25 μmol/L). The compounds were serially diluted in DMSO (0.25% final concentration). The cells were fixed (3.7% Formaldehyde and 1% glutaraldehyde) and permeabilized (1×PBS with 1% BSA and 0.2% Triton X-100) in preparation for nuclear staining. The well plates were stained for 45 minutes at RT in the dark using Hoechest 33342 nuclear stain at 0.5 μg.ml (Stock of 10 mg/ml, Invitrogen, CA, Cat # H3570). The nuclear stain was removed by aspiration and the cells were washed with wash buffer. A Cellomics Array Scan Vti plate reader was used to acquire the DNA ploidy data of the cells using Cell Cycle bioapplication. Numbers for each of "valid cell count/well", "% of 4N cells" and "% of >4N cells" were calculated with the assistance of an Activity Base 5.1 ca software and dose curves were generated using an XLFit software. With XLFit, final $EC_{50}$ IP and $EC_{50}$ transit values, as well as the Max and Min, were calculated for each curve.

Of the compounds assayed, a number of compounds exhibited activity in the 24 h cell-ploidy content assay, as provided in the Tables herein. Selected Examples exhibited an average activity in the DNA ploidy assay as follows:

"+" represents an activity ($EC_{50}$) in the range of 2.5 uM-500 nM;

"++" represents an activity ($EC_{50}$) in the range of 500-100 mM; and

"+++" represents an activity ($EC_{50}$) of less than 100 nM.

HCT116 Xenograft Model

Compounds of the present invention were evaluated in HCT116 xenografts, a human colon carcinoma model. HCT116 cells were chosen to evaluate compounds of Formulas I-IV in a tumor model based on in vitro data having showed a marked increase in polyploidy in the cells in response to Aurora B inhibition. These cells were grown as subcutaneous xenografts in female HSD (Harlan Sprague Dawley) athymic nude mice. Mice were implanted subcutaneously with $2 \times 10^6$ cells in matrigel on day 0. Treatment was initiated on day 10 with compounds of the invention at the indicated dosage p.o for 2 consecutive-days per week (intermittent schedule, such as 2 days on—5 days off) or 7-days (continuous schedule) per week, for a selected number of weeks. For example, in one study, animals were dosed with selected compound samples BID on an intermittent dosing paradigm of two days on and then 5 days off per week, for four weeks (four dosing cycles) at 15, 7.5, and 3.75 mg/kg. Tumor growth inhibition and body weights were measured throughout the study and compared to the vehicle control group. All groups were provided nutritional supplements on a daily basis throughout the study to maintain body weight. Terminal neutrophil counts were taken at the end of this study. Measures were made by ANOVA followed by Scheffe post hoc test using StatView software v5.0.1.

Materials

Tissue Culture: 10 Flasks containing a total of $7.68 \times 10^8$ HCT116 tumor cells were harvested for tumor cell implantation. HCT 116 cells were re-suspended to a cell concentration of about $2 \times 10^7$ cells/ml in serum-free McCoys 5A media +50% matrigel. Cell viability was measured to be about 99.3%.

Animals: Female Athymic Nude mice approximately 14 weeks of age (Harlan Sprague Dawley) were used for the experiment. Mice were housed five per filter-capped cage in sterile housing in an environmentally controlled room (temperature 23±2° C., relative humidity 50±20%) on a 12-hr light/dark cycle. Animals were fed a commercial rodent chow (Formulation 8640; Tek Lab, Madison, Wis.) and received filter-purified tap water ad libitum. Dietary calcium and phosphorus contents were 1.2% and 1.0%, respectively. Mice were individually identified by microchips (Biomedic Data Systems, Inc—Seaford, Del.) implanted subcutaneously at least one week prior to the study. Mice were implanted with $2 \times 10^6$ cells (100 μl) subcutaneously on the right flank on Day 0. On Day 9, tumor-bearing mice were measured and randomized into five groups (n=10). Treatment of the mice with various compound dosages began on Day 10. The duration of the dosing phase of the study was generally four weeks. During the dosing period, mouse tumor volumes were measured with a digital caliper and weighed twice per week. Tumor volumes were calculated as follows: Tumor Volume $(mm^3)=[(W^2 \times L)/2]$ where width (W) is defined as the smaller of the 2 measurements and length (L) is defined as the larger of the 2 measurements. The following Examples exhibited an inhibition of tumor growth in the 116HCT tumor xenograph model: 160 (~86% inhibition @ 3.75 mg/kg 2-day dosing scheduling QD); 165 (~63% inhibition @ 2.5 mg/kg 2-day dosing scheduling BID); and 207 (~67% inhibition @ 5.0 mg/kg 2-day dosing scheduling QD).

Indications

The compounds of the invention have Aurora kinase modulatory activity in general, and inhibitory activity in particular. In one embodiment of the invention, there is provided a method of modulating Aurora kinase enzyme in a subject, the method comprising administering to the subject an effective dosage amount of a compound of a compound of Formulas I-IV. As such, the compounds of the invention may be used to treat cellular proliferation disorders, including uncontrolled cell growth and aberrant cell cycle regulation. The compounds are also useful for treating disorders related to hyper-proliferation of cells in normal tissue, including without limitation, non-tumor bearing and metastatic tissue. For example, one use may be to protect normal hair follicles from chemotherapy induced alopecia.

In addition, compounds of the invention are useful for, but not limited to, the prevention or treatment of cancer and other Aurora kinase-mediated diseases or disorders. For example, compounds of the invention would be useful for the treatment of various solid and hematologically derived tumors, such as carcinomas, including, without limitation, cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compound of the invention may also be used to treat chemotherapy-induced thrombocytopenia, since the compounds may increase platelet count be increasing the rate of megakaryocyte maturation.

The compounds would also be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the invention are also useful in the treatment of cardiovascular conditions such as atherosclerosis, restenosis, arteriosclerosis, vascular occlusion and carotid obstructive disease.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention can also be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations

Also embraced within this invention is a class of pharmaceutical compositions, also referred to as medicaments, comprising the active compounds of Formulas I-III in association with one or more non-toxic, pharmaceutically-acceptable excipients and/or carriers, diluents and/or adjuvants (collectively referred to herein as "excipient" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable excipients, including carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable excipient, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the excipients, carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy or with neoplastic or cytotoxic agents.

If formulated as a fixed dose, such combination products employ the compounds of this invention within the accepted dosage ranges. Compounds of Formulas I-III may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

Alternatively, the compounds of the invention may also be used in co-therapies with other anti-neoplastic agents, such as other kinase inhibitors including angiogenic agents such as VEGFR. inhibitors, p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing is merely illustrative of the invention and is not intended to limit the invention to the disclosed compounds. Variations and changes, which are obvious to one skilled in the art, are intended to be within the scope and nature of the invention, which are defined in the appended claims. All mentioned references, patents, applications and publications, are hereby incorporated by reference in their entirety, as if here written.

What is claimed is:

1. A compound of Formula III:

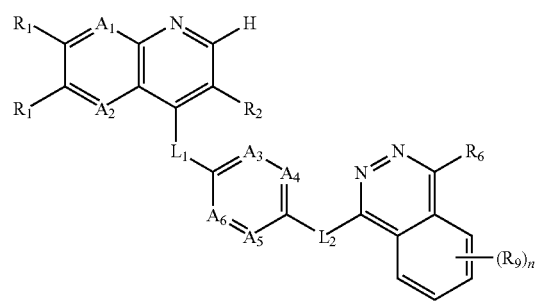

or a pharmaceutically acceptable salt thereof, wherein
$A^1$ is $CR^2$;
$A^2$ is N;
each of $A^3$, $A^4$, $A^5$ and $A^6$, independently, is $CR^3$;
$L^1$ is —O—, —$NR^4$—, —S—, —C(O)—, —S(O)—, —$SO_2$— or —$CR^4R^4$—, wherein each $R^4$, independently, is H, halo, OH, $C_{1-6}$alkoxyl, NH—$C_{1-6}$alkyl, CN or $C_{1-6}$alkyl;
$L^2$ is —$NR^4$—, wherein $R^4$ is H or $C_{1-6}$alkyl;
each $R^1$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —C(O)$R^9$, —COO$R^9$, —OC(O)$R^9$, —C(O)C(O)$R^9$, —C(O)$NR^9R^9$, —$NR^9C(O)R^9$, —$NR^9C(O)NR^9R^9$, —$NR^9(COOR^9)$, —OC(O)$NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N,or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;
each $R^2$, independently, is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)R$^9$;

each R$^3$, independently, is H, halo, haloalkyl, haloalkoxyl, CN, OH, SH, NO$_2$, NH$_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)R$^9$;

R$^6$ is R$^9$;

each R$^9$, independently, is H, halo, haloalkyl, haloalkoxyl, oxo, CN, OH, SH, NO$_2$, NH$_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, SR$^{10}$, OR$^{10}$, NR$^4$R$^{10}$, C(O)R$^{10}$, COOR$^{10}$, C(O)NR$^4$R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$R$^{10}$, NR$^4$S(O)$_2$R$^{10}$, NR$^4$S(O)$_2$NR$^4$R$^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

R$^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

2. The compound of claim 1, or a pharmaceutically acceptable salt thereof, wherein L$^1$ is —O—, —S— or —NR$^4$—, L$^2$ is —NR$^4$— and each R$^4$, independently, is as defined in claim 1.

3. The compound of claim 1, or a pharmaceutically acceptable salt thereof, wherein R$^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl.

4. The compound of claim 1, or a pharmaceutically acceptable salt thereof, wherein each of A$^3$, A$^4$, A$^5$ and A$^6$, independently, is CH.

5. The compound of claim 1, or a pharmaceutically acceptable salt thereof, wherein A$^1$ is CR$^2$, wherein R$^2$ is H;

L$^1$ is —O—, —S—or —NR$^4$—;

L$^2$ is —NR$^4$—; and

R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R$^{10}$, halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl.

6. The compound of claim 1 of formula III:

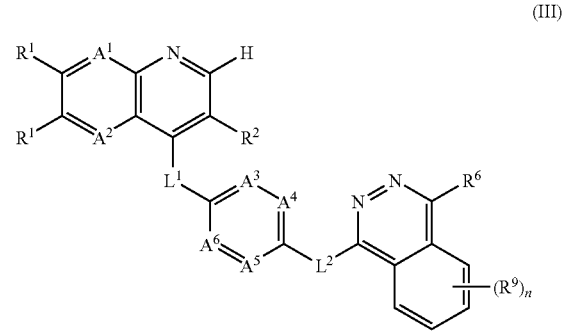

(III)

or a pharmaceutically acceptable salt thereof, wherein

A$^2$ is N;

each of A$^3$, A$^4$, A$^5$ and A$^6$, independently, is CR$^3$;

L$^1$ is —O—, —S—, or —NR$^4$—;

L$^2$ is —NR$^4$—;

each R$^1$, independently, is H, halo, haloalkyl, haloalkoxyl, oxo, CN, OH, SH, NO$_2$, NH$_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —SR$^9$, —OR$^9$, —NR$^9$R$^9$, —C(O)R$^9$, —COOR$^9$, —OC(O)R$^9$, —C(O)C(O)R$^9$, —C(O)NR$^9$R$^9$, —NR$^9$C(O)R$^9$, —NR$^9$C(O)NR$^9$R$^9$, —NR$^9$(COOR$^9$), —OC(O)NR$^9$R$^9$, —S(O)$_2$R$^9$, —S(O)$_2$R$^9$, —S(O)$_2$NR$^9$R$^9$, —NR$^9$S(O)$_2$NR$^9$R$^9$, —NR$^9$S(O)$_2$R$^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^9$;

R$^2$ is H, halo, haloalkyl, haloalkoxyl, OH, SH, NO$_2$, NH$_2$, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or —C(O)R$^9$;

each R$^3$, independently, is H, halo, haloalkyl, haloalkoxyl, CN, OH, SH, NO$_2$, NH$_2$ or C$_{1-10}$-alkyl;

each R$^4$, independently, is H or C$_{1-6}$alkyl;

R$^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

each R$^9$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{3-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, SR$^{10}$, OR$^{10}$, NR$^4$ R$^{10}$, C(O)R$^{10}$, COOR$^{10}$, C(O)NR$^4$ R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$ R$^{10}$, NR$^4$S(O)$_2$ R$^{10}$, NR$^4$S(O)$_2$NR$^4$ R$^{10}$, or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

R$^{10}$ is H, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl; and n is 0, 1, 2, 3 or 4.

7. The compound of claim 1 having a Formula III:

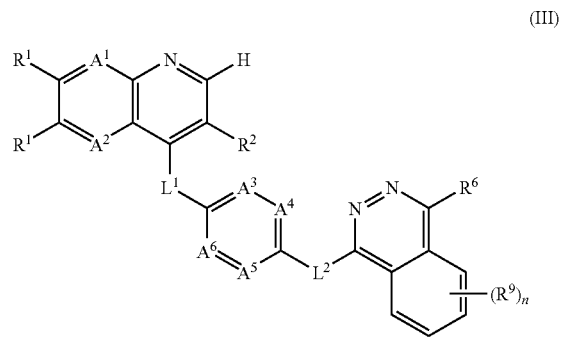

(III)

or a pharmaceutically acceptable salt thereof, wherein
A$^1$ is CR$^2$ and A$^2$ is N;
each of A$^3$, A$^4$, A$^5$ and A$^6$, independently, is CR$^3$;
L$^1$ is —O—, —NR$^4$—, —S—, —C(O)—, —S(O)—, —SO$_2$—or —CR$^4$ R$^4$—, wherein each R$^4$, independently, is H or C$_{1-6}$alkyl;
L$^2$ is —NR$^4$— wherein R$^4$ is H or CH$_3$;
each R$^l$, independently, is H, halo, haloalkyl, haloalkoxyl, CN, OH, SH, NO$_2$, NH$_2$, acetyl, C$_{1-10}$-alkyl, C$_{2-10}$alkenyl, C$_{2-10}$alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, —SR$^9$, —OR$^9$, —NR$^9$ R$^9$, —C(O)R$^9$, —COOR$^9$, —OC(O)R$^9$, —C(O)C(O)R$^9$, —C(O)NR$^9$R$^9$, —NR$^9$C(O)R$^9$, —NR$^9$C(O)NR$^9$R$^9$, —NR$^9$(COOR$^9$), —OC(O)NR$^9$ R$^9$, —S(O)$_2$ R$^9$, —S(O)$_2$R$^9$, —S(O)$_2$NR$^9$R$^9$, —NR$^9$S(O)$_2$NR$^9$R$^9$, —NR$^9$S(O)$_2$R$^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$ -alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^9$;
each R$^2$, independently, is H, halo, haloalkyl, or haloalkoxyl;
each R$^3$, independently, is H, halo, haloalkyl, haloalkoxyl, CN, OH, SH, NO$_2$, NH$_2$, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or —C(O)R$^9$;
R$^6$ is R$^9$;
each R$^9$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, SR$^{10}$, OR$^{10}$, NR$^4$ R$^{10}$, C(O)R$^{10}$, COOR$^{10}$, C(O)NR$^4$ R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$R$^{10}$, NR$^4$S(O)$_2$R$^{10}$, NR$^4$S(O)NR$^4$ R$^{10}$, or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$- cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

8. The compound of claim 4, or a pharmaceutically acceptable salt thereof, wherein
$A^1$ is $CR^2$ and $A^2$ is N;
each of $A^3$, $A^4$, $A^5$ and $A^6$, independently, is $CR^3$;
$L^1$ is —O—, —$NR^4$— or —S—;
$L^2$ is —$NR^4$—;
each $R^1$, independently, is H, halo, $CF_3$, $C_2F_5$, haloalkoxyl, CN, OH, SH, $NO_2$, $NH_2$, acetyl, methyl, methoxyl, ethyl, ethoxyl, propyl, propoxyl, isopropyl, cyclopropyl, butyl, isobutyl, tert-butyl, cyclobutyl, pentyl, cyclopentyl, hexyl, cyclohexyl, methylamine, dimethylamine, ethylamine, diethylamine, propylamine, isopropylamine, dipropylamine, diisopropylamine, —C(O)$R^9$, —COO$R^9$, —C(O)NH$R^9$, —NHC(O)$R^9$, —NHC(O)NH$R^9$, —NH(COO$R^9$), —S(O)$_2$ $R^9$, —S(O)$_2$ $R^9$, —S(O)$_2$NH$R^9$, —NHS(O)$_2$NH$R^9$, —NHS(O)$_2$$R^9$ or a ring selected from phenyl, pyridyl, pyrimidinyl, pyridazinyl, pyazinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl, cycloheptyl or pyranyl, said ring optionally substituted independently with 1-5 substituents of $R^9$;

$R^2$ is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine;

each $R^3$, independently, is H, halo, $CF_3$, CN, $NO_2$, $NH_2$, OH, methyl, methoxyl, ethyl, ethoxyl, propyl, propoxyl, isopropyl, methylamine, dimethylamine, ethylamine, diethylamine, propylamine or isopropylamine;

each $R^4$, independently, is H or $CH_3$; and $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$alkylamino-, $C_{1-10}$-dialkylamino-, benzyl or phenyl.

9. The compound of claim 1, or a pharmaceutically acceptable salt thereof, selected from, N-(4-((7-(methyloxy)-1,5-naphthyridin-4-yl)oxy)phenyl)-4-phenyl-1-phthalazinamine;

N-(4-((7-(methyloxy)-1,5-naphthyridin-4-yl)oxy)phenyl)-4-(4-methyl-1,3-thiazol-2-yl)-1-phthalazinamine;

N-(3-fluoro-4-((7-(methyloxy)-1,5-naphthyridin-4-yl)oxy)phenyl)-4-phenyl-1-phthalazinamine;

N-(4-((7-(methyloxy)-1,5-naphthyridin-4-yl)oxy)phenyl)-4-(4-methyl-2-pyridinyl)-1-phthalazinamine;

N-3-(methyloxy)-8-((4-((4-(4-methylphenyl)-1-phthalazinyl)methyl)phenyl)oxy)-1,5-naphthyridine;

4-(5-chloro-2-thienyl)-N-(4-((7(methyloxy)-1,5-naphthyridin-4-yl)oxy)phenyl)-1-phthalazinamine;

4-(1-methyl-1H-indol-2-yl)-N-(4-((7-(methyloxy)-1,5-naphthyridin-4-yl)oxy)phenyl)-1-phthalazinamine;

N-(4-((7-(methyloxy)-1,5-naphthyridin-4-yl)oxy)phenyl)-4-(4-(trifluoromethyl)phenyl)-1-phthalazinamine;

4-(4-chlorophenyl)-N-(4((7-(methyloxy)-1,5-naphthyridin-4-yl)oxy)phenyl)-1-phthalazinamine;

4-(1,3-benzodioxol-5-yl)-N-(4-((7-(methyloxy)-1,5-naphthyridin-4-yl)oxy)phenyl)-1-phthalazinamine;

4-(2,3-dihydro-1-benzofuran-5-yl)-N-(4-((7-(methyloxy)-1,5-naphthyridin-4-yl)oxy)phenyl)-1-phthalazinamine;

4-(3-chloro-4-(trifluoromethyl)phenyl)-N-(4-((7-(methyloxy)-1,5-naphthyridin-4-yl)oxy)phenyl) -1-phthalazinamine;

4-(6-fluoro-3-pyridinyl)-N-(4-((7-(methyloxy)-1,5-naphthyridin-4-yl)oxy)phenyl)-1-phthalazinamine;

4-(3-chloro-4-fluorophenyl)-N-(4((7-(methyloxy)-1,5-naphthyridin-4-yl)oxy)phenyl)-1-phthalazinamine;

4-(2-methyl-1,3-benzothiazol-5-yl)-N-(4-((7-(methyloxy)-1,5-naphthyridin-4-yl)oxy)phenyl)-1-phthalazinamine;

4-(3,4-dichlorophenyl)-N-(4-((7-(methyloxy)-1,5-naphthyridin-4-yl)oxy)phenyl)-1-phthalazinamine;

4-(1-methyl-1H-indol-5-yl)-N-(4-((7-(methyloxy)-1,5-naphthyridin-4-yl)oxy)phenyl)-1-phthalazinamine;

4-(1,3-benzodioxol-5-yl)-N-(4-((7-(methyloxy)-1,5-naphthyridin-4-yl)oxy)phenyl)-1-phthalazinamine;

N-(4-((7-(methyloxy)-1,5-naphthyridin-4-yl)oxy)phenyl)-4-(5-pyrimidinyl)-1-phthalazinamine;

4-(4-fluorophenyl)-N-(4-((7-(methyloxy)-1,5-naphthyridin-4-yl)oxy)phenyl)-1-phthalazinamine;

4-(5-chloro-2-pyridinyl)-N-(4-((7-(methyloxy)-1,5-naphthyridin-4-yl)oxy)phenyl)-1-phthalazinamine;

4-(6-chloro-3-pyridinyl)-N-(4((7-(methyloxy)-1,5-naphthyridin-4-yl)oxy)phenyl)-1-phthalazinamine;

4-(4-fluoro-3-methylphenyl)-N-(4-((7-(methyloxy)-1,5-naphthyridin-4-yl)oxy)phenyl-1-phthalazinamine;

8-((4-((4-(4-chlorophenyl)-1-phthalazinyl)amino)phenyl)oxy)-1,5-naphthyridine-3-carbonitrile;

N-(4-((7-(methyloxy)-1,5-naphthyridin-4-yl)thio)phenyl)-4-phenyl-1-phthalazinamine;

N-(4-(7-methoxy-1,5-naphthyridin-4-ylthio)phenyl)-4-(4-methylthiophen-2-yl)phthalazin-1-amine;

4-ethyl-N-(4-(7-methoxy-1,5-naphthyridin-4-ylthio)phenyl)-6-phenylpyridazin-3-amine; and 4-(5-chloro-2-pyridinyl)-N-(4-((7-(methyloxy)-1,5-naphthyridin-4-yl)thio)phenyl)-1-phthalazinamine.

10. A pharmaceutical composition comprising a pharmaceutically acceptable excipient and a therapeutically effective amount of the compound of claim 1.

11. A pharmaceutical composition comprising a pharmaceutically acceptable excipient and a therapeutically effective amount of a compound of claim 4.

12. A pharmaceutical composition comprising a pharmaceutically acceptable excipient and a therapeutically effective amount of a compound of claim 6.

13. The compound of claim 1 having the Formula III

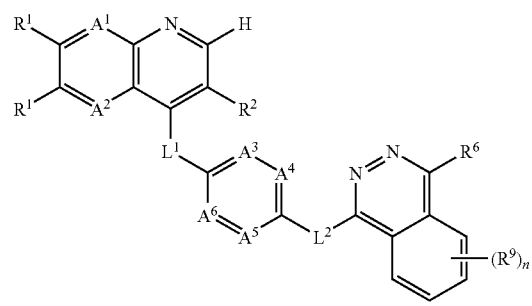

(III)

or a pharmaceutically acceptable salt thereof, wherein
$A^1$ is $CR^2$;
$A^2$ is N;
each of $A^3$, $A^4$, $A^5$ and $A^6$, independently, is $CR^3$, wherein each $R^3$, independently, is H, F, Cl, Br, $CF_3$, $-OCF_3$, CN, OH, SH, $NO_2$, $NH_2$, $CH_3$, $C_2H_5$, $-OCH_3$, $-SCH_3$, $-NHCH_3$, or $-C(O)CH_3$;
$L^1$ is $-O-$, $-NR^4-$ or $-S-$, wherein $R^4$ is H, $CH_3$ or CN;
$L^2$ is $-NH-$;
each $R^1$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $-SR^9$, $-OR^9$, $-NR^9 R^9$, $-C(O)R^9$, $-COOR^9$, $-OC(O)R^9$, $-C(O)C(O)R^9$, $-C(O)NR^9R^9$, $-NR^9C(O)R^9$, $-NR^9C(O)NR^9R^9$, $-NR^9(COOR^9)$, $-OC(O)NR^9R^9$, $-S(O)_2 R^9$, $-S(O)_2 R^9$, $-S(O)_2NR^9R^9$, $-NR^9S(O)_2NR^9R^9$, $-NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^2$, independently, is H, F, Cl, Br, $CF_3$, $C_2F_5$, $CHF_2$, $CH_2F$, $-OCF_3$, CN, OH, SH, $NO_2$, $NH_2$, $CH_3$, $C_2H_5$, $-OCH_3$, $-SCH_3$, $-NHCH_3$, or $-C(O)CH_3$;

$R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a] pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4 R^{10}$, $NR^4 (COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkyhyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

14. The compound of claim 8, or a pharmaceutically acceptable salt thereof, selected from,
- N-(4-((7-(methyloxy)-1,5-naphthyridin-4-yl)oxy)phenyl)-4-(4-methylphenyl)-1-phthalazinamine;
- N-(4-((7-(methyloxy)-1,5-naphthyridin-4-yl)oxy)phenyl)-4-(4-methyl-1,3-thiazol-2-yl)-1-phthalazinamine;
- N-(4-((7-(methyloxy)-1,5-naphthyridin-4-yl)oxy)phenyl)-4-(6-(methyloxy)-2-pyridinyl)1-1-phthalazinamine;
- N-(4-((7-(methyloxy)-1,5-naphthyridin-4-yl)oxy)phenyl)-4-(6-methyl-2-pyridinyl)1-1-phthalazinamine;
- 4-(6-((methyloxy)methyl)-2-pyridinyl)-N-(4((7-(methyloxy)-1,5-naphthyridin-4-yl)oxy)phenyl)-1-phthalazinamine;
- N-(4-((7-(methyloxy)-1,5-naphthyridin-4-yl)oxy)phenyl)-4-(5-methyl-2-thienyl)-1-phthalazinamine;
- N-(4-((7-(methyloxy)-1,5-naphthyridin-4-yl)oxy)phenyl)-4-(3-(methyloxy)phenyl)-1-phthalazinamine;
- N-(4-((7-(methyloxy)-1,5-naphthyridin-4-yl)oxy)phenyl)-4-(4-methyl-2-thienyl)-1-phthalazinamine;
- 2-chloro-5-(4-((4-((7-(methyloxy)-1,5-naphthyridin-4-yl)oxy)phenyl)amino)-1-phthalazinyl)benzonitrile;
- 4-(4-chlorophenyl)-N-(4-((7-(methyloxy)-1,5-naphthyridin-4-yl)oxy)phenyl)-1-phthalazinamine;
- N-(4-((7-(methyloxy)-1,5-naphthyridin-4-yl)oxy)phenyl)-4-(4-((trifluoromethyl)oxy)phenyl)-1-phthalazinamine;
- 4-(1H-indol-5-yl)-N-(4-((7-(methyloxy)-1,5-naphthyridin-4-yl)oxy)phenyl)-1-phthalazinamine;
- N-(6-((7-(methyloxy)-1,5-naphthyridin-4-yl)oxy)-3-pyridinyl)-4-phenyl-1-phthalazinamine;
- 4-(2-fluoro-6-methyl-3-pyridinyl)-N-(4-((7-(methyloxy)-1,5-naphthyridin-4-yl)oxy)phenyl)-1-phthalazinamine;
- 4-(4-((4-((7-(methyloxy)-1,5-naphthyridin-4-yl)oxy)phenyl)amino)-1-phthalazinyl)benzonitrile;
- N-(4-((7-(methyloxy)-1,5-naphthyridin-4-yl)oxy)phenyl)-4-(1,3-oxazol-2-yl)-1phthalazinamine;
- N-(4-((7-(methyloxy)-1,5-naphthyridin-4-yl)thio)phenyl)-4-phenyl-1-phthalazinamine;
- 4-(3-amino-4-methylphenyl)-N-(4-((7-(methyloxy)-1,5-naphthyridin-4-yl)oxy)phenyl)-1-phthalazinamine;
- 4-(3-chlorophenyl)-N-(4-((7-(methyloxy)-1,5-naphthyridin-4-yl)oxy)phenyl)-1-phthalazinamine;
- 4-(3-fluoro-4-(methyloxy)phenyl)-N-(4-((7-(methyloxy)-1,5-naphthyridin-4-yl)oxy)phenyl)-1-phthalazinamine;
- 4-(5-ethyl-2-thienyl)-N-(4-((7-(methyloxy)-1,5-naphthyridin-4-yl)oxy)phenyl)-1-phthalazinamine;
- 4-(4-chlorophenyl)-N-(4-((7-(methyloxy)-1,5-naphthyridin-4-yl)thio)phenyl)-1-phthalazinamine;
- 4-(4-chloro-3-methylphenyl)-N-(4-((7-(methyloxy)-1,5-naphthyridin-4-yl)oxy)phenyl)-1-phthalazinamine;
- 4-(3-(dimethylamino)phenyl)-N-(4-((7-(methyloxy)-1,5-naphthyridin-4-yl)oxy)phenyl)-1-phthalazinamine;
- 4,5-dimethyl-2-thienyl)-N-(4-((7-(methyloxy)-1,5-naphthyridin-4-yl)oxy)phenyl)-1-phthalazinamine;
- N-(4-(1,5-naphthyridin-4-ylthio)phenyl)-4-phenyl-1-phthalazinamine;
- 4-(4-chloro-2-thienyl)-N-(4-((7-(methyloxy)-1,5-naphthyridin-4-yl)oxy)phenyl)-1-phthalazinamine;
- N-(4-((7-(methyloxy)-1,5-naphthyridin-4-yl)oxy)phenyl)-4-(3-methylphenyl)-1-phthalazinamine;
- 4-chloro-2-pyridinyl)-N-(4-((7-(methyloxy)-1,5-naphthyridin-4-yl)thio)phenyl)-1-phthalazinamine;
- N-(4-((7-(methyloxy)-1,5-naphthyridin-4-yl)thio)phenyl)-4-(6-methyl1-2-pyridinyl)-1-phthalazinamine;
- 4-(2,3-dihydro-1-benzofuran-5-yl)-N-(4-(1,5-naphthyridin-4-ylthio)phenyl)-1-phthalazinamine;
- 4-(4-methyl-2-thienyl)-N-(4-(1,5-naphthyridin-4-yloxy)phenyl)-1-phthalazinamine;
- 4-(4-chlorophenyl)-N-(4-(1,5-naphthyridin-4-yloxy)phenyl)-1-phthalazinamine;
- 4-(4-((4-((7-methoxy-1,5-naphthyridin-4-yl)sulfanyl)phenyl)amino)-1-phthalazinyl)-1-methyl-2(1H)-pyridinone;
- 4-(4-chlorophenyl)-N-(3,5-difluoro-4-((7-methoxy-1,5-naphthyridin-4-yl)oxy)phenyl)-1-phthalazinamine;
- 4-(2-fluorophenyl)-N-(4((7-(methyloxy)-1,5-naphthyridin-4-yl)thio)phenyl)-1-phthalazinamine;
- 4-(2-methyl-2H-indazol-6-yl)-N-(4-((7-(methyloxy)-1,5-naphthyridin-4-yl)thio)phenyl)-1-phthalazinamine;
- N-(4-((7-(methyloxy)-1,5-naphthyridin-4-yl)thio)phenyl)-4-(4-methyl-1-piperazinyl)-1-phthalazinamine;
- N-(3-fluoro-4-((7-(methyloxy)-1,5-naphthyridin-4-yl)thio)phenyl)-4-phenyl-1-phthalazinamine;
- N-(4-((7-(methyloxy)-1,5-naphthyridin-4-yl)thio)phenyl)-4-(4-(methyloxy)-1-piperidinyl)-1-phthalazinamine;
- N-(4-((7-(methyloxy)-1,5-naphthyridin-4-yl)thio)phenyl)-4-(1-pyrrolidinyl)-1-phthalazinamine;
- 4-(1,3-benzodioxol-5-yl)-N-(3-fluoro-4-((7-(methyloxy)-1,5-naphthyridin-4-yl)thio)phenyl)-1-phthalazinamine; and
- 4-(1,3-benzodioxol-5-yl)-N-(4-((6-(methyloxy)-1,5-naphthyridin-4-yl)oxy)phenyl)-1-phthalazinamine.

15. The compound of claim 8, or a pharmaceutically acceptable salt thereof, having the chemical structure of

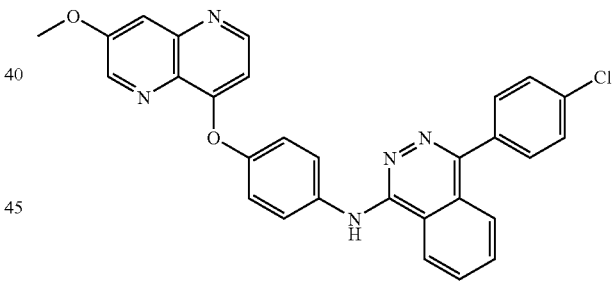

and the chemical name of 4-(4-chlorophenyl)-N-(4-((7-(methyloxy)-1,5-naphthyridin-4-yl)oxy)phenyl)-1-phthalazinamine.

16. A pharmaceutical composition comprising a pharmaceutically acceptable excipient and a therapeutically effective amount of the compound of claim 9.

17. A pharmaceutical composition comprising a pharmaceutically acceptable excipient and a therapeutically effective amount of a pharmaceutically acceptable salt form of the compound of claim 9.

* * * * *